(12) United States Patent
Bartolozzi et al.

(10) Patent No.: US 8,575,201 B2
(45) Date of Patent: Nov. 5, 2013

(54) OXADIAZOLE INHIBITORS OF LEUKOTRIENE PRODUCTION

(75) Inventors: Alessandra Bartolozzi, Norwalk, CT (US); Todd Bosanac, New Milford, CT (US); Zhidong Chen, New Milford, CT (US); Stephane De Lombaert, Branford, CT (US); Jonathon Alan Dines, Abingdon (GB); John D. Huber, New York, NY (US); Weimin W. Liu, Beijing (CN); Pui Leng Loke, Abingdon (GB); Tina Marie Morwick, Carmel, IN (US); Alan Olague, Danbury, CT (US); Doris Riether, Biberach an der Riss (DE); Heather Tye, Abingdon (GB); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 13 days.

(21) Appl. No.: 13/237,112

(22) Filed: Sep. 20, 2011

(65) Prior Publication Data

US 2012/0295896 A1    Nov. 22, 2012

Related U.S. Application Data

(60) Provisional application No. 61/533,349, filed on Sep. 12, 2011, provisional application No. 61/385,733, filed on Sep. 23, 2010.

(51) Int. Cl.
   *A01N 43/40* (2006.01)
   *A61K 31/44* (2006.01)

(52) U.S. Cl.
   USPC .................................. 514/340; 546/269.1

(58) Field of Classification Search
   USPC .................................. 514/340; 546/269.1
   See application file for complete search history.

(56) References Cited

U.S. PATENT DOCUMENTS

| | | | |
|---|---|---|---|
| 6,911,444 | B2 | 6/2005 | Lacrampe et al. |
| 7,319,108 | B2 | 1/2008 | Schwink et al. |
| 2007/0105866 | A1 | 5/2007 | Hutchinson et al. |
| 2009/0192171 | A1 | 7/2009 | Hutchinson et al. |
| 2010/0197591 | A1 | 8/2010 | Aspnes et al. |
| 2011/0206652 | A1 | 8/2011 | Kayser et al. |
| 2011/0206783 | A1* | 8/2011 | Burgey et al. ............ 424/722 |
| 2012/0214787 | A1* | 8/2012 | Bartolozzi et al. ..... 514/210.18 |
| 2012/0220561 | A1* | 8/2012 | Bartolozzi et al. ....... 514/210.2 |
| 2012/0245162 | A1* | 9/2012 | Bartolozzi et al. ....... 514/230.5 |
| 2012/0295896 | A1 | 11/2012 | Bartolozzi et al. |

FOREIGN PATENT DOCUMENTS

| | | | |
|---|---|---|---|
| WO | 2006044602 | A2 | 4/2006 |
| WO | 2007056228 | A2 | 5/2007 |
| WO | 2007120574 | A2 | 10/2007 |
| WO | 2008030369 | A1 | 3/2008 |
| WO | 2008128335 | A1 | 10/2008 |
| WO | 2008156721 | A1 | 12/2008 |
| WO | 2009048547 | A1 | 4/2009 |
| WO | 2011143466 | A1 | 11/2011 |

OTHER PUBLICATIONS

International Search Report for PCT/US2011/047356 mailed on Oct. 28, 2011.
International Search Report for PCT/US2011/048743 mailed on Nov. 2, 2011.
International Search Report for PCT/US2011/052252 mailed on Nov. 2, 2011.
International Search Report for PCT/US2011/052254 mailed on Nov. 16, 2011.
Chabner, Bruce A. et al. "Antineoplastic Agents" Chemotherapy of Neoplastic Diseases, Goodman & Gilmans, The Pharmacological Basis of Therapeutics, (2006) 11th edition, pp. 1315-1403.
Poupaert, Jacques H. "Drug Design: Basic Principles and Applications" Encyclopedia of Pharmaceutical Technology, 3rd Edition, (2007) pp. 1362-1369.
Machine Translation of JP05112564 (May 7, 1993).

* cited by examiner

*Primary Examiner* — James O Wilson
*Assistant Examiner* — Alexander R Pagano
(74) *Attorney, Agent, or Firm* — Michael P. Morris; Usha R. Patel

(57) ABSTRACT

The present invention relates to compounds of formula (I) and (IA):

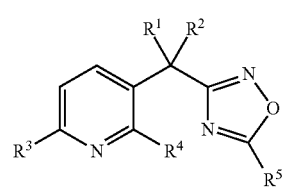

I

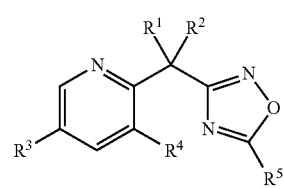

IA and pharmaceutically acceptable salts thereof, wherein $R^1$-$R^5$ are as defined herein. The invention also relates to pharmaceutical compositions comprising these compounds, methods of using these compounds in the treatment of various diseases and disorders, processes for preparing these compounds and intermediates useful in these processes.

24 Claims, No Drawings

OXADIAZOLE INHIBITORS OF LEUKOTRIENE PRODUCTION

FIELD OF THE INVENTION

This invention relates to oxadiazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoE$^{-/-}$ xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula I:

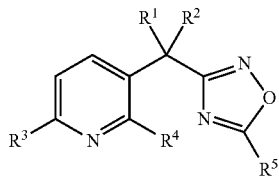

wherein:

$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;

$R^3$ is 5-11 membered heteroaryl ring containing one to three heteroatoms selected from nitrogen, oxygen and sulfur, wherein each $R^3$ is optionally independently substituted with one to three groups selected from $C_{1-5}$ alkyl, $C_{1-5}$ alkoxy, $C_{1-3}$ alkylhydroxy, —CN, amino, $C_{1-3}$ alkylamino and $C_{1-3}$ dialkylamino;

$R^4$ is hydrogen, halogen, $C_{1-3}$ alkyl or nitrile;

$R^5$ is $C_{1-6}$ alkyl, $C_{3-10}$ carbocycle, 5-11 membered heterocycle, aryl, 5-11 membered heteroaryl, —C(O)—$R^6$ or —$NR^7R^8$, wherein each $R^5$ is optionally independently substituted with one to three groups selected from $R^9$, $R^{10}$ and $R^{11}$;

$R^6$ is $C_{3-8}$ heterocycle, amino, $C_{1-3}$ alkylamino, $C_{1-3}$ dialkylamino or —NH-5-6 membered heterocycle, each optionally independently substituted with one to three groups selected from $R^9$, $R^{10}$ and $R^{11}$;

$R^7$ and $R^8$ are each independently hydrogen, —S(O)$_n$C$_{1-6}$alkyl or C$_{1-6}$ alkyl;

$R^9$, $R^{10}$ and $R^{11}$ are independently selected from
(a) —H,
(b) —OH,
(c) halogen,
(d) —CN,
(e) —CF$_3$,
(f) C$_{1-6}$alkyl optionally substituted with one to three —OH, —N(R$^{12}$)(R$^{13}$), aryl, —O—C$_{1-2}$ alkyl-aryl, 3-6 membered heterocycle, —C(O)-3-6 membered heterocycle, C$_{1-6}$alkoxy, —S(O)$_n$C$_{1-6}$alkyl, —CO$_2$R$^{12}$, halogen, —CN or —C(O)N(R$^{12}$)(R$^{13}$),
(g) C$_{1-6}$alkoxy,
(h) —N(R$^{12}$)(R$^{13}$),
(i) —S(O)$_n$C$_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) a 3-10 membered heterocyclic group optionally substituted with one to three groups selected from —OH, C$_{1-6}$ alkyl, C$_{1-6}$ alkylhydroxy, C$_{1-6}$ alkyl-CO$_2$R$^{12}$, —S(O)$_n$C$_{1-6}$alkyl, oxo, —C(O)N(R$^{12}$)(R$^{13}$), and —CO$_2$R$^{12}$,
(n') oxo,
(o) —C(O)—C$_{1-3}$ alkyl,
(p) —C(O)-3-6 membered heterocycle optionally substituted with one to three groups selected from halogen hydroxy and C$_{1-6}$alkoxy,
(q) —OR$^{12}$,
(r) 5-11 membered heteroaryl;

$R^{12}$ and $R^{13}$ are each independently selected from —H, —C$_{1-6}$alkyl, —C(O)—C$_{1-6}$ alkyl, C$_{3-10}$ carbocycle and a 3-6 membered heterocyclic group, each of which is optionally independently substituted with one to three —OH, C$_{1-6}$ alkyl, C$_{1-6}$alkoxy, —C(O)N(R$^{14}$)(R$^{15}$), —S(O)$_n$C$_{1-6}$alkyl, CN, C$_{3-10}$ carbocycle, —CO$_2$R$^{14}$, CF$_3$, 3-6 membered heterocycle, halogen; or $R^{12}$ and $R^{13}$ together with the nitrogen atom to which they are attached form a heterocyclyl ring optionally substituted with one to three —OH, CN, C$_{1-6}$alkoxy or oxo;

$R^{14}$ and $R^{15}$ are each independently selected from —H and —C$_{1-6}$alkyl;

n is 0, 1 or 2;

or a pharmaceutically acceptable salt thereof.

In a second embodiment, the present invention relates to a compound as described in the broadest embodiment above, wherein:

$R^1$ and $R^2$ together with the carbon atom to which they are attached is cyclopropyl, cyclobutyl, cyclopentyl, cyclohexyl, cycloheptyl, cyclooctyl, 2.2.1 bicycloheptyl, oxetanyl, tetrahydrofuranyl, tetrahydropyranyl, pyrrolidinyl, piperidinyl, tetrahydrothienyl, wherein each carbocycle or heterocycle is optionally independently substituted with one to two groups selected from C$_{1-6}$ alkyl and halogen;

$R^3$ is pyridinyl, pyrimidinyl, pyrazinyl, pyridazinyl, pyrrolyl, imidazolyl, thienyl, furanyl or thiazolyl, wherein each $R^3$ is optionally independently substituted with one to three groups selected from C$_{1-3}$ alkyl, C$_{1-3}$ alkoxy, C$_{1-3}$ alkylhydroxy, —CN, amino, C$_{1-3}$ alkylamino and C$_{1-3}$ dialkylamino;

$R^4$ is hydrogen, halogen or methyl;

$R^5$ is methyl, ethyl, propyl, isopropyl, butyl, isobutyl, tert, butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, dihydropyridinyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—R$^6$, hydroxy or —NR$^7$R$^8$, wherein each R$^5$ is optionally independently substituted with one to three groups selected from R$^9$, R$^{10}$ and R$^{11}$;

$R^6$ is azetidinyl, pyrrolidinyl, piperidinyl, piperazinyl, tetrahydropyranyl, morpholinyl, thiomorpholinyl, amino, C$_{1-3}$ alkylamino, C$_{1-3}$ dialkylamino or —NH-5-6 membered heterocycle, each optionally independently substituted with one to three groups selected from R$^9$, R$^{10}$ and R$^{11}$;

$R^7$ and $R^8$ are each independently hydrogen, C$_{1-5}$ alkyl or —S(O)$_n$C$_{1-6}$alkyl;

$R^9$, $R^{10}$ and $R^{11}$ are independently selected from
(a) —H,
(b) —OH,
(c) halogen,
(d) —CN,
(e) —CF$_3$,
(f) C$_{1-6}$alkyl optionally substituted with one to three —OH, —N(R$^{12}$)(R$^{13}$), phenyl, benzyl, phenethyl, azetidinyl, pyrrolidinyl, piperidinyl, piperazinyl, morpholinyl, —C(O)-3-6 membered heterocycle, C$_{1-6}$alkoxy, —S(O)$_n$ C$_{1-6}$alkyl, —CO$_2$R$^{12}$, halogen, —CN or —C(O)N(R$^{12}$)(R$^{13}$),
(g) C$_{1-6}$alkoxy, (h) —N($R^{12}$)($R^{13}$),
(i) —S(O)$_n$$C_{1-6}$ alkyl,
(j) —$CO_2R^{12}$,
(k) —C(O)N($R^{12}$)($R^{13}$),
(l) —S(O)$_2$N($R^{12}$)($R^{13}$),
(m) oxetanyl, tetrahydrofuranyl, tetrahydropyranyl, azetidinyl, pyrrolidinyl, tetrahydrothienyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$ alkylhydroxy, $C_{1-6}$ alkyl-$CO_2R^{12}$, —S(O)$_n$$C_{1-6}$alkyl, oxo, —C(O)N($R^{12}$)($R^{13}$), and —$CO_2R^{12}$,
(n') oxo,
(o) —C(O)—$C_{1-3}$ alkyl,
(p) —C(O)-3-6 membered heterocycle optionally substituted with one to three groups selected from halogen hydroxy and $C_{1-6}$alkoxy,
(q) —$OR^{12}$,
(r) imidazolyl, pyrrolyl, pyrazolyl, thienyl or furanyl;
$R^{12}$ and $R^{13}$ are each independently selected from —H, —$C_{1-6}$alkyl, —C(O)—$C_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —S(O)$_n$$C_{1-6}$alkyl, CN, cyclopropyl, cyclobutyl, cyclopentyl, cyclohexyl, —$CO_2R^{14}$, $CF_3$, 3-6 membered heterocycle, halogen; or
$R^{12}$ and $R^{13}$ together with the nitrogen atom to which they are attached form a heterocyclyl ring optionally substituted with one to three —OH, CN, $C_{1-6}$alkoxy or oxo;
$R^{14}$ and $R^{15}$ are each independently selected from —H and —$C_{1-6}$alkyl;
n is 0 or 2;
or a pharmaceutically acceptable salt thereof.

In a third embodiment, the present invention relates to a compound as described in any of the preceding embodiments above, wherein:
$R^1$ and $R^2$ together with the carbon atom to which they are attached is cyclobutyl, cyclopentyl cyclohexyl, or tetrahydropyranyl wherein each carbocycle or heterocycle is optionally independently substituted with one to two groups selected from $C_{1-3}$ alkyl and halogen;
or a pharmaceutically acceptable salt thereof.

In a fourth embodiment there is provided a compound of formula (I) as described in any of the preceding embodiments above, wherein:
$R^3$ is pyridinyl, pyrimidinyl, pyrazinyl or pyridazinyl, wherein each $R^3$ is optionally independently substituted with one to three groups selected from $C_{1-3}$ alkyl, $C_{1-3}$ alkoxy, $C_{1-3}$ alkylhydroxy, —CN, amino, $C_{1-3}$ alkylamino and $C_{1-3}$ dialkylamino;
or a pharmaceutically acceptable salt thereof.

In a fifth embodiment there is provided a compound as described in any of the preceding embodiments above, wherein:
$R^5$ is methyl, ethyl, propyl, isopropyl, butyl, isobutyl, tert-butyl, pentyl, hexyl, phenyl, piperidinyl, piperazinyl, morpholinyl, thiomorpholinyl, pyrrolidinyl, furanyl, thiazolyl, oxazolyl, isoxazolyl, pyrazolyl, imidazolyl, triazolyl, dihydropyridinyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is azetidinyl, pyrrolidinyl, piperidinyl, piperazinyl, morpholinyl, amino, $C_{1-3}$ alkylamino or $C_{1-3}$ dialkylamino;

$R^7$ and $R^8$ are each independently hydrogen, $C_{1-5}$ alkyl or —S(O)$_2$$C_{1-6}$alkyl;
$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_n$$C_{1-6}$alkyl, —$CO_2R^{12}$, halogen, —CN or —C(O)N($R^{12}$)($R^{13}$),
(g) $C_{1-6}$alkoxy,
(h) —N($R^{12}$)($R^{13}$),
(i) —S(O)$_2$$C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) oxetanyl, tetrahydrofuranyl, tetrahydropyranyl, tetrahydrothienyl, azetidinyl, pyrrolidinyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$ alkylhydroxy, $C_{1-6}$ alkyl-$CO_2R^{12}$, —S(O)$_n$$C_{1-6}$alkyl, oxo, —C(O)N($R^{12}$)($R^{13}$), and —$CO_2R^{12}$,
(n') oxo,
(o) —C(O)—$C_{1-3}$ alkyl,
(p) —C(O)-3-6 membered heterocycle optionally substituted with one to three groups selected from halogen hydroxy and $C_{1-6}$alkoxy,
(q) —$OR^{12}$,
(r) imidazolyl, pyrrolyl, pyrazolyl, thienyl or furanyl;
$R^{12}$ and $R^{13}$ are each independently selected from —H, —$C_{1-6}$alkyl, —C(O)—$C_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —S(O)$_n$$C_{1-6}$alkyl, CN, cyclopropyl, cyclobutyl, cyclopentyl, cyclohexyl, —$CO_2R^{14}$, $CF_3$, 3-6 membered heterocycle, halogen; or
$R^{12}$ and $R^{13}$ together with the nitrogen atom to which they are attached form a heterocyclyl ring optionally substituted with one to three —OH, CN, $C_{1-6}$alkoxy or oxo;
$R^{14}$ and $R^{15}$ are each independently selected from —H and —$C_{1-6}$alkyl;
n=2;
or a pharmaceutically accepted salt thereof.

In a sixth embodiment there is provided a compound of formula (I) as described in the first or second embodiment above, wherein:
$R^1$ and $R^2$ together with the carbon atom to which they are attached is cyclobutyl or tetrahydropyranyl each optionally independently substituted with one to two groups selected from methyl and fluoro;
$R^3$ is pyridinyl, pyrimidinyl, pyrazinyl or pyridazinyl, wherein each $R^3$ is optionally independently substituted with one to three groups selected from methyl, —CN, —NH—$CH_3$ and an amino group;
$R^4$ is hydrogen;
$R^5$ is phenyl, piperidinyl, piperazinyl, pyrrolidinyl, thiazolyl, oxazolyl, isoxazolyl, pyrazolyl, imidazolyl, triazolyl, dihydropyridinyl, pyridinyl, pyrimidinyl, pyrazinyl, pyridazinyl, pyrazolopyrimidinyl, imidazopyridinyl, indazolyl, or —NR⁷R⁸, wherein each R⁵ is optionally independently substituted with one to three groups selected from R⁹, R¹⁰ and R¹¹;

R⁷ and R⁸ are each independently hydrogen or $C_{1-3}$ alkyl;

R⁹, R¹⁰ and R¹¹ are independently selected from (a) —H, (b) —OH, (c) halogen, (d) —CN, (e) —CF₃, (f) $C_{1-6}$alkyl optionally substituted with one to three —OH, —N(R¹²)(R¹³), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)₂ $C_{1-6}$alkyl, —CO₂R¹², halogen, —CN or —C(O)N(R¹²)(R¹³), (g) $C_{1-6}$alkoxy, (h) —N(R¹²)(R¹³), (i) —S(O)₂$C_{1-6}$alkyl, (j) —CO₂R¹², (k) —C(O)N(R¹²)(R¹³), (l) —S(O)₂N(R¹²)(R¹³), (m) oxetanyl, tetrahydrothienyl, pyrrolidinyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$ alkylhydroxy, $C_{1-6}$ alkyl-CO₂R¹², —S(O)₂$C_{1-6}$alkyl, oxo, —C(O)N(R¹²)(R¹³), and —CO₂R¹², (n') oxo, (o) —C(O)—$C_{1-3}$ alkyl, (p) —C(O)-piperidinyl or —C(O)-pyrrolidinyl each optionally substituted with one to three groups selected from halogen hydroxy and $C_{1-6}$alkoxy, (q) —OR¹², (r) imidazolyl, pyrrolyl or pyrazolyl;

R¹² and R¹³ are each independently selected from —H, —$C_{1-6}$alkyl, —C(O)—$C_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N(R¹⁴)(R¹⁵), —S(O)₂$C_{1-6}$alkyl, CN, cyclopropyl, cyclobutyl, cyclopentyl, cyclohexyl, —CO₂R¹⁴, CF₃, 3-6 membered heterocycle, halogen; or R¹² and R¹³ together with the nitrogen atom to which they are attached form a heterocyclyl ring optionally substituted with one to three —OH, CN, $C_{1-6}$alkoxy or oxo;

R¹⁴ and R¹⁵ are each independently selected from —H and —$C_{1-6}$alkyl;

or a pharmaceutically accepted salt thereof.

In a seventh embodiment there is provided a compound as described in the embodiment above, wherein:

R¹ and R² together with the carbon atom to which they are attached is cyclobutyl;

or a pharmaceutically acceptable salt thereof.

In an eighth embodiment there is provided a compound as described in the sixth embodiment above, wherein:

R¹ and R² together with the carbon atom to which they are attached is tetrahydropyranyl;

or a pharmaceutically acceptable salt thereof.

In a ninth embodiment there is provided a compound as described in the sixth embodiment above, wherein:

R³ is selected from

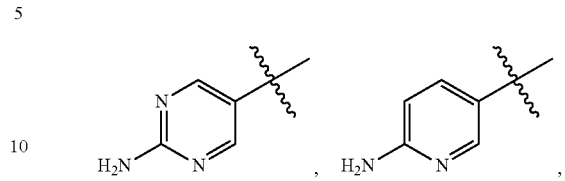

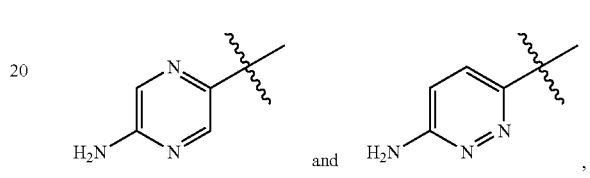

or a pharmaceutically acceptable salt thereof.

In a tenth embodiment there is provided a compound as described in the sixth embodiment above, wherein:

R⁵ is selected from imidazolyl, pyrazolyl, triazolyl, thiazolyl, oxazolyl, pyrazolopyrimidinyl, imidazopyridinyl, indazolyl, dihydropyridinyl, pyridinyl, pyrimidinyl, pyrazinyl, pyridazinyl, pyrrolidinyl, and phenyl, wherein each R⁵ is optionally independently substituted with one to three groups selected from R⁹, R¹⁰ and R¹¹;

or a pharmaceutically acceptable salt thereof.

In an eleventh embodiment there is provided a compound as described in the sixth embodiment above, wherein:

R⁵ is —NR⁷R⁸, optionally substituted with one to three groups selected from R⁹, R¹⁰ and R¹¹;

or a pharmaceutically acceptable salt thereof.

In a twelfth embodiment there is provided a compound as described in the sixth embodiment above, wherein:

R¹ and R² together with the carbon atom to which they are attached is cyclobutyl or tetrahydropyranyl;

R³ is selected from

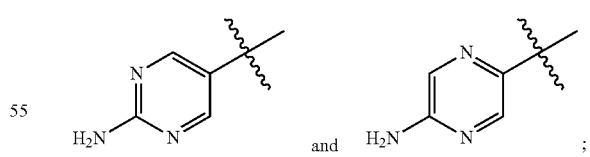

R⁴ is hydrogen;

R⁵ is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, and phenyl, wherein each R⁵ is optionally independently substituted with one to three groups selected from R⁹, R¹⁰ and R¹¹;

or a pharmaceutically acceptable salt thereof.

In a thirteenth embodiment there is provided a compound as described in the sixth embodiment above, wherein:

R¹ and R² together with the carbon atom to which they are attached is cyclobutyl or tetrahydropyranyl;

R³ is selected from

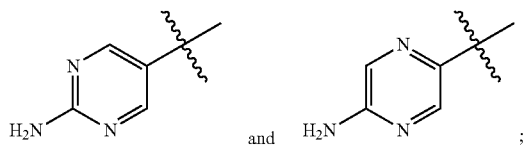 [SMILES: *c1cnc(N)nc1 ; *c1cnc(N)cn1 ; "and" ; ";"]

R⁴ is hydrogen;

R⁵ is —NR⁷R⁸ optionally substituted with one to three groups selected from R⁹, R¹⁰ and R¹¹;

or a pharmaceutically acceptable salt thereof.

In another first broadest embodiment, the present invention relates to a compound of formula IA:

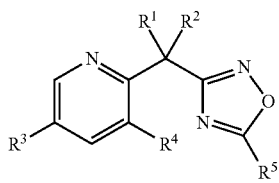

wherein:

R¹ and R² together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;

R³ is 5-11 membered heteroaryl ring containing one to three heteroatoms selected from nitrogen, oxygen and sulfur, wherein each R³ is optionally independently substituted with one to three amino groups;

R⁴ is hydrogen, $C_{1-3}$ alkyl or halogen;

R⁵ is 5-11 membered heteroaryl optionally independently substituted with one to three $C_{1-6}$ alkyl groups;

or a pharmaceutically acceptable salt thereof.

In a second embodiment, the present invention relates to a compound of formula (IA) as described in the broadest embodiment above, wherein:

R¹ and R² together with the carbon atom to which they are attached is cyclopropyl, cyclobutyl, cyclopentyl, tetrahydrofuranyl, tetrahydropyranyl, wherein each carbocycle or heterocycle is optionally independently substituted with one to two groups selected from $C_{1-6}$ alkyl and halogen;

R³ is pyridinyl, pyrimidinyl, pyrazinyl, pyridazinyl, wherein each R³ is optionally independently substituted with one to three amino groups;

R⁴ is hydrogen;

R⁵ is pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, wherein each R⁵ is optionally substituted with one to three $C_{1-6}$ alkyl groups;

or a pharmaceutically acceptable salt thereof.

In a third embodiment, the present invention relates to a compound of formula (IA) as described in any of the preceding embodiments above, wherein:

R¹ and R² together with the carbon atom to which they are attached is cyclobutyl or tetrahydropyranyl;

or a pharmaceutically acceptable salt thereof.

In a fourth embodiment there is provided a compound of formula (IA) as described in any of the preceding embodiments above, wherein:

R³ is pyrimidinyl substituted with an amino group;

or a pharmaceutically acceptable salt thereof.

In a fifth embodiment there is provided a compound of formula (IA) as described in any of the preceding embodiments above, wherein:

R⁵ is pyrazolyl or, pyridinyl, each optionally substituted with one to three $C_{1-3}$ alkyl groups;

or a pharmaceutically acceptable salt thereof.

In a sixth embodiment there is provided a compound of formula (IA) as described in the second embodiment above, wherein:

R¹ and R² together with the carbon atom to which they are attached is cyclobutyl or tetrahydropyranyl;

R³ is pyrimidinyl substituted with an amino group;

R⁴ is H

R⁵ is pyrazolyl or, pyridinyl, each optionally substituted with one to three methyl groups;

or a pharmaceutically acceptable salt thereof.

The following are representative compounds of the invention which can be made by the general synthetic schemes, the examples, and known methods in the art.

TABLE I

| Example | Structure | Name |
|---|---|---|
| 1 | 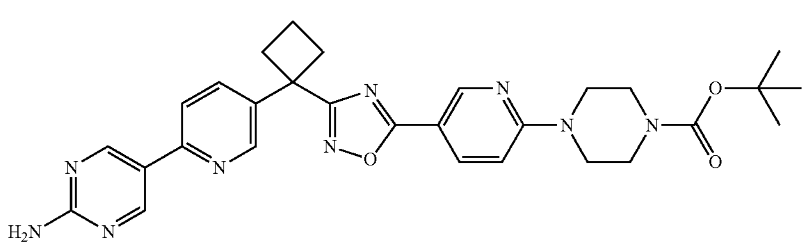 [SMILES: CC(C)(C)OC(=O)N1CCN(c2ccc(-c3nc(C4(c5ccc(-c6cnc(N)nc6)nc5)CCC4)no3)cn2)CC1] | tert-butyl 4-[5-(3-{1-[6-(2-aminopyrimidin-5-yl)pyridin-3-yl]cyclobutyl}-1,2,4-oxadiazol-5-yl)pyridin-2-yl]piperazine-1-carboxylate |

TABLE I-continued

| Example | Structure | Name |
|---|---|---|
| 2 | 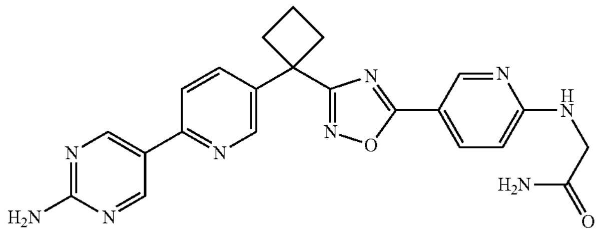 [SMILES: NC(=O)CNc1ccc(-c2nc(C3(c4ccc(-c5cnc(N)nc5)nc4)CCC3)no2)cn1] | N-2-[5-(3-{1-[6-(2-aminopyrimidin-5-yl)pyridin-3-yl]cyclobutyl}-1,2,4-oxadiazol-5-yl)pyridin-2-yl]glycinamide |
| 3 | 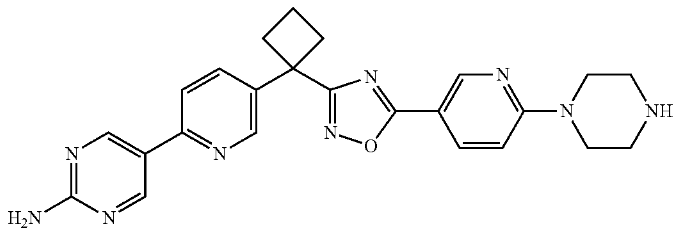 | 5-[5-(1-{5-[6-(piperazin-1-yl)pyridin-3-yl]-1,2,4-oxadiazol-3-yl}cyclobutyl)pyridin-2-yl]pyrimidin-2-amine |
| 4 | 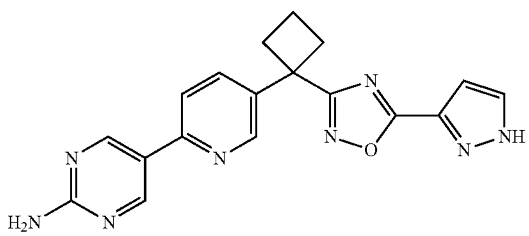 | 5-(5-{1-[5-(1H-pyrazol-3-yl)-1,2,4-oxadiazol-3-yl]cyclobutyl}pyridin-2-yl)pyrimidin-2-amine |
| 5 | 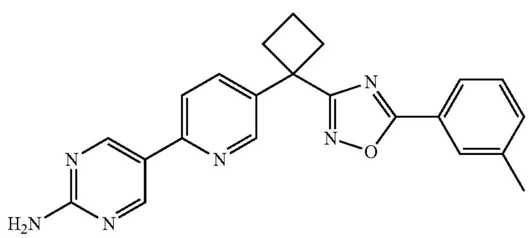 [SMILES: Cc1cccc(-c2nc(C3(c4ccc(-c5cnc(N)nc5)nc4)CCC3)no2)c1] | 5-(5-{1-[5-(3-methylphenyl)-1,2,4-oxadiazol-3-yl]cyclobutyl}pyridin-2-yl)pyrimidin-2-amine |
| 6 | 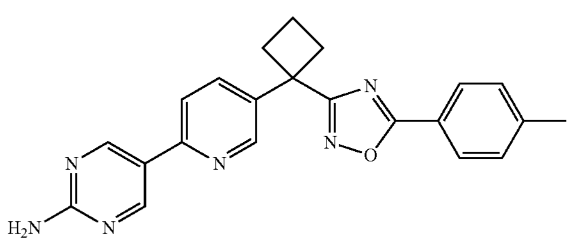 [SMILES: Cc1ccc(-c2nc(C3(c4ccc(-c5cnc(N)nc5)nc4)CCC3)no2)cc1] | 5-(5-{1-[5-(4-methylphenyl)-1,2,4-oxadiazol-3-yl]cyclobutyl}pyridin-2-yl)pyrimidin-2-amine |
| 7 | 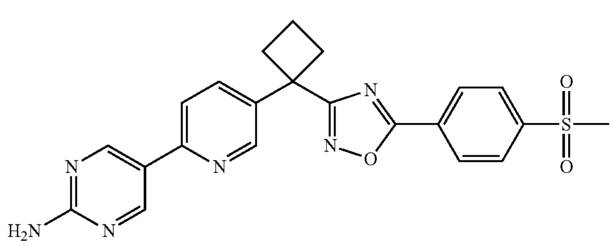 [SMILES: CS(=O)(=O)c1ccc(-c2nc(C3(c4ccc(-c5cnc(N)nc5)nc4)CCC3)no2)cc1] | 5-[5-(1-{5-[4-(methylsulfonyl)phenyl]-1,2,4-oxadiazol-3-yl}cyclobutyl)pyridin-2-yl]pyrimidin-2-amine |

TABLE I-continued

| Example | Structure | Name |
|---|---|---|
| 8 | 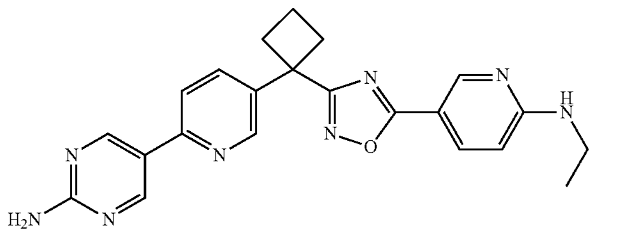 [SMILES: CCNc1ccc(-c2nc(C3(c4ccc(-c5cnc(N)nc5)nc4)CCC3)no2)cn1] | 5-[5-(1-{5-[6-(ethylamino)pyridin-3-yl]-1,2,4-oxadiazol-3-yl}cyclobutyl)pyridin-2-yl]pyrimidin-2-amine |
| 9 | 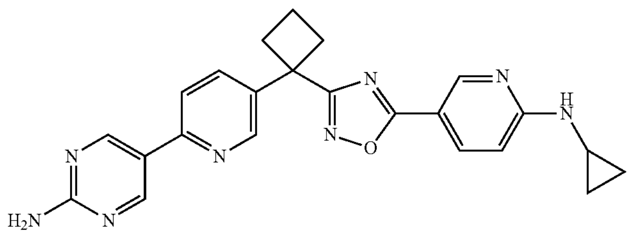 | 5-[5-(1-{5-[6-(cyclopropylamino)pyridin-3-yl]-1,2,4-oxadiazol-3-yl}cyclobutyl)pyridin-2-yl]pyrimidin-2-amine |
| 10 | 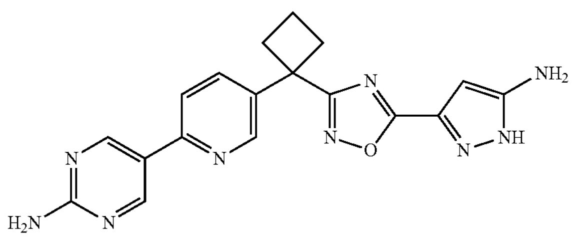 [SMILES: Nc1ncc(-c2ccc(C3(c4noc(-c5cc(N)[nH]n5)n4)CCC3)cn2)cn1] | 5-(5-{1-[5-(5-amino-1H-pyrazol-3-yl)-1,2,4-oxadiazol-3-yl]cyclobutyl}pyridin-2-yl)pyrimidin-2-amine |
| 11 | 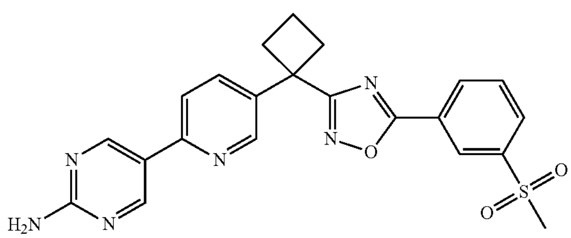 [SMILES: CS(=O)(=O)c1cccc(-c2nc(C3(c4ccc(-c5cnc(N)nc5)nc4)CCC3)no2)c1] | 5-[5-(1-{5-[3-(methylsulfonyl)phenyl]-1,2,4-oxadiazol-3-yl}cyclobutyl)pyridin-2-yl]pyrimidin-2-amine |
| 12 | 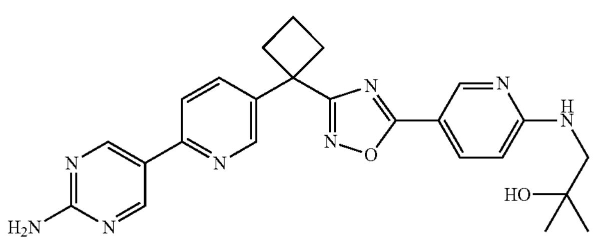 [SMILES: CC(C)(O)CNc1ccc(-c2nc(C3(c4ccc(-c5cnc(N)nc5)nc4)CCC3)no2)cn1] | 1-{[5-(3-{1-[6-(2-aminopyrimidin-5-yl)pyridin-3-yl]cyclobutyl}-1,2,4-oxadiazol-5-yl)pyridin-2-yl]amino}-2-methylpropan-2-ol |
| 13 | 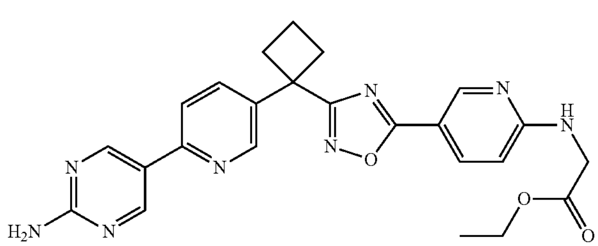 [SMILES: CCOC(=O)CNc1ccc(-c2nc(C3(c4ccc(-c5cnc(N)nc5)nc4)CCC3)no2)cn1] | ethyl N-[5-(3-{1-[6-(2-aminopyrimidin-5-yl)pyridin-3-yl]cyclobutyl}-1,2,4-oxadiazol-5-yl)pyridin-2-yl]glycinate |

TABLE I-continued

| Example | Structure | Name |
|---|---|---|
| 14 | 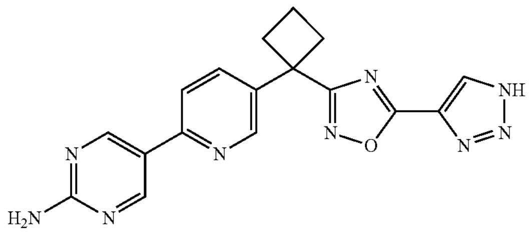 | 5-(5-{1-[5-(1H-1,2,3-triazol-4-yl)-1,2,4-oxadiazol-3-yl]cyclobutyl}pyridin-2-yl)pyrimidin-2-amine |
| 15 | 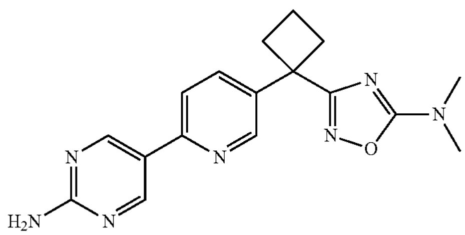 [SMILES: CN(C)c1nc(C2(c3ccc(-c4cnc(N)nc4)nc3)CCC2)no1] | 5-(5-{1-[5-(dimethylamino)-1,2,4-oxadiazol-3-yl]cyclobutyl}pyridin-2-yl)pyrimidin-2-amine |
| 16 | 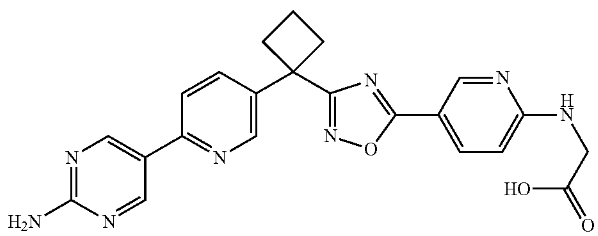 [SMILES: Nc1ncc(-c2ccc(C3(c4noc(-c5ccc(NCC(=O)O)nc5)n4)CCC3)cn2)cn1] | N-[5-(3-{1-[6-(2-aminopyrimidin-5-yl)pyridin-3-yl]cyclobutyl}-1,2,4-oxadiazol-5-yl)pyridin-2-yl]glycine |
| 17 | 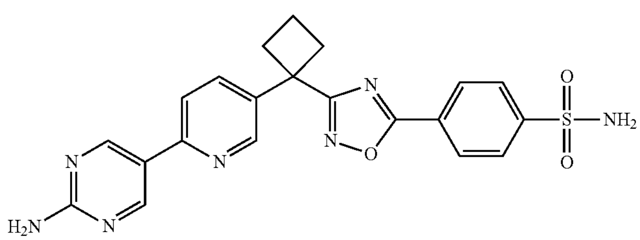 [SMILES: Nc1ncc(-c2ccc(C3(c4noc(-c5ccc(S(N)(=O)=O)cc5)n4)CCC3)cn2)cn1] | 4-(3-{1-[6-(2-aminopyrimidin-5-yl)pyridin-3-yl]cyclobutyl}-1,2,4-oxadiazol-5-yl)benzenesulfonamide |
| 18 | 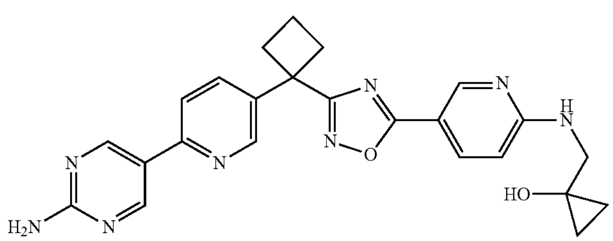 [SMILES: Nc1ncc(-c2ccc(C3(c4noc(-c5ccc(NCC6(O)CC6)nc5)n4)CCC3)cn2)cn1] | 1-(([5-(3-{1-[6-(2-aminopyrimidin-5-yl)pyridin-3-yl]cyclobutyl}-1,2,4-oxadiazol-5-yl)pyridin-2-yl]amino}methyl)cyclopropanol |
| 19 | 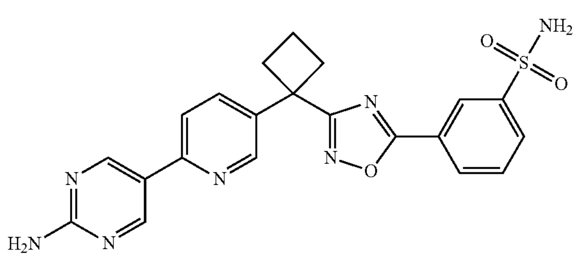 [SMILES: Nc1ncc(-c2ccc(C3(c4noc(-c5cccc(S(N)(=O)=O)c5)n4)CCC3)cn2)cn1] | 3-(3-{1-[6-(2-aminopyrimidin-5-yl)pyridin-3-yl]cyclobutyl}-1,2,4-oxadiazol-5-yl)benzenesulfonamide |

TABLE I-continued

| Example | Structure | Name |
|---|---|---|
| 20 | 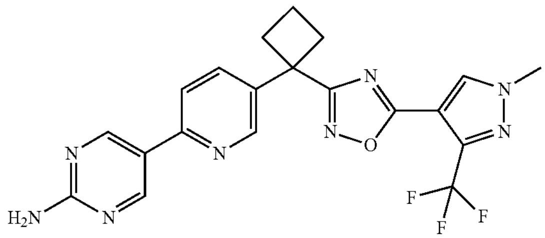 [SMILES: Cn1cc(-c2nc(C3(c4ccc(-c5cnc(N)nc5)nc4)CCC3)no2)c(C(F)(F)F)n1] | 5-[5-(1-{5-[1-methyl-3-(trifluoromethyl)-1H-pyrazol-4-yl]-1,2,4-oxadiazol-3-yl}cyclobutyl)pyridin-2-yl]pyrimidin-2-amine |
| 21 | 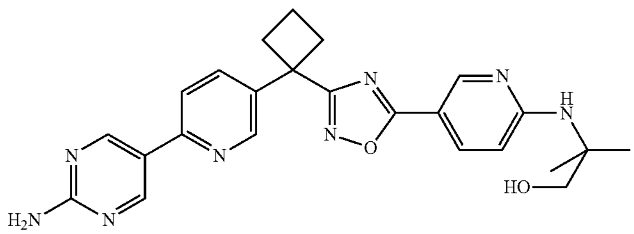 [SMILES: CC(C)(CO)Nc1ccc(-c2nc(C3(c4ccc(-c5cnc(N)nc5)nc4)CCC3)no2)cn1] | 2-{[5-(3-{1-[6-(2-aminopyrimidin-5-yl)pyridin-3-yl]cyclobutyl}-1,2,4-oxadiazol-5-yl)pyridin-2-yl]amino}-2-methylpropan-1-ol |
| 22 | 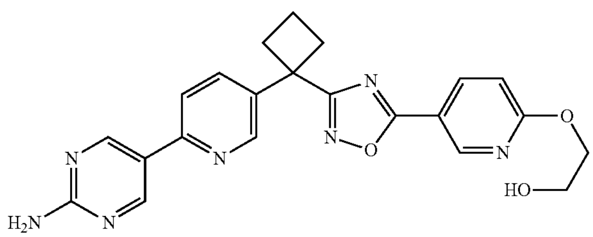 [SMILES: Nc1ncc(-c2ccc(C3(c4noc(-c5ccc(OCCO)nc5)n4)CCC3)cn2)cn1] | 2-{[5-(3-{1-[6-(2-aminopyrimidin-5-yl)pyridin-3-yl]cyclobutyl}-1,2,4-oxadiazol-5-yl)pyridin-2-yl]oxy}ethanol |
| 23 | 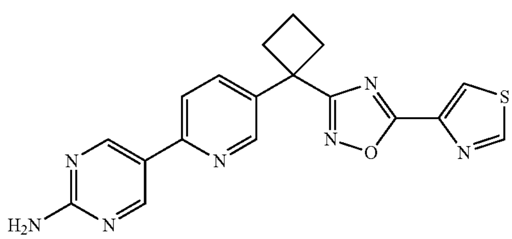 | 5-(5-{1-[5-(1,3-thiazol-4-yl)-1,2,4-oxadiazol-3-yl]cyclobutyl}pyridin-2-yl)pyrimidin-2-amine |
| 24 | 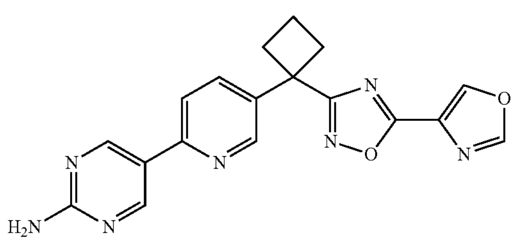 [SMILES: Nc1ncc(-c2ccc(C3(c4noc(-c5cocn5)n4)CCC3)cn2)cn1] | 5-(5-{1-[5-(1,3-oxazol-4-yl)-1,2,4-oxadiazol-3-yl]cyclobutyl}pyridin-2-yl)pyrimidin-2-amine |
| 25 | 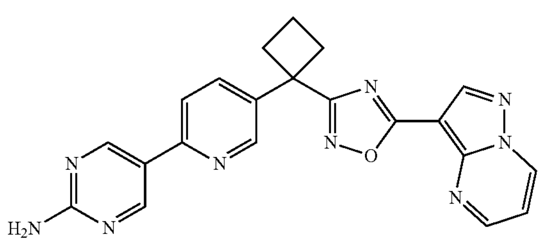 [SMILES: Nc1ncc(-c2ccc(C3(c4noc(-c5cnn6cccnc56)n4)CCC3)cn2)cn1] | 5-(5-{1-[5-(pyrazolo[1,5-a]pyrimidin-3-yl)-1,2,4-oxadiazol-3-yl]cyclobutyl}pyridin-2-yl)pyrimidin-2-amine |

TABLE I-continued

| Example | Structure | Name |
|---|---|---|
| 26 | 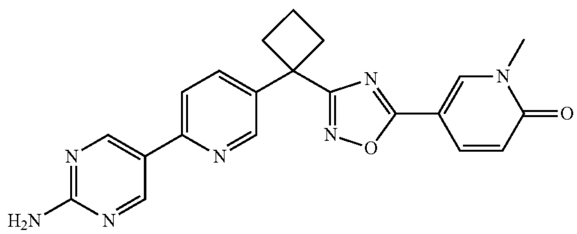 [SMILES: Cn1cc(-c2nc(C3(c4ccc(-c5cnc(N)nc5)nc4)CCC3)no2)ccc1=O] | 5-(3-{1-[6-(2-aminopyrimidin-5-yl)pyridin-3-yl]cyclobutyl}-1,2,4-oxadiazol-5-yl)-1-methylpyridin-2(1H)-one |
| 27 | 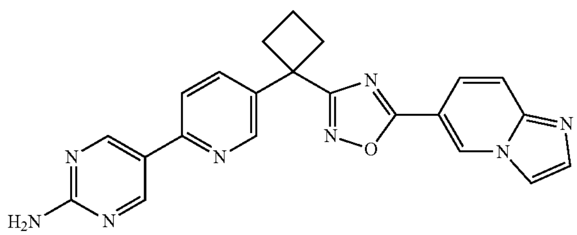 [SMILES: Nc1ncc(-c2ccc(C3(c4noc(-c5ccc6nccn6c5)n4)CCC3)cn2)cn1] | 5-(5-{1-[5-(imidazo[1,2-a]pyridin-6-yl)-1,2,4-oxadiazol-3-yl]cyclobutyl}pyridin-2-yl)pyrimidin-2-amine |
| 28 | 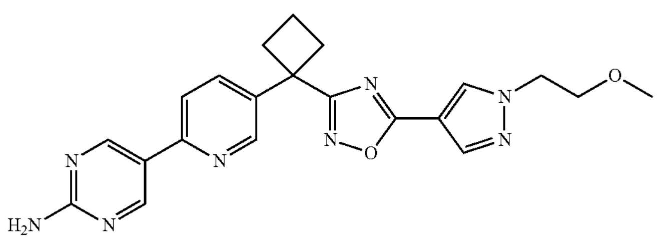 [SMILES: COCCn1cc(-c2nc(C3(c4ccc(-c5cnc(N)nc5)nc4)CCC3)no2)cn1] | 5-[5-(1-{5-[1-(2-methoxyethyl)-1H-pyrazol-4-yl]-1,2,4-oxadiazol-3-yl}cyclobutyl)pyridin-2-yl]pyrimidin-2-amine |
| 29 | 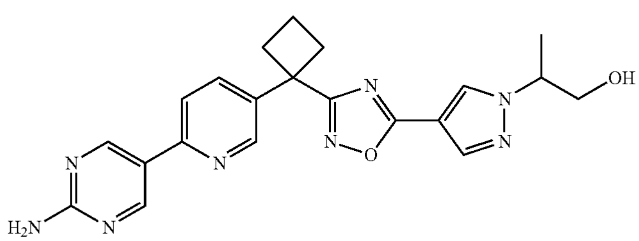 [SMILES: CC(CO)n1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]propan-1-ol |
| 30 | 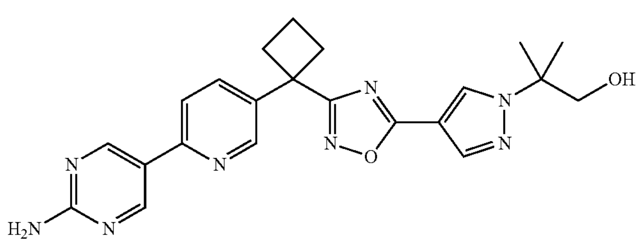 [SMILES: CC(C)(CO)n1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]-2-methylpropan-1-ol |
| 31 | 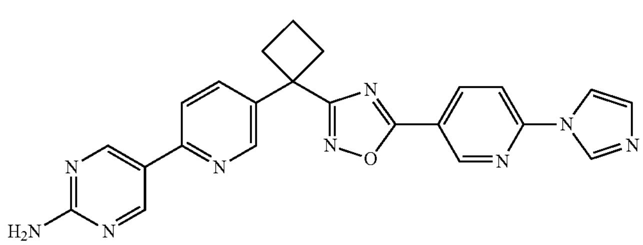 [SMILES: Nc1ncc(-c2ccc(C3(c4noc(-c5ccc(-n6ccnc6)nc5)n4)CCC3)cn2)cn1] | 5-[5-(1-{5-[6-(1H-imidazol-1-yl)pyridin-3-yl]-1,2,4-oxadiazol-3-yl}cyclobutyl)pyridin-2-yl]pyrimidin-2-amine |

TABLE I-continued

| Example | Name |
|---|---|
| 32 | 4-(3-{1-[6-(2-aminopyrimidin-5-yl)pyridin-3-yl]cyclobutyl}-1,2,4-oxadiazol-5-yl)phenol |
| 33 | 2-{[5-(3-{1-[6-(2-aminopyrimidin-5-yl)pyridin-3-yl]cyclobutyl}-1,2,4-oxadiazol-5-yl)pyridin-2-yl]amino}propane-1,3-diol |
| 34 | 1-[5-(3-{1-[6-(2-aminopyrimidin-5-yl)pyridin-3-yl]cyclobutyl}-1,2,4-oxadiazol-5-yl)pyridin-2-yl]-N,N-dimethyl-L-prolinamide |
| 35 | 1-[5-(3-{1-[6-(2-aminopyrimidin-5-yl)pyridin-3-yl]cyclobutyl}-1,2,4-oxadiazol-5-yl)pyridin-2-yl]-L-proline |
| 36 | methyl 1-[5-(3-{1-[6-(2-aminopyrimidin-5-yl)pyridin-3-yl]cyclobutyl}-1,2,4-oxadiazol-5-yl)pyridin-2-yl]-L-prolinate |
| 37 | 5-(5-{1-[5-(4-methyl-4H-1,2,4-triazol-3-yl)-1,2,4-oxadiazol-3-yl]cyclobutyl}pyridin-2-yl)pyrimidin-2-amine |

TABLE I-continued

| Example | Structure | Name |
|---|---|---|
| 38 | 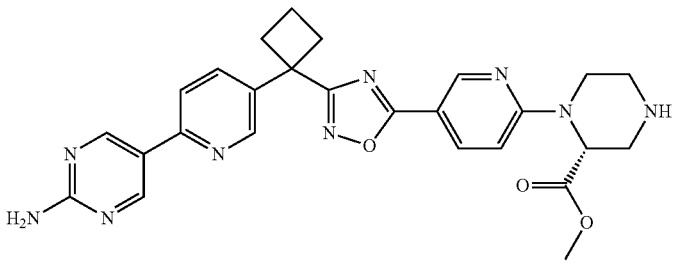 [SMILES: COC(=O)[C@H]1CNCCN1c1ccc(-c2nc(C3(c4ccc(-c5cnc(N)nc5)nc4)CCC3)no2)cn1] | methyl (2R)-1-[5-(3-{1-[6-(2-aminopyrimidin-5-yl)pyridin-3-yl]cyclobutyl}-1,2,4-oxadiazol-5-yl)pyridin-2-yl]piperazine-2-carboxylate |
| 39 | 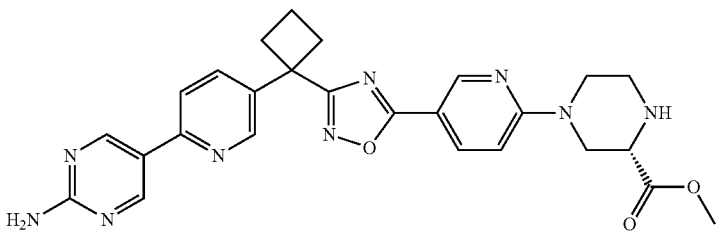 | methyl (2S)-[5-(3-{1-[6-(2-aminopyrimidin-5-yl)pyridin-3-yl]cyclobutyl}-1,2,4-oxadiazol-5-yl)pyridin-2-yl]piperazine-2-carboxylate |
| 40 | 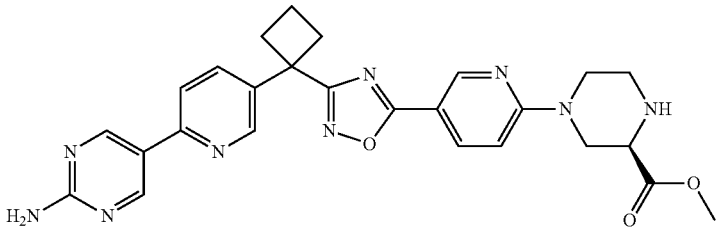 | methyl (2R)-4-[5-(3-{1-[6-(2-aminopyrimidin-5-yl)pyridin-3-yl]cyclobutyl}-1,2,4-oxadiazol-5-yl)pyridin-2-yl]piperazine-2-carboxylate |
| 41 | 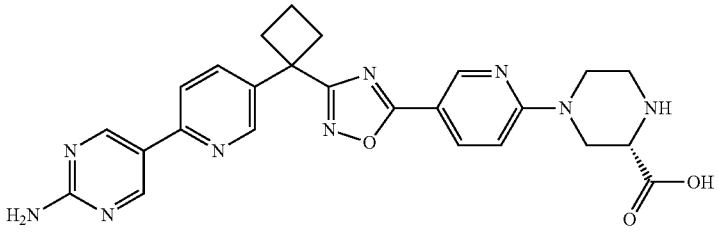 [SMILES: COC(=O)[C@@H]1CN(c2ccc(-c3nc(C4(c5ccc(-c6cnc(N)nc6)nc5)CCC4)no3)cn2)CCN1] | (2S)-4-[5-(3-{1-[6-(2-aminopyrimidin-5-yl)pyridin-3-yl]cyclobutyl}-1,2,4-oxadiazol-5-yl)pyridin-2-yl]piperazine-2-carboxylic acid |
| 42 | 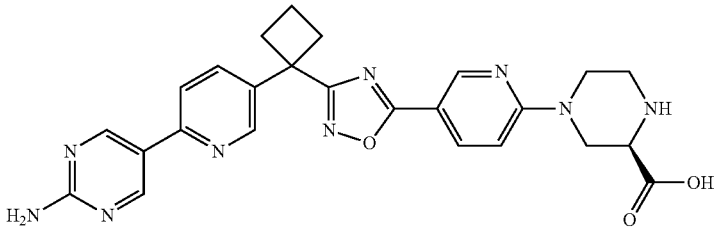 [SMILES: COC(=O)[C@H]1CN(c2ccc(-c3nc(C4(c5ccc(-c6cnc(N)nc6)nc5)CCC4)no3)cn2)CCN1] | (2R)-4-[5-(3-{1-[6-(2-aminopyrimidin-5-yl)pyridin-3-yl]cyclobutyl}-1,2,4-oxadiazol-5-yl)pyridin-2-yl]piperazine-2-carboxylic acid |
| 43 | 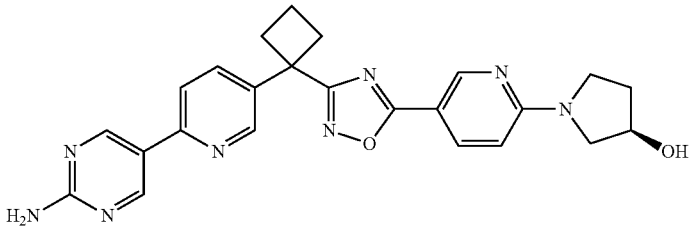 [SMILES: Nc1ncc(-c2ccc(C3(c4noc(-c5ccc(N6CC[C@@H](O)C6)nc5)n4)CCC3)cn2)cn1] | (3R)-1-[5-(3-{1-[6-(2-aminopyrimidin-5-yl)pyridin-3-yl]cyclobutyl}-1,2,4-oxadiazol-5-yl)pyridin-2-yl]pyrrolidin-3-ol |

TABLE I-continued

| Example | Structure | Name |
|---|---|---|
| 44 | 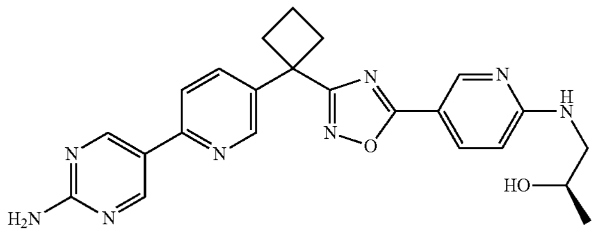 [SMILES: C[C@@H](O)CNc1ccc(-c2nc(C3(c4ccc(-c5cnc(N)nc5)nc4)CCC3)no2)cn1] | (2R)-1-{[5-(3-{1-[6-(2-aminopyrimidin-5-yl)pyridin-3-yl]cyclobutyl}-1,2,4-oxadiazol-5-yl)pyridin-2-yl]amino}propan-2-ol |
| 45 | 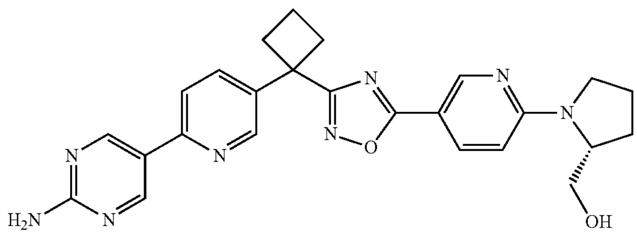 [SMILES: Nc1ncc(-c2ccc(C3(c4noc(-c5ccc(N6CCC[C@@H]6CO)nc5)n4)CCC3)cn2)cn1] | {(2R)-1-[5-(3-{1-[6-(2-aminopyrimidin-5-yl)pyridin-3-yl]cyclobutyl}-1,2,4-oxadiazol-5-yl)pyridin-2-yl]pyrrolidin-2-yl}methanol |
| 46 | 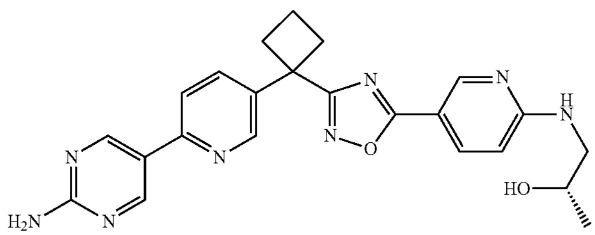 [SMILES: C[C@H](O)CNc1ccc(-c2nc(C3(c4ccc(-c5cnc(N)nc5)nc4)CCC3)no2)cn1] | (2S)-1-{[5-(3-{1-[6-(2-aminopyrimidin-5-yl)pyridin-3-yl]cyclobutyl}-1,2,4-oxadiazol-5-yl)pyridin-2-yl]amino}propan-2-ol |
| 47 | 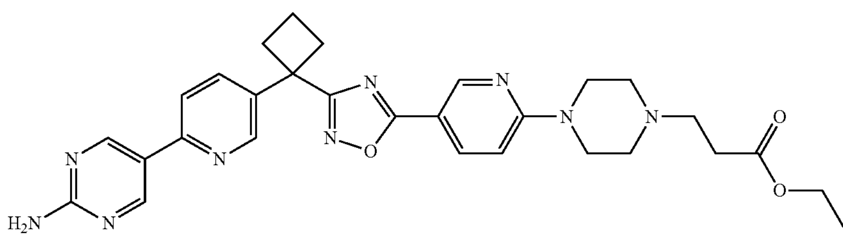 [SMILES: CCOC(=O)CCN1CCN(c2ccc(-c3nc(C4(c5ccc(-c6cnc(N)nc6)nc5)CCC4)no3)cn2)CC1] | ethyl 3-{4-[5-(3-{1-[6-(2-aminopyrimidin-5-yl)pyridin-3-yl]cyclobutyl}-1,2,4-oxadiazol-5-yl)pyridin-2-yl]piperazin-1-yl}propanoate |
| 48 | 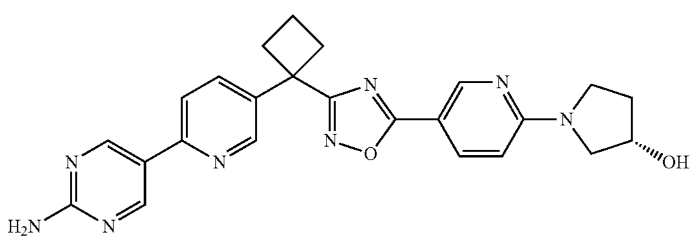 [SMILES: Nc1ncc(-c2ccc(C3(c4noc(-c5ccc(N6CC[C@H](O)C6)nc5)n4)CCC3)cn2)cn1] | (3S)-1-[5-(3-{1-[6-(2-aminopyrimidin-5-yl)pyridin-3-yl]cyclobutyl}-1,2,4-oxadiazol-5-yl)pyridin-2-yl]pyrrolidin-3-ol |
| 49 | 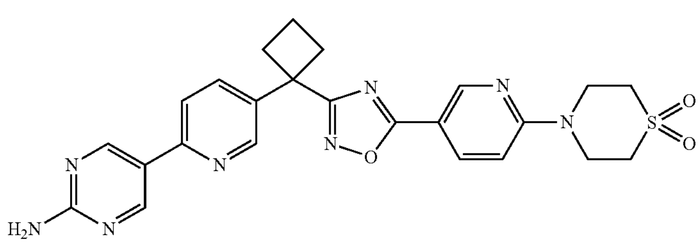 [SMILES: Nc1ncc(-c2ccc(C3(c4noc(-c5ccc(N6CCS(=O)(=O)CC6)nc5)n4)CCC3)cn2)cn1] | 5-[5-(1-{5-[6-(1,1-dioxidothiomorpholin-4-yl)pyridin-3-yl]-1,2,4-oxadiazol-3-yl}cyclobutyl)pyridin-2-yl]pyrimidin-2-amine |

TABLE I-continued

| Example | Structure | Name |
|---|---|---|
| 50 | 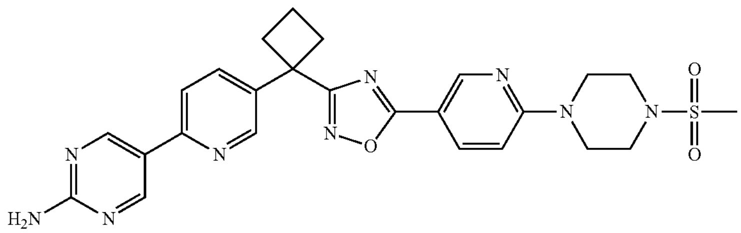 [SMILES: CS(=O)(=O)N1CCN(c2ccc(-c3nc(C4(c5ccc(-c6cnc(N)nc6)nc5)CCC4)no3)cn2)CC1] | 5-{5-[1-(5-{6-[4-(methylsulfonyl)piperazin-1-yl]pyridin-3-yl}-1,2,4-oxadiazol-3-yl)cyclobutyl]pyridin-2-yl}pyrimidin-2-amine |
| 51 | 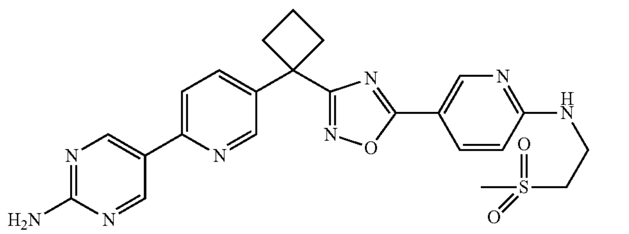 [SMILES: CS(=O)(=O)CCNc1ccc(-c2nc(C3(c4ccc(-c5cnc(N)nc5)nc4)CCC3)no2)cn1] | 5-(5-{1-[5-(6-{[2-(methylsulfonyl)ethyl]amino}pyridin-3-yl)-1,2,4-oxadiazol-3-yl]cyclobutyl}pyridin-2-yl)pyrimidin-2-amine |
| 52 | 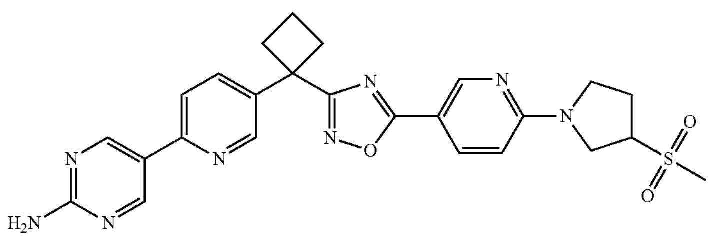 [SMILES: CS(=O)(=O)C1CCN(c2ccc(-c3nc(C4(c5ccc(-c6cnc(N)nc6)nc5)CCC4)no3)cn2)C1] | 5-{5-[1-(5-{6-[3-(methylsulfonyl)pyrrolidin-1-yl]pyridin-3-yl}-1,2,4-oxadiazol-3-yl)cyclobutyl]pyridin-2-yl}pyrimidin-2-amine |
| 53 | 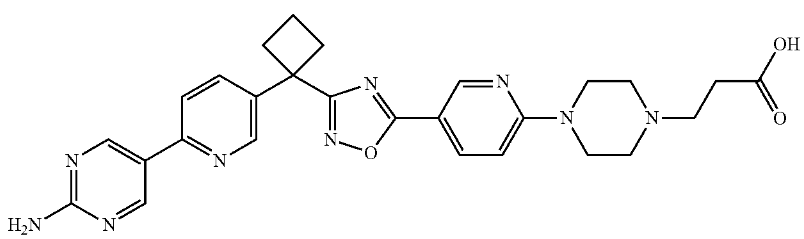 [SMILES: Nc1ncc(-c2ccc(C3(c4noc(-c5ccc(N6CCN(CCC(=O)O)CC6)nc5)n4)CCC3)cn2)cn1] | 3-{4-[5-(3-{1-[6-(2-aminopyrimidin-5-yl)pyridin-3-yl]cyclobutyl}-1,2,4-oxadiazol-5-yl)pyridin-2-yl]piperazin-1-yl}propanoic acid |
| 54 | 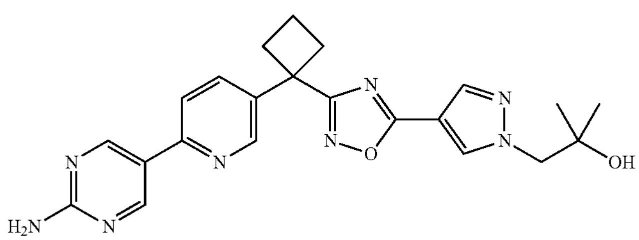 [SMILES: CC(C)(O)Cn1cc(-c2nc(C3(c4ccc(-c5cnc(N)nc5)nc4)CCC3)no2)cn1] | 1-[4-(3-{1-[6-(2-aminopyrimidin-5-yl)pyridin-3-yl]cyclobutyl}-1,2,4-oxadiazol-5-yl)-1H-pyrazol-1-yl]-2-methylpropan-2-ol |
| 55 | 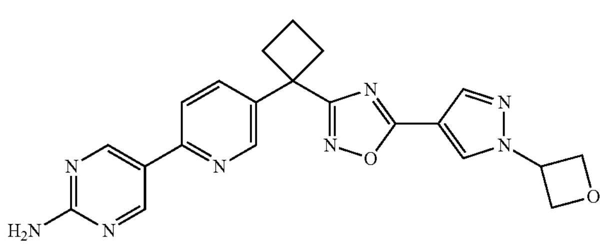 | 5-[5-(1-{5-[1-(oxetan-3-yl)-1H-pyrazol-4-yl]-1,2,4-oxadiazol-3-yl}cyclobutyl)pyridin-2-yl]pyrimidin-2-amine |

TABLE I-continued

| Example | Structure | Name |
|---|---|---|
| 56 | 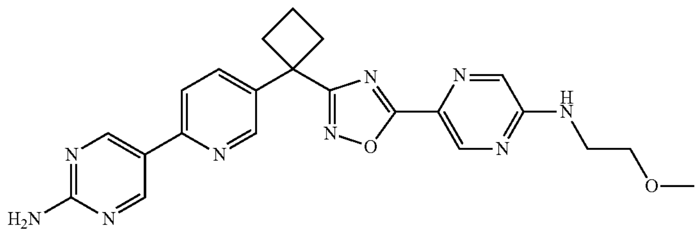 [SMILES: COCCNc1cnc(-c2nc(C3(c4ccc(-c5cnc(N)nc5)nc4)CCC3)no2)cn1] | 5-{5-[1-(5-{5-[(2-methoxyethyl)amino]pyrazin-2-yl}-1,2,4-oxadiazol-3-yl)cyclobutyl]pyridin-2-yl}pyrimidin-2-amine |
| 57 | 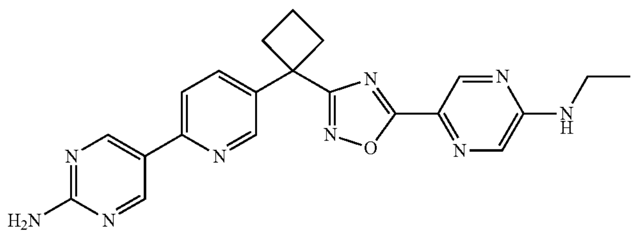 [SMILES: CCNc1cnc(-c2nc(C3(c4ccc(-c5cnc(N)nc5)nc4)CCC3)no2)cn1] | 5-[5-(1-{5-[5-(ethylamino)pyrazin-2-yl]-1,2,4-oxadiazol-3-yl}cyclobutyl)pyridin-2-yl]pyrimidin-2-amine |
| 58 | 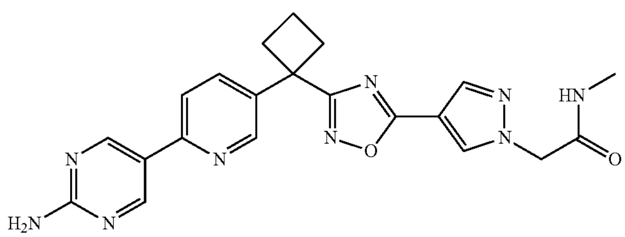 [SMILES: CNC(=O)Cn1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]-N-methylacetamide |
| 59 | 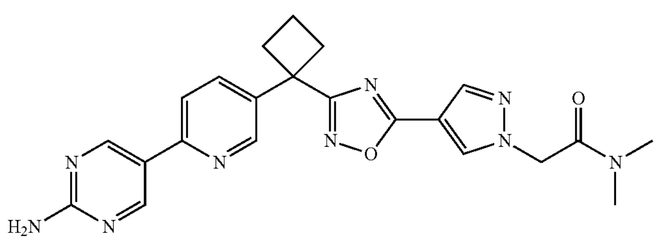 [SMILES: CN(C)C(=O)Cn1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]-N,N-dimethylacetamide |
| 60 | 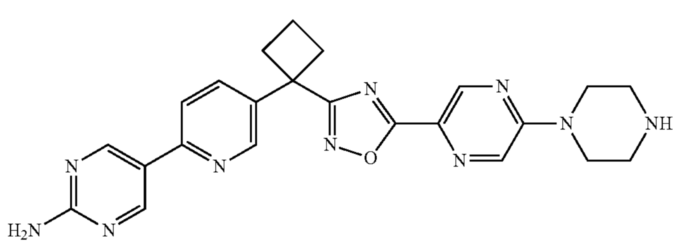 [SMILES: Nc1ncc(-c2ccc(C3(c4noc(-c5cnc(N6CCNCC6)cn5)n4)CCC3)cn2)cn1] | 5-[5-(1-{5-[5-(piperazin-1-yl)pyrazin-2-yl]-1,2,4-oxadiazol-3-yl}cyclobutyl)pyridin-2-yl]pyrimidin-2-amine |
| 61 | 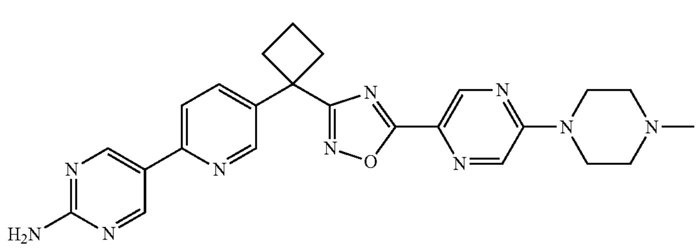 [SMILES: CN1CCN(c2cnc(-c3nc(C4(c5ccc(-c6cnc(N)nc6)nc5)CCC4)no3)cn2)CC1] | 5-[5-(1-{5-[5-(4-methylpiperazin-1-yl)pyrazin-2-yl]-1,2,4-oxadiazol-3-yl}cyclobutyl)pyridin-2-yl]pyrimidin-2-amine |

US 8,575,201 B2

31    32

TABLE I-continued

| Example | Structure | Name |
|---|---|---|
| 62 | 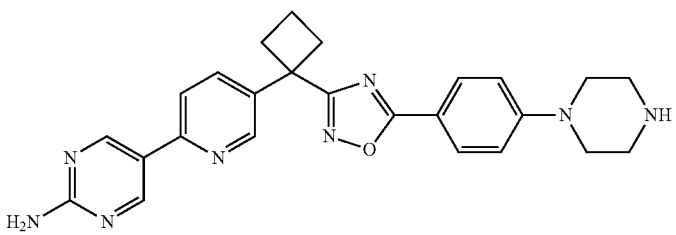 | 5-[5-(1-{5-[4-(piperazin-1-yl)phenyl]-1,2,4-oxadiazol-3-yl}cyclobutyl)pyridin-2-yl]pyrimidin-2-amine |
| 63 | 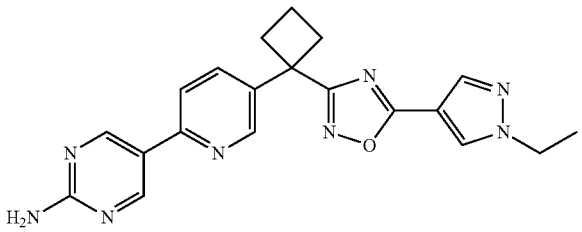 | 5-(5-{1-[5-(1-ethyl-1H-pyrazol-4-yl)-1,2,4-oxadiazol-3-yl]cyclobutyl}pyridin-2-yl)pyrimidin-2-amine |
| 64 | 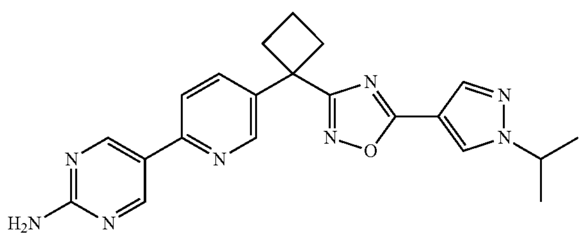 | 5-[5-(1-{5-[1-(propan-2-yl)-1H-pyrazol-4-yl]-1,2,4-oxadiazol-3-yl}cyclobutyl)pyridin-2-yl]pyrimidin-2-amine |
| 65 | 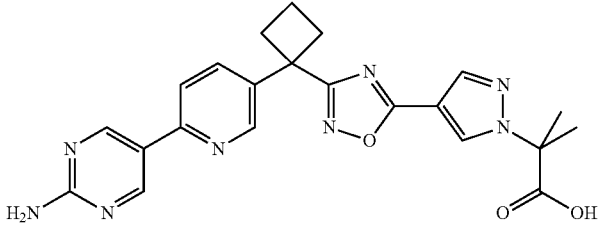 [SMILES: CC(C)(C(=O)O)n1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]-2-methylpropanoic acid |
| 66 | 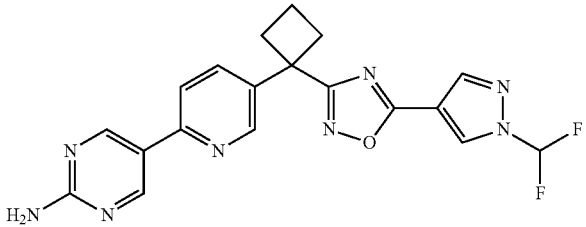 | 5-[5-(1-{5-[1-(difluoromethyl)-1H-pyrazol-4-yl]-1,2,4-oxadiazol-3-yl}cyclobutyl)pyridin-2-yl]pyrimidin-2-amine |
| 67 | 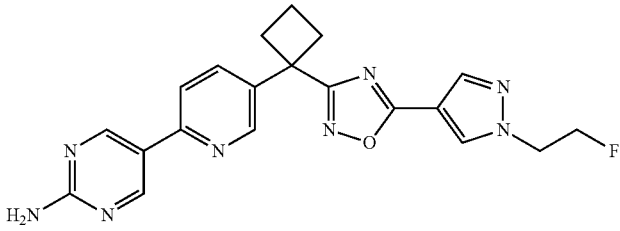 [SMILES: Nc1ncc(-c2ccc(C3(c4noc(-c5cnn(CCF)c5)n4)CCC3)cn2)cn1] | 5-[5-(1-{5-[1-(2-fluoroethyl)-1H-pyrazol-4-yl]-1,2,4-oxadiazol-3-yl}cyclobutyl)pyridin-2-yl]pyrimidin-2-amine |

US 8,575,201 B2

33 34

TABLE I-continued

| Example | Structure | Name |
|---------|-----------|------|
| 68 | 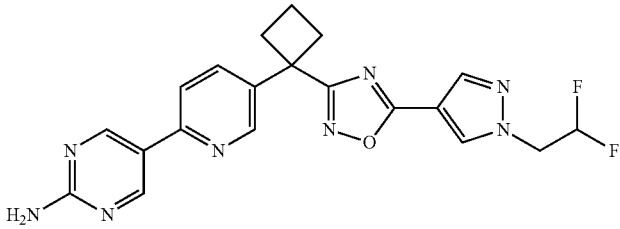 [SMILES: Nc1ncc(-c2ccc(C3(c4noc(-c5cnn(CC(F)F)c5)n4)CCC3)cn2)cn1] | 5-[5-(1-{5-[1-(2,2-difluoroethyl)-1H-pyrazol-4-yl]-1,2,4-oxadiazol-3-yl}cyclobutyl)pyridin-2-yl]pyrimidin-2-amine |
| 69 | 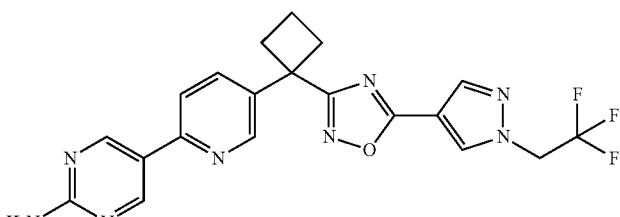 | 5-[5-(1-{5-[1-(2,2,2-trifluoroethyl)-1H-pyrazol-4-yl]-1,2,4-oxadiazol-3-yl}cyclobutyl)pyridin-2-yl]pyrimidin-2-amine |
| 70 | 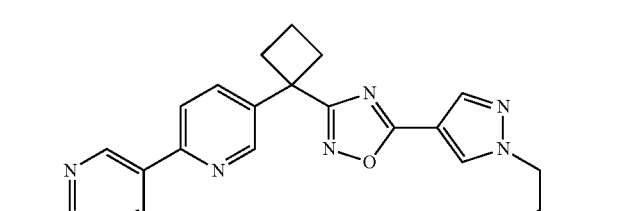 | 2-[4-(3-{1-[6-(2-aminopyrimidin-5-yl)pyridin-3-yl]cyclobutyl}-1,2,4-oxadiazol-5-yl)-1H-pyrazol-1-yl]acetamide |
| 71 | 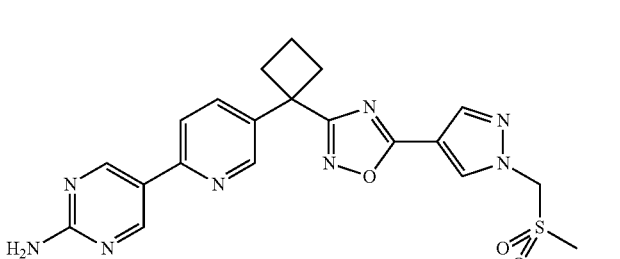 | 5-{5-[1-(5-{1-[(methylsulfonyl)methyl]-1H-pyrazol-4-yl}-1,2,4-oxadiazol-3-yl)cyclobutyl]pyridin-2-yl}pyrimidin-2-amine |
| 72 | 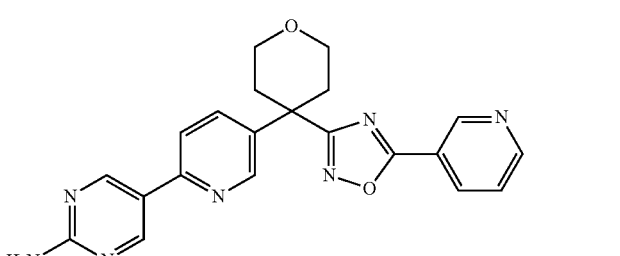 | 5-(5-{4-[5-(pyridin-3-yl)-1,2,4-oxadiazol-3-yl]tetrahydro-2H-pyran-4-yl}pyridin-2-yl)pyrimidin-2-amine |
| 73 | 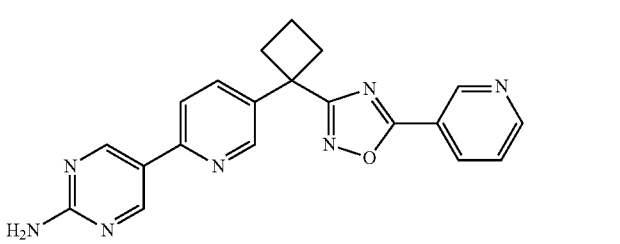 [SMILES: Nc1ncc(-c2ccc(C3(c4noc(-c5cccnc5)n4)CCC3)cn2)cn1] | 5-(5-{1-[5-(pyridin-3-yl)-1,2,4-oxadiazol-3-yl]cyclobutyl}pyridin-2-yl)pyrimidin-2-amine |

TABLE I-continued

| Example | Structure | Name |
|---|---|---|
| 74 | 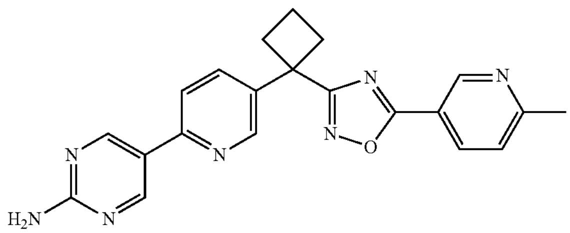 [SMILES: Cc1ccc(-c2nc(C3(c4ccc(-c5cnc(N)nc5)nc4)CCC3)no2)cn1] | 5-(5-{1-[5-(6-methylpyridin-3-yl)-1,2,4-oxadiazol-3-yl]cyclobutyl}pyridin-2-yl)pyrimidin-2-amine |
| 75 | 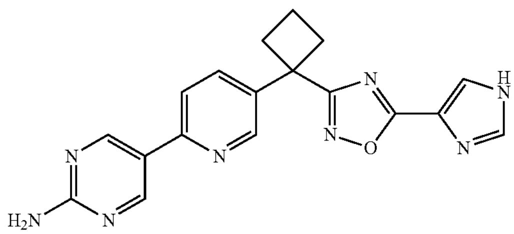 [SMILES: Nc1ncc(-c2ccc(C3(c4noc(-c5c[nH]cn5)n4)CCC3)cn2)cn1] | 5-(5-{1-[5-(1H-imidazol-4-yl)-1,2,4-oxadiazol-3-yl]cyclobutyl}pyridin-2-yl)pyrimidin-2-amine |
| 76 | 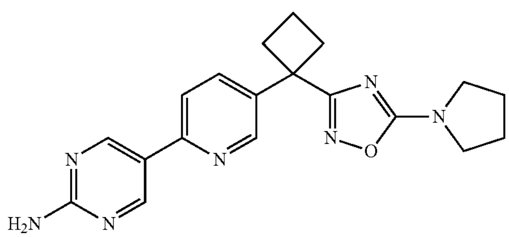 [SMILES: Nc1ncc(-c2ccc(C3(c4noc(N5CCCC5)n4)CCC3)cn2)cn1] | 5-(5-{1-[5-(pyrrolidin-1-yl)-1,2,4-oxadiazol-3-yl]cyclobutyl}pyridin-2-yl)pyrimidin-2-amine |
| 77 | 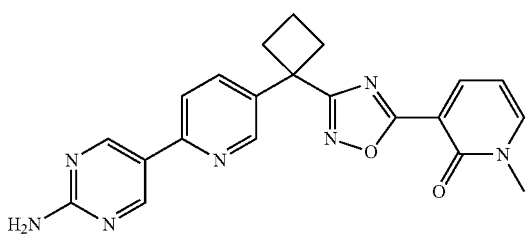 [SMILES: Cn1cccc(-c2nc(C3(c4ccc(-c5cnc(N)nc5)nc4)CCC3)no2)c1=O] | 3-(3-{1-[6-(2-aminopyrimidin-5-yl)pyridin-3-yl]cyclobutyl}-1,2,4-oxadiazol-5-yl)-1-methylpyridin-2(1H)-one |
| 78 | 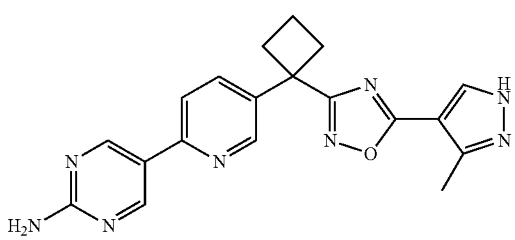 [SMILES: Cc1n[nH]cc1-c1nc(C2(c3ccc(-c4cnc(N)nc4)nc3)CCC2)no1] | 5-(5-{1-[5-(3-methyl-1H-pyrazol-4-yl)-1,2,4-oxadiazol-3-yl]cyclobutyl}pyridin-2-yl)pyrimidin-2-amine |
| 79 | 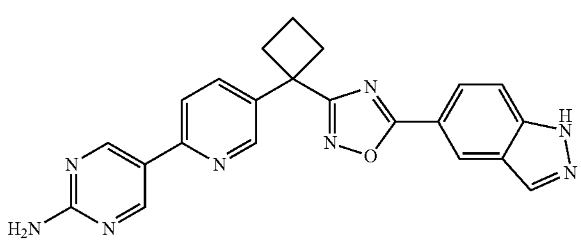 [SMILES: Nc1ncc(-c2ccc(C3(c4noc(-c5ccc6[nH]ncc6c5)n4)CCC3)cn2)cn1] | 5-(5-{1-[5-(1H-indazol-5-yl)-1,2,4-oxadiazol-3-yl]cyclobutyl}pyridin-2-yl)pyrimidin-2-amine |

TABLE I-continued

| Example | Structure | Name |
|---|---|---|
| 80 | 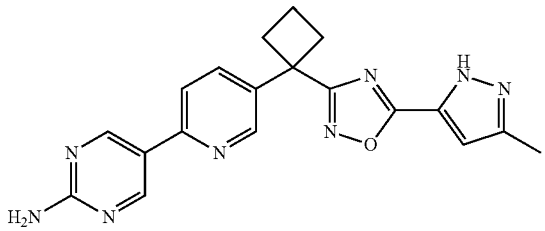 [SMILES: Cc1cc(-c2nc(C3(c4ccc(-c5cnc(N)nc5)nc4)CCC3)no2)[nH]n1] | 5-(5-{1-[5-(3-methyl-1H-pyrazol-5-yl)-1,2,4-oxadiazol-3-yl]cyclobutyl}pyridin-2-yl)pyrimidin-2-amine |
| 81 | 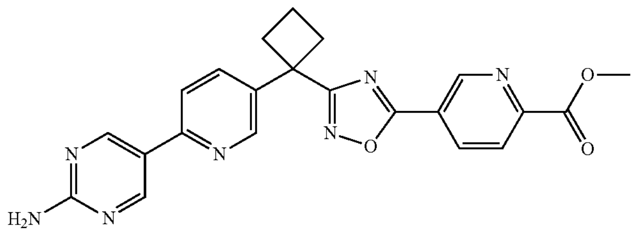 [SMILES: COC(=O)c1ccc(-c2nc(C3(c4ccc(-c5cnc(N)nc5)nc4)CCC3)no2)cn1] | methyl 5-(3-{1-[6-(2-aminopyrimidin-5-yl)pyridin-3-yl]cyclobutyl}-1,2,4-oxadiazol-5-yl)pyridine-2-carboxylate |
| 82 | 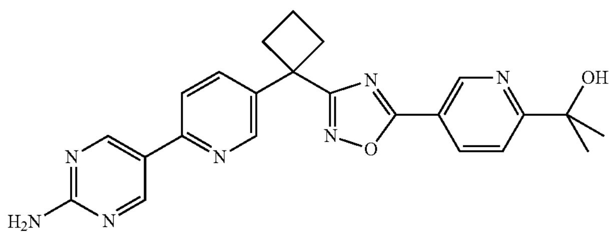 [SMILES: CC(C)(O)c1ccc(-c2nc(C3(c4ccc(-c5cnc(N)nc5)nc4)CCC3)no2)cn1] | 2-[5-(3-{1-[6-(2-aminopyrimidin-5-yl)pyridin-3-yl]cyclobutyl}-1,2,4-oxadiazol-5-yl)pyridin-2-yl]propan-2-ol |
| 83 | 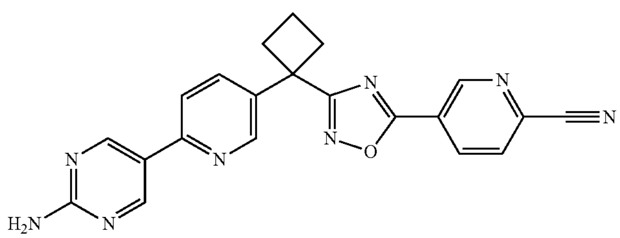 [SMILES: N#Cc1ccc(-c2nc(C3(c4ccc(-c5cnc(N)nc5)nc4)CCC3)no2)cn1] | 5-(3-{1-[6-(2-aminopyrimidin-5-yl)pyridin-3-yl]cyclobutyl}-1,2,4-oxadiazol-5-yl)pyridine-2-carbonitrile |
| 84 | 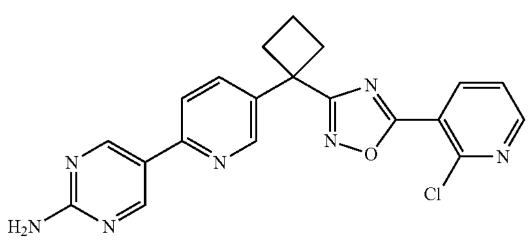 | 5-(5-{1-[5-(2-chloropyridin-3-yl)-1,2,4-oxadiazol-3-yl]cyclobutyl}pyridin-2-yl)pyrimidin-2-amine |
| 85 | 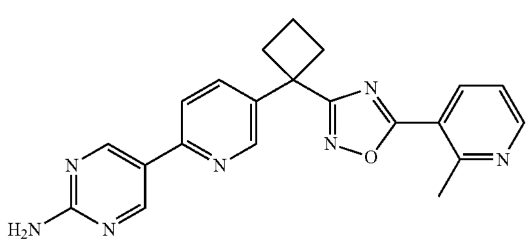 [SMILES: Cc1ncccc1-c1nc(C2(c3ccc(-c4cnc(N)nc4)nc3)CCC2)no1] | 5-(5-{1-[5-(2-methylpyridin-3-yl)-1,2,4-oxadiazol-3-yl]cyclobutyl}pyridin-2-yl)pyrimidin-2-amine |

TABLE I-continued

| Example | Structure | Name |
|---|---|---|
| 86 | 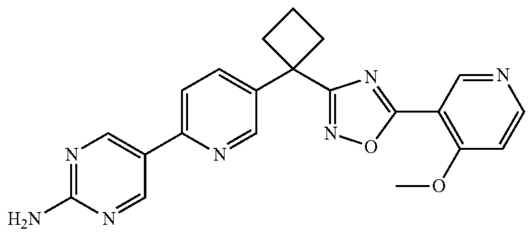 [SMILES: COc1ccncc1-c1nc(C2(c3ccc(-c4cnc(N)nc4)nc3)CCC2)no1] | 5-(5-{1-[5-(4-methoxypyridin-3-yl)-1,2,4-oxadiazol-3-yl]cyclobutyl}pyridin-2-yl)pyrimidin-2-amine |
| 87 | 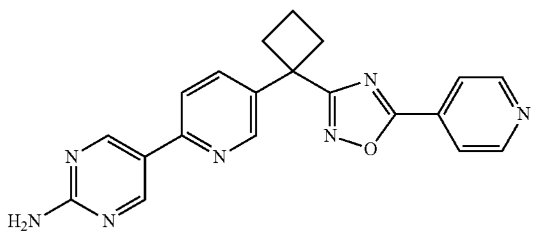 | 5-(5-{1-[5-(pyridin-4-yl)-1,2,4-oxadiazol-3-yl]cyclobutyl}pyridin-2-yl)pyrimidin-2-amine |
| 88 | 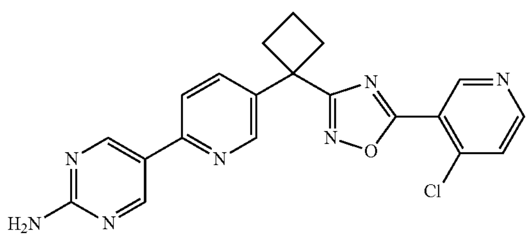 [SMILES: Nc1ncc(-c2ccc(C3(c4noc(-c5cnccc5Cl)n4)CCC3)cn2)cn1] | 5-(5-{1-[5-(4-chloropyridin-3-yl)-1,2,4-oxadiazol-3-yl]cyclobutyl}pyridin-2-yl)pyrimidin-2-amine |
| 89 | 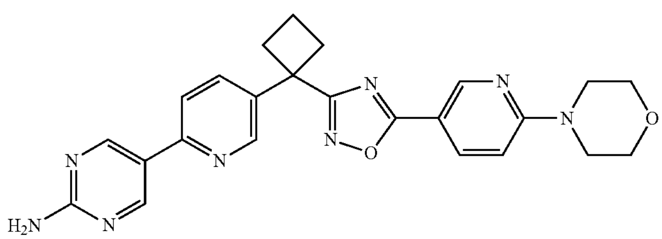 [SMILES: Nc1ncc(-c2ccc(C3(c4noc(-c5ccc(N6CCOCC6)nc5)n4)CCC3)cn2)cn1] | 5-[5-(1-{5-[6-(morpholin-4-yl)pyridin-3-yl]-1,2,4-oxadiazol-3-yl}cyclobutyl)pyridin-2-yl]pyrimidin-2-amine |
| 90 | 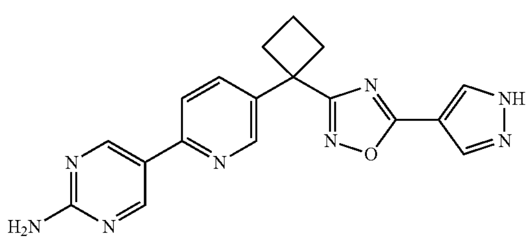 | 5-(5-{1-[5-(1H-pyrazol-4-yl)-1,2,4-oxadiazol-3-yl]cyclobutyl}pyridin-2-yl)pyrimidin-2-amine |
| 91 | 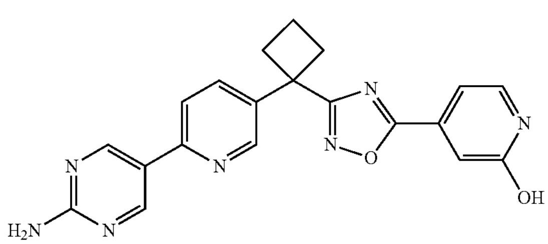 [SMILES: Nc1ncc(-c2ccc(C3(c4noc(-c5ccnc(O)c5)n4)CCC3)cn2)cn1] | 4-(3-{1-[6-(2-aminopyrimidin-5-yl)pyridin-3-yl]cyclobutyl}-1,2,4-oxadiazol-5-yl)pyridin-2-ol |

TABLE I-continued

| Example | Structure | Name |
|---|---|---|
| 92 | 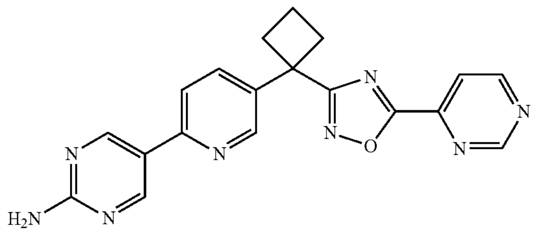 [SMILES: Nc1ncc(-c2ccc(C3(c4noc(-c5ccncn5)n4)CCC3)cn2)cn1] | 5-(5-{1-[5-(pyrimidin-4-yl)-1,2,4-oxadiazol-3-yl]cyclobutyl}pyridin-2-yl)pyrimidin-2-amine |
| 93 | 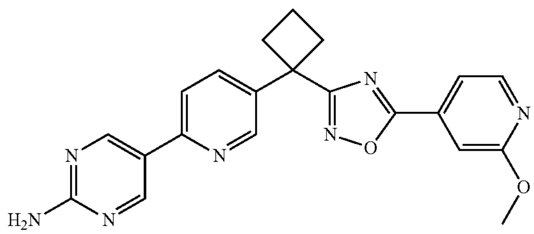 [SMILES: COc1cc(-c2nc(C3(c4ccc(-c5cnc(N)nc5)nc4)CCC3)no2)ccn1] | 5-(5-{1-[5-(2-methoxypyridin-4-yl)-1,2,4-oxadiazol-3-yl]cyclobutyl}pyridin-2-yl)pyrimidin-2-amine |
| 94 | 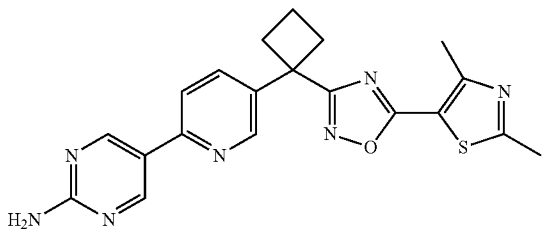 [SMILES: Cc1nc(C)c(-c2nc(C3(c4ccc(-c5cnc(N)nc5)nc4)CCC3)no2)s1] | 5-(5-{1-[5-(2,4-dimethyl-1,3-thiazol-5-yl)-1,2,4-oxadiazol-3-yl]cyclobutyl}pyridin-2-yl)pyrimidin-2-amine |
| 95 | 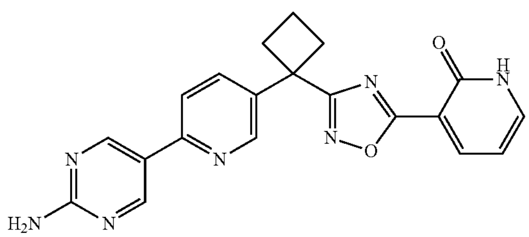 | 3-(3-{1-[6-(2-aminopyrimidin-5-yl)pyridin-3-yl]cyclobutyl}-1,2,4-oxadiazol-5-yl)pyridin-2(1H)-one |
| 96 | 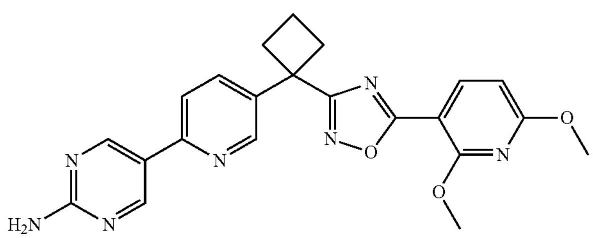 | 5-(5-{1-[5-(2,6-dimethoxypyridin-3-yl)-1,2,4-oxadiazol-3-yl]cyclobutyl}pyridin-2-yl)pyrimidin-2-amine |
| 97 | 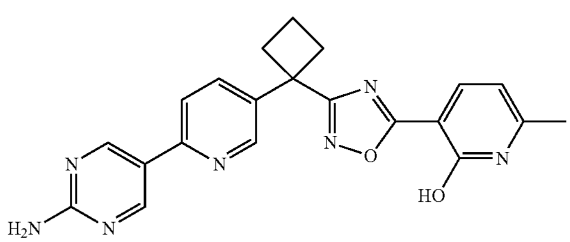 [SMILES: Cc1ccc(-c2nc(C3(c4ccc(-c5cnc(N)nc5)nc4)CCC3)no2)c(O)n1] | 3-(3-{1-[6-(2-aminopyrimidin-5-yl)pyridin-3-yl]cyclobutyl}-1,2,4-oxadiazol-5-yl)-6-methylpyridin-2-ol |

TABLE I-continued

| Example | Structure | Name |
|---|---|---|
| 98 | 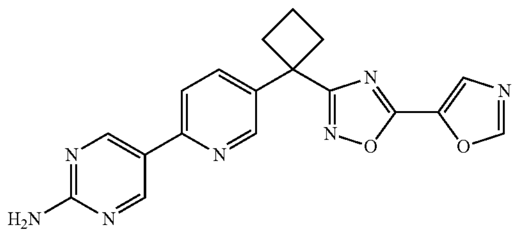 [SMILES: Nc1ncc(-c2ccc(C3(c4noc(-c5cnco5)n4)CCC3)cn2)cn1] | 5-(5-{1-[5-(1,3-oxazol-5-yl)-1,2,4-oxadiazol-3-yl]cyclobutyl}pyridin-2-yl)pyrimidin-2-amine |
| 99 | 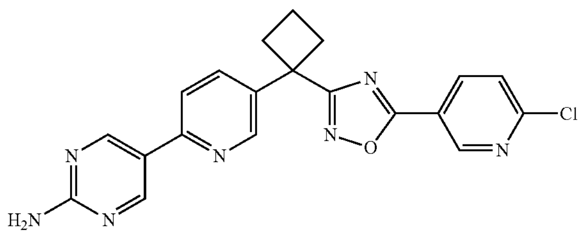 [SMILES: Nc1ncc(-c2ccc(C3(c4noc(-c5ccc(Cl)nc5)n4)CCC3)cn2)cn1] | 5-(5-{1-[5-(6-chloropyridin-3-yl)-1,2,4-oxadiazol-3-yl]cyclobutyl}pyridin-2-yl)pyrimidin-2-amine |
| 100 | 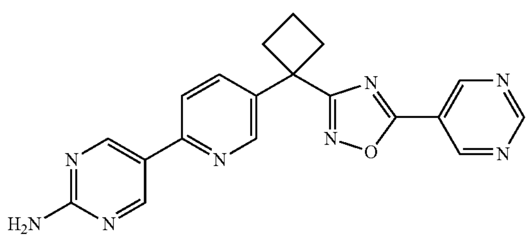 [SMILES: Nc1ncc(-c2ccc(C3(c4noc(-c5cncnc5)n4)CCC3)cn2)cn1] | 5-(5-{1-[5-(pyrimidin-5-yl)-1,2,4-oxadiazol-3-yl]cyclobutyl}pyridin-2-yl)pyrimidin-2-amine |
| 101 | 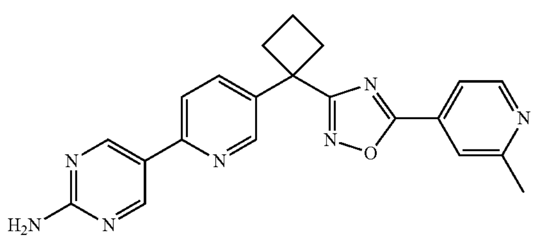 [SMILES: Cc1cc(-c2nc(C3(c4ccc(-c5cnc(N)nc5)nc4)CCC3)no2)ccn1] | 5-(5-{1-[5-(2-methylpyridin-4-yl)-1,2,4-oxadiazol-3-yl]cyclobutyl}pyridin-2-yl)pyrimidin-2-amine |
| 102 | 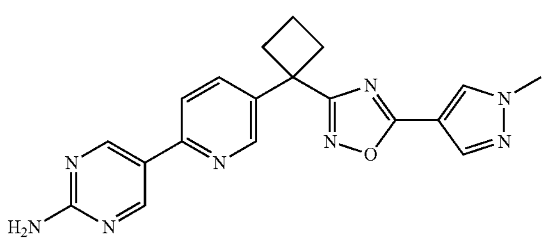 [SMILES: Cn1cc(-c2nc(C3(c4ccc(-c5cnc(N)nc5)nc4)CCC3)no2)cn1] | 5-(5-{1-[5-(1-methyl-1H-pyrazol-4-yl)-1,2,4-oxadiazol-3-yl]cyclobutyl}pyridin-2-yl)pyrimidin-2-amine |
| 103 | 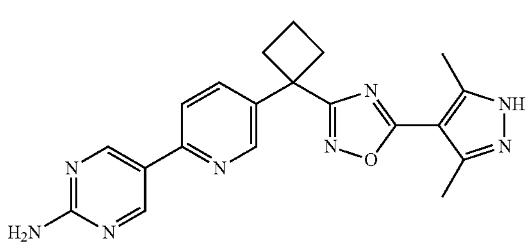 [SMILES: Cc1n[nH]c(C)c1-c1nc(C2(c3ccc(-c4cnc(N)nc4)nc3)CCC2)no1] | 5-(5-{1-[5-(3,5-dimethyl-1H-pyrazol-4-yl)-1,2,4-oxadiazol-3-yl]cyclobutyl}pyridin-2-yl)pyrimidin-2-amine |

TABLE I-continued

| Example | Structure | Name |
|---|---|---|
| 104 | 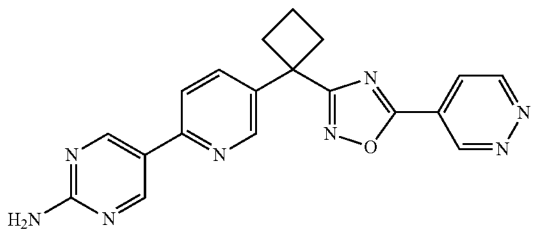 | 5-(5-{1-[5-(pyridazin-4-yl)-1,2,4-oxadiazol-3-yl]cyclobutyl}pyridin-2-yl)pyrimidin-2-amine |
| 105 | 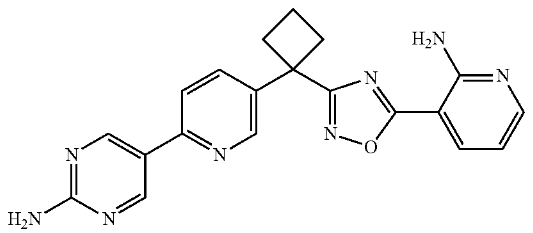 [SMILES: Nc1ncc(-c2ccc(C3(c4noc(-c5cccnc5N)n4)CCC3)cn2)cn1] | 5-(5-{1-[5-(2-aminopyridin-3-yl)-1,2,4-oxadiazol-3-yl]cyclobutyl}pyridin-2-yl)pyrimidin-2-amine |
| 106 | 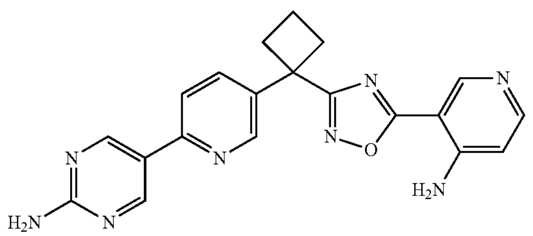 [SMILES: Nc1ncc(-c2ccc(C3(c4noc(-c5cnccc5N)n4)CCC3)cn2)cn1] | 5-(5-{1-[5-(4-aminopyridin-3-yl)-1,2,4-oxadiazol-3-yl]cyclobutyl}pyridin-2-yl)pyrimidin-2-amine |
| 107 | 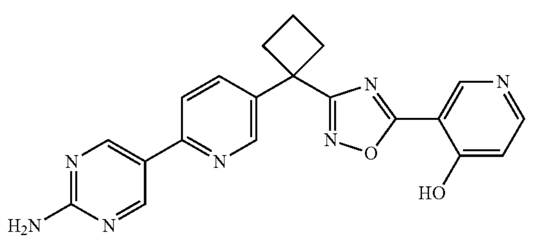 | 3-(3-{1-[6-(2-aminopyrimidin-5-yl)pyridin-3-yl]cyclobutyl}-1,2,4-oxadiazol-5-yl)pyridin-4-ol |
| 108 | 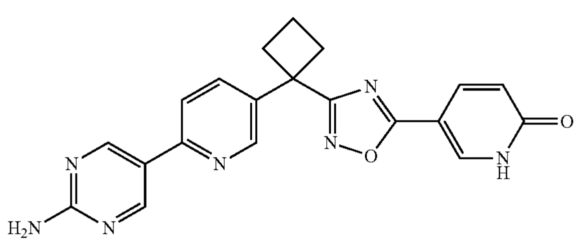 [SMILES: Nc1ncc(-c2ccc(C3(c4noc(-c5ccc(=O)[nH]c5)n4)CCC3)cn2)cn1] | 5-(3-{1-[6-(2-aminopyrimidin-5-yl)pyridin-3-yl]cyclobutyl}-1,2,4-oxadiazol-5-yl)pyridin-2(1H)-one |
| 109 | 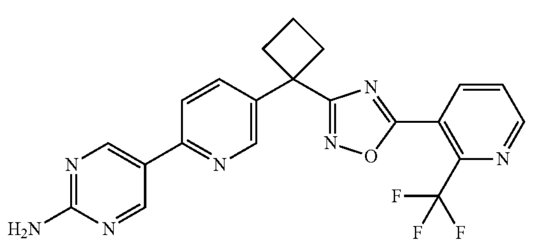 [SMILES: Nc1ncc(-c2ccc(C3(c4noc(-c5cccnc5C(F)(F)F)n4)CCC3)cn2)cn1] | 5-[5-(1-{5-[2-(trifluoromethyl)pyridin-3-yl]-1,2,4-oxadiazol-3-yl}cyclobutyl)pyridin-2-yl]pyrimidin-2-amine |

TABLE I-continued

| Example | Structure | Name |
|---|---|---|
| 110 | 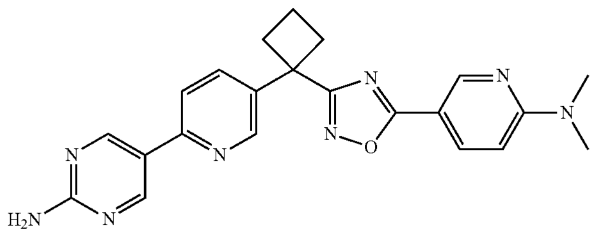 [SMILES: CN(C)c1ccc(-c2nc(C3(c4ccc(-c5cnc(N)nc5)nc4)CCC3)no2)cn1] | 5-[5-(1-{5-[6-(dimethylamino)pyridin-3-yl]-1,2,4-oxadiazol-3-yl}cyclobutyl)pyridin-2-yl]pyrimidin-2-amine |
| 111 | 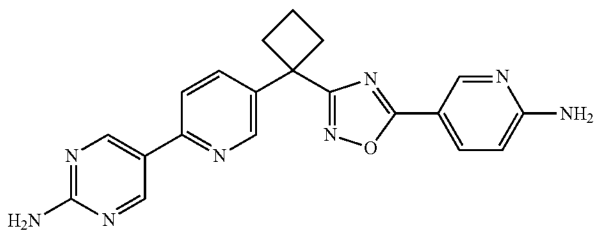 [SMILES: Nc1ccc(-c2nc(C3(c4ccc(-c5cnc(N)nc5)nc4)CCC3)no2)cn1] | 5-(5-{1-[5-(6-aminopyridin-3-yl)-1,2,4-oxadiazol-3-yl]cyclobutyl}pyridin-2-yl)pyrimidin-2-amine |
| 112 | 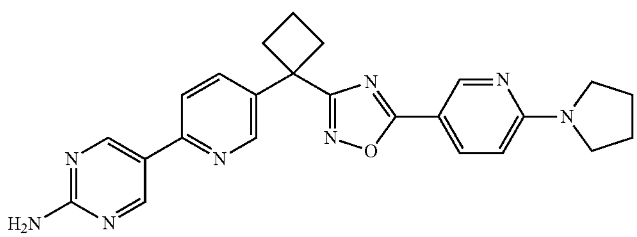 [SMILES: Nc1ncc(-c2ccc(C3(c4noc(-c5ccc(N6CCCC6)nc5)n4)CCC3)cn2)cn1] | 5-[5-(1-{5-[6-(pyrrolidin-1-yl)pyridin-3-yl]-1,2,4-oxadiazol-3-yl}cyclobutyl)pyridin-2-yl]pyrimidin-2-amine |
| 113 | 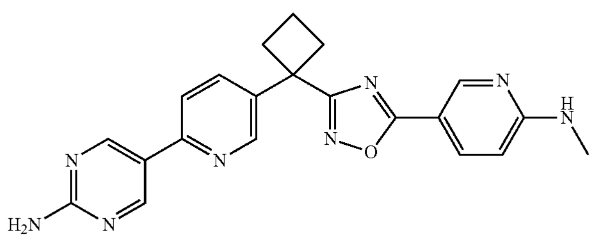 [SMILES: CNc1ccc(-c2nc(C3(c4ccc(-c5cnc(N)nc5)nc4)CCC3)no2)cn1] | 5-[5-(1-{5-[6-(methylamino)pyridin-3-yl]-1,2,4-oxadiazol-3-yl}cyclobutyl)pyridin-2-yl]pyrimidin-2-amine |
| 114 | 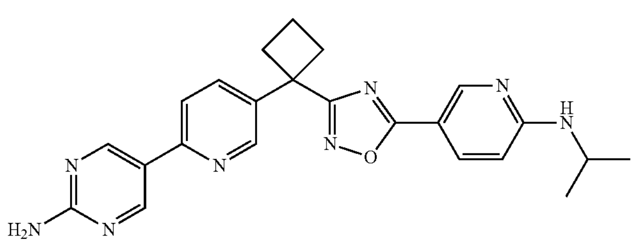 [SMILES: CC(C)Nc1ccc(-c2nc(C3(c4ccc(-c5cnc(N)nc5)nc4)CCC3)no2)cn1] | 5-[5-(1-{5-[6-(propan-2-ylamino)pyridin-3-yl]-1,2,4-oxadiazol-3-yl}cyclobutyl)pyridin-2-yl]pyrimidin-2-amine |
| 115 | 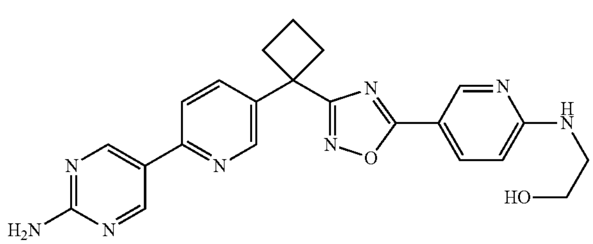 | 2-{[5-(3-{1-[6-(2-aminopyrimidin-5-yl)pyridin-3-yl]cyclobutyl}-1,2,4-oxadiazol-5-yl)pyridin-2-yl]amino}ethanol |

TABLE I-continued

| Example | Structure | Name |
|---|---|---|
| 116 | 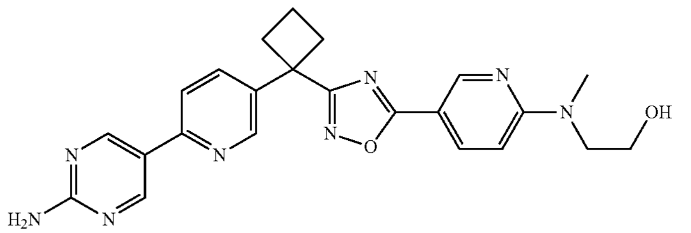 [SMILES: CN(CCO)c1ccc(-c2nc(C3(c4ccc(-c5cnc(N)nc5)nc4)CCC3)no2)cn1] | 2-{[5-(3-{1-[6-(2-aminopyrimidin-5-yl)pyridin-3-yl]cyclobutyl}-1,2,4-oxadiazol-5-yl)pyridin-2-yl](methyl)amino}ethanol |
| 117 | 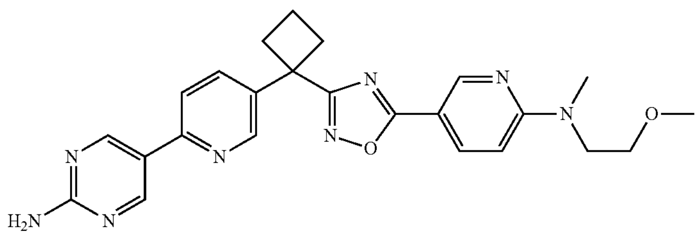 [SMILES: COCCN(C)c1ccc(-c2nc(C3(c4ccc(-c5cnc(N)nc5)nc4)CCC3)no2)cn1] | 5-{5-[1-(5-{6-[(2-methoxyethyl)(methyl)amino]pyridin-3-yl}-1,2,4-oxadiazol-3-yl)cyclobutyl]pyridin-2-yl}pyrimidin-2-amine |
| 118 | 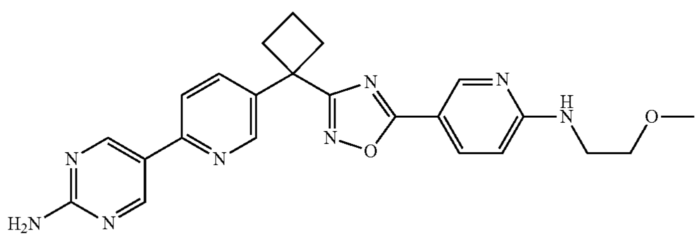 | 5-{5-[1-(5-{6-[(2-methoxyethyl)amino]pyridin-3-yl}-1,2,4-oxadiazol-3-yl)cyclobutyl]pyridin-2-yl}pyrimidin-2-amine |
| 119 | 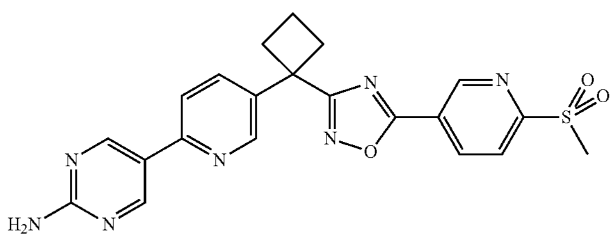 [SMILES: CS(=O)(=O)c1ccc(-c2nc(C3(c4ccc(-c5cnc(N)nc5)nc4)CCC3)no2)cn1] | 5-[5-(1-{5-[6-(methylsulfonyl)pyridin-3-yl]-1,2,4-oxadiazol-3-yl}cyclobutyl)pyridin-2-yl]pyrimidin-2-amine |
| 120 | 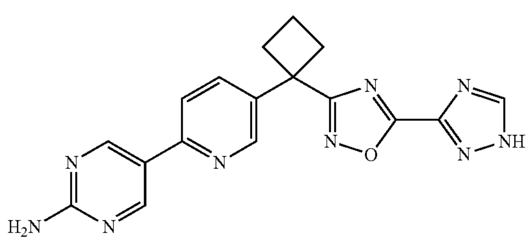 [SMILES: Nc1ncc(-c2ccc(C3(c4noc(-c5nc[nH]n5)n4)CCC3)cn2)cn1] | 5-(5-{1-[5-(1H-1,2,4-triazol-3-yl)-1,2,4-oxadiazol-3-yl]cyclobutyl}pyridin-2-yl)pyrimidin-2-amine |
| 121 | 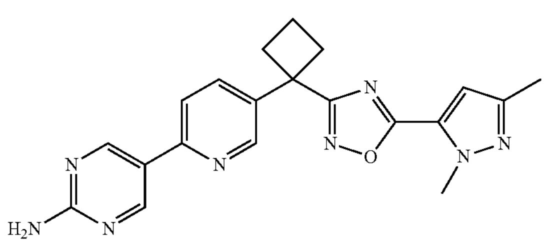 [SMILES: Cc1cc(-c2nc(C3(c4ccc(-c5cnc(N)nc5)nc4)CCC3)no2)n(C)n1] | 5-(5-{1-[5-(1,3-dimethyl-1H-pyrazol-5-yl)-1,2,4-oxadiazol-3-yl]cyclobutyl}pyridin-2-yl)pyrimidin-2-amine |

TABLE I-continued

| Example | Structure | Name |
|---|---|---|
| 122 | 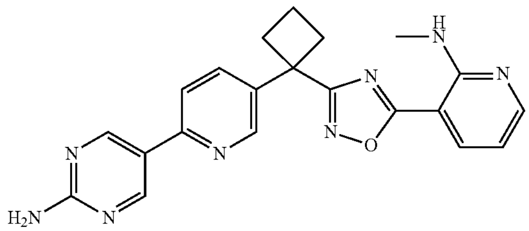 | 5-[5-(1-{5-[2-(methylamino)pyridin-3-yl]-1,2,4-oxadiazol-3-yl}cyclobutyl)pyridin-2-yl]pyrimidin-2-amine |
| 123 | 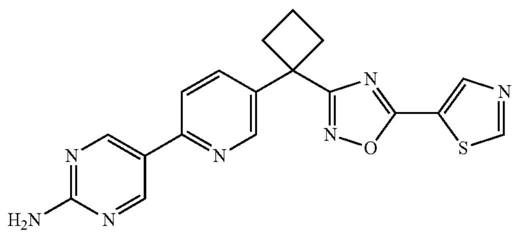 [SMILES: Nc1ncc(-c2ccc(C3(c4noc(-c5cncs5)n4)CCC3)cn2)cn1] | 5-(5-{1-[5-(1,3-thiazol-5-yl)-1,2,4-oxadiazol-3-yl]cyclobutyl}pyridin-2-yl)pyrimidin-2-amine |
| 124 | 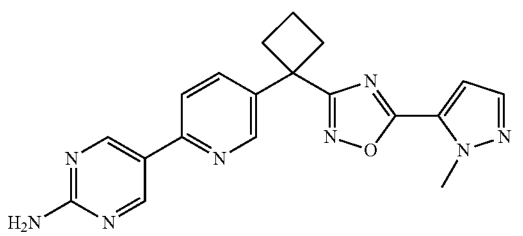 [SMILES: Cn1nccc1-c1nc(C2(c3ccc(-c4cnc(N)nc4)nc3)CCC2)no1] | 5-(5-{1-[5-(1-methyl-1H-pyrazol-5-yl)-1,2,4-oxadiazol-3-yl]cyclobutyl}pyridin-2-yl)pyrimidin-2-amine |
| 125 | 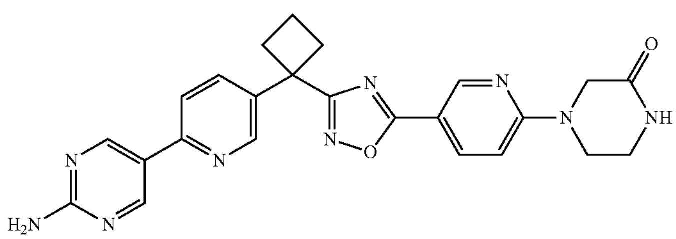 [SMILES: Nc1ncc(-c2ccc(C3(c4noc(-c5ccc(N6CCNC(=O)C6)nc5)n4)CCC3)cn2)cn1] | 4-[5-(3-{1-[6-(2-aminopyrimidin-5-yl)pyridin-3-yl]cyclobutyl}-1,2,4-oxadiazol-5-yl)pyridin-2-yl]piperazin-2-one |
| 126 | 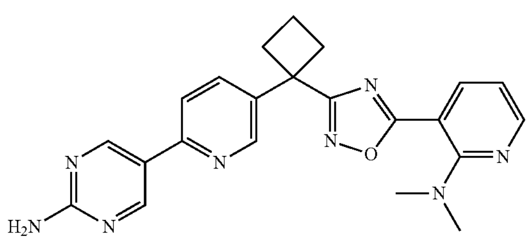 | 5-[5-(1-{5-[2-(dimethylamino)pyridin-3-yl]-1,2,4-oxadiazol-3-yl}cyclobutyl)pyridin-2-yl]pyrimidin-2-amine |
| 127 | 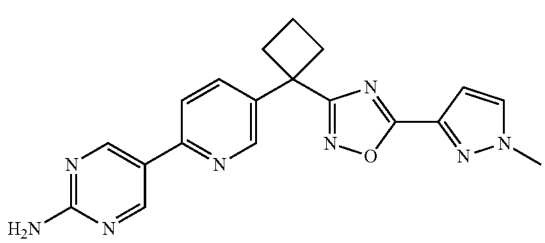 [SMILES: Cn1ccc(-c2nc(C3(c4ccc(-c5cnc(N)nc5)nc4)CCC3)no2)n1] | 5-(5-{1-[5-(1-methyl-1H-pyrazol-3-yl)-1,2,4-oxadiazol-3-yl]cyclobutyl}pyridin-2-yl)pyrimidin-2-amine |

TABLE I-continued

| Example | Structure | Name |
|---|---|---|
| 128 | 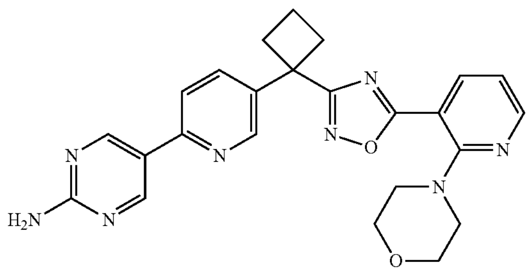 [SMILES: Nc1ncc(-c2ccc(C3(c4noc(-c5cccnc5N5CCOCC5)n4)CCC3)cn2)cn1] | 5-[5-(1-{5-[2-(morpholin-4-yl)pyridin-3-yl]-1,2,4-oxadiazol-3-yl}cyclobutyl)pyridin-2-yl]pyrimidin-2-amine |
| 129 | 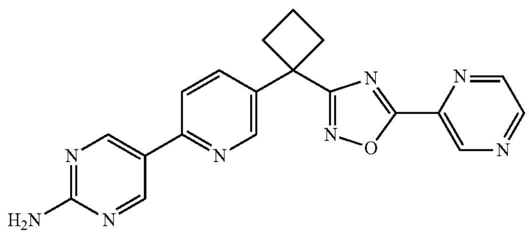 [SMILES: Nc1ncc(-c2ccc(C3(c4noc(-c5cnccn5)n4)CCC3)cn2)cn1] | 5-(5-{1-[5-(pyrazin-2-yl)-1,2,4-oxadiazol-3-yl]cyclobutyl}pyridin-2-yl)pyrimidin-2-amine |
| 130 | 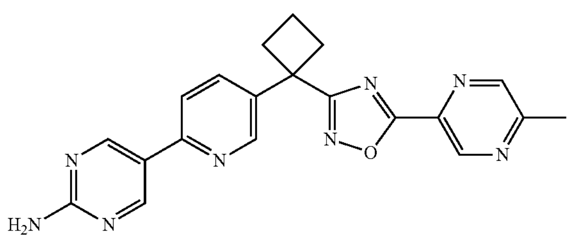 [SMILES: Cc1cnc(-c2nc(C3(c4ccc(-c5cnc(N)nc5)nc4)CCC3)no2)cn1] | 5-(5-{1-[5-(5-methylpyrazin-2-yl)-1,2,4-oxadiazol-3-yl]cyclobutyl}pyridin-2-yl)pyrimidin-2-amine |
| 131 | 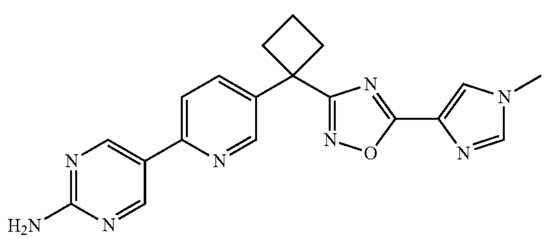 [SMILES: Cn1cnc(-c2nc(C3(c4ccc(-c5cnc(N)nc5)nc4)CCC3)no2)c1] | 5-(5-{1-[5-(1-methyl-1H-imidazol-4-yl)-1,2,4-oxadiazol-3-yl]cyclobutyl}pyridin-2-yl)pyrimidin-2-amine |
| 132 | 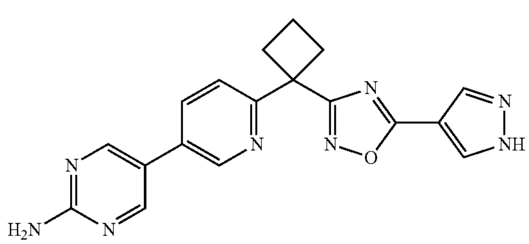 [SMILES: Nc1ncc(-c2ccc(C3(c4noc(-c5cn[nH]c5)n4)CCC3)nc2)cn1] | 5-(6-{1-[5-(1H-pyrazol-4-yl)-1,2,4-oxadiazol-3-yl]cyclobutyl}pyridin-3-yl)pyrimidin-2-amine |
| 133 | 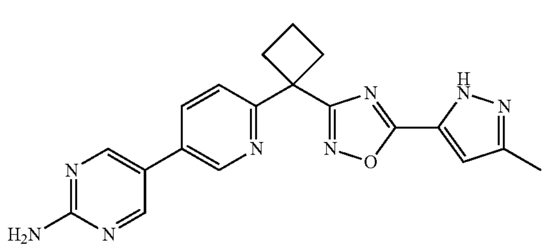 [SMILES: Cc1cc(-c2nc(C3(c4ccc(-c5cnc(N)nc5)cn4)CCC3)no2)[nH]n1] | 5-(6-{1-[5-(3-methyl-1H-pyrazol-5-yl)-1,2,4-oxadiazol-3-yl]cyclobutyl}pyridin-3-yl)pyrimidin-2-amine |

TABLE I-continued

| Example | Structure | Name |
|---|---|---|
| 134 | 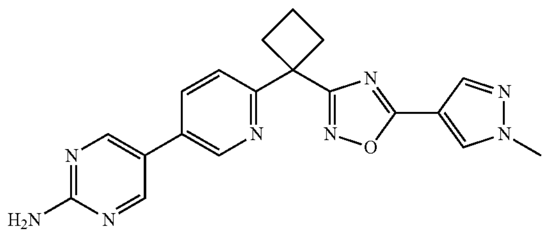 | 5-(6-{1-[5-(1-methyl-1H-pyrazol-4-yl)-1,2,4-oxadiazol-3-yl]cyclobutyl}pyridin-3-yl)pyrimidin-2-amine |
| 135 | 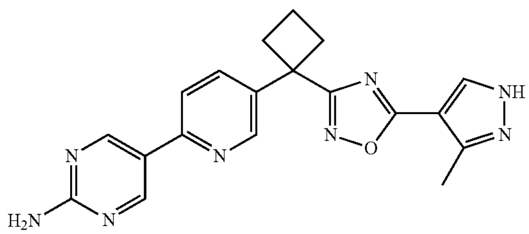 [SMILES: Cc1n[nH]cc1-c1nc(C2(c3ccc(-c4cnc(N)nc4)nc3)CCC2)no1] | 5-(6-{1-[5-(3-methyl-1H-pyrazol-4-yl)-1,2,4-oxadiazol-3-yl]cyclobutyl}pyridin-3-yl)pyrimidin-2-amine |
| 136 | 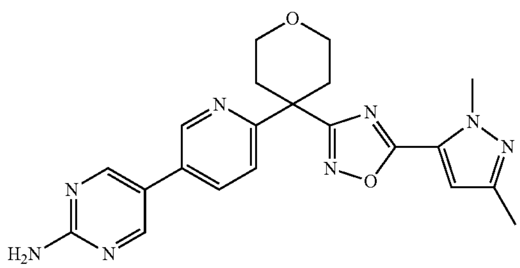 [SMILES: Cc1cc(-c2nc(C3(c4ccc(-c5cnc(N)nc5)cn4)CCOCC3)no2)n(C)n1] | 5-(6-{4-[5-(1,3-dimethyl-1H-pyrazol-5-yl)-1,2,4-oxadiazol-3-yl]tetrahydro-2H-pyran-4-yl}pyridin-3-yl)pyrimidin-2-amine |
| 137 | 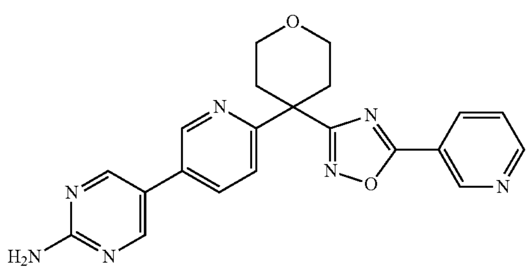 [SMILES: Nc1ncc(-c2ccc(C3(c4noc(-c5cccnc5)n4)CCOCC3)nc2)cn1] | 5-(6-{4-[5-(pyridin-3-yl)-1,2,4-oxadiazol-3-yl]tetrahydro-2H-pyran-4-yl}pyridin-3-yl)pyrimidin-2-amine |
| 138 | 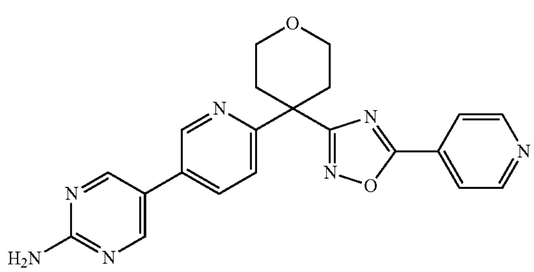 [SMILES: Nc1ncc(-c2ccc(C3(c4noc(-c5ccncc5)n4)CCOCC3)nc2)cn1] | 5-(6-{4-[5-(pyridin-4-yl)-1,2,4-oxadiazol-3-yl]tetrahydro-2H-pyran-4-yl}pyridin-3-yl)pyrimidin-2-amine |
| 139 | 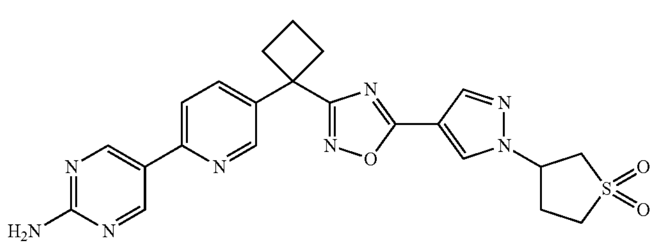 [SMILES: Nc1ncc(-c2ccc(C3(c4noc(-c5cnn(C6CCS(=O)(=O)C6)c5)n4)CCC3)cn2)cn1] | 5-[5-(1-{5-[1-(1,1-dioxidotetrahydrothiophen-3-yl)-1H-pyrazol-4-yl]-1,2,4-oxadiazol-3-yl}cyclobutyl)pyridin-2-yl]pyrimidin-2-amine |

TABLE I-continued

| Example | Structure | Name |
|---|---|---|
| 140 | 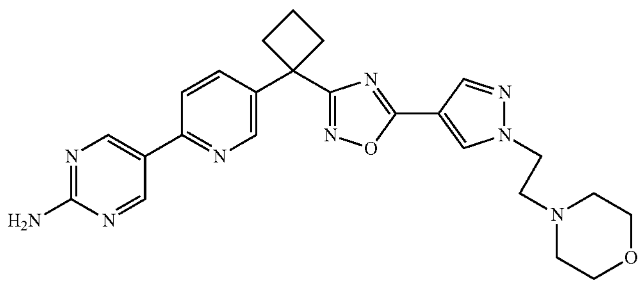 [SMILES: Nc1ncc(-c2ccc(C3(c4noc(-c5cnn(CCN6CCOCC6)c5)n4)CCC3)cn2)cn1] | 5-{5-[1-(5-{1-[2-(morpholin-4-yl)ethyl]-1H-pyrazol-4-yl}-1,2,4-oxadiazol-3-yl)cyclobutyl]pyridin-2-yl}pyrimidin-2-amine |
| 141 | 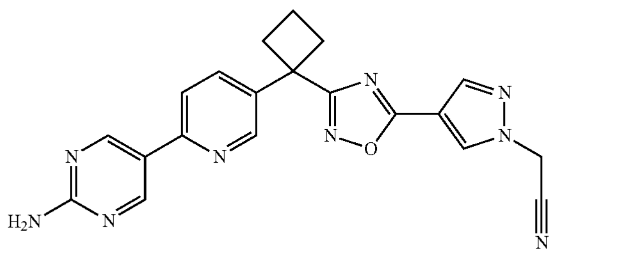 [SMILES: N#CCn1cc(-c2nc(C3(c4ccc(-c5cnc(N)nc5)nc4)CCC3)no2)cn1] | [4-(3-{1-[6-(2-aminopyrimidin-5-yl)pyridin-3-yl]cyclobutyl}-1,2,4-oxadiazol-5-yl)-1H-pyrazol-1-yl]acetonitrile |
| 142 | 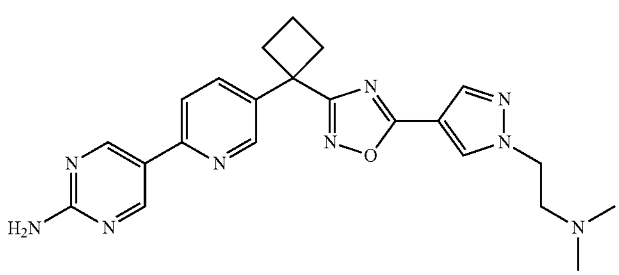 [SMILES: CN(C)CCn1cc(-c2nc(C3(c4ccc(-c5cnc(N)nc5)nc4)CCC3)no2)cn1] | 5-{5-[1-(5-{1-[2-(dimethylamino)ethyl]-1H-pyrazol-4-yl}-1,2,4-oxadiazol-3-yl)cyclobutyl]pyridin-2-yl}pyrimidin-2-amine |
| 143 | 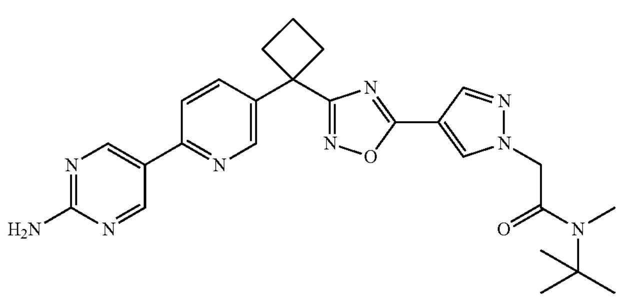 [SMILES: CN(C(=O)Cn1cc(-c2nc(C3(c4ccc(-c5cnc(N)nc5)nc4)CCC3)no2)cn1)C(C)(C)C] | 2-[4-(3-{1-[6-(2-aminopyrimidin-5-yl)pyridin-3-yl]cyclobutyl}-1,2,4-oxadiazol-5-yl)-1H-pyrazol-1-yl]-N-tert-butyl-N-methylacetamide |
| 144 | 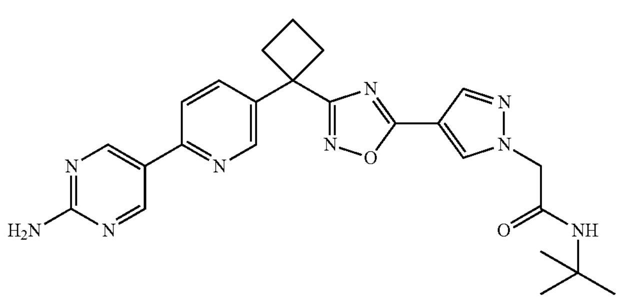 [SMILES: CC(C)(C)NC(=O)Cn1cc(-c2nc(C3(c4ccc(-c5cnc(N)nc5)nc4)CCC3)no2)cn1] | 2-[4-(3-{1-[6-(2-aminopyrimidin-5-yl)pyridin-3-yl]cyclobutyl}-1,2,4-oxadiazol-5-yl)-1H-pyrazol-1-yl]-N-tert-butylacetamide |

TABLE I-continued

| Example | Structure | Name |
|---|---|---|
| 145 | 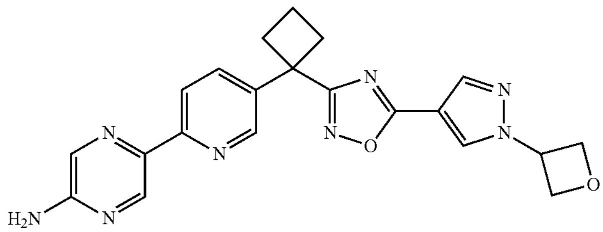 [SMILES: Nc1cnc(-c2ccc(C3(c4noc(-c5cnn(C6COC6)c5)n4)CCC3)cn2)cn1] | 5-(5-{1-[5-(1-oxetan-3-yl-1H-pyrazol-4-yl)-[1,2,4]oxadiazol-3-yl]-cyclobutyl}-pyridin-2-yl)-pyrazin-2-ylamine |
| 146 | 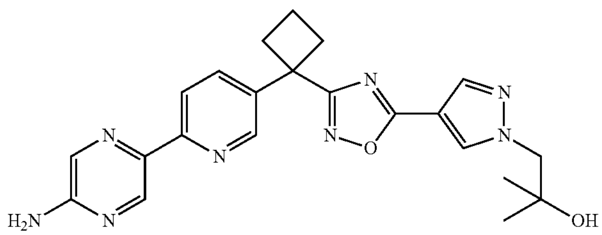 [SMILES: CC(C)(O)Cn1cc(-c2nc(C3(c4ccc(-c5cnc(N)cn5)nc4)CCC3)no2)cn1] | 1-[4-(3-{1-[6-(5-amino-pyrazin-2-yl)-pyridin-3-yl]-cyclobutyl}-[1,2,4]oxadiazol-5-yl)-pyrazol-1-yl]-2-methyl-propan-2-ol |
| 147 | 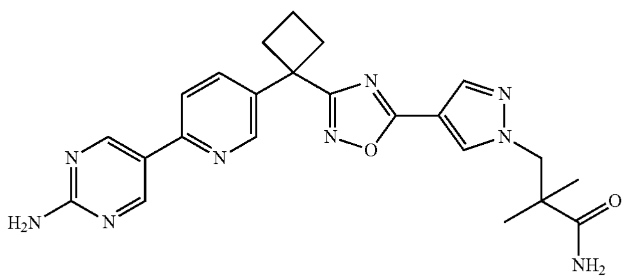 [SMILES: CC(C)(Cn1cc(-c2nc(C3(c4ccc(-c5cnc(N)nc5)nc4)CCC3)no2)cn1)C(N)=O] | 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionamide |
| 148 | 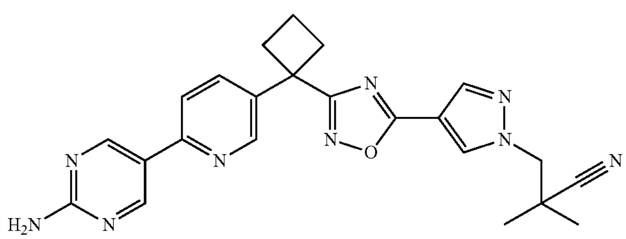 [SMILES: CC(C)(C#N)Cn1cc(-c2nc(C3(c4ccc(-c5cnc(N)nc5)nc4)CCC3)no2)cn1] | 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionitrile |
| 149 | 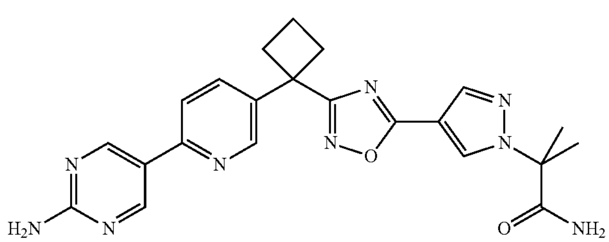 [SMILES: CC(C)(C(N)=O)n1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-isobutyramide |
| 150 | 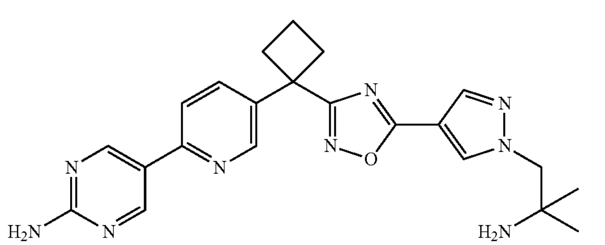 [SMILES: CC(C)(N)Cn1cc(-c2nc(C3(c4ccc(-c5cnc(N)nc5)nc4)CCC3)no2)cn1] | 5-[5-(1-{5-[1-(2-amino-2-methyl-propyl)-1H-pyrazol-4-yl]-[1,2,4]oxadiazol-3-yl}-cyclobutyl)-pyridin-2-yl]-pyrimidin-2-ylamine |

TABLE I-continued

| Example | Structure | Name |
|---|---|---|
| 151 | 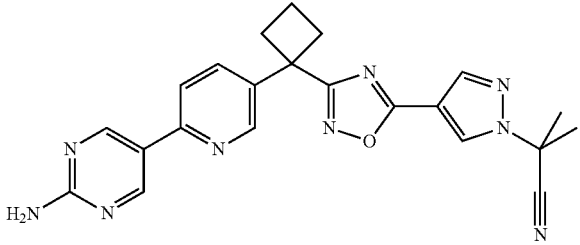 [SMILES: CC(C)(C#N)n1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-2-methyl-propionitrile |
| 152 | 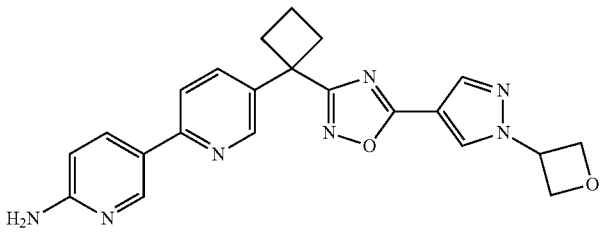 | 5-{1-[5-(1-oxetan-3-yl-1H-pyrazol-4-yl)-[1,2,4]oxadiazol-3-yl]-cyclobutyl}-[2,3']bipyridinyl-6'-ylamine |
| 153 | 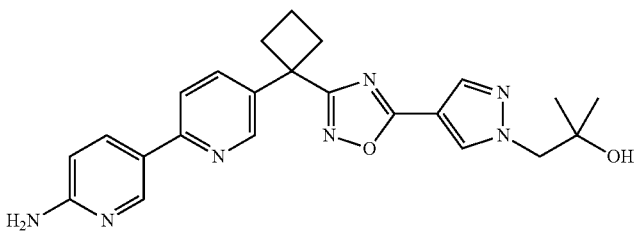 | 1-(4-{3-[1-(6'-amino-[2,3']bipyridinyl-5-yl)-cyclobutyl]-[1,2,4]oxadiazol-5-yl}-pyrazol-1-yl)-2-methyl-propan-2-ol |
| 154 | 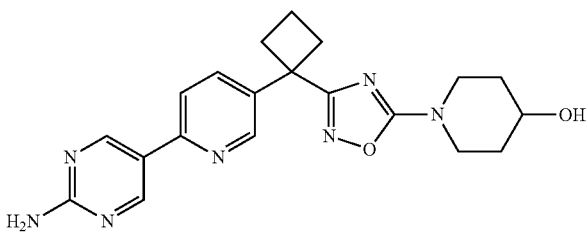 [SMILES: Nc1ncc(-c2ccc(C3(c4noc(N5CCC(O)CC5)n4)CCC3)cn2)cn1] | 1-(3-{1-[6-(2-amino-pyrimidin-5-yl)-pyridin-3-yl]-cyclobutyl}-[1,2,4]oxadiazol-5-yl)-piperidin-4-ol |
| 155 | 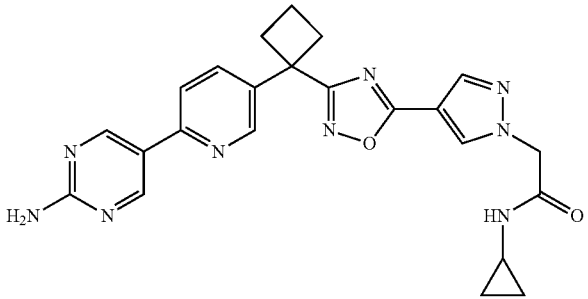 [SMILES: Nc1ncc(-c2ccc(C3(c4noc(-c5cnn(CC(=O)NC6CC6)c5)n4)CCC3)cn2)cn1] | 2-[4-(3-{1-[6-(2-Amino-pyrimidin-5-yl)-pyridin-3-yl]-cyclobutyl}-[1,2,4]oxadiazol-5-yl)-pyrazol-1-yl]-N-cyclopropyl-acetamide |

TABLE I-continued

| Example | Structure | Name |
|---|---|---|
| 156 | 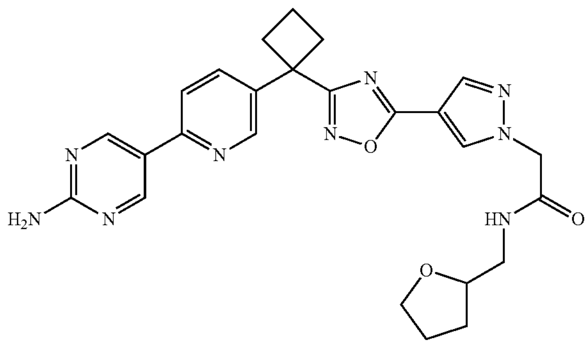 [SMILES: Nc1ncc(-c2ccc(C3(c4noc(-c5cnn(CC(=O)NCC6CCCO6)c5)n4)CCC3)cn2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-(tetrahydro-furan-2-ylmethyl)-acetamide |
| 157 | 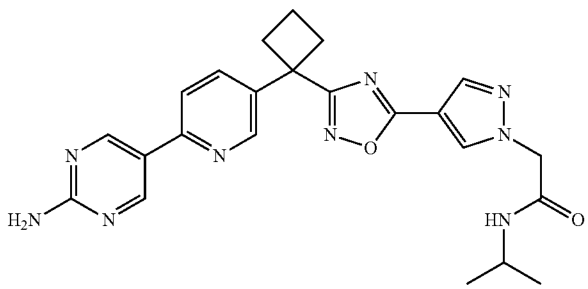 [SMILES: CC(C)NC(=O)Cn1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-isopropyl-acetamide |
| 158 | 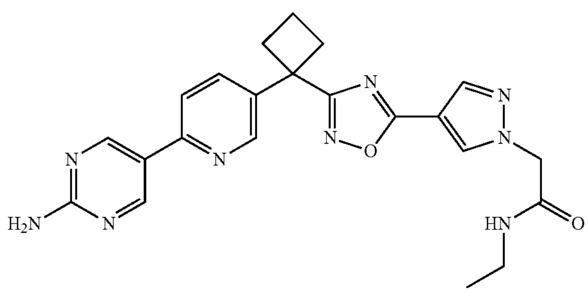 [SMILES: CCNC(=O)Cn1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-ethyl-acetamide |
| 159 | 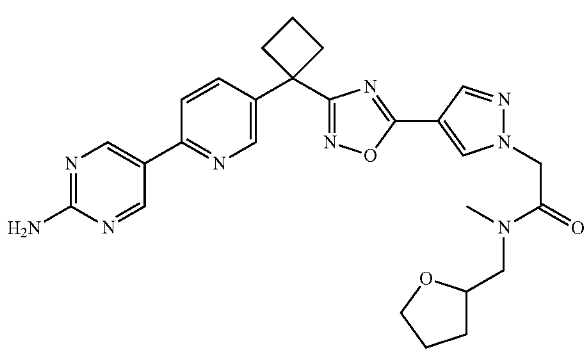 [SMILES: CN(CC1CCCO1)C(=O)Cn1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-methyl-N-(tetrahydro-furan-2-ylmethyl)-acetamide |
| 160 | 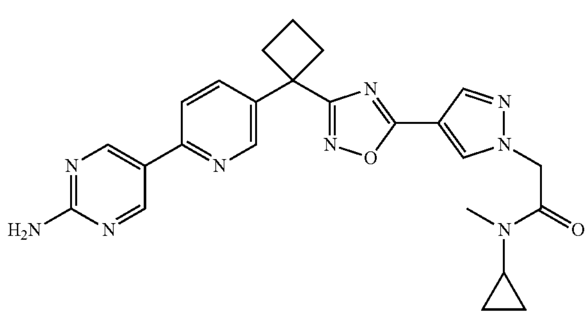 [SMILES: CN(C(=O)Cn1cc(-c2nc(C3(c4ccc(-c5cnc(N)nc5)nc4)CCC3)no2)cn1)C1CC1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-cyclopropyl-N-methyl-acetamide |

TABLE I-continued

| Example | Structure | Name |
|---|---|---|
| 161 | 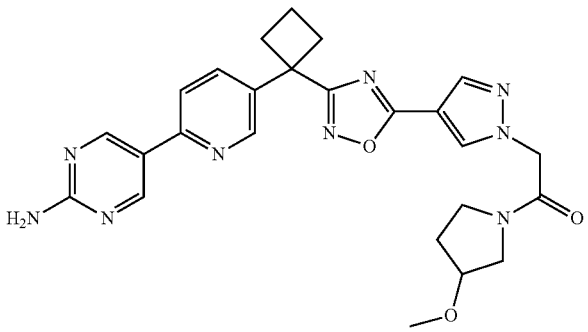 [SMILES: COC1CCN(C(=O)Cn2cc(-c3nc(C4(c5ccc(-c6cnc(N)nc6)nc5)CCC4)no3)cn2)C1] | 2-[4-(3-{1-[6-(2-amino-pyrimidin-5-yl)-pyridin-3-yl]-cyclobutyl}-[1,2,4]oxadiazol-5-yl)-pyrazol-1-yl]-1-(3-methoxy-pyrrolidin-1-yl)-ethanone |
| 162 | 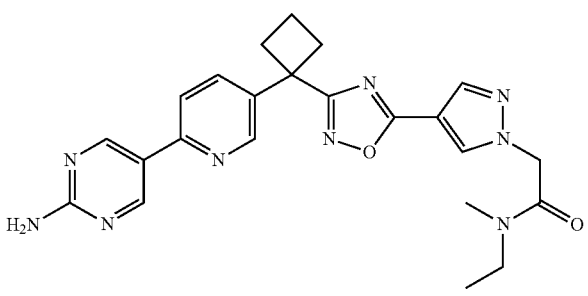 [SMILES: CCN(C)C(=O)Cn1cc(-c2nc(C3(c4ccc(-c5cnc(N)nc5)nc4)CCC3)no2)cn1] | 2-[4-(3-{1-[6-(2-amino-pyrimidin-5-yl)-pyridin-3-yl]-cyclobutyl}-[1,2,4]oxadiazol-5-yl)-pyrazol-1-yl]-N-ethyl-N-methyl-acetamide |
| 163 | 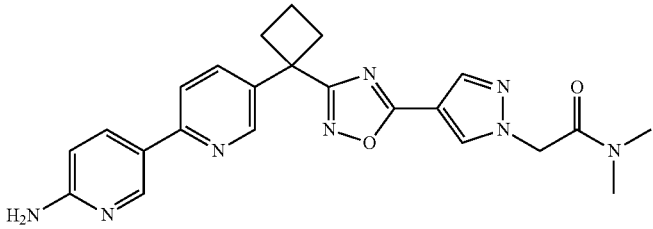 [SMILES: CN(C)C(=O)Cn1cc(-c2nc(C3(c4ccc(-c5ccc(N)nc5)nc4)CCC3)no2)cn1] | 2-(4-{3-[1-(6'-amino-[2,3']bipyridinyl-5-yl)-cyclobutyl]-[1,2,4]oxadiazol-5-yl}-pyrazol-1-yl)-N,N-dimethyl-acetamide |
| 164 | 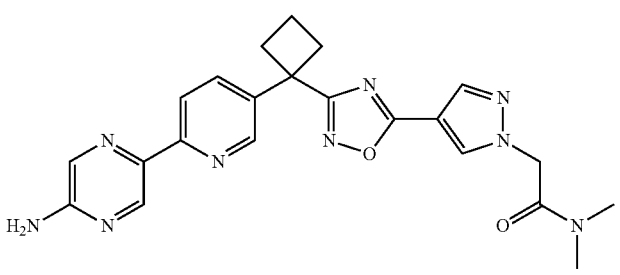 [SMILES: CN(C)C(=O)Cn1cc(-c2nc(C3(c4ccc(-c5cnc(N)cn5)nc4)CCC3)no2)cn1] | 2-[4-(3-{1-[6-(5-amino-pyrazin-2-yl)-pyridin-3-yl]-cyclobutyl}-[1,2,4]oxadiazol-5-yl)-pyrazol-1-yl]-N,N-dimethyl-acetamide |
| 165 | 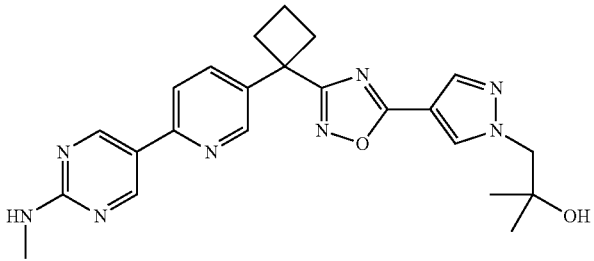 [SMILES: CNc1ncc(-c2ccc(C3(c4noc(-c5cnn(CC(C)(C)O)c5)n4)CCC3)cn2)cn1] | 2-Methyl-1-[4-(3-{1-[6-(2-methylamino-pyrimidin-5-yl)-pyridin-3-yl]-cyclobutyl}-[1,2,4]oxadiazol-5-yl)-pyrazol-1-yl]-propan-2-ol |

TABLE I-continued

| Example | Structure | Name |
|---|---|---|
| 166 | 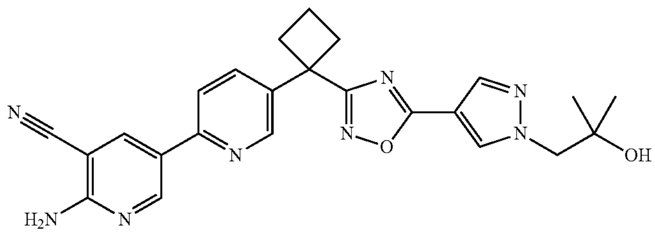 [SMILES: CC(C)(O)Cn1cc(-c2nc(C3(c4ccc(-c5cnc(N)c(C#N)c5)nc4)CCC3)no2)cn1] | 6-Amino-5-(1-{5-[1-(2-hydroxy-2-methyl-propyl)-1H-pyrazol-4-yl]-[1,2,4]oxadiazol-3-yl}-cyclobutyl)-[2,3']bipyridinyl-5'-carbonitrile |
| 167 | 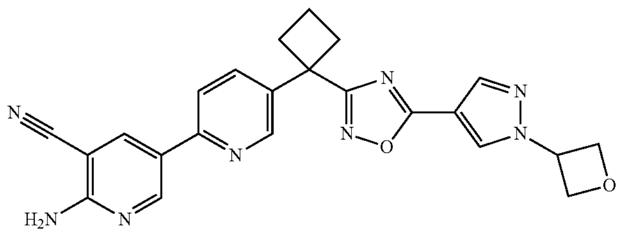 | 6'-Amino-5-{1-[5-(1-oxetan-3-yl-1H-pyrazol-4-yl)-[1,2,4]oxadiazol-3-yl]-cyclobutyl}-[2,3']bipyridinyl-5'-carbonitrile |
| 168 | 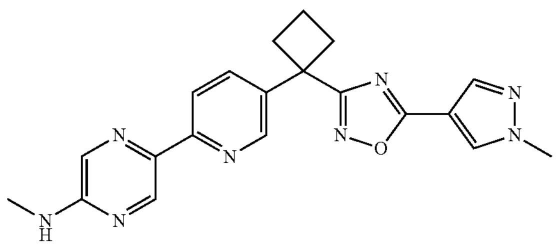 | Methyl-[5-(5-{1-[5-(1-methyl-1H-pyrazol-4-yl)-[1,2,4]oxadiazol-3-yl]-cyclobutyl}-pyridin-2-yl)-pyrazin-2-yl]-amine |
| 169 | 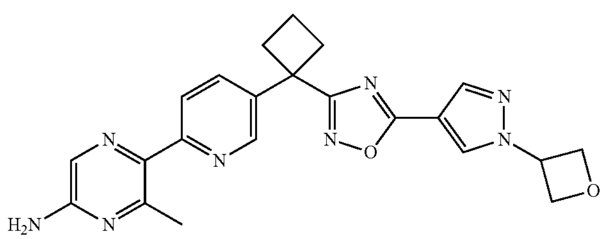 [SMILES: Cc1nc(N)cnc1-c1ccc(C2(c3noc(-c4cnn(C5COC5)c4)n3)CCC2)cn1] | 6-Methyl-5-(5-{1-[5-(1-oxetan-3-yl-1H-pyrazol-4-yl)-[1,2,4]oxadiazol-3-yl]-cyclobutyl}-pyridin-2-yl)-pyrazin-2-ylamine |
| 170 | 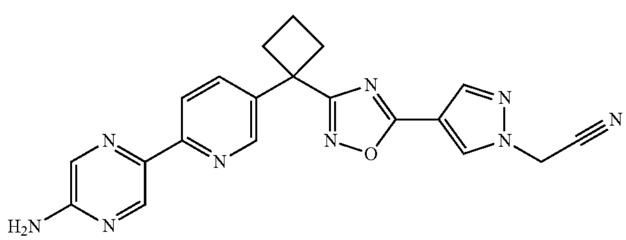 [SMILES: N#CCn1cc(-c2nc(C3(c4ccc(-c5cnc(N)cn5)nc4)CCC3)no2)cn1] | [4-(3-{1-[6-(5-Amino-pyrazin-2-yl)-pyridin-3-yl]-cyclobutyl}-[1,2,4]oxadiazol-5-yl)-pyrazol-1-yl]-acetonitrile |
| 171 | 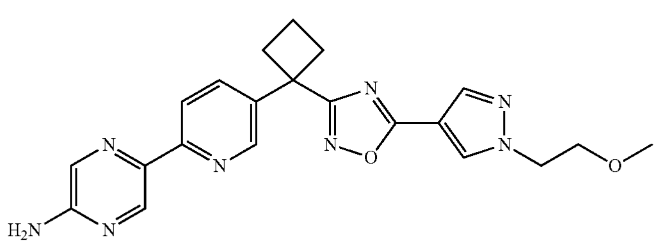 [SMILES: COCCn1cc(-c2nc(C3(c4ccc(-c5cnc(N)cn5)nc4)CCC3)no2)cn1] | 5-[5-(1-{5-[1-(2-Methoxy-ethyl)-1H-pyrazol-4-yl]-[1,2,4]oxadiazol-3-yl}-cyclobutyl)-pyridin-2-yl]-pyrazin-2-ylamine |

TABLE I-continued

| Example | Structure | Name |
|---|---|---|
| 172 | 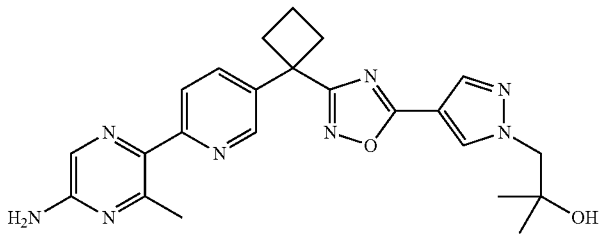 [SMILES: Cc1nc(N)cnc1-c1ccc(C2(c3noc(-c4cnn(CC(C)(C)O)c4)n3)CCC2)cn1] | 1-[4-(3-{1-[6-(5-Amino-3-methyl-pyrazin-2-yl)-pyridin-3-yl]-cyclobutyl}-[1,2,4]oxadiazol-5-yl)-pyrazol-1-yl]-2-methyl-propan-2-ol |
| 173 | 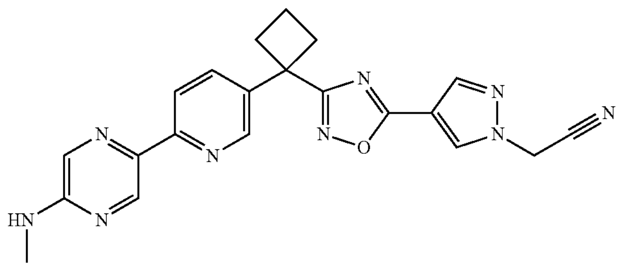 [SMILES: CNc1cnc(-c2ccc(C3(c4noc(-c5cnn(CC#N)c5)n4)CCC3)cn2)cn1] | [4-(3-{1-[6-(5-Methylamino-pyrazin-2-yl)-pyridin-3-yl]-cyclobutyl}-[1,2,4]oxadiazol-5-yl)-pyrazol-1-yl]-acetonitrile |
| 174 | 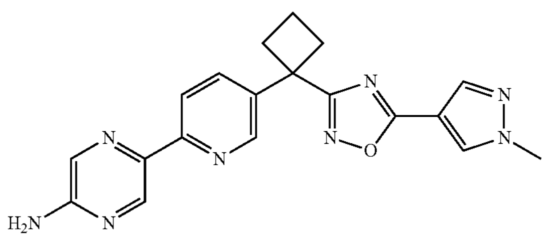 [SMILES: Cn1cc(-c2nc(C3(c4ccc(-c5cnc(N)cn5)nc4)CCC3)no2)cn1] | 5-(5-{1-[5-(1-Methyl-1H-pyrazol-4-yl)-[1,2,4]oxadiazol-3-yl]-cyclobutyl}-pyridin-2-yl)-pyrazin-2-ylamine |
| 175 | 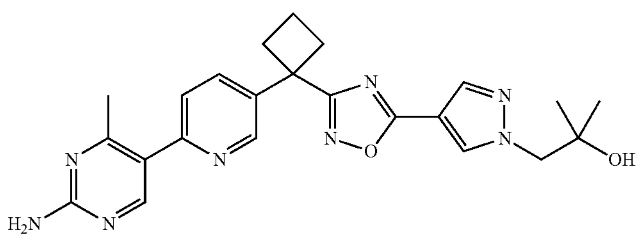 [SMILES: Cc1nc(N)ncc1-c1ccc(C2(c3noc(-c4cnn(CC(C)(C)O)c4)n3)CCC2)cn1] | 1-[4-(3-{1-[6-(2-Amino-4-methyl-pyrimidin-5-yl)-pyridin-3-yl]-cyclobutyl}-[1,2,4]oxadiazol-5-yl)-pyrazol-1-yl]-2-methyl-propan-2-ol |
| 176 | 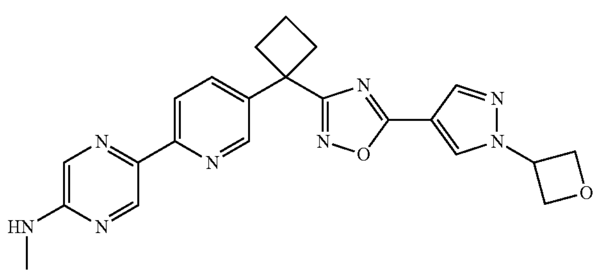 [SMILES: CNc1cnc(-c2ccc(C3(c4noc(-c5cnn(C6COC6)c5)n4)CCC3)cn2)cn1] | Methyl-[5-(5-{1-[5-(1-oxetan-3-yl-1H-pyrazol-4-yl)-[1,2,4]oxadiazol-3-yl]-cyclobutyl}-pyridin-2-yl)-pyrazin-2-yl]-amine |
| 177 | | 2-Methyl-1-[4-(3-{1-[6-(5-methylamino-pyrazin-2-yl)-pyridin-3-yl]-cyclobutyl}-[1,2,4]oxadiazol-5-yl)-pyrazol-1-yl]-propan-2-ol | or the pharmaceutically acceptable salts thereof.

In one embodiment, the invention relates to any of the compounds depicted in Table 1 above and the pharmaceutically acceptable salt thereof.

Representative compounds of the invention show activity in the FLAP binding assay and in the human whole blood $LTB_4$ production inhibition assay, described in the assessment of biological properties section, as shown in Table II.

TABLE II

| Example | FLAP SPA $IC_{50}$ (nM) | hWB $LTB_4$ $IC_{50}$ (nM) |
|---|---|---|
| 1 | 3.8 | 280 |
| 2 | 5.0 | 740 |
| 3 | 2.7 | 150 |
| 4 | 17 | 430 |
| 5 | 8.8 | 1100 |
| 6 | 5.8 | 830 |
| 7 | 11 | 690 |
| 8 | 2.0 | 110 |
| 9 | 2.9 | 320 |
| 10 | 30 | 650 |
| 11 | 78 | 2200 |
| 12 | 2.1 | 140 |
| 13 | 3.9 | 170 |
| 14 | 140 | >5000 |
| 15 | 280 | 2600 |
| 16 | 11 | 2200 |
| 17 | 8.7 | >5000 |
| 18 | 1.8 | 95 |
| 19 | 58 | >5000 |
| 20 | 9.2 | 530 |
| 21 | 2.6 | 250 |
| 22 | 2.5 | 140 |
| 23 | 26 | 430 |
| 24 | 110 | 1000 |
| 25 | 4.0 | 46 |
| 26 | 110 | 730 |
| 27 | 12.4 | 420 |
| 28 | 17 | 210 |
| 29 | 35 | 320 |
| 30 | 33 | 400 |
| 31 | 1.9 | 300 |
| 32 | 2.9 | 140 |
| 33 | 2.2 | 2600 |
| 34 | 40 | 1800 |
| 35 | 43 | >5000 |
| 36 | 5.9 | 1400 |
| 37 | 110 | 790 |
| 38 | 3.2 | 75 |
| 39 | 3.7 | 86 |
| 40 | 3.3 | 92 |
| 41 | 7.7 | >5000 |
| 42 | 7.7 | >5000 |
| 43 | 1.2 | 170 |
| 44 | 2.7 | 100 |
| 45 | 3.1 | 750 |
| 46 | 2.4 | 110 |
| 47 | 3.4 | 170 |
| 48 | 2.2 | 140 |
| 49 | 3.7 | 180 |
| 50 | 2.7 | 150 |
| 51 | 4.8 | 150 |
| 52 | 2.6 | 180 |
| 53 | 2.6 | 2600 |
| 54 | 28 | 120 |
| 55 | 13 | 52 |
| 56 | 3.2 | 24 |
| 57 | 2.4 | 34 |
| 58 | 22 | 250 |
| 59 | 83 | 610 |
| 60 | 7.9 | 150 |
| 61 | 1.8 | 41 |
| 62 | 2.6 | 72 |
| 63 | 8.8 | 190 |
| 64 | 7.2 | 170 |
| 65 | 590 | >5000 |
| 66 | 7.4 | 200 |
| 67 | 9.5 | 69 |
| 68 | 6.1 | 160 |
| 69 | 7.6 | 170 |
| 70 | 150 | 2100 |
| 71 | 58 | 390 |
| 72 | 610 | 2300 |
| 73 | 25 | 460 |
| 74 | 4.5 | 210 |
| 75 | 19 | 580 |
| 76 | 92 | 920 |
| 77 | 51 | 490 |
| 78 | 4.7 | 220 |
| 79 | 4.0 | 68 |
| 80 | 5.5 | 160 |
| 81 | 25 | 790 |
| 82 | 17 | 480 |
| 83 | 52 | 410 |
| 84 | 4.1 | 280 |
| 85 | 21 | 1000 |
| 86 | 18 | 1100 |
| 87 | 55 | 1000 |
| 88 | 7.3 | 490 |
| 89 | 2.7 | 180 |
| 90 | 7.0 | 140 |
| 91 | 24 | 330 |
| 92 | 130 | 2200 |
| 93 | 9.6 | 400 |
| 94 | 8.1 | 650 |
| 95 | 29 | >5000 |
| 96 | 7.3 | 1100 |
| 97 | 19 | >5000 |
| 98 | 110 | >5000 |
| 99 | 7.5 | 660 |
| 100 | 120 | 960 |
| 101 | 24 | 820 |
| 102 | 13 | 270 |
| 103 | 14 | 1000 |
| 104 | 110 | 2100 |
| 105 | 17 | 570 |
| 106 | 31 | 840 |
| 107 | 190 | 4000 |
| 108 | 48 | 720 |
| 109 | 14 | 1500 |
| 110 | 2.4 | 310 |
| 111 | 4.2 | 74 |
| 112 | 3.3 | 570 |
| 113 | 2.4 | 100 |
| 114 | 1.5 | 280 |
| 115 | 1.9 | 49 |
| 116 | 4.3 | 140 |
| 117 | 3.0 | 120 |
| 118 | 2.8 | 84 |
| 119 | 62 | 230 |
| 120 | 200 | >5000 |
| 121 | 28 | 1800 |
| 122 | 28 | 3800 |
| 123 | 31 | 790 |
| 124 | 11 | 210 |
| 125 | 1.8 | 160 |
| 126 | 34 | >5000 |
| 127 | 40 | 640 |
| 128 | 66 | 2700 |
| 129 | 47 | 630 |
| 130 | 26 | 350 |
| 131 | 52 | 300 |
| 132 | 46 | 370 |
| 133 | 43 | 340 |
| 134 | 81 | 790 |
| 135 | 27 | 400 |
| 136 | 540 | >5000 |
| 137 | 580 | 3000 |
| 138 | 970 | >5000 |
| 139 | 28 | 340 |
| 140 | 15 | 110 |
| 141 | 11 | 85 |
| 142 | 16 | 250 |
| 143 | 14 | 260 |
| 144 | 14 | 190 |
| 145 | 8.3 | 29 |
| 146 | 15 | 43 |

TABLE II-continued

| Example | FLAP SPA IC$_{50}$ (nM) | hWB LTB$_4$ IC$_{50}$ (nM) |
|---|---|---|
| 147 | 65 | 340 |
| 148 | 25 | 200 |
| 149 | 160 | 430 |
| 150 | 68 | 370 |
| 151 | 18 | 94 |
| 152 | 13 | 100 |
| 153 | 34 | 190 |
| 154 | 170 | 590 |
| 155 | 63 | 550 |
| 156 | 97 | 620 |
| 157 | 79 | 560 |
| 158 | 100 | 550 |
| 159 | 83 | 510 |
| 160 | 95 | 540 |
| 161 | 250 | 1100 |
| 162 | 130 | 490 |
| 163 | 110 | 300 |
| 164 | 43 | 170 |
| 165 | 73 | 280 |
| 166 | 200 | 740 |
| 167 | 140 | 680 |
| 168 | 33 | 99 |
| 169 | — | 21 |
| 170 | 48 | 51 |
| 171 | 50 | 76 |
| 172 | — | 51 |
| 173 | — | 18 |
| 174 | 39 | 74 |
| 175 | 830 | 620 |
| 176 | 23 | 73 |
| 177 | 32 | 160 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term $C_{1-3}$ hydroxy also means $C_{1-3}$alkylhydroxy or $C_{1-3}$alkyl-OH.

The term "$C_{3-10}$ carbocycle" or "$C_{3-10}$ cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0] nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo [2.2.2]octanyl, and bicyclo[3.2.1]octanyl. Non-limiting examples of 6 to 10-membered spirocyclic carbocyclic radicals include but are not limited to spiro[3,3]heptanyl, spiro [3,4]octanyl and spiro[4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, dihydropyridinyl, pyranyl, tetrahydropyranyl, dioxanyl, thiomorpholinyl, 1,1-dioxo-$1\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, pyrazolopyrimidinyl, imidazopyrimidinyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically.

This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, R$^1$, R$^2$, R$^3$, R$^4$ and R$^5$ in the Formulas below shall have the meaning of R$^1$, R$^2$, R$^3$, R$^4$ and R$^5$ in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (I) may be synthesized according to Scheme 1:

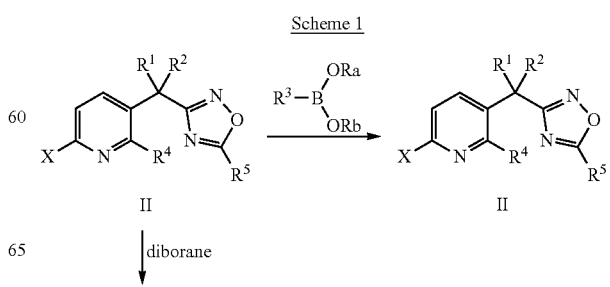

-continued

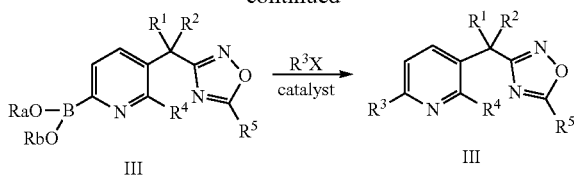

As illustrated in scheme 1, reaction of a compound of formula II with a boronic acid or the corresponding boronic acid ester shown in the above scheme, in a suitable solvent, in the presence of a suitable a suitable catalyst, provides a compound of formula (I). Ra and Rb are hydrogen or Ra and Rb together with the oxygen atoms to which they are attached form a 5-6 membered ring optionally substituted with 2-4 methyl groups. Alternatively, reaction of a compound of formula II with a diborane, under standard reaction conditions, provides a compound of formula III. Coupling the intermediate of formula III with a halide or triflate $R^3X$, in a suitable solvent, in the presence of a suitable catalyst, provides a compound of formula (I). X is chloro, bromo, triflate, or iodo.

The compounds of Formula (I) may be prepared according to Scheme 2:

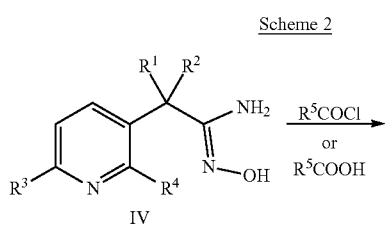

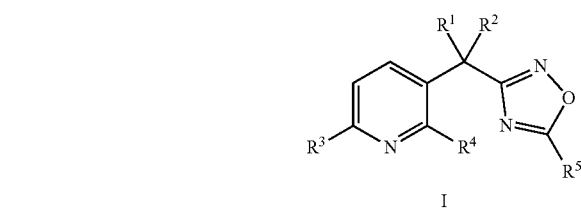

As illustrated in scheme 2, reaction of a compound of formula IV with an acid chloride $R^5COCl$, in a suitable solvent, in the presence of a suitable base, provides a compound of formula (I).

Alternatively, reaction of a compound of formula IV with an acid $R^5COOH$, in a suitable solvent, in the presence of carbonyl diimidazole, or other suitable amide coupling reagent, provides a compound of formula (I).

Additionally, reaction of a compound of formula IV with trichloromethyl anhydride, provides a compound of formula (I) wherein $R^5$ is trichloromethyl. The trichloromethyl group may be further converted to another group by using procedures known to one skilled in the art.

The intermediate of formula II may be synthesized as outlined in Scheme 3:

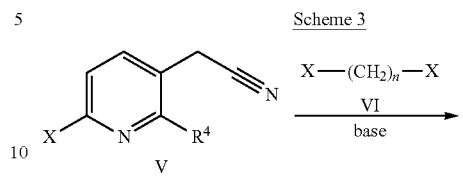

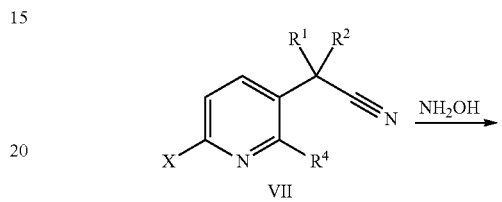

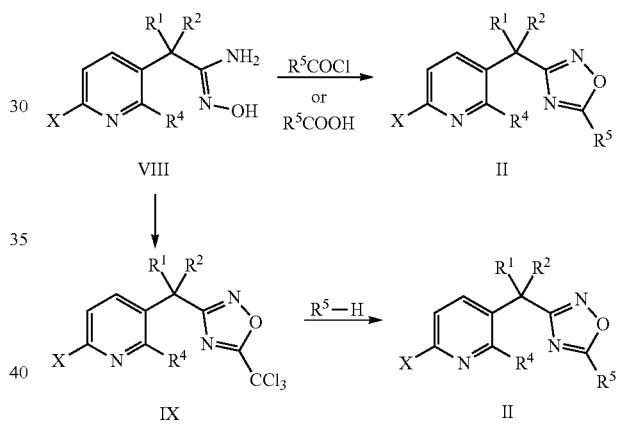

As illustrated in scheme 3, reaction of a nitrile of formula V with a dihalide VI wherein one of the carbon atoms in the alkyl chain may be optionally substituted with O, S or N, in a suitable solvent, in the presence of a suitable base such as sodium hydride, provides a substituted nitrile of formula VII. $R^1$ and $R^2$ together with the carbon atom to which they are attached form a $C_{3-8}$ carbocyclic or heterocyclic ring. X is chloro, bromo, or iodo. Reaction of the compound of formula VII with hydroxylamine, under standard reaction conditions, provides a compound of formula VIII. Reaction of the compound of formula VIII with an acid chloride $R^5COCl$, in a suitable solvent, in the presence of a suitable base, provides a compound of formula II. Alternatively, reaction of a compound of formula VIII with an acid $R^5COOH$, in a suitable solvent, in the presence of carbonyl diimidazole, or other suitable amide coupling reagent, provides a compound of formula II.

Intermediate of formula VIII may also be converted to the trichloromethyl intermediate of formula IX by reacting it with a reagent such as trichloromethyl anhydride, under standard conditions. Reaction of the intermediate IX with $R^5H$ when $R^5H$ contains a primary or secondary amino group, in a suitable solvent provides an intermediate of formula II The intermediate of formula IV may be synthesized according to Scheme 4:

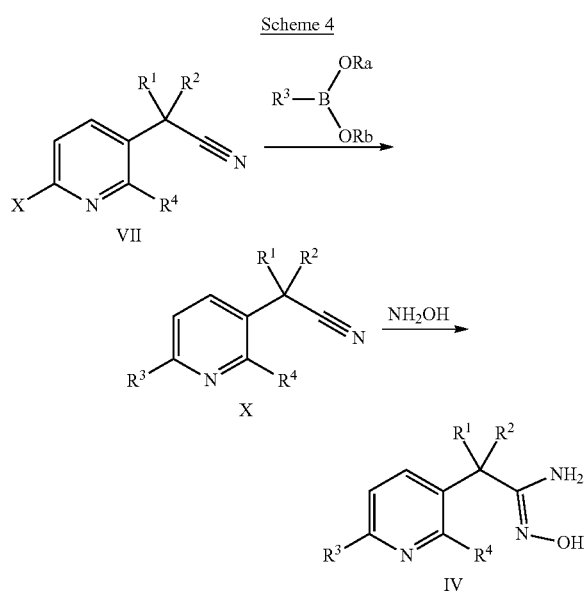

As illustrated above in scheme 4, reaction of a nitrile of formula VII with a boronic acid or the corresponding boronic acid ester shown in the above scheme, in a suitable solvent, in the presence of a suitable catalyst, provides a compound of formula X. Ra and Rb are hydrogen or Ra and Rb together with the oxygen atoms to which they are attached form a 5-6 membered ring optionally substituted with 2-4 methyl groups. Alternatively, coupling may also be achieved by reacting $R^3$—$(Sn(CH_3)_3)_2$ with a starting material of formula VII, in the presence of a suitable catalyst, to provide a compound of formula X. Reaction of a compound of formula X with hydroxylamine, under standard reaction conditions, provides a compound of formula IV.

The nitrile intermediate of formula XIII may be synthesized according to Scheme 5:

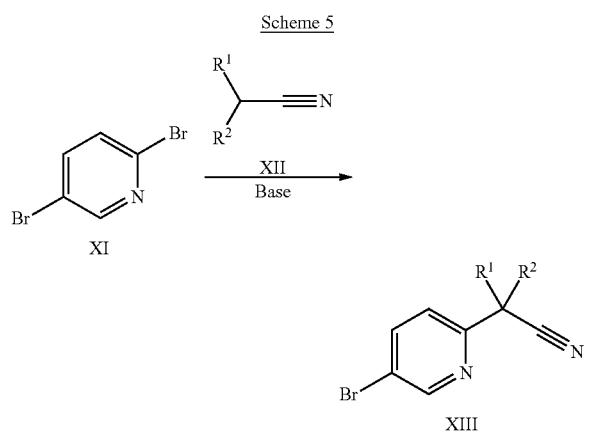

As illustrated above in scheme 5, reaction of a dihalide of formula XI with a nitrile of formula XII, under standard reaction conditions, in the presence of a suitable base, provides an intermediate of formula XIII. The intermediate of formula XIII may be converted to a compound of formula (IA) by the sequence of reactions shown in scheme 3.

Compounds of formula (IA) may be synthesized using any of the above schemes by using the appropriate staring materials and reagents.

Further modification of the initial product of Formula (I) and (IA), by methods known in the art, such as alkylation of heterocycles, and illustrated in the Examples below, may be used to prepare additional compounds of this invention.

Synthetic Examples

The following are representative compounds of the invention which can be made by the general synthetic schemes, the examples, and known methods in the art.

Preparation of Intermediates

Nitrile Intermediates

Synthesis of 1-(6-chloro-pyridin-3-yl)-cyclobutanecarbonitrile (Intermediate I-1.1)

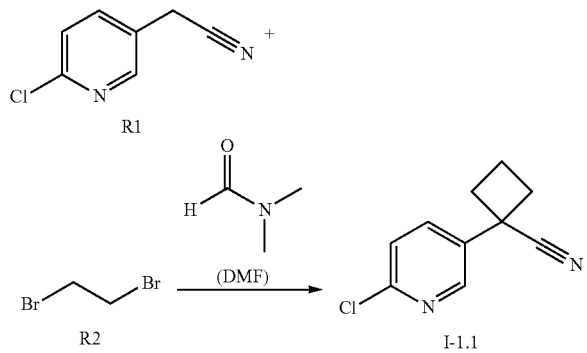

To a solution of compound R1 (65 g, 0.426 mol) in DMF (500 mL) at 0° C. is added NaH (60% in oil suspension, 37.5 g, 0.937 mol) portion-wise over 20 minutes. The mixture is stirred for a further 20 minutes and R2 (44.1 mL, 0.435 mol) is added. The reaction mixture is warmed to room temperature and stirling is continued for 1 hour. The reaction is then quenched by the addition of water (200 mL) and concentrated in vacuo. The residue is partitioned between ethyl acetate (EtOAc) and saturated aqueous $NaHCO_3$ and the phases are separated. The organic phase is dried over $Na_2SO_4$, filtered and concentrated in vacuo. The residue is purified by flash column chromatography ($SiO_2$, 20-60% ethyl acetate/heptane) to yield intermediate I-1.1 (63 g); m/z 193 [M+1].

The following intermediate is synthesized in a similar fashion from the appropriate reagents:

| Intermediate | Structure | m/z [M + H] |
|---|---|---|
| I-1.2 | 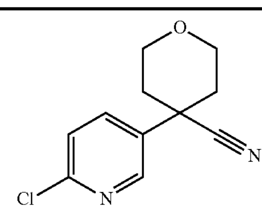 | 223 |

Synthesis of 1-(5-Bromo-pyridin-2-yl)-cyclobutanecarbonitrile (Intermediate I-1.3)

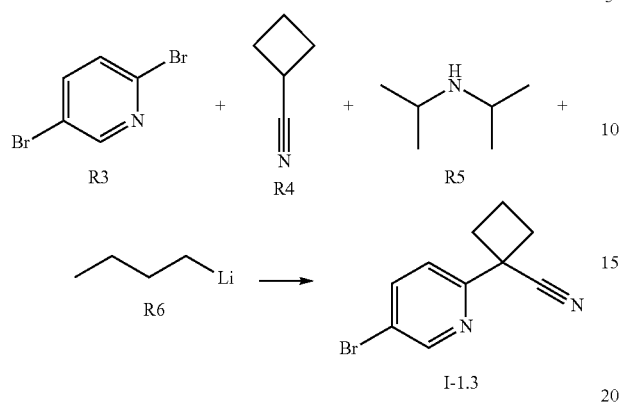

R5 (1.41 mL, 10.0 mmol) is added to THF (20 mL) and the resulting mixture is cooled to −10° C. To the resulting mixture is added R6 (1.6M in hexanes, 6.25 mL, 10.0 mmol) and the reaction is stirred for 30 minutes. The mixture is then cooled to −78° C. and R4 (811 mg, 10.0 mmol) is then added and the reaction is stirred at −78° C. for 45 minutes. At this time a mixture of R3 (1.90 g, 8.02 mmol) in THF (5 mL) is added and the mixture is allowed to warm to room temperature and stirred overnight. The resulting mixture is concentrated and the residue is partitioned between water and ethyl acetate. The phases are separated and the aqueous phase is extracted with ethyl acetate. The organic phases are combined, washed with brine, dried over $Na_2SO_4$, and concentrated. The crude residue is purified by flash chromatography ($SiO_2$, ethyl acetate/heptane gradient) to yield intermediate I-1.3 (1.10 g); m/z 237.2, 239.1 [M+H for $^{79}Br$ and $^{81}Br$].

The following intermediate is synthesized in a similar fashion from the appropriate reagents:

| Intermediate | Structure | m/z [M + H] |
|---|---|---|
| I-1.4 | 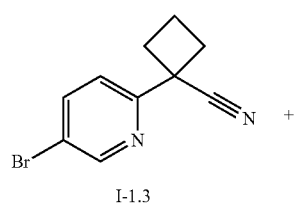 | 267 |

Synthesis of 1-[5-(2-Amino-pyrimidin-5-yl)-pyridin-2-yl]-cyclobutanecarbonitrile (Intermediate I-1.5)

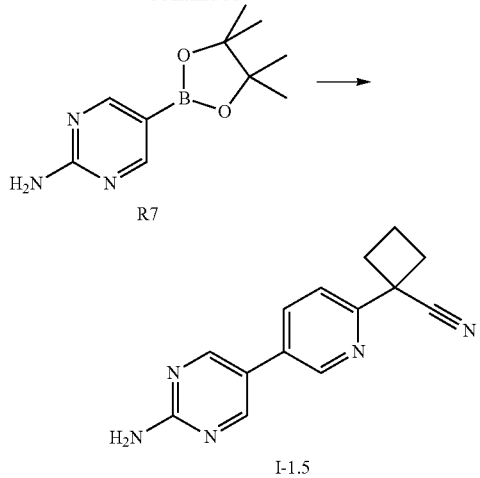

R7 (553 mg, 2.00 mmol) and palladium (II) acetate-dicyclohexylphenylphosphine PE fibers (FibreCat 1007, 167 mg, 0.100 mmol) are combined in a microwave vial. I-1.3 (474 mg, 2.50 mmol), THF (10.0 mL), and 2M aqueous $Na_2CO_3$ (4.00 mL) are then added and the reaction is heated in the microwave at 120° C. for 45 minutes. The resulting mixture is diluted with water and ethyl acetate and filtered. The organic phase is collected, washed with brine, dried over $Na_2SO_4$, and concentrated. The crude residue is purified by flash chromatography ($SiO_2$, ethyl acetate/heptane gradient) to yield intermediate I-1.5 (300 mg); m/z 252.2 [M+H].

Synthesis of 1-[6-(2-amino-pyrimidin-5-yl)-pyridin-3-yl]-cyclobutanecarbonitrile (Intermediate I-1.6)

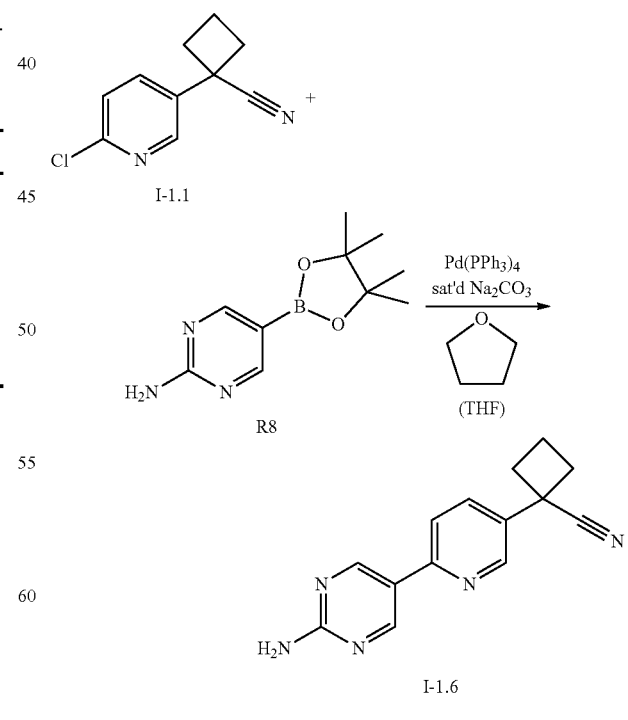

To a suspension of I-1.1 (3.00 g, 15.6 mmol) and R8 (4.13 g, 18.7 mmol) in THF (30 mL) is added $Pd(PPh_3)_4$ (1.8 g, 1.56 mmol) and saturated aqueous Na$_2$CO$_3$ (10 mL). The mixture is heated to reflux overnight. The reaction mixture is concentrated in vacuo and purified by flash chromatography (SiO$_2$, 0-3% methanol/CH$_2$Cl$_2$) to afford the title intermediate I-1.6 (3.7 g); m/z 252 [M+H].

The following intermediate is synthesized in a similar fashion from the appropriate reagents:

| Intermediate | Structure | m/z [M + H] |
|---|---|---|
| I-1.7 | | 279.9 |
| I-1.9 | 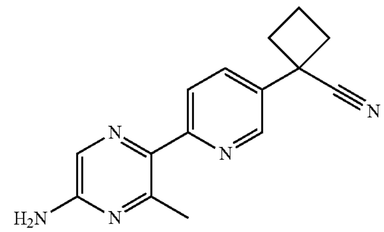 [SMILES: Cc1nc(N)cnc1-c1ccc(C2(C#N)CCC2)cn1] | 266.4 |
| I-1.10 | 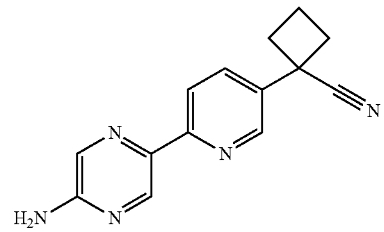 [SMILES: N#CC1(c2ccc(-c3cnc(N)cn3)nc2)CCC1] | 252.4 |

Carboxamidine Intermediate

Synthesis of 1-[6-(5-Methylamino-pyrazin-2-yl)-pyridin-3-yl]-cyclobutanecarbonitrile (Intermediate I-1.8)

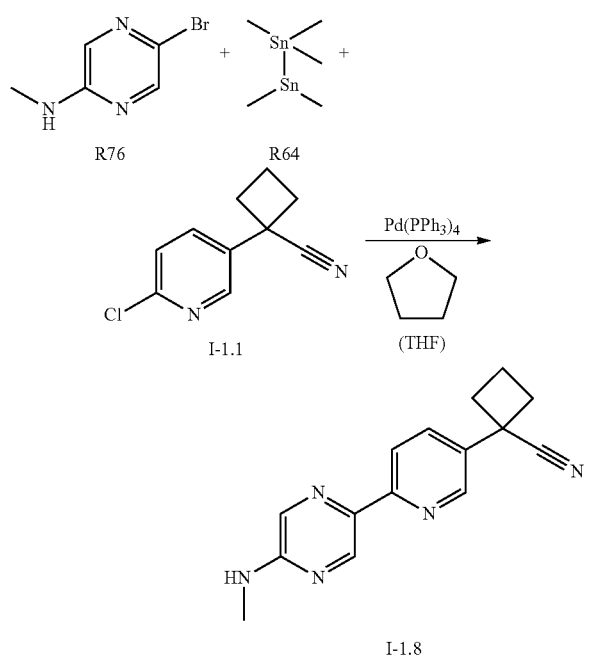

Synthesis of 1-(6-chloro-pyridin-3-yl)-N-hydroxy-cyclobutanecarboxamidine (Intermediate I-2.1)

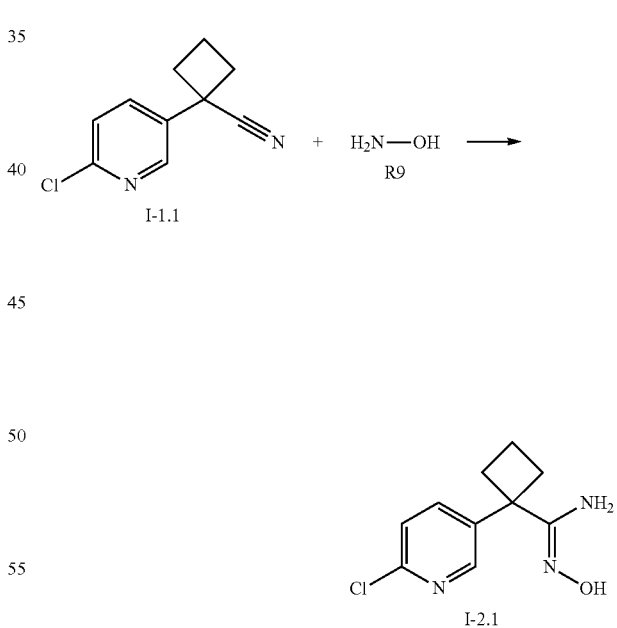

R76 (500 mg, 2.66 mmol) is treated with R64 (0.96 g, 2.93 mmol) and THF (12 mL) and the resulting mixture is degassed with argon and treated with Pd(PPh$_3$)$_4$ (307 mg, 0.266 mmol mmol). The mixture is heated at 95° C. for 2 hours at which time it is treated with I-1.1 (0.61 g, 3.19 mmol) and Pd(PPh$_3$)$_4$ (307 mg, 0.266 mmol mmol) again and heated at 95° C. overnight. The reaction mixture is concentrated in vacuo and purified by flash chromatography (SiO$_2$, 0-8% methanol/CH$_2$Cl$_2$) to afford the title intermediate I-1.8 (1.00 g); m/z 267.2 [M+H]. The following intermediates are synthesized in a similar fashion from the appropriate reagents:

To a solution of I-1.1 (30 g, 0.156 mol) in ethanol (400 mL) is added R9 (50% aqueous solution, 95.4 mL, 1.56 mol). The reaction mixture is stirred at 80° C. for 18 h. The reaction is cooled to room temperature, the ethanol is evaporated in vacuo, and the concentrated mixture is extracted with CH$_2$Cl$_2$ (DCM). The combined organics are dried with Na$_2$SO$_4$, filtered and concentrated in vacuo to give the title intermediate I-2.1 (29.8 g); m/z 226 [M+H].

The following intermediates are synthesized in a similar fashion from the appropriate reagents:

| Intermediate | Structure | m/z [M + H] |
|---|---|---|
| I-2.2 | 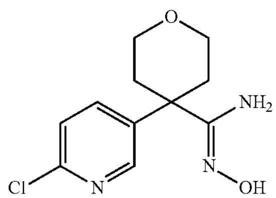 [SMILES: N/C(=N\O)C1(c2ccc(Cl)nc2)CCOCC1] | 256 |
| I-2.3 | 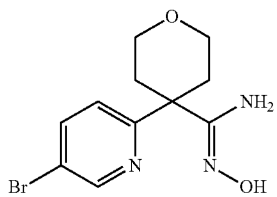 [SMILES: N/C(=N\O)C1(c2ccc(Br)cn2)CCOCC1] | 256 |

Synthesis of 1-[6-(2-amino-pyrimidin-5-yl)-pyridin-3-yl]-N-hydroxy-cyclobutanecarboxamidine (Intermediate I-3.1)

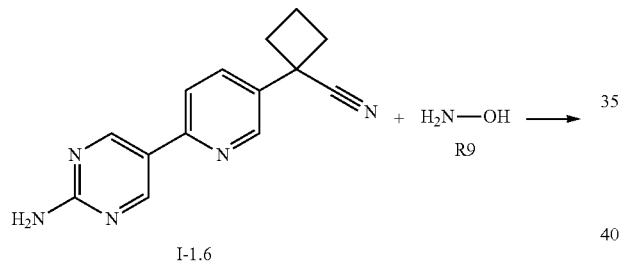

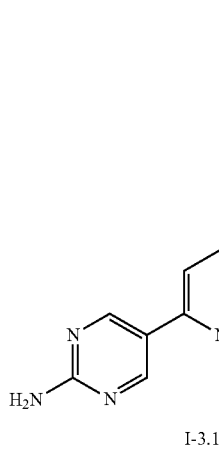

To a solution of I-1.6 (8.85 g, 35.2 mmol) in ethanol (40 mL) is added R9 (50% aqueous solution, 20 mL, 326 mmol). The reaction mixture is stirred at reflux for 18 hours. The reaction mixture is cooled to room temperature, the ethanol is evaporated in vacuo, and the precipitate is collected via filtration to yield the title intermediate I-3.1 (8.80 g); m/z 285 [M+H].

The following intermediates are synthesized in a similar fashion from the appropriate reagents:

| Intermediate | Structure | m/z [M + H] |
|---|---|---|
| I-3.2 | 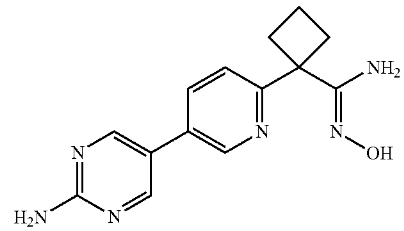 [SMILES: N/C(=N\O)C1(c2ccc(-c3cnc(N)nc3)cn2)CCC1] | 285.2 |
| I-3.3 | 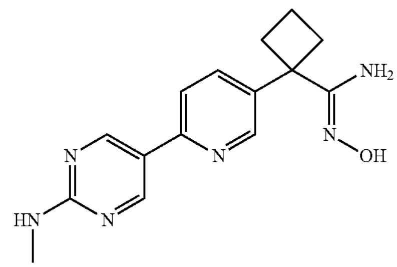 [SMILES: CNc1ncc(-c2ccc(C3(/C(N)=N/O)CCC3)cn2)cn1] | 299.2 |
| I-3.4 | 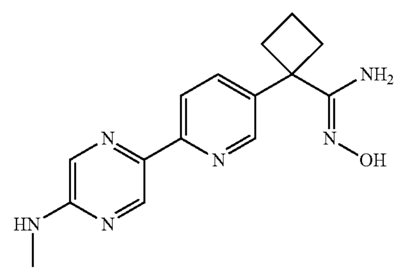 [SMILES: CNc1cnc(-c2ccc(C3(/C(N)=N/O)CCC3)cn2)cn1] | 299.2 |
| I-3.5 | 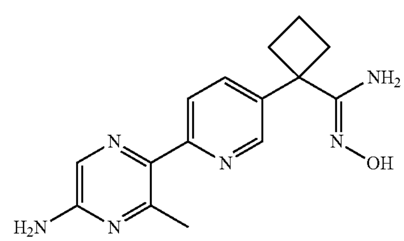 [SMILES: Cc1nc(N)cnc1-c1ccc(C2(/C(N)=N/O)CCC2)cn1] | 299.9 |
| I-3.6 | 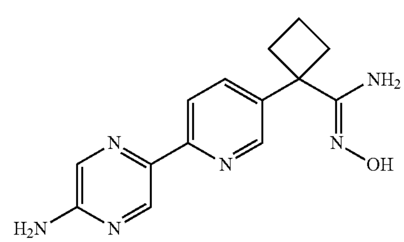 [SMILES: N/C(=N\O)C1(c2ccc(-c3cnc(N)cn3)nc2)CCC1] | 285.1 |

Pyridyl Halide Intermediates

Synthesis of 2-Chloro-5-[1-(5-pyridin-3-yl-1,2,4-oxadiazol-3-yl)-cyclobutyl]-pyridine (Intermediate I-4.1)

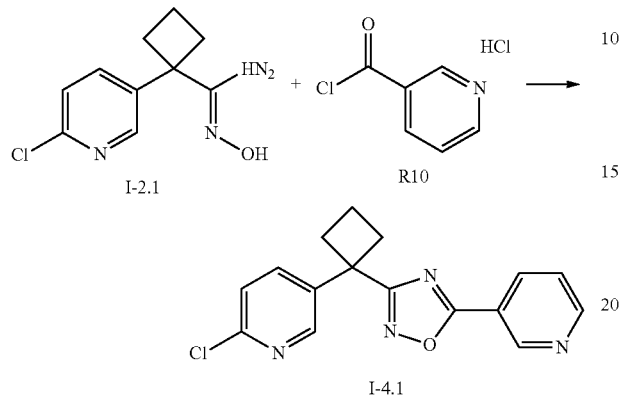

R10 (356 mg, 2.00 mmol) is treated with pyridine (2 mL) and I-2.1 (500 mg, 1.33 mmol) and the resulting mixture is heated at 110° C. until the starting material is consumed. The reaction is cooled to room temperature and the solvent is removed in vacuo. The residue is diluted with ethyl acetate and saturated aqueous NaHCO$_3$ and the phases are separated. The aqueous phase is extracted twice more with ethyl acetate and the combined organics are washed twice with saturated aqueous NaHCO$_3$ and once with brine. The organics are collected, dried over Na$_2$SO$_4$, filtered, and the solvent is removed in vacuo to give I-4.1 (285 mg); m/z 313 [M+H].

Synthesis of 2-Chloro-5-{1-[5-(1H-pyrazol-4-yl)-1,2,4-oxadiazol-3-yl]-cyclobutyl}-pyridine (Intermediate I-4.2)

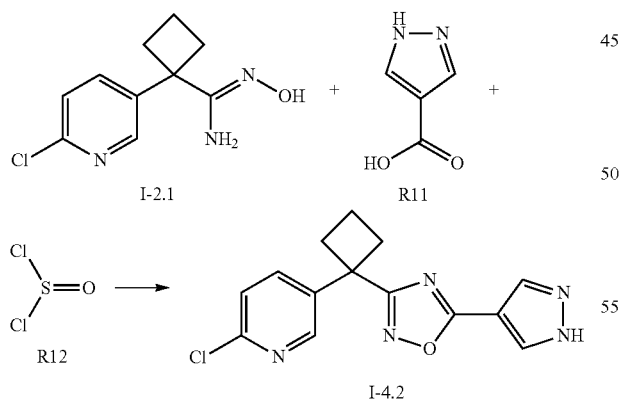

R11 (156 mg, 1.40 mmol) is treated with pyridine (10.0 mL) and R12 (116 μL, 1.60 mmol) and the resulting mixture is stirred for 30 minutes. I-2.1 (300 mg, 1.33 mmol) is then added and the reaction is stirred at 110° C. for 18 hours. The resulting mixture is cooled to room temperature and the solvent is removed in vacuo. The residue is partitioned between CH$_2$Cl$_2$ and saturated aqueous NaHCO$_3$ and the phases are separated. The organic phase is dried over Na$_2$SO$_4$, filtered, and the solvent is removed in vacuo to give I-4.2 (187 mg); m/z 301.9 [M+H].

Synthesis of 2-(4-{3-[1-(6-chloro-pyridin-3-yl)-cyclobutyl]-1,2,4-oxadiazol-5-yl}-pyrazol-1-yl)-N-methyl-acetamide (Intermediate I-4.3)

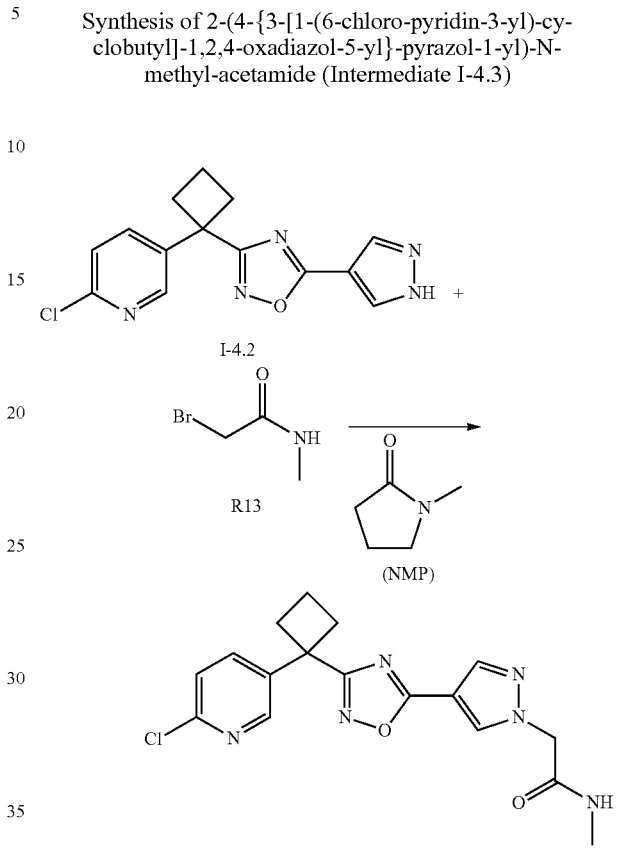

I-4.2 (23 wt % with NMP, 691 mg, 0.527 mmol) is treated with DMF (4.0 mL), R13 (84.1 mg, 0.553 mmol), and K$_2$CO$_3$ (109 mg, 0.790 mmol) and the reaction is heated at 80° C. for 17 hours at which time R13 (8 mg, 0.0.026 mmol) and K$_2$CO$_3$ (3.6 mg, 0.026 mmol) are again added and the reaction is heated at 80° C. for 16 hours. The solvent is removed in vacuo and the residue is partitioned between water and ethyl acetate. The layers are separated and the aqueous is again extracted with ethyl acetate. The combined organic phases are washed with brine and the solvent is removed in vacuo to give I-4.3 (195 mg); m/z 373.3 [M+H].

Synthesis of (4-{3-[1-(6-chloro-pyridin-3-yl)-cyclobutyl]-1,2,4-oxadiazol-5-yl}-pyrazol-1-yl)-acetic acid ethyl ester (Intermediate I-4.4)

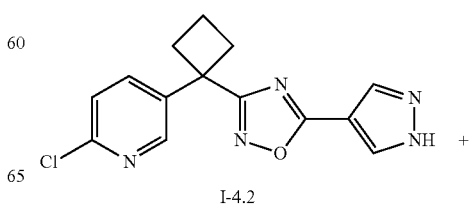

-continued

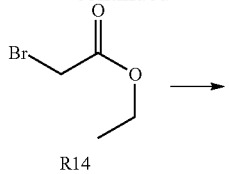

R14

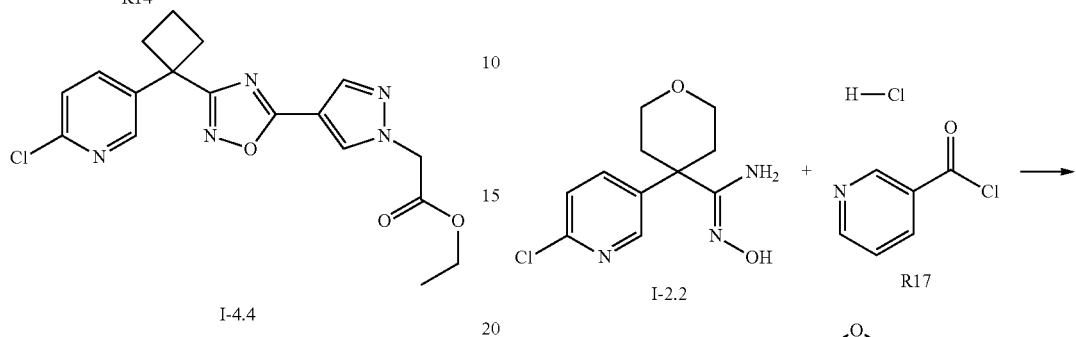

I-4.4

I-4.4 is prepared according to the method for I-4.3 using R15 in place of R13 to give I-4.4 (259 mg); m/z 388 [M+H].

Synthesis of 2-(4-{3-[1-(6-chloro-pyridin-3-yl)-cyclobutyl]-1,2,4-oxadiazol-5-yl}-pyrazol-1-yl)-N,N-dimethyl-acetamide (Intermediate I-4.5)

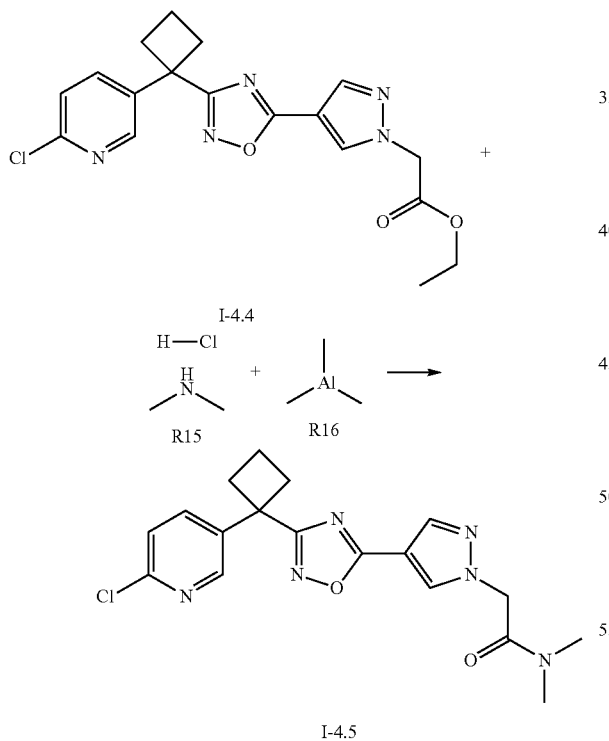

R15 (164 mg, 2.00 mmol) is treated with toluene (6 mL) and R16 (2M in toluene, 0.280 mL, 2.00 mmol) and the resulting mixture is stirred for 30 minutes. I-4.4 (259 mg, 0.669 mmol) is then added and the mixture is stirred at 100° C. for 2 hours. The reaction is cooled to room temperature and water is added. The layers are separated and the organics are dried with $Na_2SO_4$, filtered, and the solvent removed in vacuo to provide I-4.5 (200 mg); m/z 387 [M+H].

Synthesis of 2-chloro-5-[4-(5-pyridin-3-yl-1,2,4-oxadiazol-3-yl)-tetrahydro-pyran-4-yl]-pyridine (Intermediate I-4.6)

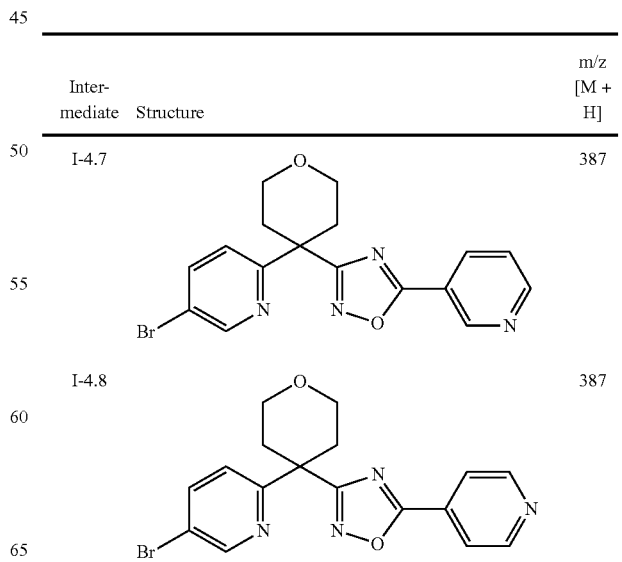

I-2.2 (500 mg, 1.96 mmol) is treated with pyridine (5 mL), and R17 (522 mg, 2.93 mmol) and heated at 110° C. for 1 hour. The reaction is cooled to room temperature and the solvent is removed in vacuo. The residue is diluted with ethyl acetate and saturated aqueous $NaHCO_3$ and the phases are separated. The aqueous phase is extracted twice more with ethyl acetate and the combined organics are washed with saturated $NaHCO_3$ twice, then brine. The organic phase is collected, dried with $Na_2SO_4$, filtered, and the solvent removed in vacuo to provide I-4.6 (525 mg); m/z 343 [M+H].

The following intermediate are synthesized in a similar fashion from the appropriate reagents:

| Intermediate | Structure | m/z [M + H] |
| --- | --- | --- |
| I-4.7 | 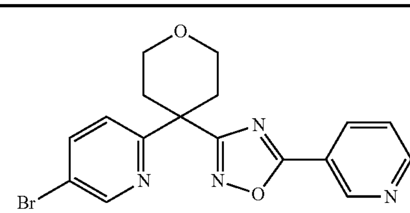 | 387 |
| I-4.8 | 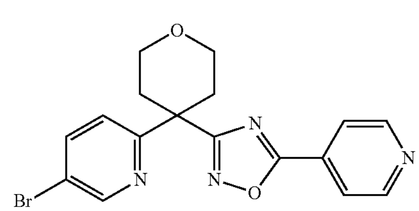 [SMILES: Brc1ccc(C2(c3noc(-c4ccncc4)n3)CCOCC2)nc1] | 387 |

| Intermediate | Structure | m/z [M+H] |
|---|---|---|
| I-4.9 | 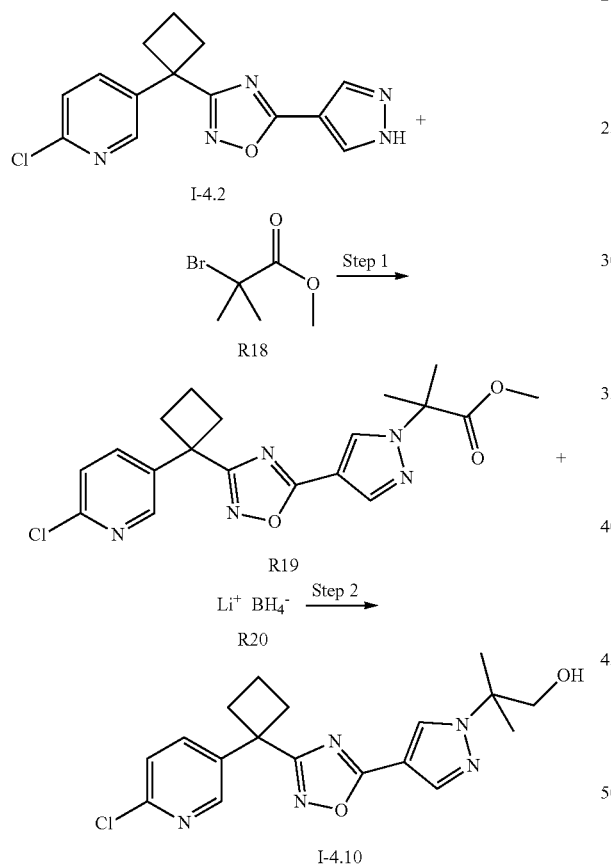 | 405 |

Synthesis of 2-(4-{3-[1-(6-chloro-pyridin-3-yl)-cyclobutyl]-1,2,4-oxadiazol-5-yl}-pyrazol-1-yl)-2-methyl-propan-1-ol (Intermediate I-4.10)

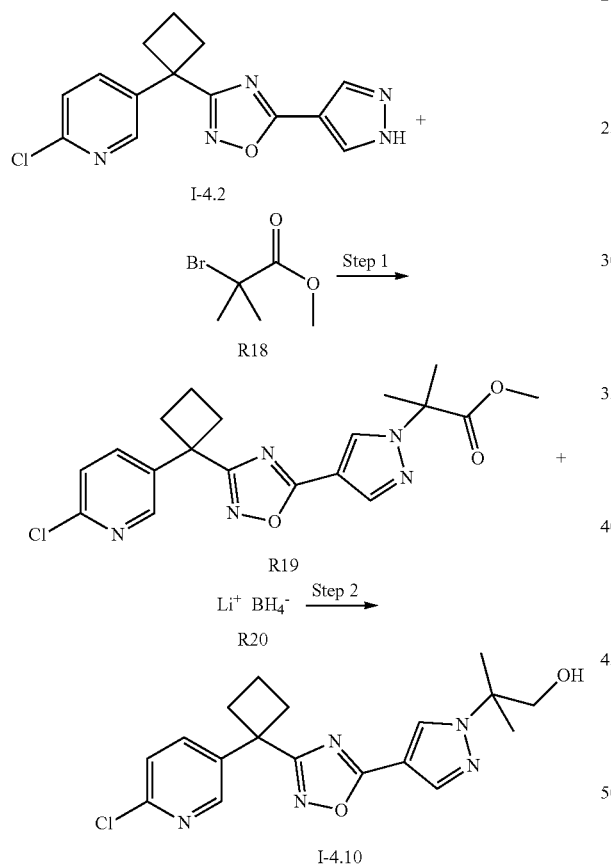

Step 1: Synthesis of 2-(4-{3-[1-(6-chloro-pyridin-3-yl)-cyclobutyl]-1,2,4-oxadiazol-5-yl}-pyrazol-1-yl)-2-methyl-propionic acid methyl ester (R19)

R19 is prepared according to the method for I-4.6 using R18 in place of R13; m/z 402 [M+H].

Step 2: Synthesis of 2-(4-{3-[1-(6-chloro-pyridin-3-yl)-cyclobutyl]-1,2,4-oxadiazol-5-yl}-pyrazol-1-yl)-2-methyl-propan-1-ol (I-4.10)

R19 (83.1 mg, 0.207 mmol) is treated with THF (2.0 mL) and cooled to 0° C. R20 (9.0 mg, 0.41 mmol) is then added and the reaction is warmed to room temperature and stirred for 2 hours at which time the solvent is removed in vacuo. The residue is partitioned between saturated aqueous NaHCO$_3$ and ethyl acetate and the organic layer is collected, dried with Na$_2$SO$_4$, filtered, and the solvent removed in vacuo to afford I-4.10 (78 mg); m/z 374 [M+H].

Synthesis of 2-(4-{3-[1-(6-chloro-pyridin-3-yl)-cyclobutyl]-1,2,4-oxadiazol-5-yl}-pyrazol-1-yl)-2-methyl-propan-1-ol (Intermediate I-4.11)

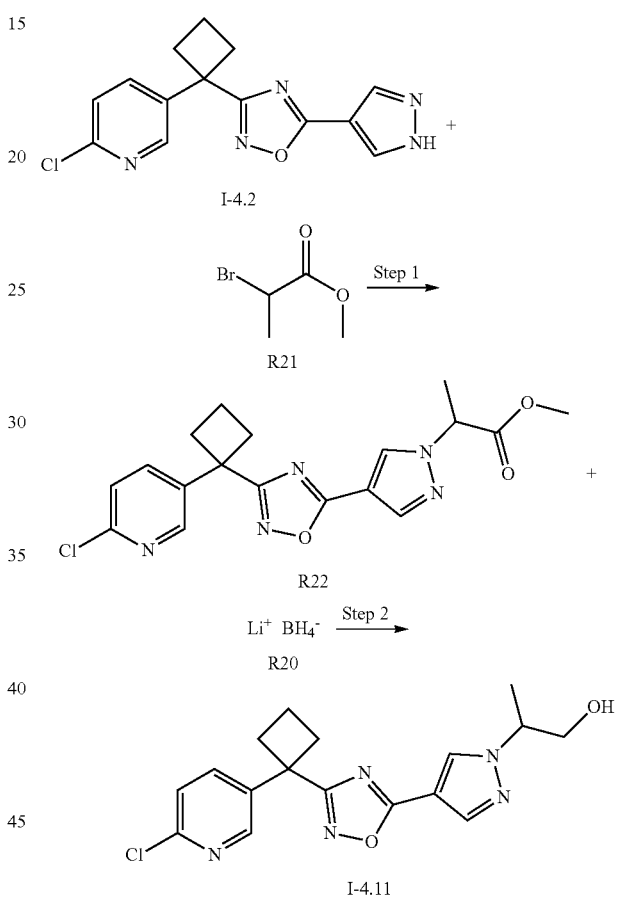

I-4.11 is prepared according to the procedure for I-4.10 using the appropriate reagents; m/z 360 [M+H].

Synthesis of (5-{3-[1-(6-Chloro-pyridin-3-yl)-cyclobutyl]-1,2,4-oxadiazol-5-yl}-pyrazin-2-yl)-(2-methoxy-ethyl)-amine (Intermediate I-4.12)

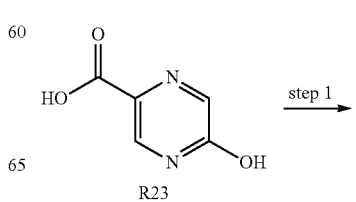

93

-continued

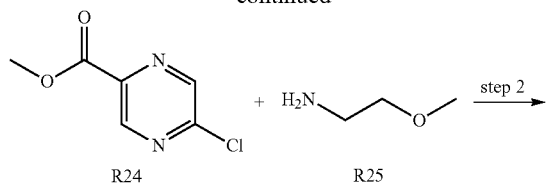

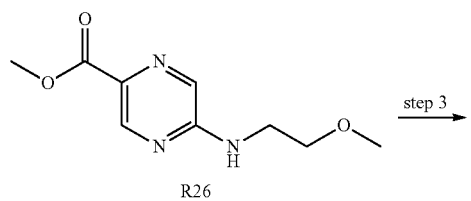

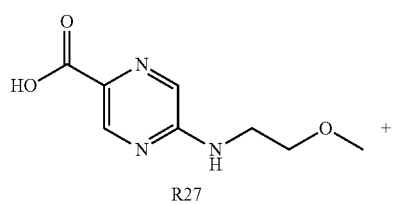

94

Step 1: synthesis of 5-chloro-pyrazine-2-carboxylic acid methyl ester (R24)

R23 (2.00 g, 14.3 mmol) is treated with R12 (10.0 mL) and to the resulting mixture is added DMF (0.1 mL) dropwise. The reaction mixture is then heated at reflux for 4 hours. The solvent is removed in vacuo and the residue is treated with methanol (10.0 mL) and pyridine (1.39 mL, 17.1 mmol) and the resulting mixture is stirred overnight. The solvent is removed in vacuo and the residue is purified by flash chromatography (SiO$_2$, 20% ethyl acetate/cyclohexane) to give R24 (1.12 g); m/z 173 [M+H].

Step 2: synthesis of 5-(2-methoxy-ethylamino)-pyrazine-2-carboxylic acid methyl ester (R26)

R24 (200 mg, 1.16 mmol) is treated with dimethyl sulfoxide (DMSO) (4.00 mL) and R25 (151 mL, 1.74 mmol) and the resulting mixture is heated at 80° C. for 2 hours. The mixture is diluted with water (5 mL) and acidified to approximately pH 2 with 2M aqueous HCl. The resulting mixture is extracted 3 times with ethyl acetate and the combined organic phases are washed with saturated brine, collected, dried over MgSO$_4$, filtered, and the solvent is removed in vacuo. The crude residue is purified by flash chromatography (SiO$_2$, 90% ethyl acetate/cyclohexane) to give R26 (143 mg); m/z 212 [M+H].

Step 3: synthesis of 5-(2-methoxy-ethylamino)-pyrazine-2-carboxylic acid (R22)

R26 (143 mg, 0.701 mmol) is treated with THF (1.50 mL), water (1.50 mL) and lithium hydroxide (25.2 mg, 1.05 mmol) and the resulting mixture is stirred at room temperature overnight. The solvent is removed in vacuo to give crude R27 (138 mg); m/z 196 [M+H].

Step 4: synthesis of (5-{3-[1-(6-Chloro-pyridin-3-yl)-cyclobutyl]-1,2,4-oxadiazol-5-yl}-pyrazin-2-yl)-(2-methoxy-ethyl)-amine (Intermediate I-4.12)

R27 (138 mg, 0.700 mmol) is treated with DMF (7.00 mL), HATU (266 mg, 0.700 mmol), and triethylamine (TEA) (0.10 mL, 0.700 mmol) and the resulting mixture is stirred for 5 minutes at which time I-2.1 (158 mg, 0.700 mmol) is added and the reaction is stirred at 90° C. overnight. The solvent is removed in vacuo and the resulting residue is partitioned between ethyl acetate and saturated aqueous NaHCO$_3$ and the layers are separated. The aqueous phase is extracted twice more with ethyl acetate and the combined organics are washed with water, brine, collected, dried over MgSO$_4$, filtered, and the solvent is removed in vacuo. The crude residue Synthesis of 2-Chloro-5-{1-[5-(1-oxetan-3-yl-1H-pyrazol-4-yl)-[1,2,4]oxadiazol-3-yl]-cyclobutyl}-pyridine (Intermediate 4.13)

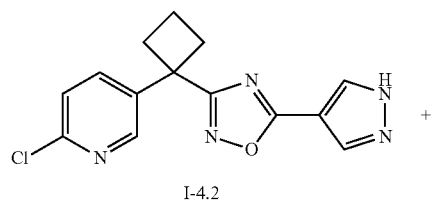

I-4.2

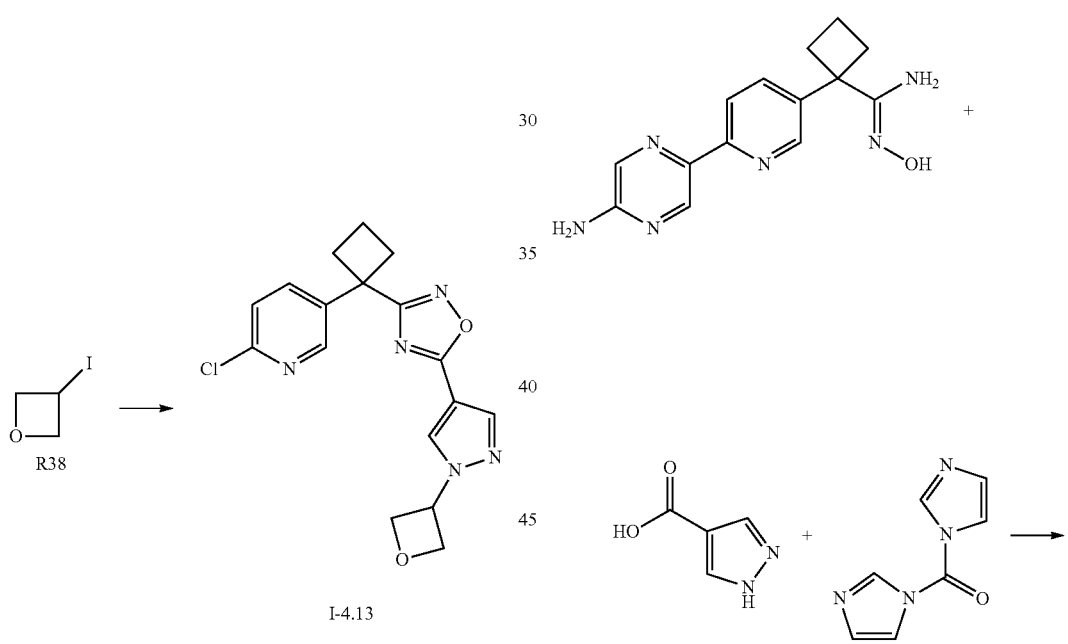

I-4.13

I-4.13 is prepared according to the method for I-4.3 using R38 in place of R13 to afford the title compound (500 mg).

Synthesis of 1-(4-{3-[1-(6-Chloro-pyridin-3-yl)-cyclobutyl]-[1,2,4]oxadiazol-5-yl}-pyrazol-1-yl)-2-methyl-propan-2-ol (Intermediate I-4.14)

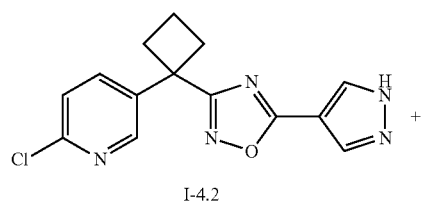

I-4.2

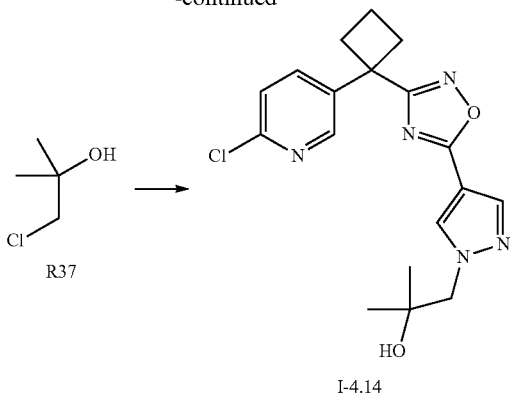

I-4.14

I-4.14 is prepared according to the method for I-4.3 using R37 in place of R13 to afford the title compound (600 mg).

Synthesis of 5-(5-{1-[5-(1H-Pyrazol-4-yl)-[1,2,4]oxadiazol-3-yl]-cyclobutyl}-pyridin-2-yl)-pyrazin-2-ylamine (Intermediate I-5.1)

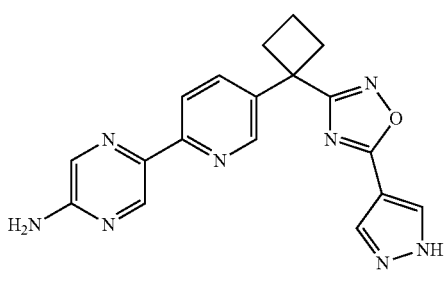

I-5.1

I-5.1 is prepared according to method 10 to afford the title compound (470 mg).

The following intermediates are synthesized in a similar fashion from the appropriate reagents:

| Intermediate | Structure | m/z [M + H] |
|---|---|---|
| I-5.2 | 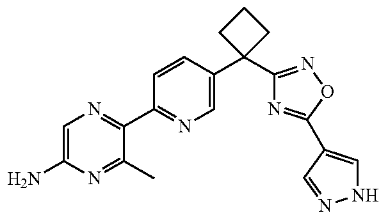 [SMILES: Cc1nc(N)cnc1-c1ccc(C2(c3noc(-c4cn[nH]c4)n3)CCC2)cn1] | 375.2 |
| I-5.3 | 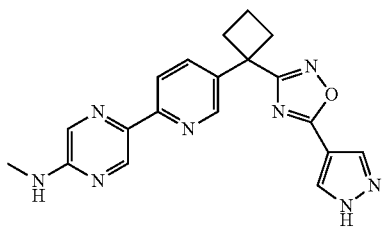 [SMILES: CNc1cnc(-c2ccc(C3(c4noc(-c5cn[nH]c5)n4)CCC3)cn2)cn1] | 374.9 |

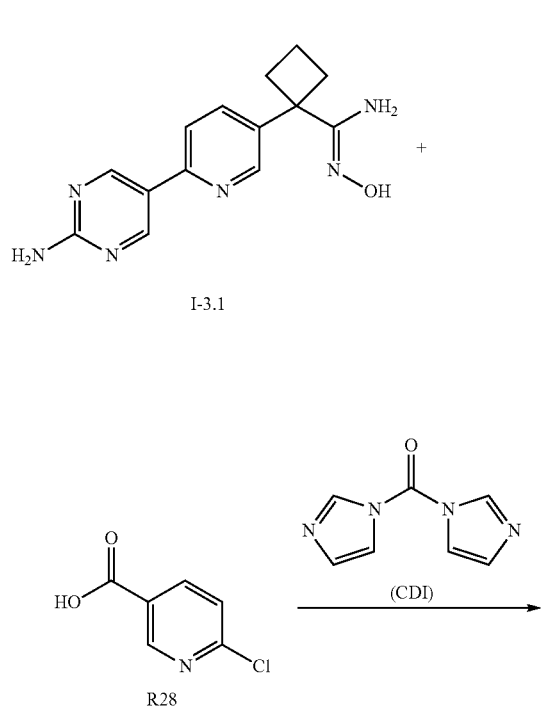

Method 1

Synthesis of 5-(5-{1-[5-(6-chloropyridin-3-yl)-1,2,4-oxadiazol-3-yl]-cyclobutyl}pyridin-2-yl)-pyrimidin-2-amine (Example 99, Table 1)

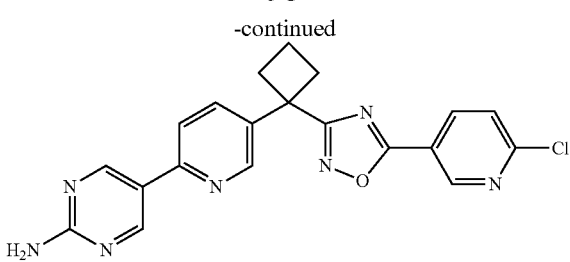

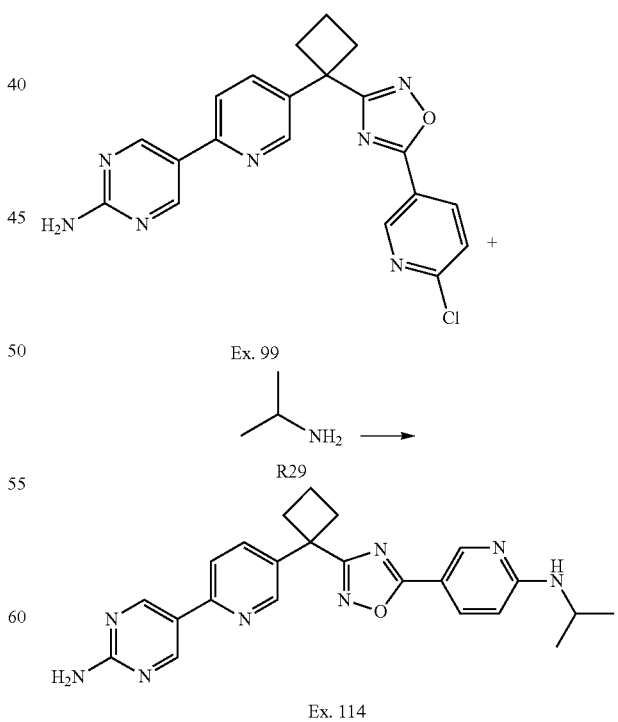

R28 (5.41 g, 19.0 mmol) is treated with THF (25 mL) and CDI (3.09 g, 19.0 mmol) and heated at 50° C. for 20 minutes at which time I-3.1 is added and the reaction is refluxed overnight. The reaction is cooled to room temperature and the resulting precipitate is collected by filtration and recrystallized from acetonitrile to afford the title compound (5.68 g); m/z 406.2 [M+H].

Examples in table 1 listed with method 1 are synthesized in a similar fashion. Example 32 uses NMP as solvent and the second stage is heated at 100° C. overnight. Example 57 uses DMF as solvent and is heated at 100° C. for 3 hours. Examples 81 and 83 use NMP as solvent, the first stage is run at room temperature, and the second stage is at 70° C. for 30 minutes. Examples 88 and 94 use NMP as solvent and the second stage is run at 80° C. for 2 hours. Example 120 uses NMP as the solvent and the second stage is run at 130° C. for 2 hours. Example 132 uses dimethylacetamide as solvent and is heated at 140° C. for 55 minutes.

Method 2

Synthesis of 5-[5-(1-{5-[6-(propan-2-ylamino)pyridin-3-yl]-1,2,4-oxadiazol-3-yl}-cyclobutyl)pyridin-2-yl]pyrimidin-2-amine (Example 114, Table 1)

Example 99 (50 mg, 0.123 mmol) is treated with THF (2 mL) and R29 (0.5 mL) and the resulting mixture is heated at 100° C. for 2 hours. The solvent is removed in vacuo and the resulting residue is suspended in water. The precipitate is collected by filtration and recrystallized from acetonitrile/methanol to afford the title compound (50 mg); m/z 429.6 [M+H].

Examples in table 1 listed with method 2 are synthesized in a similar fashion. Examples 43, 45, and 47-49 are run at 60° C. overnight; example 125 is run in NMP at 100° C. for 3 days with 3 equivalents of TEA added; example 21 is run in THF at 100° C. for 3 days; example 111 is run at 100° C. for 24 hours; examples 50 and 52 are run in NMP at 100° C. overnight; examples 34 and 116-118 are run neat at 80° C. for 2 hours; example 112 is run neat at 100° C. for 2 days; example 13 is run in NMP at 100° C. for 6 hours with 3 equivalents of TEA added; example 51 is run in NMP at 100° C. overnight with 3 equivalents of TEA added; example 2 is run in NMP at 100° C. for 6 hours.

Method 3

Synthesis of 3-{4-[5-(3-{1-[6-(2-aminopyrimidin-5-yl)pyridin-3-yl]cyclobutyl}-1,2,4-oxadiazol-5-yl)pyridin-2-yl]piperazin-1-yl}propanoic acid (Example 53, Table 1)

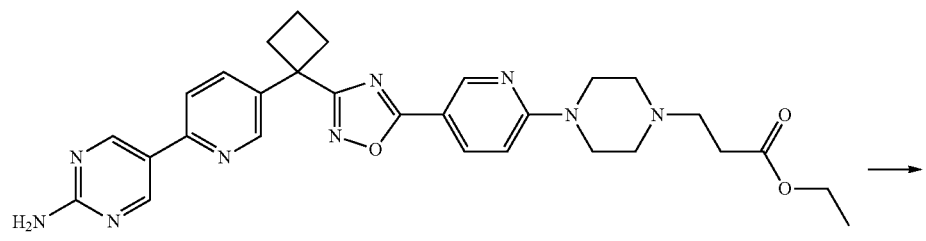

Ex. 47

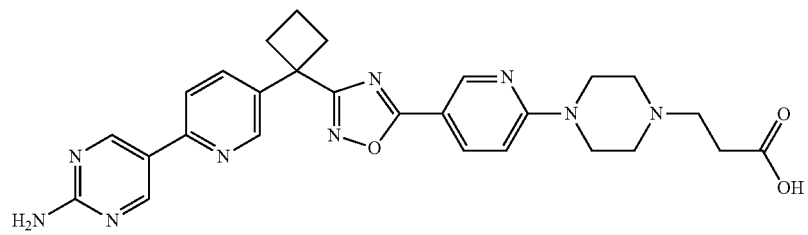

Ex. 53

Example 47 (400 mg, 0.720 mmol) is treated with THF (2 mL), methanol (2 mL) and 5M aqueous NaOH (2 mL) and stirred overnight. The solvent is removed in vacuo and the resulting residue is acidified with concentrated aqueous HCl and the solvents are again removed in vacuo. The residue is purified by reverse-phase preparative HPLC to afford the title compound (162 mg); m/z 528.2 [M+H].

Method 4

Synthesis of methyl (2R)-1-[5-(3-{1-[6-(2-aminopyrimidin-5-yl)pyridin-3-yl]cyclobutyl}-1,2,4-oxadiazol-5-yl)pyridin-2-yl]piperazine-2-carboxylate (Example 38, Table 1)

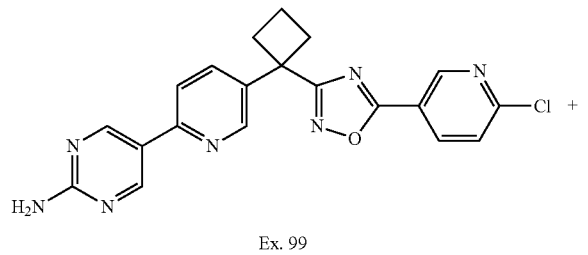

Ex. 99

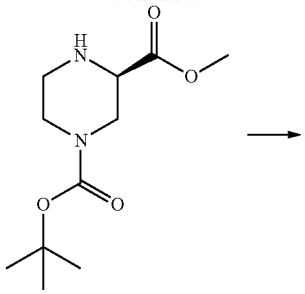

R30

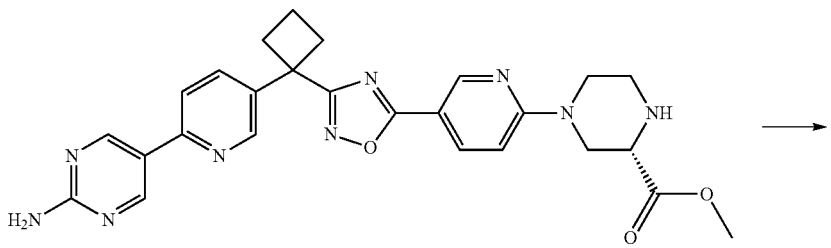

Ex. 38

Example 99 (120 mg, 0.296 mmol) is treated with R30 (361 mg, 1.48 mmol) and NMP (0.150 mL) and heated at 80° C. for 48 hours. The resulting mixture is cooled to room temperature and treated with 4N HCl in 1,4-dioxane (1.50 mL) and stirred for 1.5 hours. The resulting mixture is purified by reverse-phase preparative HPLC (C-18 silica, 10-30% acetonitrile/water/0.1% trifluoroacetic acid over 20 minutes) to afford the title compound as a trifluoroacetic acid salt (110 mg), m/z 514.8 [M+H].

Examples in table 1 listed with method 4 are synthesized in a similar fashion.

Method 5

Synthesis of (2S)-4-[5-(3-{1-[6-(2-aminopyrimidin-5-yl)pyridin-3-yl]cyclobutyl}-1,2,4-oxadiazol-5-yl)pyridin-2-yl]piperazine-2-carboxylic acid (Example 41, Table 1)

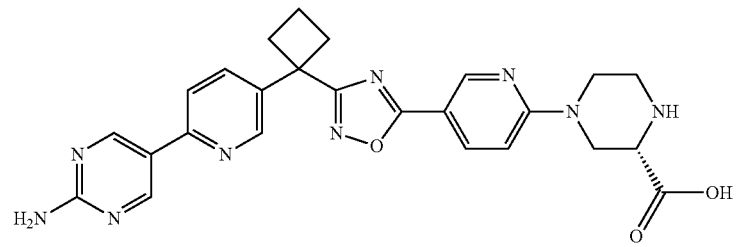

Ex. 39

Ex. 41

Example 39 (135 mg, 0.215 mmol) is treated with methanol (1.00 mL) and 5M aqueous NaOH (1.00 mL) and the resulting mixture is heated at 70° C. for 2 hours. The mixture is then cooled to room temperature and filtered to afford the title compound (35 mg); m/z 500.7 [M+H].

Examples in table 1 listed with method 5 are synthesized in a similar fashion. Example 16 used sodium methoxide in place of NaOH with water as a co-solvent.

Method 6

Synthesis of methyl 1-[5-(3-{1-[6-(2-aminopyrimidin-5-yl)pyridin-3-yl]cyclobutyl}-1,2,4-oxadiazol-5-yl)pyridin-2-yl]-L-prolinate (Example 36, Table 1) and 1-[5-(3-{1-[6-(2-aminopyrimidin-5-yl)pyridin-3-yl]cyclobutyl}-1,2,4-oxadiazol-5-yl)pyridin-2-yl]-L-proline (Example 35, Table 1)

Example 99 (100 mg, 0.246 mmol) is treated with R31 (204 mg, 1.23 mmol), NMP (0.5 mL), and TEA (0.5 mL) and the resulting mixture is heated at 80° C. for 2 hours. The crude mixture containing both title products is directly purified by reverse-phase preparative HPLC(C-18 silica, 10-50% acetonitrile/water/0.1% trifluoroacetic acid over 20 minutes) to afford the title compounds example 35 (24 mg), m/z 499.8 [M+H] and example 36 (24 mg), m/z 512.8 [M+H].

Method 7

Synthesis of 5-[5-(1-{5-[6-(1H-imidazol-1-yl)pyridin-3-yl]-1,2,4-oxadiazol-3-yl}cyclobutyl)pyridin-2-yl]pyrimidin-2-amine (Example 31, Table 1)

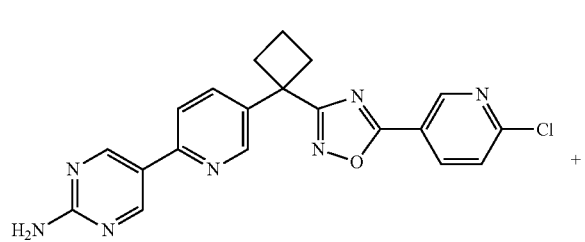

Ex. 99

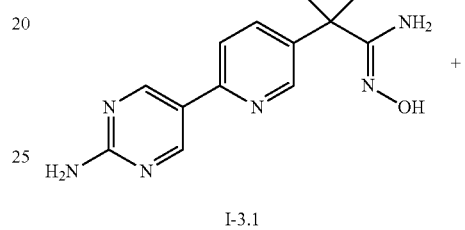

I-3.1

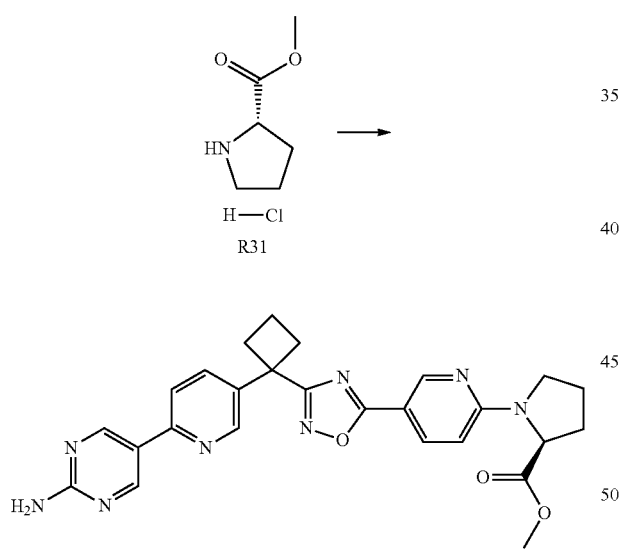

Ex. 36

+

Ex. 35

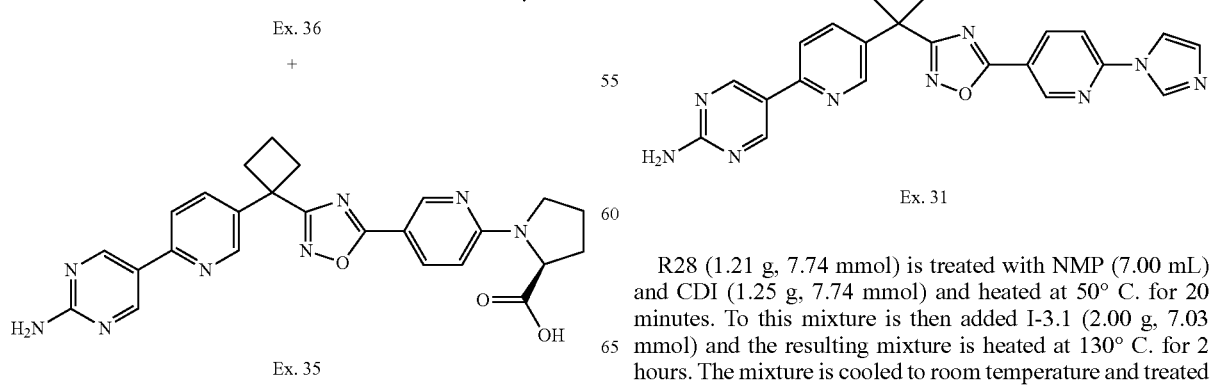

Ex. 31

R28 (1.21 g, 7.74 mmol) is treated with NMP (7.00 mL) and CDI (1.25 g, 7.74 mmol) and heated at 50° C. for 20 minutes. To this mixture is then added I-3.1 (2.00 g, 7.03 mmol) and the resulting mixture is heated at 130° C. for 2 hours. The mixture is cooled to room temperature and treated with water (70 mL) and the solid is collected by filtration.

This crude mixture is purified by flash chromatography (SiO₂, 0-10% methanol/CH₂Cl₂) to afford the title compound (245 mg); m/z 438.6 [M+H].

Method 8

Synthesis of 5-[5-(1-{5-[5-(4-methylpiperazin-1-yl)pyrazin-2-yl]-1,2,4-oxadiazol-3-yl}cyclobutyl)pyridin-2-yl]pyrimidin-2-amine (Example 61, Table 1)

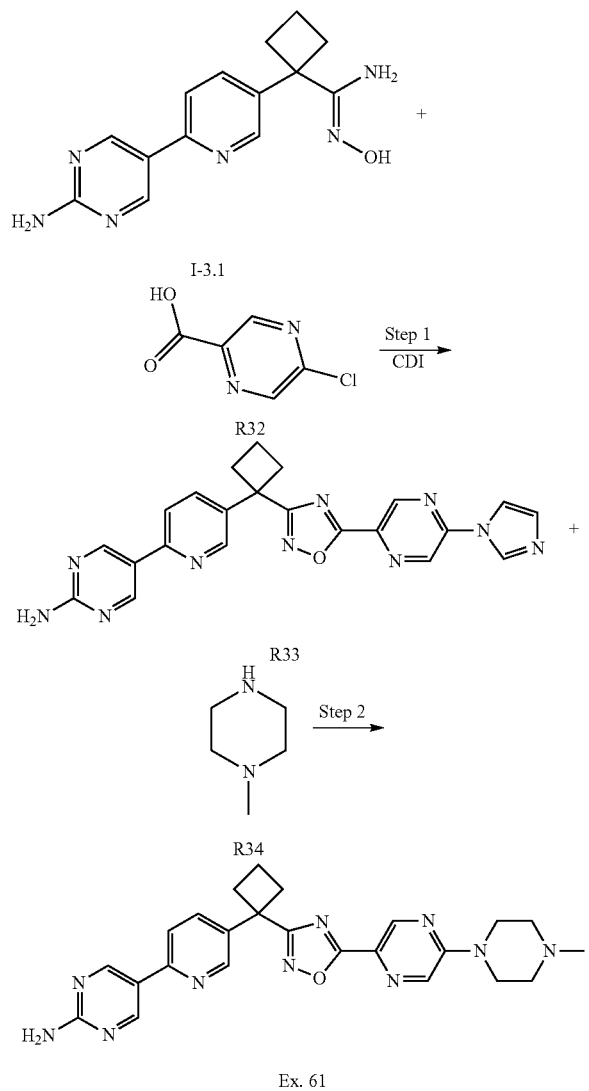

Step 1: synthesis of 5-(5-{1-[5-(5-imidazol-1-yl-pyrazin-2-yl)-1,2,4-oxadiazol-3-yl]-cyclobutyl}-pyridin-2-yl)-pyrimidin-2-ylamine (R33)

R32 (300 mg, 1.89 mmol) is treated with DMF (5.00 mL) and CDI (306 mg, 1.89 mmol) and stirred at 50° C. for 20 minutes. To this mixture is added I-3.1 (488 mg, 1.72 mmol) and the resulting mixture is heated at 110° C. for 2 hours. The solvent is removed in vacuo and the resulting residue is partitioned between ethyl acetate and saturated aqueous NaHCO₃. The phases are separated and the resulting precipitate in the aqueous phase is collected by filtration. The organic phase is dried over Na₂SO₄, filtered, and the solvent is removed in vacuo. The collected solids from the aqueous layer and the residue from the organics are combined to afford R33 (384 mg); m/z 439.0 [M+H].

Step 2: synthesis of 5-[5-(1-{5-[5-(4-methylpiperazin-1-yl)pyrazin-2-yl]-1,2,4-oxadiazol-3-yl}cyclobutyl)pyridin-2-yl]pyrimidin-2-amine (example 61)

R33 (284 mg, 0.389 mmol) is treated with DMSO (1.00 mL), K₂CO₃ (53.7 mg, 0.389 mmol), and R34 (64.7 µL, 0.583 mmol) and the mixture is heated at 80° C. for 1 hour. The mixture is cooled to room temperature and diluted with water (3 mL) and rendered basic (pH>9) by addition of 2M aqueous NaOH. The resulting mixture is extracted 3 times with CH₂Cl₂ and the combined organic phases are washed with brine, dried over Na₂SO₄, filtered, and the solvent is removed in vacuo. This crude mixture is purified by flash chromatography (SiO₂, 0-10% methanol/CH₂Cl₂) to afford the title compound (90.8 mg); m/z 470.2 [M+H].

Method 9

Synthesis of 5-[5-(1-{5-[6-(methylsulfonyl)pyridin-3-yl]-1,2,4-oxadiazol-3-yl}-cyclobutyl)pyridin-2-yl]pyrimidin-2-amine Example 119, Table 1)

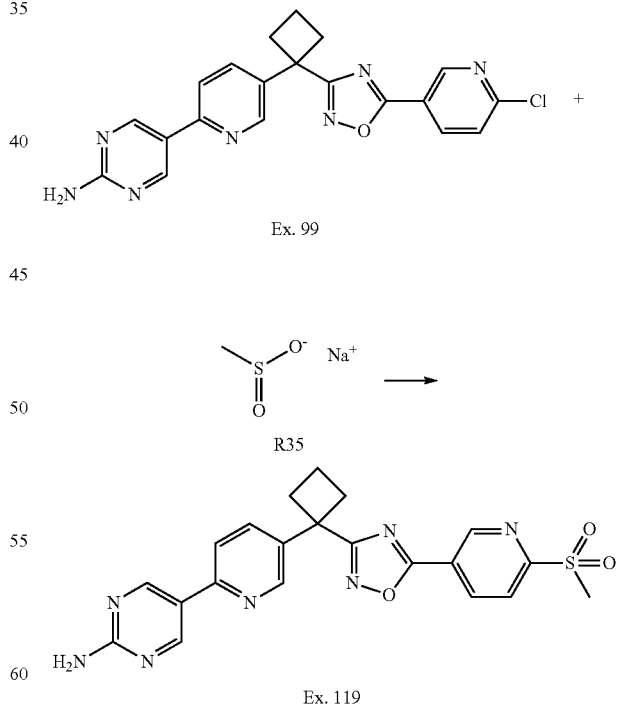

Example 99 (50.0 mg, 0.123 mmol) is treated with NMP (0.75 mL) and R35 (148 mg) and the resulting mixture is heated at 80° C. for 2 hours. The mixture is cooled to room temperature and filtered. The filtrate is purified by reverse-phase HPLC (15-65% acetonitrile/water/0.1% trifluoroacetic acid) to afford the title compound (23.0 mg); m/z 450.2 [M+H].

Method 10

Synthesis of 5-(5-{1-[5-(1-methyl-1H-pyrazol-4-yl)-1,2,4-oxadiazol-3-yl]cyclobutyl}pyridin-2-yl)pyrimidin-2-amine (Example 102, Table 1)

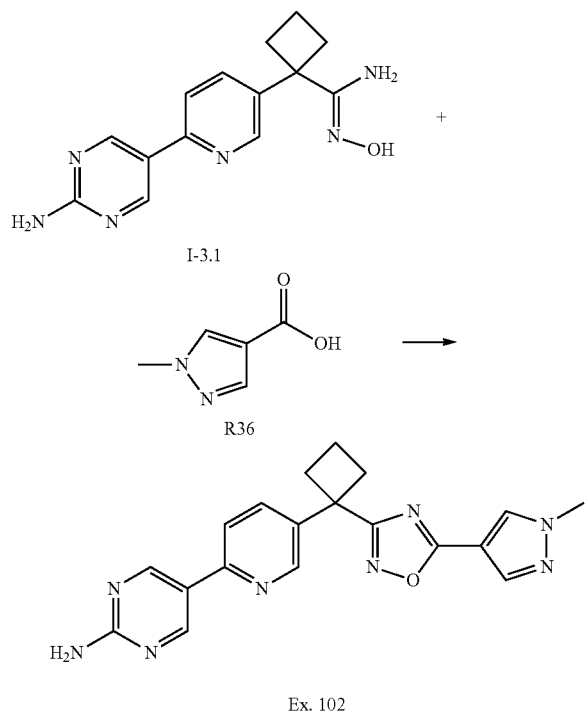

R36 (53.2 mg, 0.422 mmol) is treated with NMP (1.50 mL), diisopropylethylamine (DIEA) (0.08 mL, 0.42 mmol) and HATU (161 mg, 0.422 mmol) and stirred for 15 minutes. To this mixture is added I-3.1 (100 mg, 0.352 mmol) and the resulting mixture is heated at 100° C. for 4 hours. The reaction mixture is directly purified by reverse-phase HPLC (10 to 35% acetonitrile/water/0.1% trifluoroacetic acid) to afford the title compound (46.0 mg); m/z 375.2 [M+H].

Examples in table 1 listed with method 10 are synthesized in a similar fashion. Example 1 is heated at 130° C. for 6 hours. Examples 4, 123-124, and 127 use TEA in place of DIEA and are heated at 100° C. for 16 hours. Examples 5-7, 11, 17, 19, 93, 96-98, 101, and 129-130 use TEA in place of DIEA and are heated at 80° C. overnight. Example 14 uses TEA in place of DIEA and is heated at 100° C. for 1 hour. Example 20 uses TEA in place of DIEA and is heated at 100° C. for 2 hours. Examples 23-26 use TEA in place in DMF and are heated at 110° C. for 2 hours. Example 27 uses TEA in place of DIEA in DMF and is heated at 80° C. overnight. Example 28 uses TEA in place of DIEA and is heated at 110° C. overnight. Example 74 uses no base and is heated at 80° C. for 2 hours. Example 86 uses TEA in place of DIEA in DMF and is heated at 120° C. for 1 hour. Examples 91 and 92 use TEA in place of DIEA in DMF and is heated at 80° C. for 2 hours. Example 100 and 109 use TEA in place of DIEA and is heated at 80° C. for 2 hours. Example 104 is heated at 130° C. for 2 hours. Examples 75, 77-80, and 131 use TEA in place of DIEA in DMF and are stirred at room temperature overnight prior to heating at 110° C. for 4 hours. Example 133 uses dimethylacetamide as solvent and is heated at 100° C. for 1.5 hours. Example 134 uses dioxane as solvent and is heated at 90° C. for 16 hours, then 100° C. for 8 hours. Example 135 uses dimethylacetamide as solvent and is heated first at 100° C. for 1.5 hours, then 45° C. for 16 hours, then 90° C. for 5 hours.

Method 11

Synthesis of 1-[4-(3-{1-[6-(2-aminopyrimidin-5-yl)pyridin-3-yl]cyclobutyl}-1,2,4-oxadiazol-5-yl)-1H-pyrazol-1-yl]-2-methylpropan-2-ol (Example 54, Table 1)

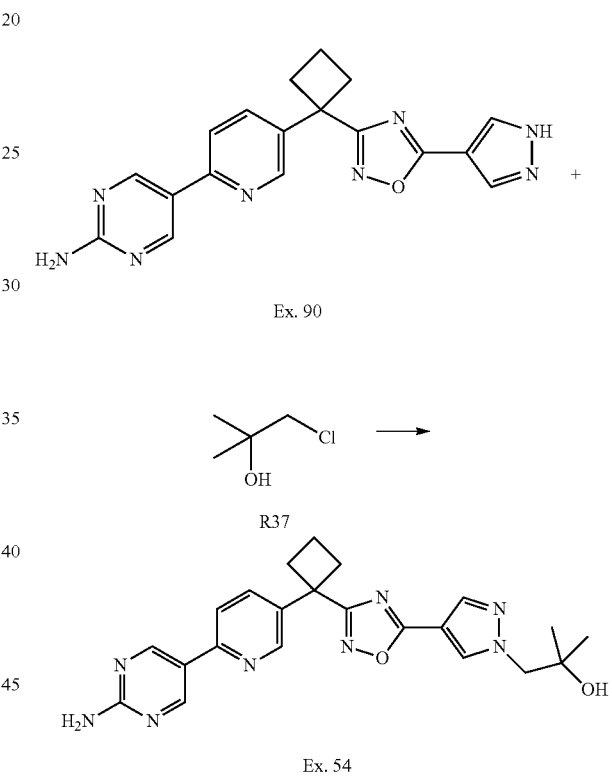

Example 90 (5.00 g, 13.9 mmol) is treated with R37 (4.00 g, 36.8 mmol), K$_2$CO$_3$ (2.88 g, 20.8 mmol) and DMF (50 mL) and the resulting mixture is heated at 80° C. for 60 hours. The reaction mixture is diluted with ethyl acetate and washed with water and brine. The organic phase is dried over Na$_2$SO$_4$, filtered, and the solvent is removed in vacuo. This crude mixture is purified by flash chromatography (SiO$_2$, 0-5% 2M NH$_3$ in methanol/CH$_2$Cl$_2$) to afford the title compound (2.58 g); m/z 433.4 [M+H].

Examples in table 1 listed with method 11 are synthesized in a similar fashion. Examples 63-64, 67-68, and 171 are stirred at room temperature for 18 hours. Example 69 is stirred first at room temperature for 18 hours, then 65° C. for 18 hours. Example 70 is stirred at room temperature for 4 hours. Examples 170 and 173 are stirred at room temperature for 18 hours. Example 172 is stirred at 75° C. for 18 hours.

Method 12

Synthesis of 5-[5-(1-{5-[1-(oxetan-3-yl)-1H-pyrazol-4-yl]-1,2,4-oxadiazol-3-yl}-cyclobutyl)pyridin-2-yl]pyrimidin-2-amine (Example 55, Table 1)

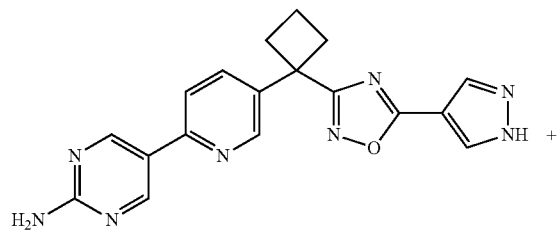

Ex. 90

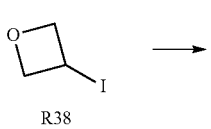

R38

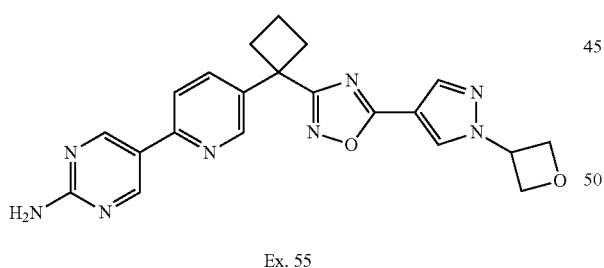

Ex. 55

Example 90 (500 mg, 1.39 mmol) is treated with R38 (510 mg, 2.77 mmol), K₂CO₃ (383 mg, 2.77 mmol) and DMF (8 mL) and the resulting mixture is heated at 50° C. for 18 hours. A second charge of R38 (510 mg, 2.77 mmol) is then added and the mixture is heated at 80° C. for 18 hours. The reaction mixture is diluted with ethyl acetate and washed with water and brine. The organic phase is dried over Na₂SO₄, filtered, and the solvent is removed in vacuo. The crude mixture is purified by flash chromatography (SiO₂, 0-5% 2M NH₃ in methanol/CH₂Cl₂) to give a residue which is recrystallized from acetonitrile to afford the title compound (265 mg); m/z 417.4 [M+H].

Examples in table 1 listed with method 12 are synthesized in a similar fashion. Example 176 uses a single treatment at 80° C. for 18 hours.

Method 13

Synthesis of 5-(5-{1-[5-(4-methyl-4H-1,2,4-triazol-3-yl)-1,2,4-oxadiazol-3-yl]cyclobutyl}pyridin-2-yl)pyrimidin-2-amine (Example 37, Table 1)

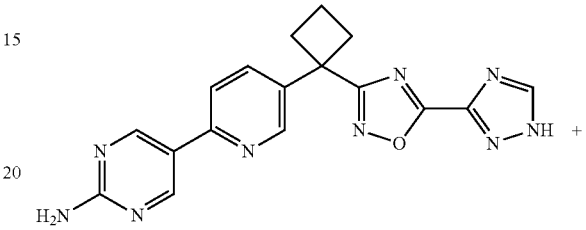

Ex. 120

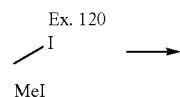

MeI

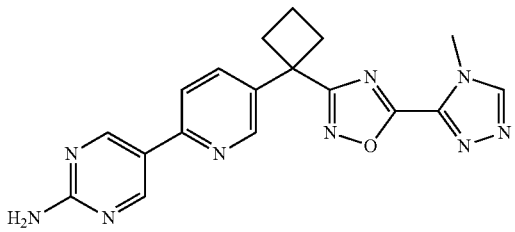

Ex. 37

Example 120 (147 mg, 0.407 mmol) is treated with K₂CO₃ (84.3 mg, 0.610 mmol), DMF (1.0 mL), and MeI (69.3 mg, 0.488 mmol) and the resulting mixture is stirred for 30 minutes. The mixture is purified directly by preparative reverse-phase HPLC (10-35% acetonitrile/water with 0.1% TFA) to afford the title compound (28.0 mg); m/z 376.6 [M+H].

Method 14

Synthesis of 5-{5-[1-(5-{1-[(methylsulfonyl)methyl]-1H-pyrazol-4-yl}-1,2,4-oxadiazol-3-yl)cyclobutyl]pyridin-2-yl}pyrimidin-2-amine (Example 71, Table 1)

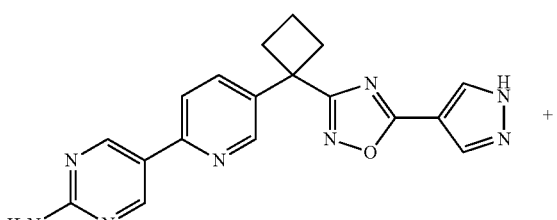

Ex. 90 filtered, and the solvent is removed in vacuo to afford the title compound (6.0 mg); m/z 453.4 [M+H].

Method 15

Synthesis of 5-[5-(1-{5-[1-(difluoromethyl)-1H-pyrazol-4-yl]-1,2,4-oxadiazol-3-yl}cyclobutyl)pyridin-2-yl]pyrimidin-2-amine (Example 66, Table 1)

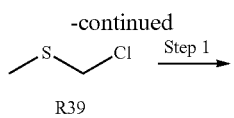

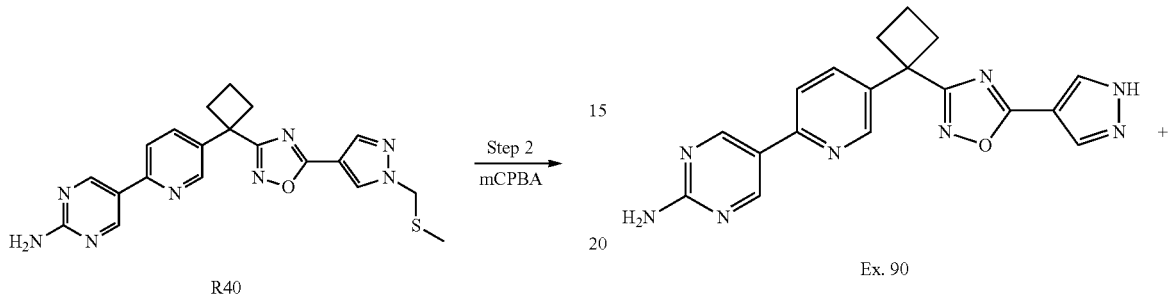

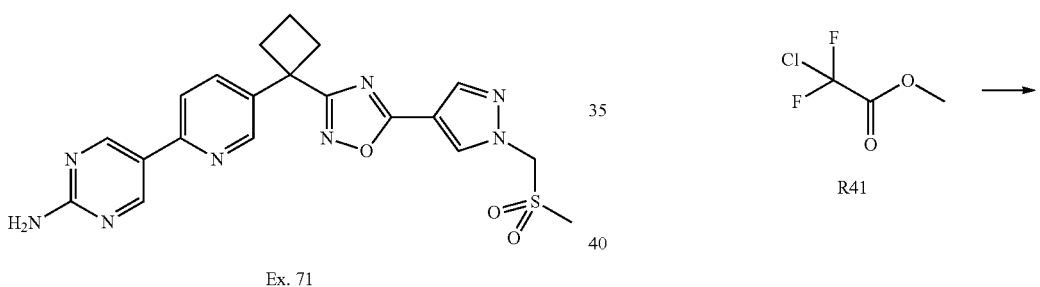

Step 1: synthesis of 5-(5-{1-[5-(1-methylsulfanylmethyl-1H-pyrazol-4-yl)-1,2,4-oxadiazol-3-yl]-cyclobutyl}-pyridin-2-yl)-pyrimidin-2-ylamine (R40)

R40 is synthesized according to method 11 at room temperature for 16 hours.

Step 2: synthesis of 5-{5-[1-(5-{1-[(methylsulfonyl)methyl]-1H-pyrazol-4-yl}-1,2,4-oxadiazol-3-yl)cyclobutyl]pyridin-2-yl}pyrimidin-2-amine (Example 71)

Crude R40 (120 mg, 0.285 mmol) is treated with CH$_2$Cl$_2$ (2.0 mL) and meta-chloroperbenzoic acid (mCPBA) (155 mg, 0.628 mmol) and stirred for 3 hours. The resulting mixture is diluted with saturated aqueous NaHCO$_3$ and CH$_2$Cl$_2$ and the phases are separated. The organic phase is dried over MgSO$_4$, filtered, and the solvent is removed in vacuo. The crude residue is purified by preparative reverse-phase HPLC (10-50% acetonitrile/water with 0.1% TFA). The resulting residue is partitioned between NaHCO$_3$ and CH$_2$Cl$_2$ and the phases are separated. The organic phase is dried over MgSO$_4$,

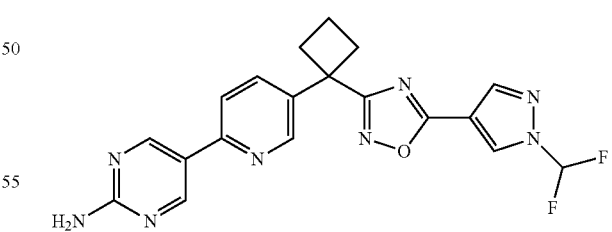

Example 90 (150 mg, 0.416 mmol) is treated with R41 (72.0 mg, 0.498 mmol), Cs$_2$CO$_3$ (676 mg, 2.08 mmol), and DMF (4.0 mL) and the resulting mixture is stirred at 60° C. for 24 hours. The resulting mixture is diluted with ethyl acetate and water and the phases are separated. The organic phase is washed with brine, dried over Na$_2$SO$_4$, filtered, and the solvent is removed in vacuo. The crude residue is purified by flash chromatography (SiO$_2$, 0-8% 2M NH$_3$ in methanol/ CH$_2$Cl$_2$) to afford the title compound (42 mg); m/z 411.4 [M+H].

Method 16

Synthesis of 2-[4-(3-{1-[6-(2-aminopyrimidin-5-yl) pyridin-3-yl]cyclobutyl}-1,2,4-oxadiazol-5-yl)-1H-pyrazol-1-yl]-2-methylpropanoic acid (Example 65, Table 1)

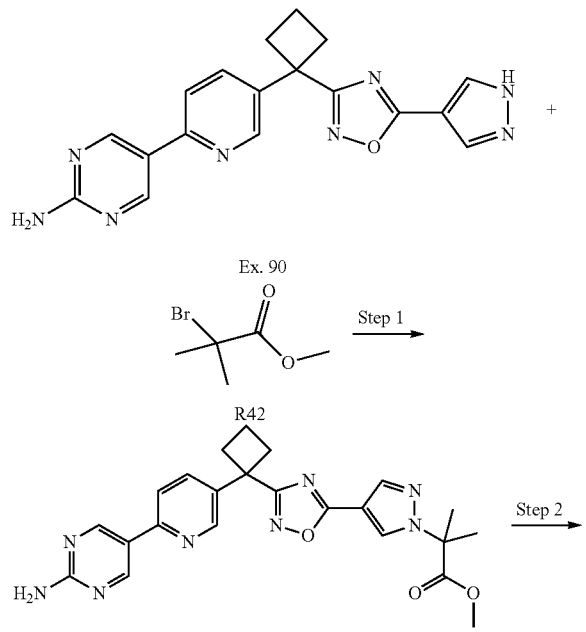

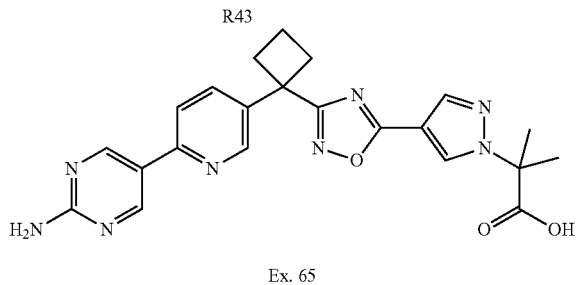

Step 1: synthesis of 2-[4-(3-{1-[6-(2-Amino-pyrimidin-5-yl)-pyridin-3-yl]-cyclobutyl}-1,2,4-oxadiazol-5-yl)-pyrazol-1-yl]-2-methyl-propionic acid methyl ester (R43)

R43 is synthesized according to method 11 with stirring at room temperature for 72 hours (819 mg); m/z 461.4 [M+H].

Step 2: synthesis of 2-[4-(3-{1-[6-(2-aminopyrimidin-5-yl)pyridin-3-yl]cyclobutyl}-1,2,4-oxadiazol-5-yl)-1H-pyrazol-1-yl]-2-methylpropanoic acid (Example 65)

R43 (200 mg, 0.434 mmol) is treated with THF (2.0 mL), methanol (2.0 mL), and 2M NaOH (2.0 mL) and the resulting mixture is stirred at 50° C. for 16 hours. The resulting mixture is extracted with ethyl acetate four times, and the combined organic phases are dried over Na$_2$SO$_4$, filtered, and the solvent is removed in vacuo. The aqueous phase is concentrated and the resulting solids are extracted with methanol and the extracts combined with the organic phase residue. The combined crude residue is purified by preparative reverse-phase HPLC (153 mg); m/z 447.3 [M+H].

Method 17

Synthesis of 2-[5-(3-{1-[6-(2-aminopyrimidin-5-yl) pyridin-3-yl]cyclobutyl}-1,2,4-oxadiazol-5-yl)pyridin-2-yl]propan-2-ol (Example 82, Table 1)

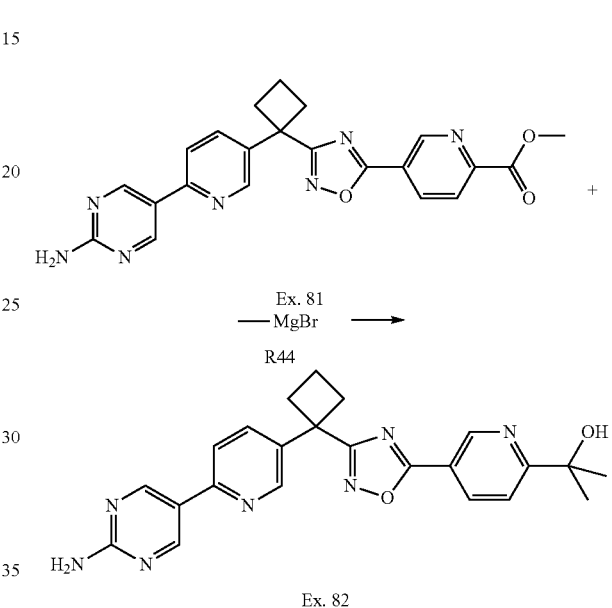

Example 81 (59.0 mg, 0.137 mmol) is treated with THF (2.0 mL) and R44 (1.4M in toluene:THF 3:1, 0.49 mL, 0.69 mmol) and the resulting mixture is stirred for 2 hours. The mixture is then partitioned between water and CH$_2$Cl$_2$ and the phases are separated. The organic phase is washed with brine, dried over Na$_2$SO$_4$, filtered, and the solvent is removed in vacuo. The resulting mixture is purified directly by preparative reverse-phase HPLC (25-75% acetonitrile/water with 0.1% TFA) to afford the title compound (6.0 mg); m/z [M+H].

Method 18

Synthesis of 5-(5-{1-[5-(5-amino-1H-pyrazol-3-yl)-1,2,4-oxadiazol-3-yl]cyclobutyl}pyridin-2-yl)pyrimidin-2-amine (Example 10, Table 1)

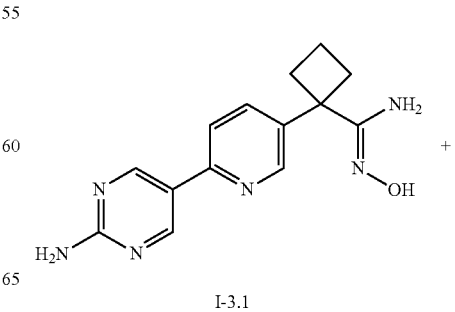

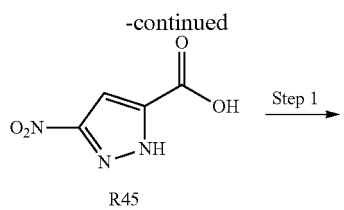

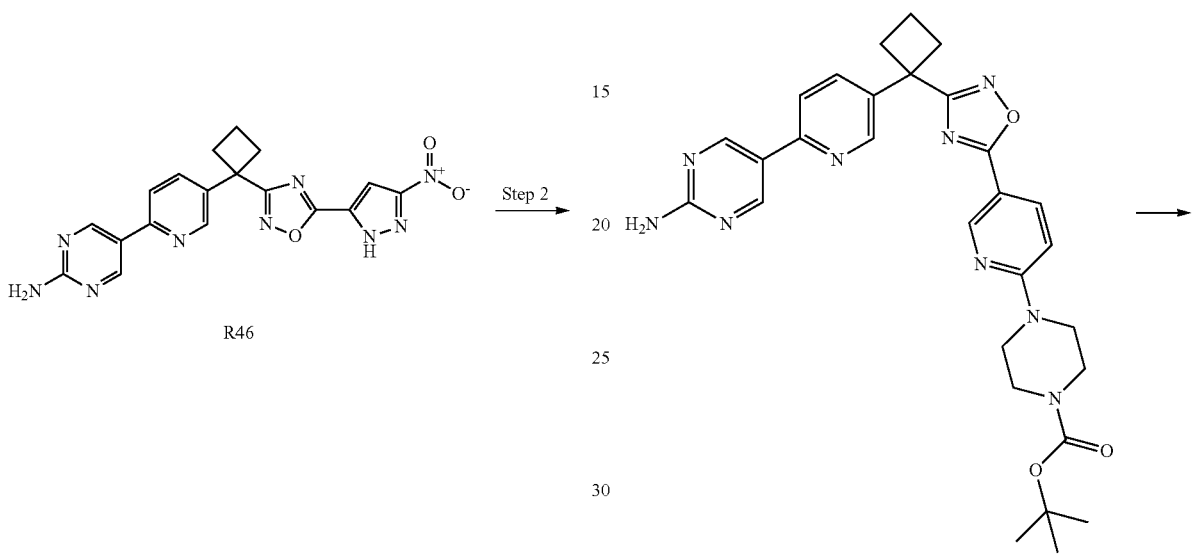

resulting residue is treated with acetonitrile and heated at 70° C. for 2 hours and then filtered to afford the title compound (10 mg); m/z 376.6 [M+H].

Method 19

Synthesis of 5-[5-(1-{5-[6-(piperazin-1-yl)pyridin-3-yl]-1,2,4-oxadiazol-3-yl}cyclobutyl)pyridin-2-yl]pyrimidin-2-amine (Example 3, table 1)

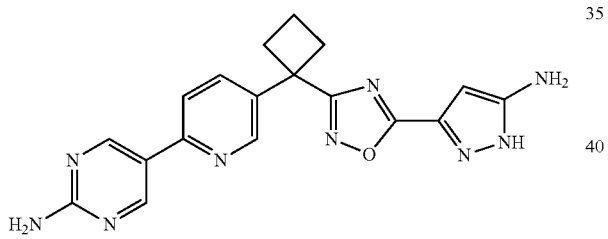

Step 1: synthesis of 5-(5-{1-[5-(5-nitro-2H-pyrazol-3-yl)-1,2,4-oxadiazol-3-yl]-cyclobutyl}-pyridin-2-yl)-pyrimidin-2-ylamine (R46)

R46 is synthesized according to the procedure for method 10 heating for 1 hour (180 mg); m/z 406.6 [M+H].

Step 2: Synthesis of 5-(5-{1-[5-(5-amino-1H-pyrazol-3-yl)-1,2,4-oxadiazol-3-yl]cyclobutyl}pyridin-2-yl)pyrimidin-2-amine (Example 10)

R46 (180 mg, 0.444 mmol) is treated with ammonium formate (280 mg, 4.44 mmol), palladium on carbon (10 wt % palladium, 50.0 mg, 0.047 mmol), and methanol (8.0 mL) and the resulting mixture is heated at 65° C. for 3 hours. The mixture is cooled to room temperature, filtered through celite, and concentrated in vacuo and the residue is purified by flash chromatography (SiO$_2$, 0-10% methanol/CH$_2$Cl$_2$). The

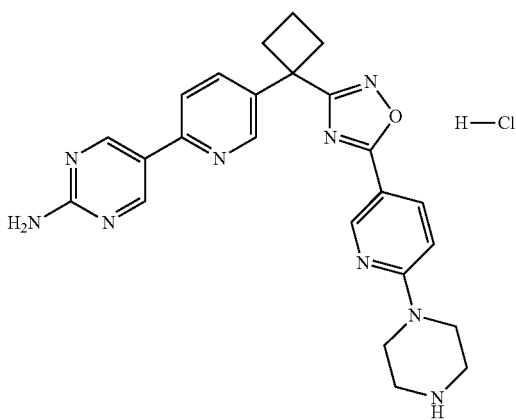

Example 1 (115 mg, 0.207 mmol) is treated with 4.0M HCl in dioxane and stirred for 6 hours. The resulting solid is collected by filtration and dried to afford the title compound as the hydrochloride salt (55.0 mg); m/z 456.7 [M+H].

Examples in table 1 listed with method 19 are synthesized in a similar fashion.

Method 20

Synthesis of 5-[5-(1-{5-[5-(piperazin-1-yl)pyrazin-2-yl]-1,2,4-oxadiazol-3-yl}cyclobutyl)pyridin-2-yl]pyrimidin-2-amine (Example 60, Table 1)

Step 2: synthesis of 2,3,5,6-Tetrahydro-[1,2']bipyrazinyl-4,5'-dicarboxylic acid 4-tert-butyl ester (R50)

R49 (890 mg, 2.76 mmol) is treated with ethanol (25 mL) and 5N NaOH (2.76 mL, 13.8 mmol). The mixture is stirred

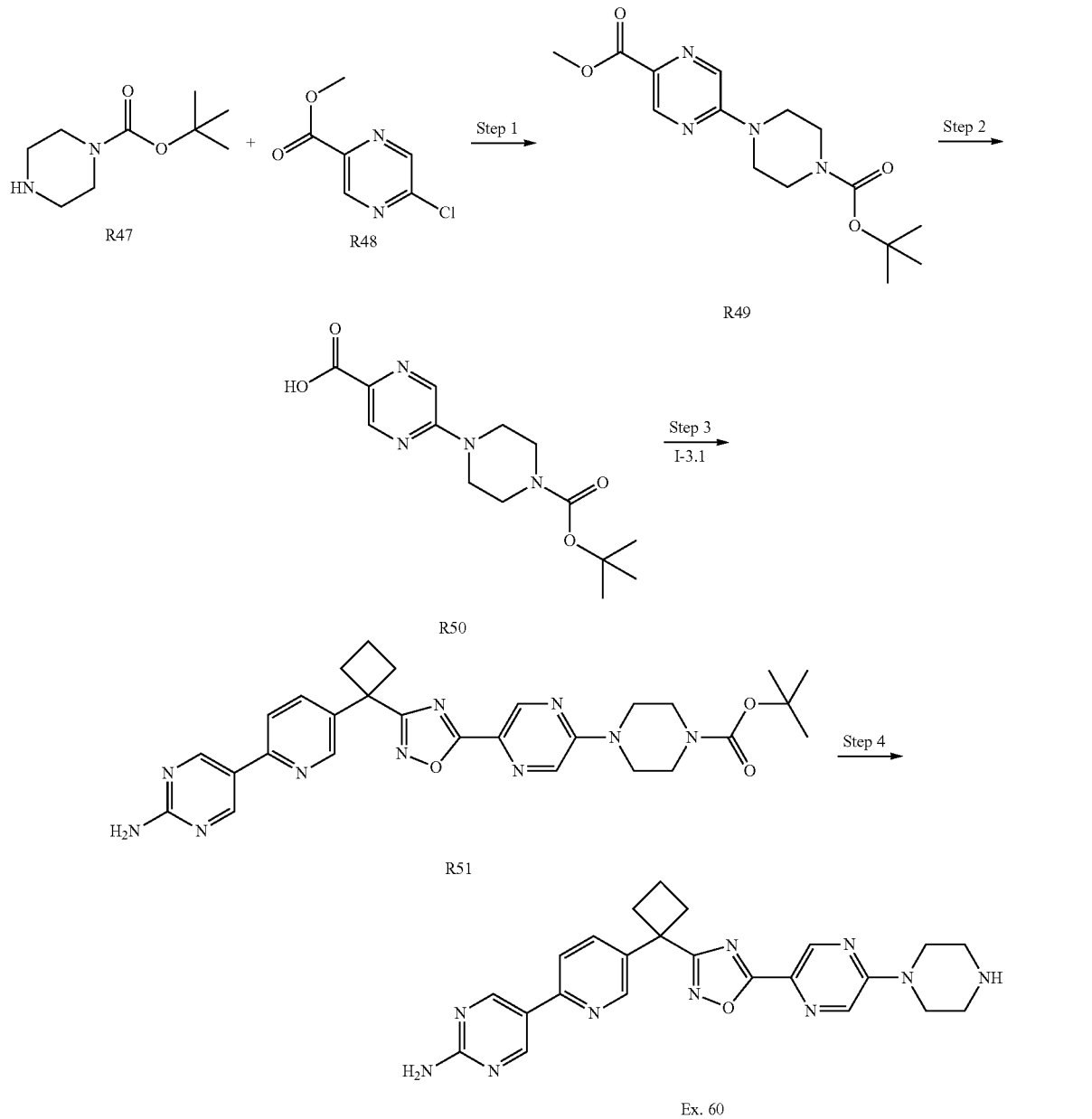

Step 1: synthesis of 2,3,5,6-tetrahydro-[1,2]bipyrazinyl-4,5'-dicarboxylic acid 4-tert-butyl ester 5'-methyl ester (R49)

R47 (646 mg, 3.47 mmol) is treated with R48 (598 mg, 3.49 mmol), TEA (580 µL, 4.16 mmol), and NMP (10.0 mL) and the mixture is heated at 60° C. for 30 minutes. The reaction is cooled to room temperature and poured into ice water and the resulting solid is collected by filtration to afford R49 (1.03 g); m/z 323.1 [M+H].

for several minutes at which time water (approximately 10 mL) is added and the reaction is stirred for 24 hours. The resulting mixture is diluted with water, acidified with acetic acid., and extracted twice with $CH_2Cl_2$. The combined organic phases are washed with brine, dried over $MgSO_4$, filtered, and the solvent is removed in vacuo to afford R50 (690 mg); m/z 309.4 [M+H].

Step 3: synthesis of 5'-(3-{1-[6-(2-amino-pyrimidin-5-yl)-pyridin-3-yl]-cyclobutyl}-1,2,4-oxadiazol-5-yl)-2,3,5,6-tetrahydro-1,2'-bipyrazinyl-4-carboxylic acid tert-butyl ester (R51)

R50 (690 mg, 2.24 mmol) is treated with THF (10.00 mL) and CDI (370.7 mg, 2.29 mmol) and stirred at 50° C. for 30 minutes. To this mixture is added I-3.1 (600 mg, 2.11 mmol) and the resulting mixture is heated at 80° C. for 3 hours. The mixture is cooled to room temperature, acetic acid (1.8 mL) is added, and the mixture is heated at 80° C. for 16 hours. The resulting mixture is cooled to room temperature, diluted with water and ethyl acetate and the phases are separated. The aqueous phase is extracted twice with ethyl acetate and the combined organic phases are washed twice each with water and saturated aqueous NaHCO$_3$, dried over MgSO$_4$, filtered, and the solvent is removed in vacuo to afford R51 (970 mg).

Step 4: synthesis of 5-[5-(1-{5-[5-(piperazin-1-yl)pyrazin-2-yl]-1,2,4-oxadiazol-3-yl}cyclobutyl)pyridin-2-yl]pyrimidin-2-amine (Example 60)

Methanol (10.0 mL) is cooled to −5° C. and treated with acetyl chloride (1.00 mL). To this mixture is added R51 (0.50 g, 0.90 mmol) and the resulting mixture is stirred for 16 hours. The resulting mixture is treated with 7N ammonia in methanol until basic by pH paper and concentrated in vacuo. The resulting solid is treated with acetonitrile and diluted with water. The mixture is filtered and the filtrate is treated with saturated NaHCO$_3$ (3 mL) and the solid is collected by filtration to afford the title compound (90.00 mg). m/z 457.3 [M+H].

Method 21

Synthesis of 5-(5-{1-[5-(2-chloropyridin-3-yl)-1,2,4-oxadiazol-3-yl]cyclobutyl}pyridin-2-yl)pyrimidin-2-amine (Example 84, Table 1)

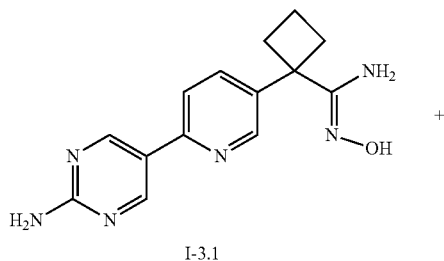

I-3.1

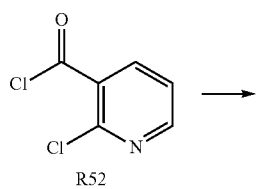

R52

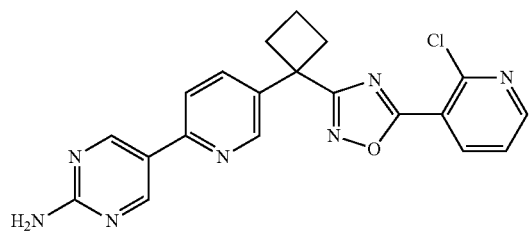

Ex. 84

I-3.1 (280 mg, 0.985 mmol) is treated with NMP (1 mL), DIEA (0.5 mL) and R52 (180 mg, 1.00 mmol) and the resulting mixture is stirred at 120° C. for 1 hour. The crude residue is purified by flash chromatography (SiO$_2$, 0-10% methanol/CH$_2$Cl$_2$) to afford the title compound (20 mg); m/z 406.4 [M+H].

Examples in table 1 listed with method 21 are synthesized in a similar fashion.

Method 22

Synthesis of 5-(5-{1-[5-(2-aminopyridin-3-yl)-1,2,4-oxadiazol-3-yl]cyclobutyl}pyridin-2-yl)pyrimidin-2-amine (Example 105, Table 1)

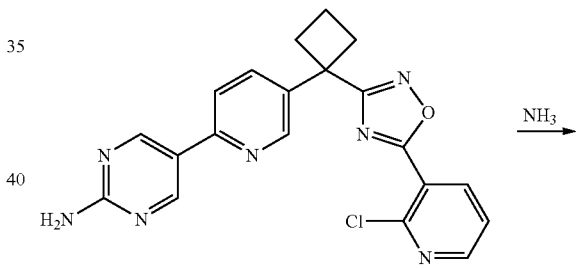

Ex. 84

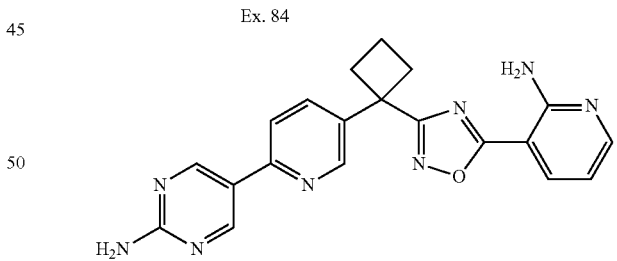

Ex. 105

Example 84 (50 mg, 0.12 mmol) is treated with THF (2.0 mL) and the mixture is cooled to −40° C. Ammonia gas is bubbled through this solution for 5 minutes and the resulting mixture is heated in a sealed vessel at 100° C. for 24 hours. The solvent is removed in vacuo, the residue is treated with water (2.0 mL), and the resulting precipitate is collected by filtration and purified by flash chromatography (SiO$_2$, 0-10% methanol/CH$_2$Cl$_2$) to afford the title compound (20 mg); m/z 387.6 [M+H].

Examples listed in table 1 under method 22 are synthesized in a similar fashion from appropriate reagents.

Method 23

Synthesis of 5-[5-(1-{5-[2-(methylamino)pyridin-3-yl]-1,2,4-oxadiazol-3-yl}cyclobutyl)pyridin-2-yl]pyrimidin-2-amine (Example 122, Table 1)

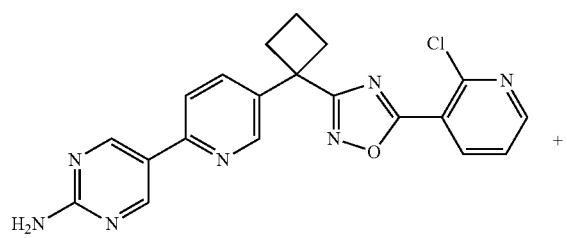

Ex. 84

+

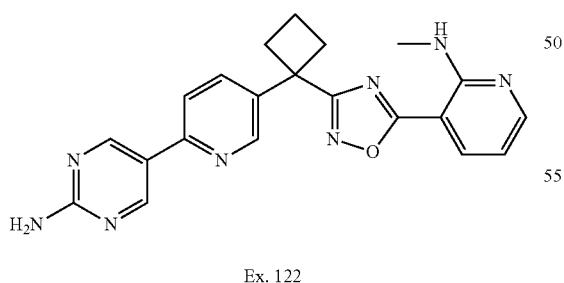

R53

→

Ex. 122

Example 84 (50 mg, 0.12 mmol) is treated with 2M methylamine in THF (2.0 mL, 0.4 mmol) and heated in a sealed vessel at 100° C. for 2 hours. The resulting mixture is diluted with water (2.0 mL) and the resulting precipitate is collected by filtration and purified by preparative reverse-phase HPLC (50 mg); m/z 401.7 [M+H].

Examples in table 1 listed with method 22 are synthesized in a similar fashion.

Method 24

Synthesis of 3-(3-{1-[6-(2-aminopyrimidin-5-yl)pyridin-3-yl]cyclobutyl}-1,2,4-oxadiazol-5-yl)pyridin-2(1H)-one (Example 95, Table 1)

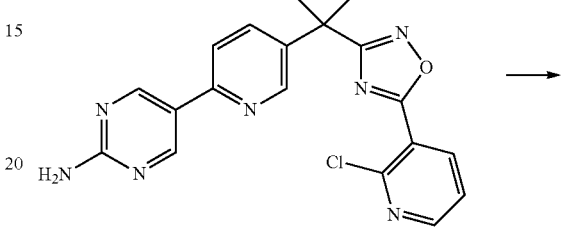

Ex. 84

→

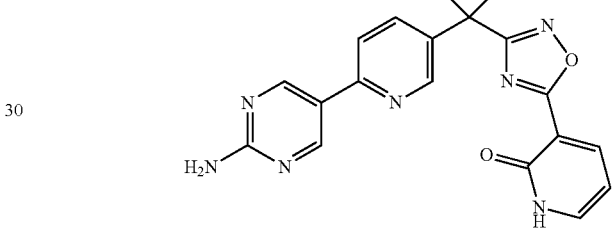

Ex. 95

Example 84 (50 mg, 0.12 mmol) is treated with 1,4-dioxane (2.0 mL) and lithium hydroxide (10% in water, 3 drops) and the mixture is heated at 70° C. for 24 hours. The resulting mixture is diluted with water (2.0 mL) and the precipitate is collected by filtration and purified by preparative reverse-phase HPLC (30 mg); m/z 388.5 [M+H]. Examples in table 1 listed with method 24 are synthesized in a similar fashion from appropriate reagents.

Method 25

Synthesis of 5-(5-{1-[5-(pyrrolidin-1-yl)-1,2,4-oxadiazol-3-yl]cyclobutyl}pyridin-2-yl)pyrimidin-2-amine (Example 76, Table 1)

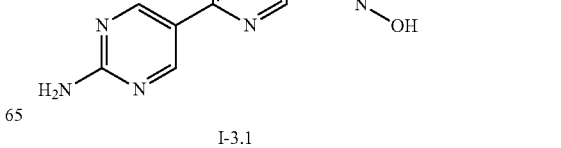

I-3.1

+

123
-continued

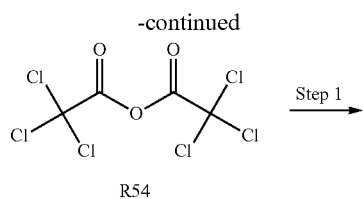

R54

Step 1 →

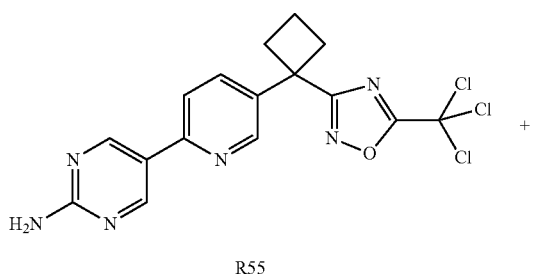

R55

+

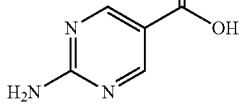

R56

Step 2 →

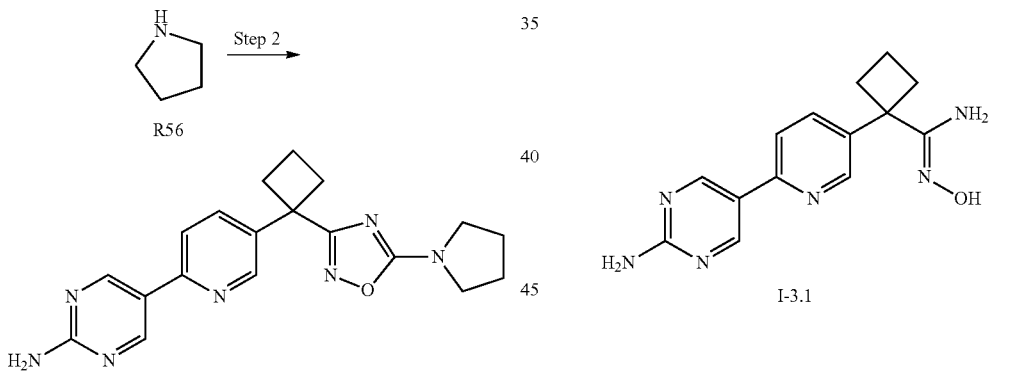

Ex. 76

Step 1: synthesis of 5-{5-[1-(5-trichloromethyl-1,2,4-oxadiazol-3-yl)-cyclobutyl]-pyridin-2-yl}-pyrimidin-2-ylamine (R55)

I-3.1 (300 mg, 1.06 mmol) is treated with toluene (10.0 mL) and R54 (0.23 mL, 1.3 mmol) and the reaction is stirred at 110° C. for 2 hours. The resulting mixture is cooled to room temperature and partitioned between ethyl acetate and water. The phases are separated and the organic phase is washed with water and saturated aqueous NaHCO₃. The organic phase is dried over MgSO₄, filtered, and the solvent is removed in vacuo to afford R55 (354 mg); m/z 413 [M+H].

124

Step 2: synthesis of 5-(5-{1-[5-(pyrrolidin-1-yl)-1,2,4-oxadiazol-3-yl]cyclobutyl}pyridin-2-yl)pyrimidin-2-amine (example 76)

R56 (0.07 mL, 0.9 mmol) is treated with DMF (5.0 mL) and R55 (354 mg, 0.860 mmol) and the resulting mixture is stirred for 30 minutes. The reaction is diluted with water and ethyl acetate and the phases are separated. The organic phase is washed twice more with water, dried over MgSO₄, filtered, and the solvent is removed in vacuo. The crude residue is purified by flash chromatography (SiO₂, 3% methanol/CH₂Cl₂) to afford the title compound (76.9 mg); m/z 364 [M+H].

Method 26

Synthesis of 5-(5-{1-[5-(dimethylamino)-1,2,4-oxadiazol-3-yl]cyclobutyl}pyridin-2-yl)pyrimidin-2-amine (Example 15, Table 1)

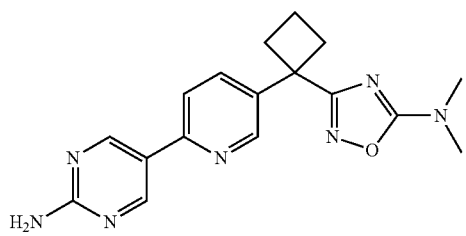

R57

+

I-3.1

Ex. 15

R57 (75.0 mg, 0.539 mmol) is treated with HATU (284 mg, 0.746 mmol), TEA (0.30 mL, 2.16 mmol), and NMP (5.00 mL) and the mixture is stirred for 5 minutes. I-3.1 (153 mg, 0.539 mmol) is then added and the mixture is heated at 80° C.

for 16 hours. The mixture is purified directly by preparative reverse-phase HPLC to afford the title compound (161 mg); m/z 338.2 [M+H].

Method 27

Synthesis of 2-[4-(3-{1-[6-(2-amino-pyrimidin-5-yl)-pyridin-3-yl]-cyclobutyl}-1,2,4-oxadiazol-5-yl)-pyrazol-1-yl]-N,N-dimethyl-acetamide (Example 59, Table 1)

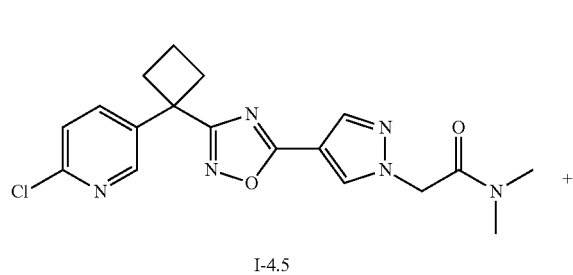

I-4.5

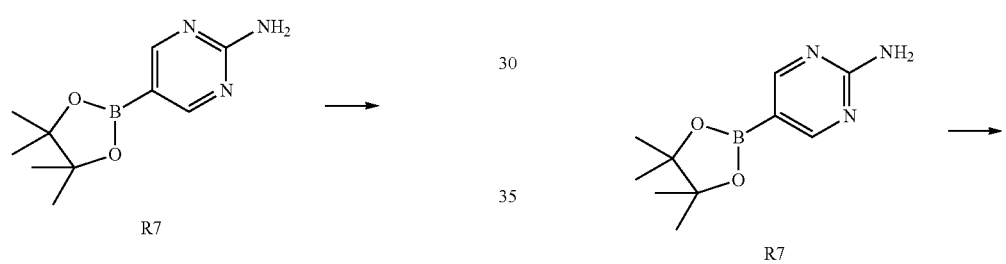

Ex. 59

I-4.5 (200 mg, 0.516 mmol) is treated with DMF (2.0 mL), R7 (342 mg, 1.55 mmol), 2M Na₂CO₃ (0.52 mL, 1.03 mmol), and bis(triphenylphosphine)palladium(II) dichloride (72 mg, 0.103 mmol) and the resulting mixture is heated at 80° C. overnight. The reaction is passed through a PTFE filter, the solvent is removed in vacuo, and the residue is partitioned between CH₂Cl₂ and water. The phases are separated and the organic phase is washed with saturated aqueous NaHCO₃, dried over Na₂SO₄, filtered, and the solvent is removed in vacuo. The crude residue is purified by reverse phase preparative HPLC to afford the title compound (40 mg); m/z 446 [M+H].

Examples in table 1 listed with method 27 are synthesized in a similar fashion from the appropriate intermediates I-4. Examples 152, 153, 166, and 175 use tetrakistriphenylphosphinepalladium(0) as catalyst.

Method 28

Synthesis of 5-{5-[1-(5-Pyridin-3-yl-1,2,4-oxadiazol-3-yl)-cyclobutyl]-pyridin-2-yl}-pyrimidin-2-ylamine (Example 73, Table 1)

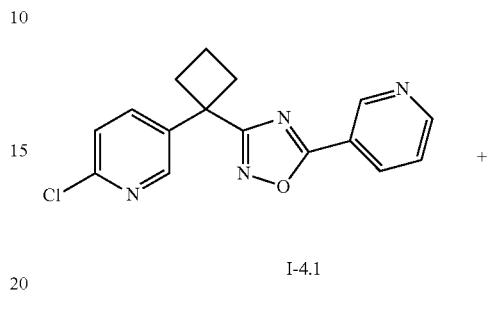

I-4.1

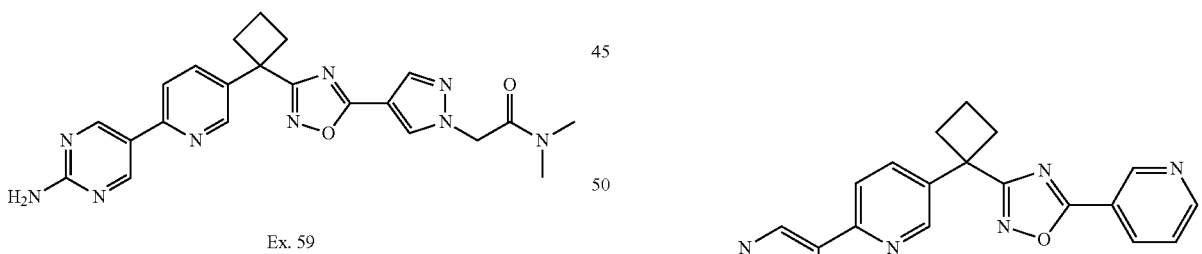

Ex. 73

I-4.1 (115 mg, 0.37 mmol) is treated with toluene/ethanol mixture (1:4 3.0 mL), R7 (61 mg, 0.44 mmol), 2M Na₂CO₃ (0.40 mL, 0.81 mmol), 1,1'-bis-diphenylphosphinoferrocene (20 mg, 0.04 mmol), and dichloro(1,1'-bis-diphenylphosphinoferrocene)palladium(II) (30 mg, 0.04 mmol) and the resulting mixture is heated at 90° C. for 3 hours. The resulting mixture is cooled to room temperature, filtered through celite and the crude residue is purified by preparative reverse-phase HPLC to afford the title compound (34 mg); m/z 372 [M+H].

Examples in table 1 listed with method 28 are synthesized in a similar fashion from the appropriate intermediate I-4.

Method 29

Synthesis of 5-{5-[1-(5-{1-[2-(morpholin-4-yl)ethyl]-1H-pyrazol-4-yl}-1,2,4-oxadiazol-3-yl)cyclobutyl]pyridin-2-yl}pyrimidin-2-amine (Example 140)

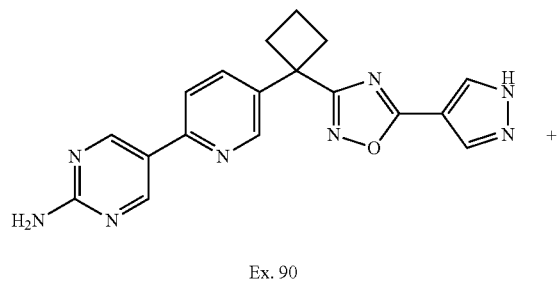

Ex. 90

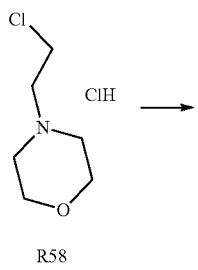

R58

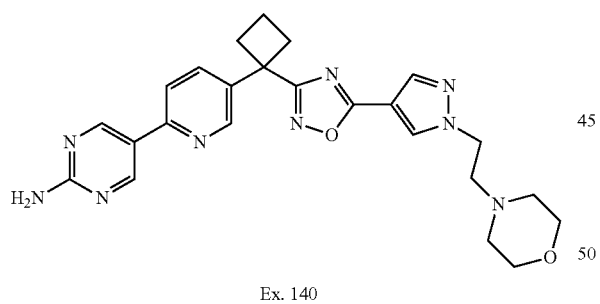

Ex. 140

Example 90 (75.0 mg, 0.208 mmol) is treated with DMF (1.50 mL), Cs₂CO₃ (153 mg, 0.468 mmol), and R58 (77.5 mg, 0.416 mmol) and the resulting mixture is stirred at 60° C. for 1 hour. At this time R58 (25 mg, 0.134 mmol) and Cs₂CO₃ (50 mg, 0.153 mmol) are added and the reaction is heated at 70° C. for 1 hour. The mixture is purified directly by reverse-phase HPLC (10 to 70% acetonitrile/water/0.1% trifluoroacetic acid) to afford the title compound (18.0 mg); m/z 474.4 [M+H].

Examples in table 1 listed with method 29 are synthesized in a similar fashion. Example 139 is heated at 70° C. for 1 hour and no second addition of reagents is needed. Example 141 is heated at 60° C. for 1 hour, then 1.5 equivalents of halide and 2.25 equivalents of base are added and heating was continued for an additional hour. Example 142 was heated at 70° C. for 1 hour, then room temperature over a weekend.

Method 30

Synthesis of 2-[4-(3-{1-[6-(2-aminopyrimidin-5-yl)pyridin-3-yl]cyclobutyl}-1,2,4-oxadiazol-5-yl)-1H-pyrazol-1-yl]-N-tert-butyl-N-methylacetamide (Example 143)

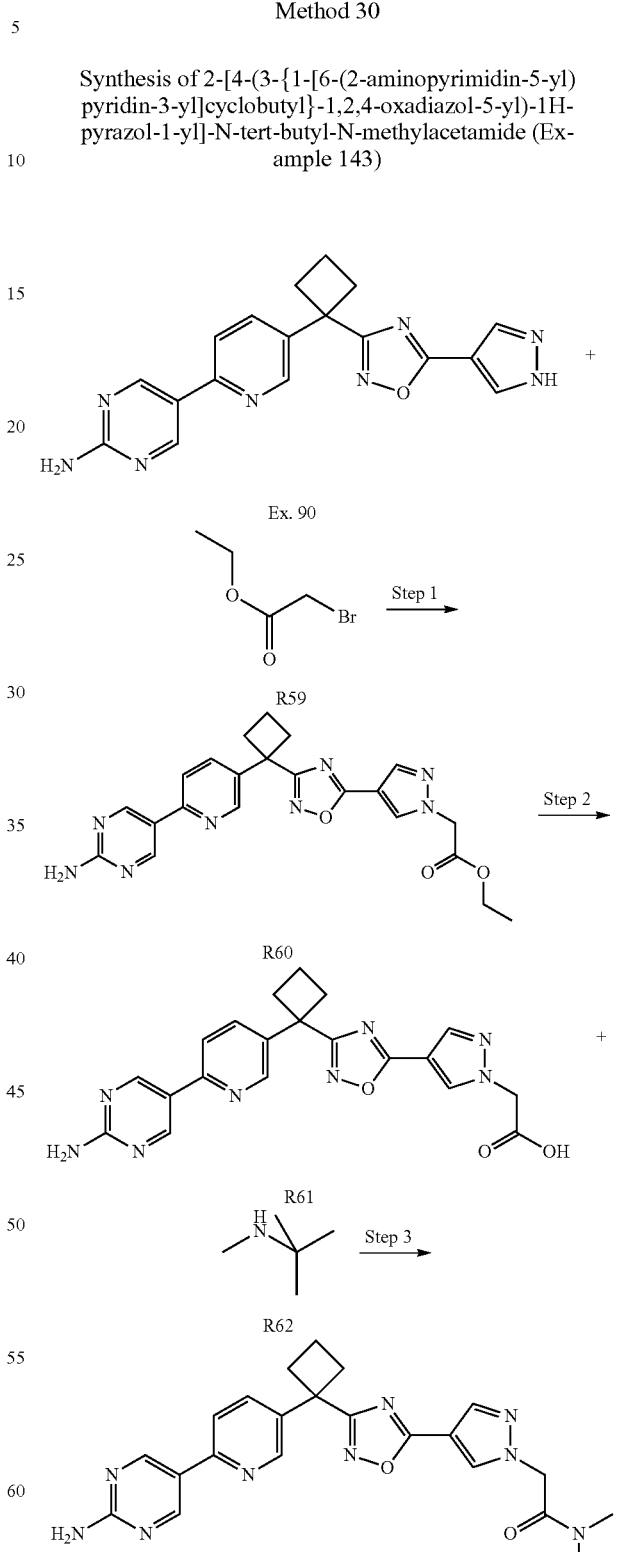

Step 1: Synthesis of [4-(3-{1-[6-(2-Amino-pyrimidin-5-yl)-pyridin-3-yl]-cyclobutyl}-1,2,4-oxadiazol-5-yl)-pyrazol-1-yl]-acetic acid ethyl ester (R60)

R60 is prepared according to the procedure for Example 65 step 1 using R59; m/z 447.4.

Step 2: Synthesis of [4-(3-{1-[6-(2-Amino-pyrimidin-5-yl)-pyridin-3-yl]-cyclobutyl}-1,2,4-oxadiazol-5-yl)-pyrazol-1-yl]-acetic acid (R61)

R61 is prepared according to the procedure for Example 65 step 2 using R60.

Step 3: Synthesis of 2-[4-(3-{1-[6-(2-Amino-pyrimidin-5-yl)-pyridin-3-yl]-cyclobutyl}-1,2,4-oxadiazol-5-yl)-pyrazol-1-yl]-N-tert-butyl-N-methyl-acetamide (Example 143)

R61 (13.2 mg, 0.180 mmol) is added to a reaction vial. A stock solution of HATU (1.71 g) in dimethylacetamide (20 mL) is prepared and added (0.800 mL, 0.180 mmol) followed by a stock solution of R61 (502 mg) and DIEA (0.627 mL) in dimethylacetamide (DMA) (9.0 mL) (0.965 mL, 0.12 mmol R60 and 0.36 mmol DIEA). The resulting mixture is shaken overnight at room temperature and the residue is purified by reverse-phase HPLC (acetonitrile/water/0.1% formic acid) to afford the title compound (23.1 mg); m/z 488.4 [M+H].

Examples in table 1 listed with method 30 are synthesized in a similar fashion.

Method 31

Synthesis of 5-{1-[5-(1-Oxetan-3-yl-1H-pyrazol-4-yl)-[1,2,4]oxadiazol-3-yl]-cyclobutyl}-[2,3']bipyridinyl-6'-ylamine (Example 145)

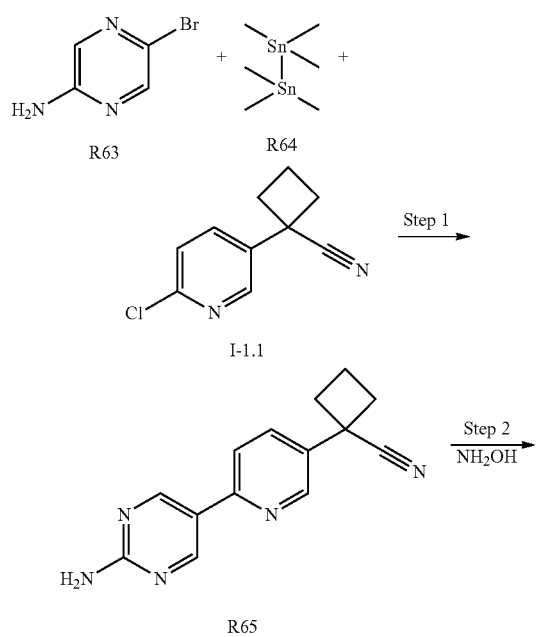

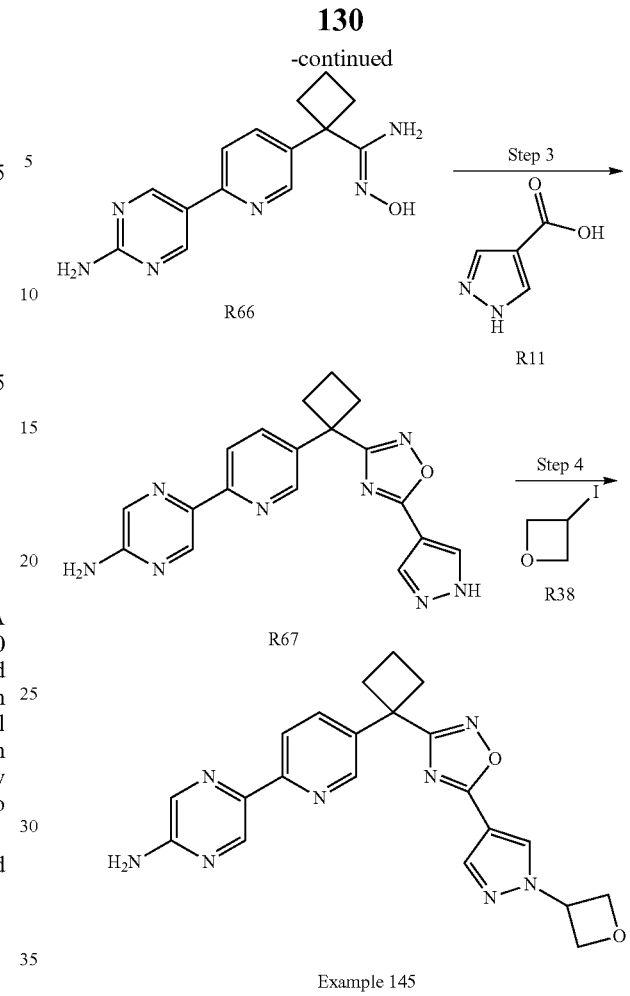

Example 145

Step 1: Synthesis of 1-[6-(5-amino-pyrazin-2-yl)-pyridin-3-yl]-cyclobutanecarbonitrile (R65)

In a 20 ml microwave reaction vessel are combined R63 (250 mg, 1.44 mmol) and R64 (520 mg, 1.59 mmol) in toluene (8 ml). The mixture is degassed using argon after which tetrakis(triphenylphosphine) palladium (0) (100 mg, 0.09 mmol) is added. The reaction is degassed once more, capped and warmed to 115° C. for 1 h. Upon cooling to ambient temperature, I-1.1 is introduced along with tetrakis(triphenylphosphine) palladium (0) (120 mg, 0.10 mmol). The vessel is capped and warmed to 115° C. overnight. After this time the reaction is cooled and concentrated. The crude is suspended in DCM/MeOH, treated with silica gel and concentrated. The resulting solid is purified via flash chromatography (Silica gel, 0-10% MeOH/DCM) to give R65 (220 mg); m/z 252.2 [M+H].

Step 2: Synthesis of 1-[6-(5-amino-pyrazin-2-yl)-pyridin-3-yl]-N-hydroxy-cyclobutanecarboxamidine (R66)

To a stirred suspension of R65 (220 mg, 0.88 mmol) in ethanol (4 ml) is added hydroxylamine (50% aq. solution, 1 ml). The resulting mixture is stirred at 80° C. overnight and cooled to room temperature. The reaction is concentrated and the remaining residue is diluted with water. The precipitated yellow solid is collected via filtration and washed with water to give R66 (115 mg).

Step 3: Synthesis of 5-(5-{1-[5-(1H-pyrazol-4-yl)-[1,2,4]oxadiazol-3-yl]-cyclobutyl}-pyridin-2-yl)-pyrazin-2-ylamine (R67)

To a suspension of R11 (68 mg, 0.61 mmol) in THF (5 ml) is added CDI (98 mg, 0.61 mmol) at room temperature. The mixture is stirred at 50° C. for 30 minutes after which time R66 (115 mg, 0.40 mmol) is added. The resulting mixture is heated at 80° C. for 3 hours, cooled to room temperature and treated with acetic acid (AcOH) (8 ml). The reaction is warmed to 80° C. and stirred overnight. Upon cooling to room temperature, the reaction is concentrated and diluted with water. The product is extracted into DCM (2×). The combined organics are washed with brine, dried (MgSO4), filtered and concentrated. The remaining residue is purified via flash chromatography (Silica gel, 0-10% MeOH/DCM) to afford R67 (50 mg); m/z 361.2 [M+H].

Step 4: Synthesis of 5-{1-[5-(1-Oxetan-3-yl-1H-pyrazol-4-yl)-[1,2,4]oxadiazol-3-yl]-cyclobutyl}-[2,3]bipyridinyl-6'-ylamine (Example 145)

A mixture of R67 (50 mg, 0.14 mmol), R38 (51 mg, 0.28 mmol) and potassium carbonate (38 mg, 0.28 mmol) in DMF (2 ml) are stirred at 80° C. over night. After this time the reaction is cooled to room temperature and poured into water and EtOAc. The layers are separated and the aqueous phase is extracted twice more with EtOAc. The combined organics are dried (MgSO4), filtered and concentrated. The remaining residue is purified via flash chromatography (Silica gel, 0-8% MeOH/DCM) to afford the title compound (35 mg); m/z 417.3 [M+H].

Examples in table 1 listed with method 31 are synthesized in a similar fashion.

Method 32

Synthesis of 1-(3-{1-[6-(2-Amino-pyrimidin-5-yl)-pyridin-3-yl]-cyclobutyl}-[1,2,4]oxadiazol-5-yl)-piperidin-4-ol (Example 154)

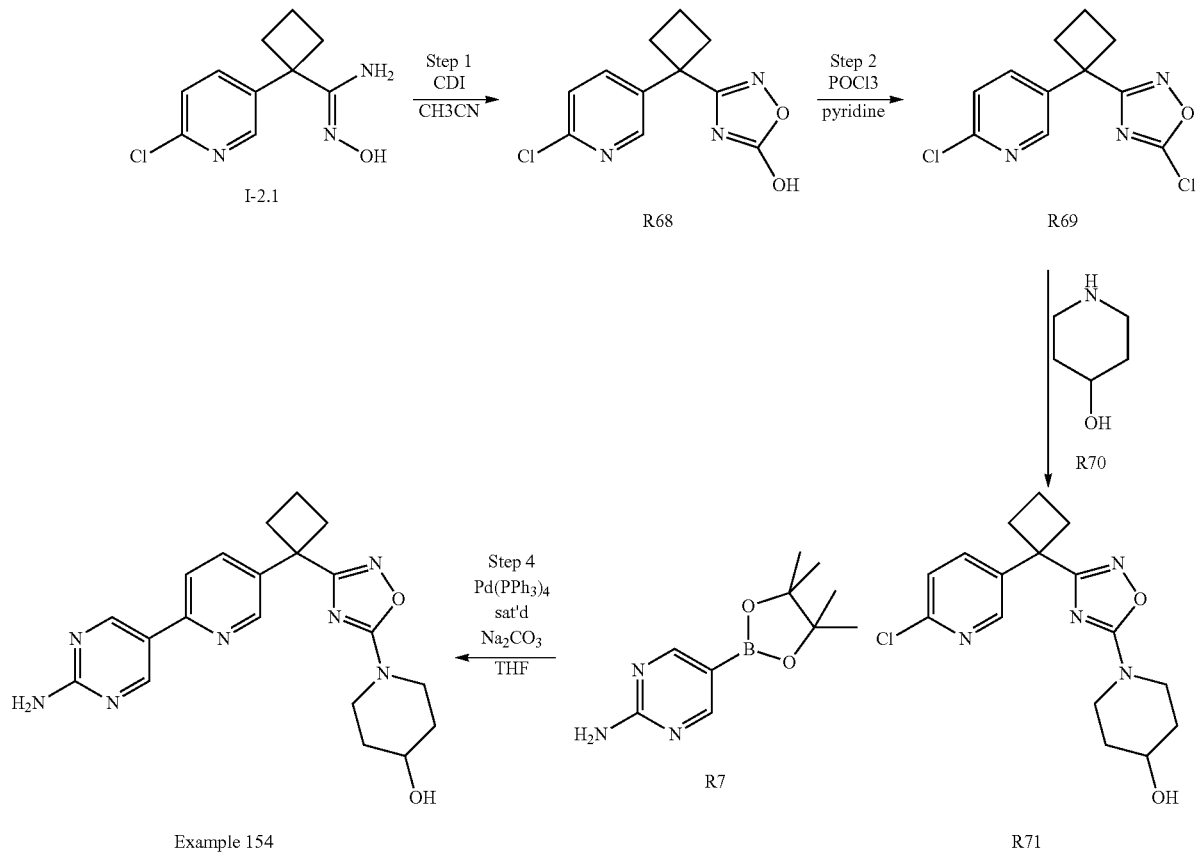

Step 1: Synthesis of 3-[1-(6-chloro-pyridin-3-yl)-cyclobutyl]-[1,2,4]oxadiazol-5-ol (R68)

To a solution of I-2.1 (2 g, 8.862 mmol) in CH3CN (50 mL) is added CDI (3.593 g, 22.16 mmol) in a pressure flask. The reaction mixture is stirred at 75° C. for 18 hours. After this time, the reaction mixture is concentrated in vacuo and the resulting residue is quenched 1N HCl aqueous solution and extracted with ethyl acetate twice. The organics are combined and washed with brine, dried over Na2SO4, filtered and concentrated in vacuo to afford the title compound (2.13 g) as an off white solid; m/z 252.4 [M+1].

Step 2: Synthesis of 2-Chloro-5-[1-(5-chloro-[1,2,4]oxadiazol-3-yl)-cyclobutyl]-pyridine (R69)

To a solution of R68 (300 mg, 1.192 mmol) in DCM (4 mL) is added POCl3 (0.175 mL, 1.910 mmol) and pyridine (0.481 mL, 5.960 mmol) in a pressure flask. The reaction mixture is heated in a microwave at 120° C. for 1 hour. After this time, the reaction mixture is poured into ice water and extracted

133 with DCM twice. The organics are combined and washed with brine, dried over Na$_2$SO$_4$, filtered and concentrated in vacuo. The crude is purified by flash chromatography (SiO$_2$, 5-40% EtOAc/heptanes) to afford the title compound (98 mg) as a light yellow oil; m/z 270.2 [M].

Step 3: Synthesis of 1-{3-[1-(6-chloro-pyridin-3-yl)-cyclobutyl]-[1,2,4]oxadiazol-5-yl}-piperidin-4-ol (R71)

To a solution of R68 (98 mg, 0.363 mmol) in DMSO (1.5 mL) is added R70 (44.1 mg, 0.436 mmol) and DIEA (0.158 mL, 0.908 mmol). The reaction mixture is stirred at room temperature for 1 hour. After this time, the reaction mixture is quenched with water and extracted with EtOAc twice. The organics are combined and washed with brine, dried over Na$_2$SO$_4$, filtered and concentrated in vacuo to afford the title compound (121 mg) as a light yellow oil; m/z 335.1 [M+1].

Step 4: Synthesis of 1-(3-{1-[6-(2-amino-pyrimidin-5-yl)-pyridin-3-yl]-cyclobutyl}-[1,2,4]oxadiazol-5-yl)-piperidin-4-ol (Example 154)

To a mixture of R7 (96.4 mg, 0.436 mmol) and Pd(PPh$_3$)$_4$ (42 mg, 0.036 mmol) in a microwave vial is added the DMF (4 mL) solution of R71 (121 mg, 0.363 mmol) and 2M Na$_2$CO$_3$ aqueous solution (0.726 mL). The reaction mixture is purged with argon and then heated in a microwave at 110° C. for 45 minutes. After this time, the reaction mixture is quenched with water and extracted with EtOAc twice. The organics are combined and washed with brine, dried over Na$_2$SO$_4$, filtered and concentrated in vacuo. The crude is purified by flash chromatography (SiO$_2$, 1.2-10% MeOH/DCM) to afford the title compound (22 mg) as a white solid; m/z 394.2 [M+1].

Method 33

Synthesis of 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionamide (Example 147)

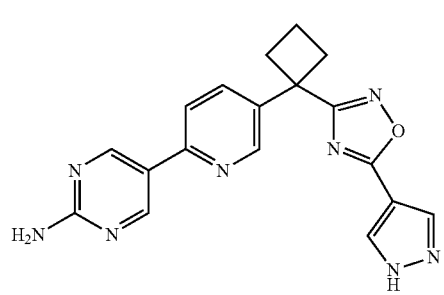

Example 90

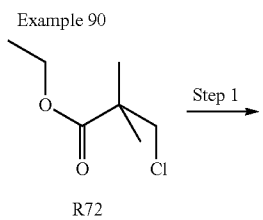

R72

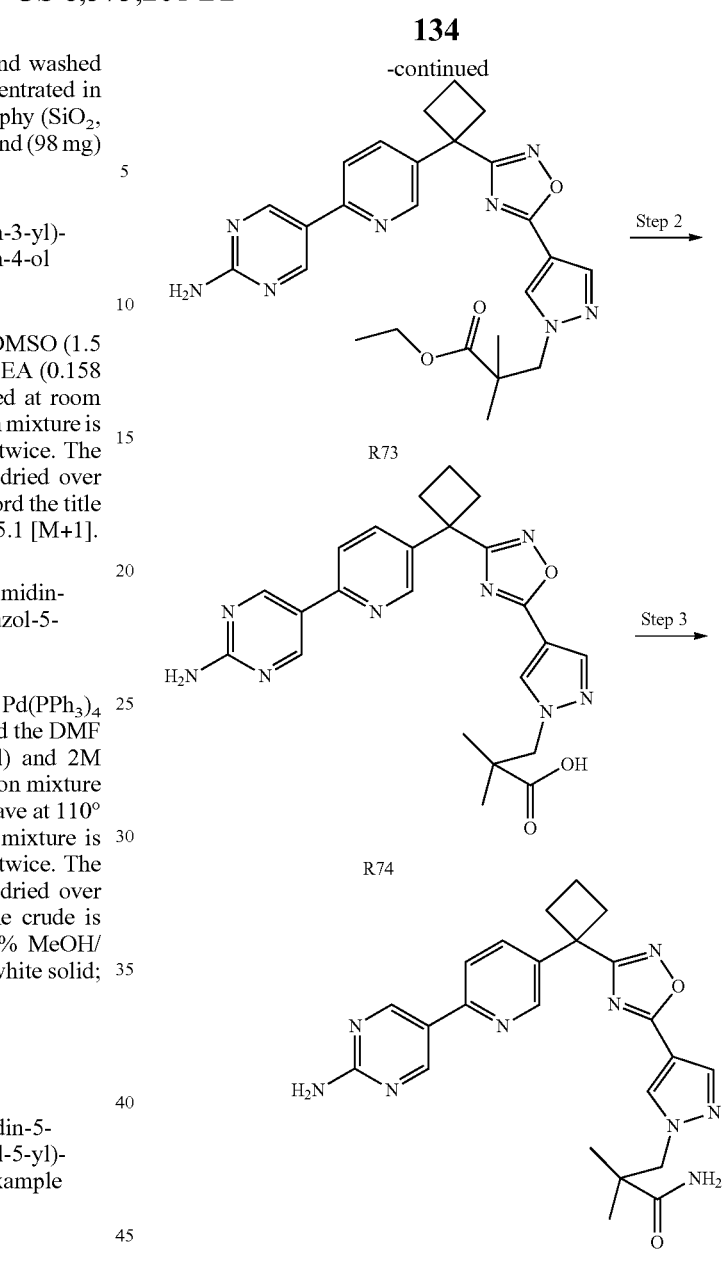

Step 1: Synthesis of 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionic acid ethyl ester (R73)

To a solution of Example 90 (300 mg, 0.832 mmol) in NMP (10.0 mL) is added R72 (343 mg, 2.08 mmol) and Cs$_2$CO$_3$ (325 mg, 0.999 mmol) and the resulting mixture is stirred at 100° C. for 4 hours. At this time another charge of R72 (27 mg, 0.164 mmol) is added and the reaction is heated at 100° C. overnight. The resulting mixture is cooled and diluted with ethyl acetate and water. The phases are then separated and the organic phase is washed with water and brine, collected, dried over Na$_2$SO$_4$, filtered, and concentrated in vacuo. The residue is purified by flash chromatography eluting 0-10% methanol/DCM to give the title compound (170 mg); m/z 489.4 [M+H].

Step 2: Synthesis of 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionic acid (R74)

R73 (170 mg, 0.348 mmol) is treated with THF (1.60 mL), water (0.80 mL), methanol (0.40 mL), and lithium hydroxide monohydrate (43.9 mg, 1.04 mmol) and the resulting mixture is stirred at 45° C. for 1 hour. The reaction is quenched with 1N HCl (1.04 mL, 1.04 mmol) and the mixture is concentrated in vacuo to give the title compound (160 mg).

Step 3: Synthesis of 3-[4 (3-{1-[6-(2 amino-pyrimidin-5-yl)-pyridin-3-yl]-cyclobutyl}-[1,2,4]oxadiazol-5-yl)-pyrazol-1-yl]-2,2-dimethyl-propionamide (Example 147)

R74 (160 mg, 0.348 mmol) is treated with HATU (186 mg, 0.488 mmol) and DMF (3.5 mL). Ammonia gas is then bubbled through this mixture for 2 minutes twice with 5 minutes in between and the vessel is capped and stirred for 1 hour. The resulting mixture is then purified directly by reverse-phase preparative HPLC (20-80% acetonitrile/water/ 0.1% trifluoroacetic acid (TFA)) to give the title compound (122 mg). Examples in table 1 listed with method 33 are synthesized in a similar fashion.

Method 34

Synthesis of 3-[4-(3-{1-[6-(2-amino-pyrimidin-5-yl)-pyridin-3-yl]-cyclobutyl}-[1,2,4]oxadiazol-5-yl)-pyrazol-1-yl]-2,2-dimethyl-propionitrile (Example 148)

TFAA (73 µL, 0.522 mmol) is treated with $CH_2Cl_2$ (1.0 mL) and pyridine (42.2 µL, 0.522 mmol) and cooled to 0° C. To this mixture is added a solution of Example 147 (48.0 mg, 0.104 mmol) in $CH_2Cl_2$ (0.5 mL) and the resulting mixture is warmed to room temperature and stirred for 1 hour. The reaction is then quenched by the addition of saturated $NaHCO_3$ and stirred for 30 minutes. The mixture is diluted with $CH_2Cl_2$ and water and the layers separated. The aqueous layer is extracted again with $CH_2Cl_2$ and the combined organics are dried over $Na_2SO_4$, filtered, and concentrated. The crude residue is then treated with THF (1.0 mL), water (0.5 mL), methanol (0.2 mL), and lithium hydroxide monohydrate (8.6 mg, 0.21 mmol) and the resulting mixture is heated at 40° C. for 30 minutes. The mixture is then diluted with saturated $NaHCO_3$ and ethyl acetate and the layers separated. The aqueous is then extracted with ethyl acetate again and the combined organics are dried over $Na_2SO_4$, filtered, and concentrated. The resulting residue is triturated with acetonitrile to give the title compound (12.0 mg).

Examples in table 1 listed with method 34 are synthesized in a similar fashion.

Method 35

Synthesis of 5-[5-(1-{5-[1-(2-amino-2-methyl-propyl)-1H-pyrazol-4-yl]-[1,2,4]oxadiazol-3-yl}-cyclobutyl)-pyridin-2-yl]-pyrimidin-2-ylamine (Example 150)

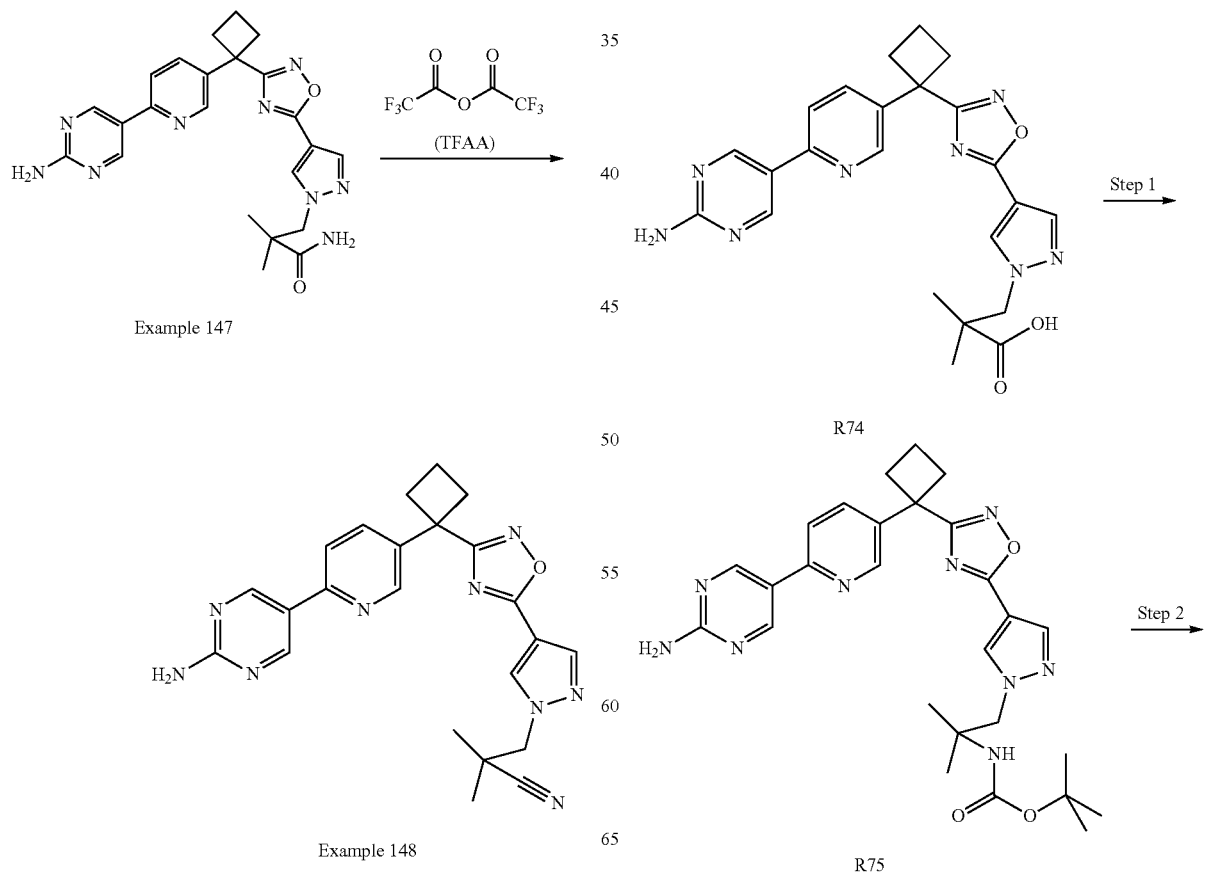

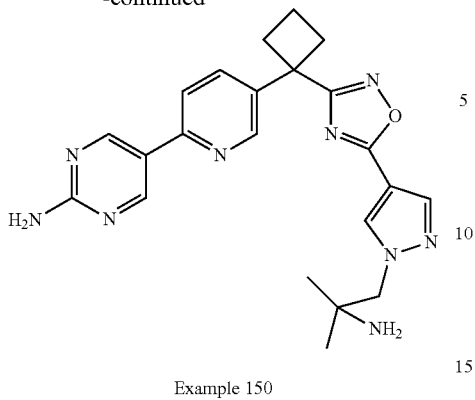

Example 150

Step 1: Synthesis of {2-[4-(3-{1-[6-(2-amino-pyrimidin-5-yl)-pyridin-3-yl]-cyclobutyl}-[1,2,4]oxadiazol-5-yl)-pyrazol-1-yl]-1,1-dimethyl-ethyl}-carbamic acid tert-butyl ester (R75)

R74 (110 mg, 0.202 mmol) is treated with toluene (1.00 mL), DIEA (70.3 µL, 0.403 mmol), t-butanol (1.00 mL), and diphenylphosphoryl azide (69.4 mg, 0.252 mmol) and the resulting mixture is stirred at 85° C. overnight. An additional charge of t-butanol (0.5 mL) is then added and the heating is continued again overnight. The resulting mixture is diluted with ethyl acetate and washed with water and then saturated $NaHCO_3$. The organics are dried over $Na_2SO_4$, filtered, and concentrated and the resulting residue is purified by flash chromatography eluting 0-10% methanol/$CH_2Cl_2$ to give the title compound (33.0 mg).

Step 2 Synthesis of 5-[5 (1-{5-[1-(2 amino-2-methyl-propyl)-1H-pyrazol-4-yl]-[1,2,4]oxadiazol-3-yl}-cyclobutyl)-pyridin-2-yl]-pyrimidin-2-ylamine (Example 150)

R75 (33.0 mg, 0.062 mmol) is treated with $CH_2Cl_2$ (1.0 mL) and TFA (0.25 mL) and the resulting mixture is stirred for 1.5 hours. The mixture is then concentrated to dryness and purified directly by reverse-phase preparative HPLC to give the title compound (21.0 mg).

TABLE 1

Final compounds.

| Example | Structure | Method | Retention time | m/z | LCMS method |
|---|---|---|---|---|---|
| 1 | 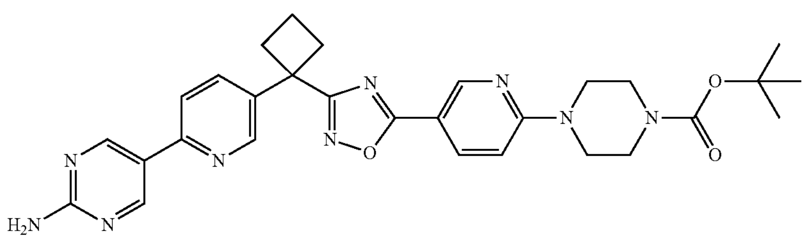 [SMILES: CC(C)(C)OC(=O)N1CCN(c2ccc(-c3nc(C4(c5ccc(-c6cnc(N)nc6)nc5)CCC4)no3)cn2)CC1] | 10 | 6.56 | 556.8 | E |
| 2 | 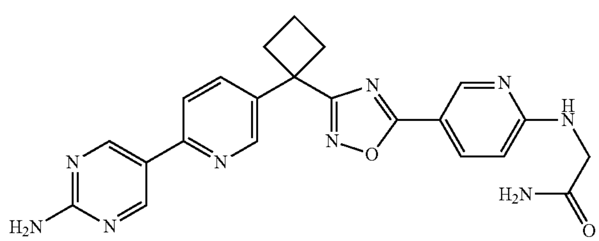 | 2 | 4.10 | 444.7 | E |
| 3 | 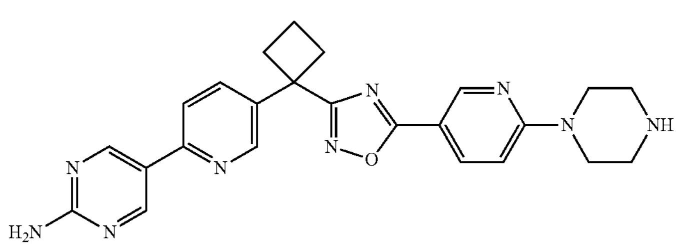 | 19 | 3.79 | 456.7 | E |

TABLE 1-continued

Final compounds.

| Example | Structure | Method | Retention time | m/z | LCMS method |
|---|---|---|---|---|---|
| 4 | 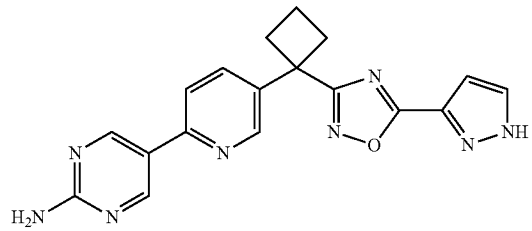 | 10 | 4.35 | 361.6 | E |
| 5 | 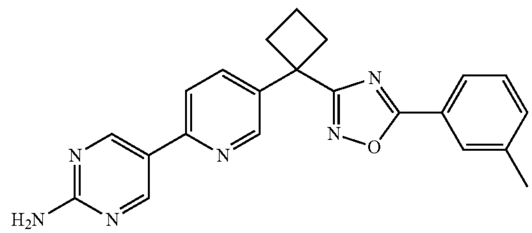 | 10 | 2.33 | 385.1 | I |
| 6 | 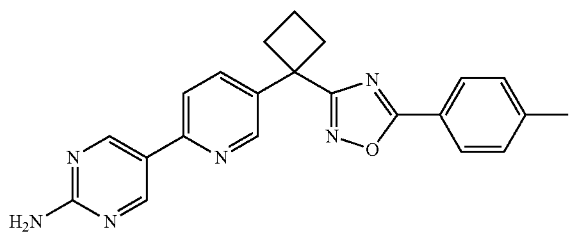 [SMILES: Cc1ccc(-c2nc(C3(c4ccc(-c5cnc(N)nc5)nc4)CCC3)no2)cc1] | 10 | 2.27 | 385.0 | I |
| 7 | 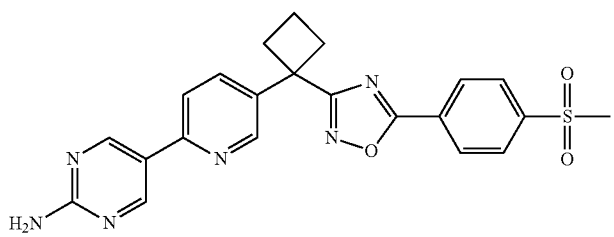 | 10 | 1.58 | 448.9 | I |
| 8 | 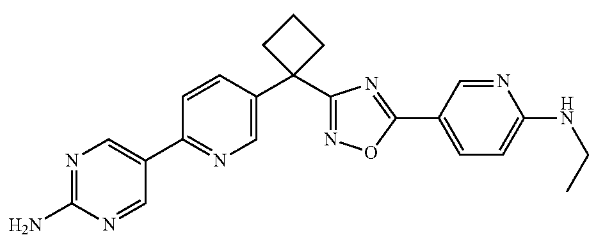 [SMILES: CCNc1ccc(-c2nc(C3(c4ccc(-c5cnc(N)nc5)nc4)CCC3)no2)cn1] | 2 | 4.51 | 415.6 | E |
| 9 | 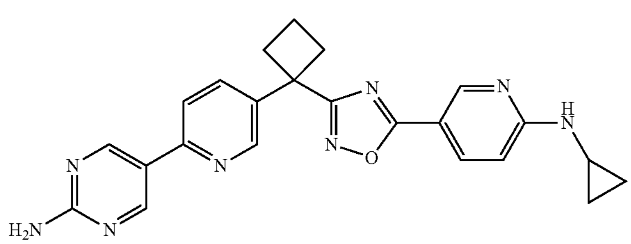 [SMILES: Nc1ncc(-c2ccc(C3(c4noc(-c5ccc(NC6CC6)nc5)n4)CCC3)cn2)cn1] | 2 | 6.11 | 427.6 | B |

TABLE 1-continued

Final compounds.

| Example | Structure | Method | Retention time | m/z | LCMS method |
|---|---|---|---|---|---|
| 10 | 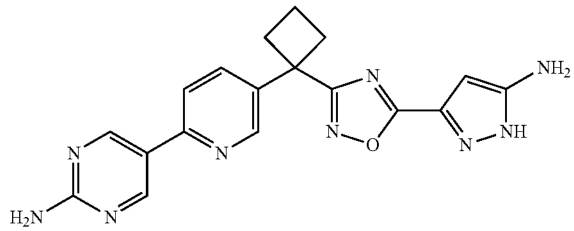 | 18 | 3.97 | 376.6 | E |
| 11 | 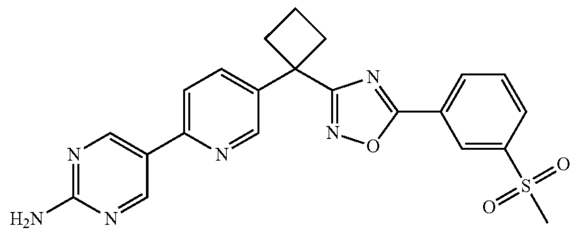 [SMILES: CS(=O)(=O)c1cccc(-c2nc(C3(c4ccc(-c5cnc(N)nc5)nc4)CCC3)no2)c1] | 10 | 2.14 | 449.2 | C |
| 12 | 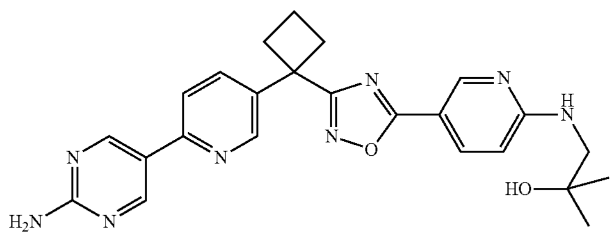 [SMILES: CC(C)(O)CNc1ccc(-c2nc(C3(c4ccc(-c5cnc(N)nc5)nc4)CCC3)no2)cn1] | 2 | 5.95 | 459.6 | B |
| 13 | 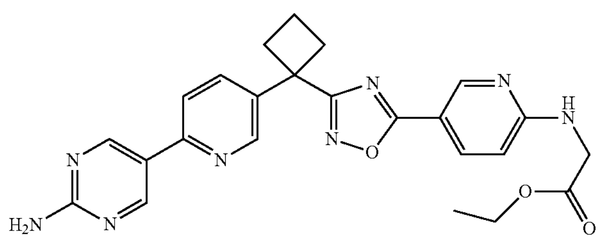 [SMILES: CCOC(=O)CNc1ccc(-c2nc(C3(c4ccc(-c5cnc(N)nc5)nc4)CCC3)no2)cn1] | 2 | 6.70 | 473.6 | B |
| 14 | 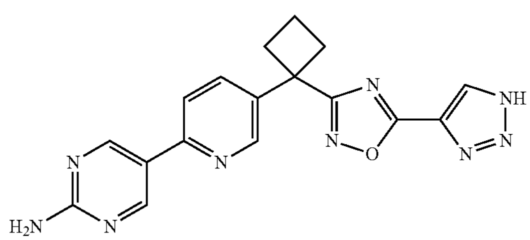 | 10 | 4.23 | 362.6 | E |
| 15 | 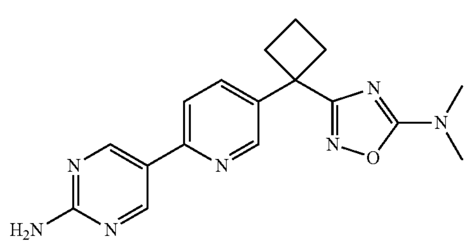 [SMILES: CN(C)c1nc(C2(c3ccc(-c4cnc(N)nc4)nc3)CCC2)no1] | 26 | 1.87 | 338.2 | C |

TABLE 1-continued

Final compounds.

| Example | Structure | Method | Retention time | m/z | LCMS method |
|---|---|---|---|---|---|
| 16 | 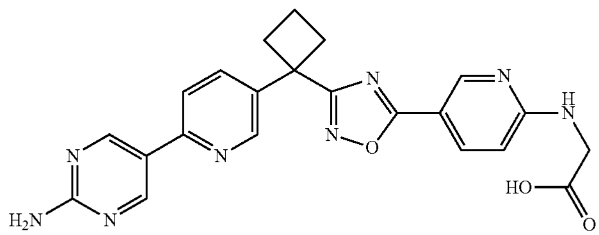 [SMILES: Nc1ncc(-c2ccc(C3(c4noc(-c5ccc(NCC(=O)O)nc5)n4)CCC3)cn2)cn1] | 5 | 4.36 | 445.7 | E |
| 17 | 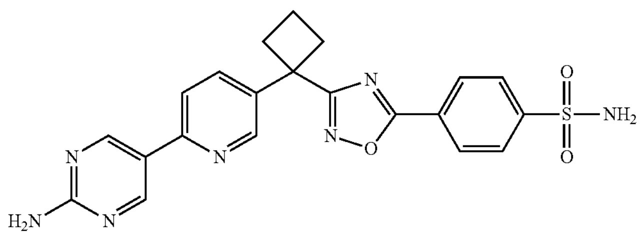 [SMILES: Nc1ncc(-c2ccc(C3(c4noc(-c5ccc(S(N)(=O)=O)cc5)n4)CCC3)cn2)cn1] | 10 | 1.97 | 450.2 | C |
| 18 | 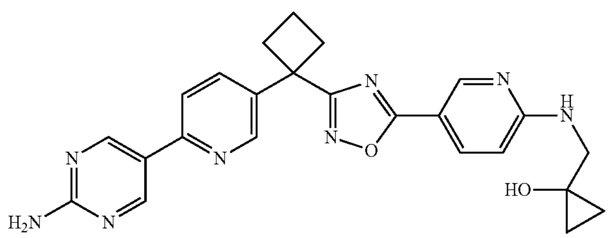 [SMILES: Nc1ncc(-c2ccc(C3(c4noc(-c5ccc(NCC6(O)CC6)nc5)n4)CCC3)cn2)cn1] | 2 | 5.93 | 457.6 | B |
| 19 | 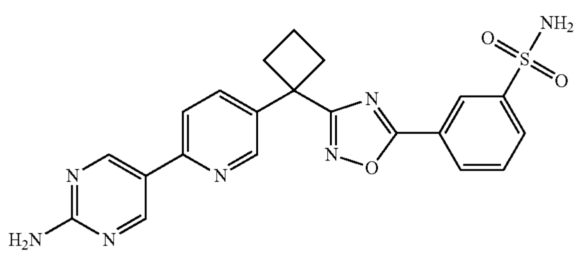 [SMILES: Nc1ncc(-c2ccc(C3(c4noc(-c5cccc(S(N)(=O)=O)c5)n4)CCC3)cn2)cn1] | 10 | 2.01 | 450.2 | C |
| 20 | 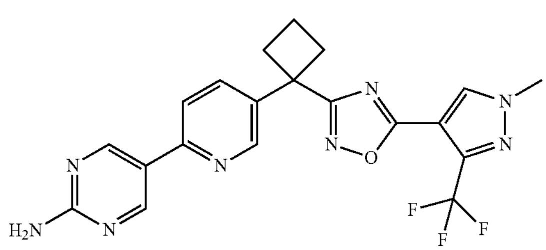 [SMILES: Cn1cc(-c2nc(C3(c4ccc(-c5cnc(N)nc5)nc4)CCC3)no2)c(C(F)(F)F)n1] | 10 | 7.04 | 443.6 | B |
| 21 | 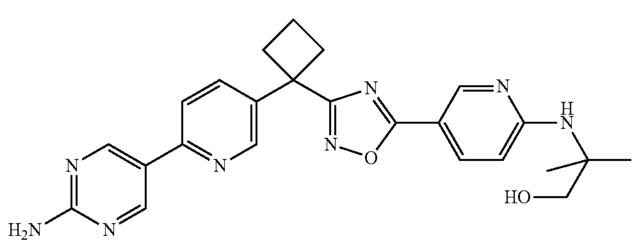 [SMILES: CC(C)(CO)Nc1ccc(-c2nc(C3(c4ccc(-c5cnc(N)nc5)nc4)CCC3)no2)cn1] | 2 | 6.19 | 459.6 | B |

TABLE 1-continued

Final compounds.

| Example | Structure | Method | Retention time | m/z | LCMS method |
|---|---|---|---|---|---|
| 22 | 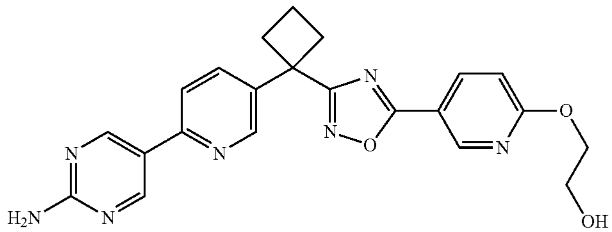 [SMILES: Nc1ncc(-c2ccc(C3(c4noc(-c5ccc(OCCO)nc5)n4)CCC3)cn2)cn1] | 2 | 6.17 | 432.6 | B |
| 23 | 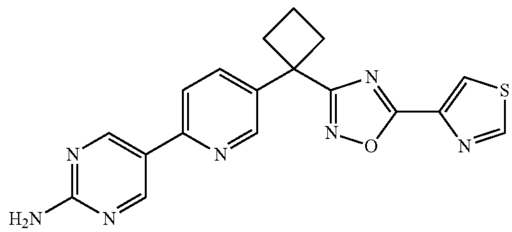 | 10 | 3.33 | 378 | G |
| 24 | 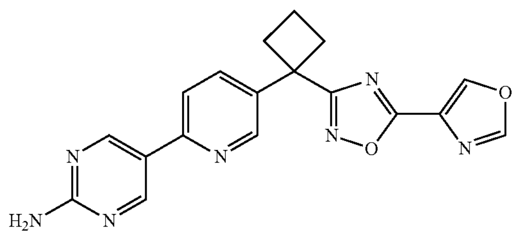 | 10 | 3.23 | 362 | G |
| 25 | 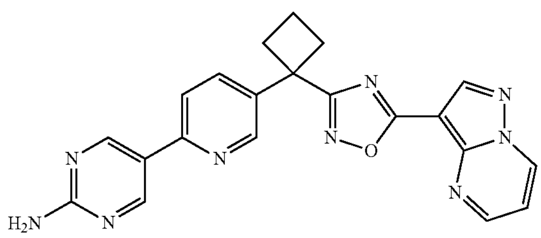 [SMILES: Nc1ncc(-c2ccc(C3(c4noc(-c5cnn6cccnc56)n4)CCC3)cn2)cn1] | 10 | 3.23 | 412 | G |
| 26 | 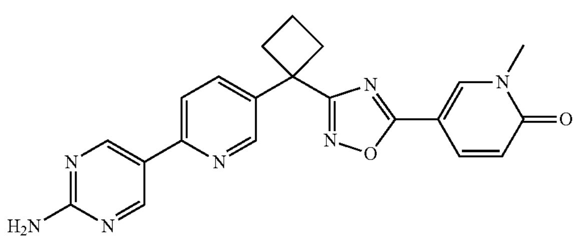 [SMILES: Cn1cc(-c2nc(C3(c4ccc(-c5cnc(N)nc5)nc4)CCC3)no2)ccc1=O] | 10 | 3.22 | 402 | G |
| 27 | 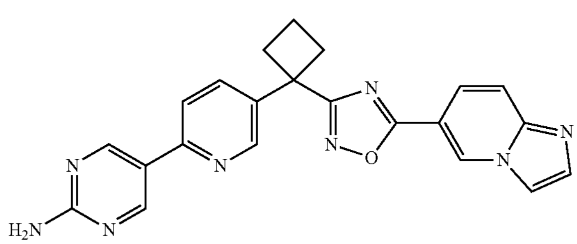 [SMILES: Nc1ncc(-c2ccc(C3(c4noc(-c5ccc6nccn6c5)n4)CCC3)cn2)cn1] | 10 | 2.76 | 411 | G |

TABLE 1-continued
Final compounds.
| Example | Structure | Method | Retention time | m/z | LCMS method |
|---|---|---|---|---|---|
| 28 | 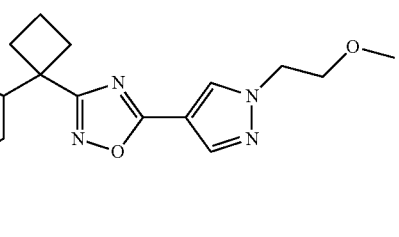 | 10 | 3.42 | 418 | G |
| 29 | 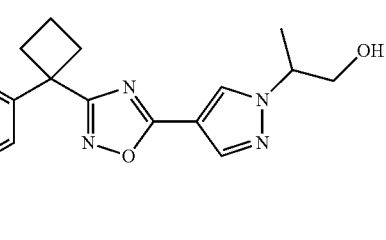 | 27 | 3.19 | 419 | G |
| 30 | 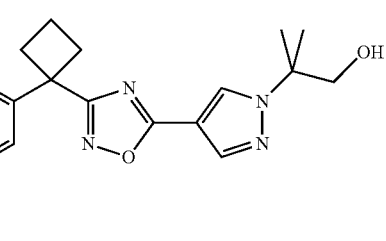 | 27 | 3.37 | 433 | G |
| 31 | 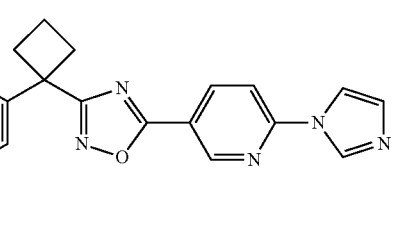 | 7 | 4.02 | 438.6 | E |
| 32 | 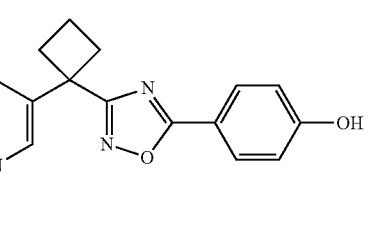 | 1 | 2.05 | 387.2 | C |
| 33 | 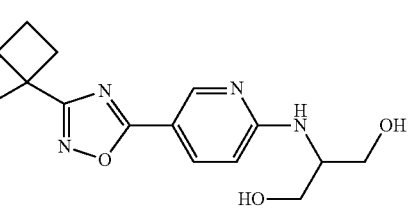 | 2 | 3.93 | 461.7 | E |

TABLE 1-continued

Final compounds.

| Example | Structure | Method | Retention time | m/z | LCMS method |
|---|---|---|---|---|---|
| 34 | 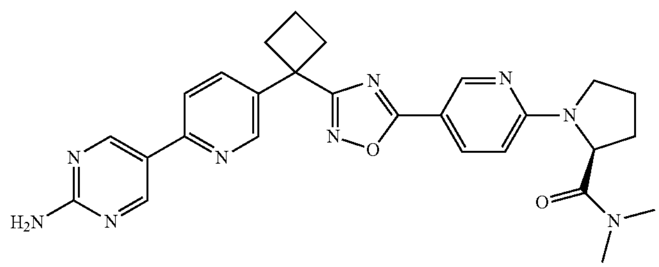 [SMILES: CN(C)C(=O)[C@@H]1CCCN1c1ccc(-c2nc(C3(c4ccc(-c5cnc(N)nc5)nc4)CCC3)no2)cn1] | 2 | 4.82 | 512.8 | E |
| 35 | 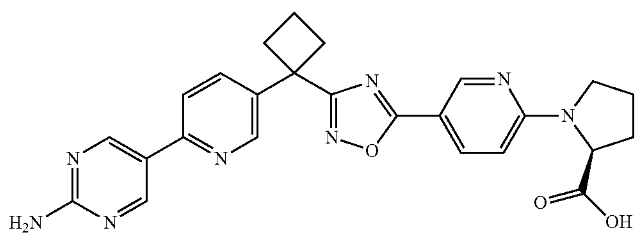 [SMILES: Nc1ncc(-c2ccc(C3(c4noc(-c5ccc(N6CCC[C@H]6C(=O)O)nc5)n4)CCC3)cn2)cn1] | 6 | 4.88 | 485.7 | E |
| 36 | 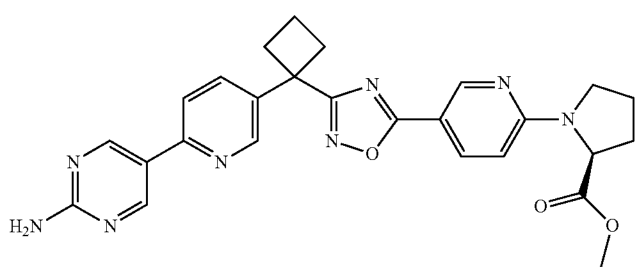 [SMILES: COC(=O)[C@@H]1CCCN1c1ccc(-c2nc(C3(c4ccc(-c5cnc(N)nc5)nc4)CCC3)no2)cn1] | 6 | 5.70 | 499.8 | E |
| 37 | 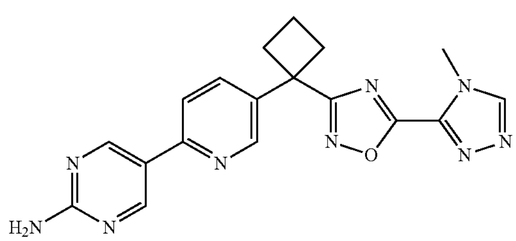 [SMILES: Cn1cnnc1-c1nc(C2(c3ccc(-c4cnc(N)nc4)nc3)CCC2)no1] | 13 | 4.24 | 376.6 | E |
| 38 | 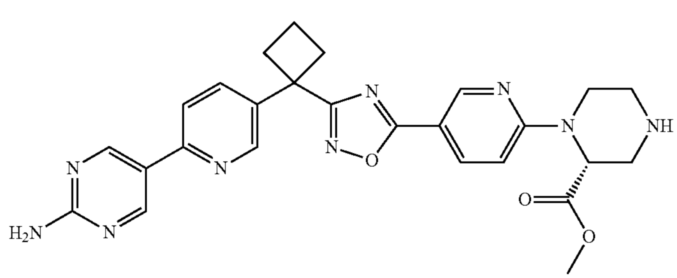 [SMILES: COC(=O)[C@H]1CNCCN1c1ccc(-c2nc(C3(c4ccc(-c5cnc(N)nc5)nc4)CCC3)no2)cn1] | 4 | 3.98 | 514.8 | E |

TABLE 1-continued

Final compounds.

| Example | Structure | Method | Retention time | m/z | LCMS method |
|---|---|---|---|---|---|
| 39 | 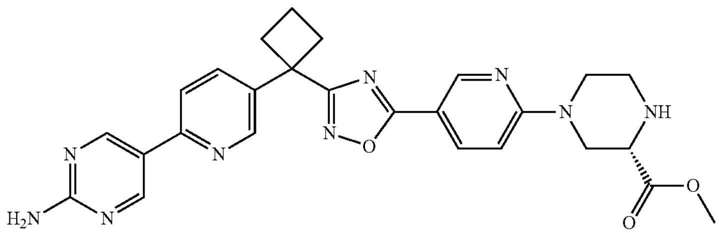 [SMILES: COC(=O)[C@@H]1CN(c2ccc(-c3nc(C4(c5ccc(-c6cnc(N)nc6)nc5)CCC4)no3)cn2)CCN1] | 4 | 3.97 | 514.8 | E |
| 40 | 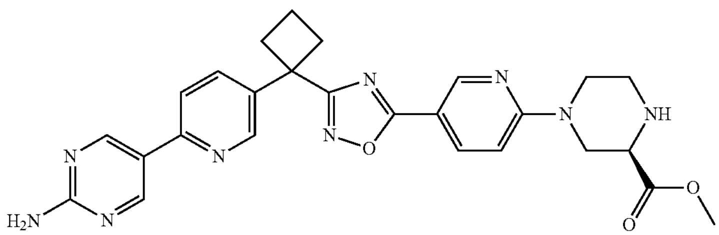 [SMILES: COC(=O)[C@H]1CN(c2ccc(-c3nc(C4(c5ccc(-c6cnc(N)nc6)nc5)CCC4)no3)cn2)CCN1] | 4 | 3.99 | 514.8 | E |
| 41 | 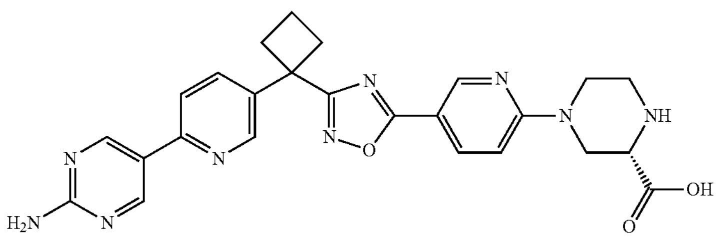 [SMILES: Nc1ncc(-c2ccc(C3(c4noc(-c5ccc(N6CCN[C@H](C(=O)O)C6)nc5)n4)CCC3)cn2)cn1] | 5 | 3.87 | 500.7 | E |
| 42 | 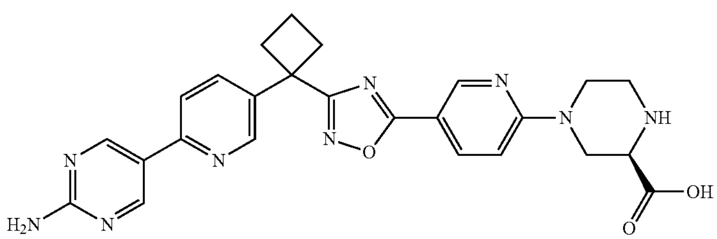 | 5 | 3.89 | 500.7 | E |
| 43 | 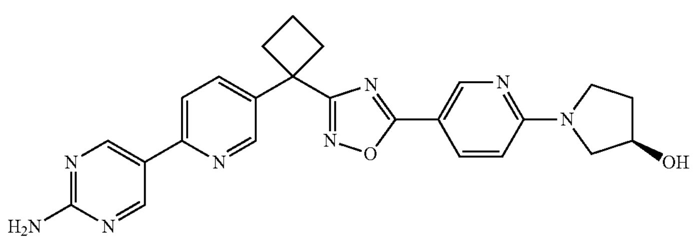 [SMILES: Nc1ncc(-c2ccc(C3(c4noc(-c5ccc(N6CC[C@@H](O)C6)nc5)n4)CCC3)cn2)cn1] | 2 | 1.86 | 457.2 | C |
| 44 | 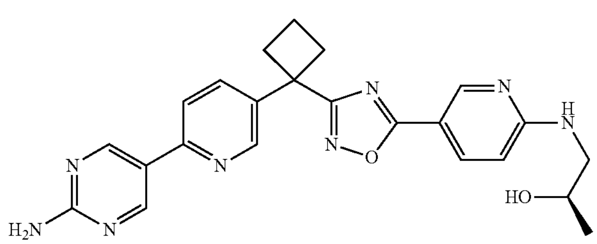 [SMILES: C[C@@H](O)CNc1ccc(-c2nc(C3(c4ccc(-c5cnc(N)nc5)nc4)CCC3)no2)cn1] | 2 | 4.23 | 445.7 | E |

TABLE 1-continued
Final compounds.
| Example | Structure | Method | Retention time | m/z | LCMS method |
|---|---|---|---|---|---|
| 45 | 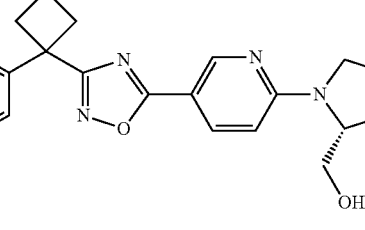 | 2 | 1.33 | 471.2 | F |
| 46 | 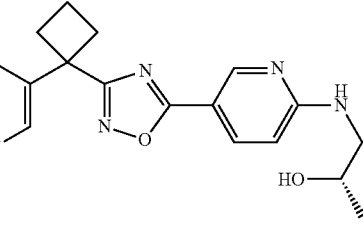 | 2 | 4.23 | 445.7 | B |
| 47 | 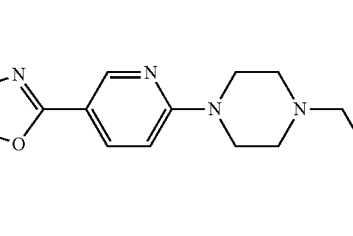 | 2 | 1.12 | 556.2 | F |
| 48 | 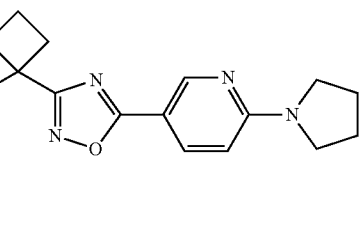 | 2 | 1.26 | 457.2 | F |
| 49 | 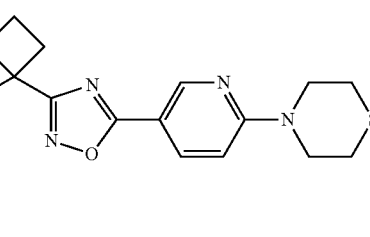 | 2 | 2.05 | 505.2 | C |
| 50 | 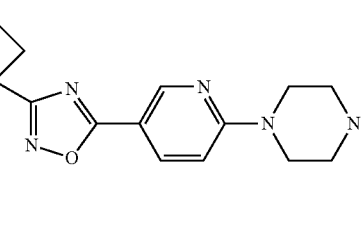 | 2 | 2.22 | 534.2 | C |

TABLE 1-continued

Final compounds.

| Example | Structure | Method | Retention time | m/z | LCMS method |
|---|---|---|---|---|---|
| 51 | 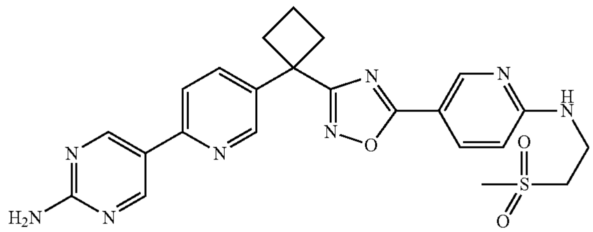 [SMILES: CS(=O)(=O)CCNc1ccc(-c2nc(C3(c4ccc(-c5cnc(N)nc5)nc4)CCC3)no2)cn1] | 2 | 1.84 | 493.2 | C |
| 52 | 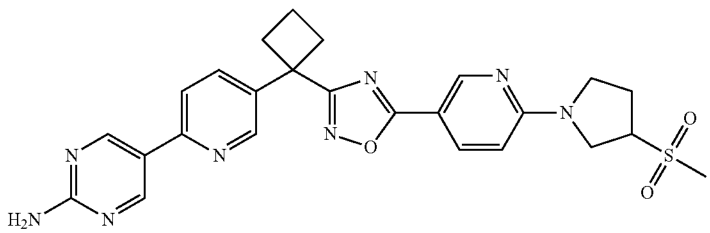 [SMILES: CS(=O)(=O)C1CCN(c2ccc(-c3nc(C4(c5ccc(-c6cnc(N)nc6)nc5)CCC4)no3)cn2)C1] | 2 | 1.97 | 519.2 | C |
| 53 | 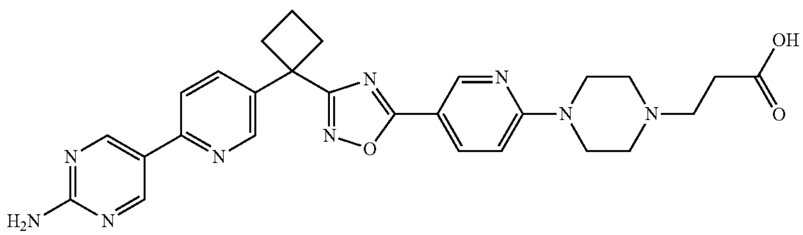 [SMILES: Nc1ncc(-c2ccc(C3(c4noc(-c5ccc(N6CCN(CCC(=O)O)CC6)nc5)n4)CCC3)cn2)cn1] | 3 | 1.10 | 528.2 | F |
| 54 | 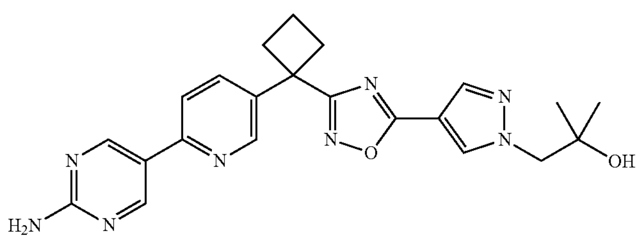 [SMILES: CC(C)(O)Cn1cc(-c2nc(C3(c4ccc(-c5cnc(N)nc5)nc4)CCC3)no2)cn1] | 11 | 1.27 | 433.4 | A |
| 55 | 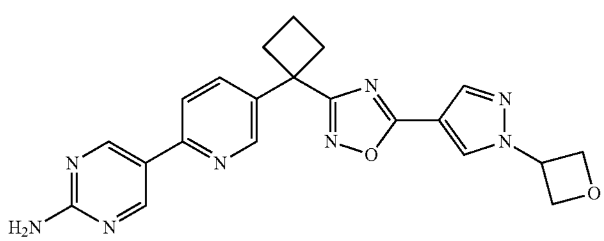 [SMILES: Nc1ncc(-c2ccc(C3(c4noc(-c5cnn(C6COC6)c5)n4)CCC3)cn2)cn1] | 12 | 1.27 | 417.4 | A |
| 56 | 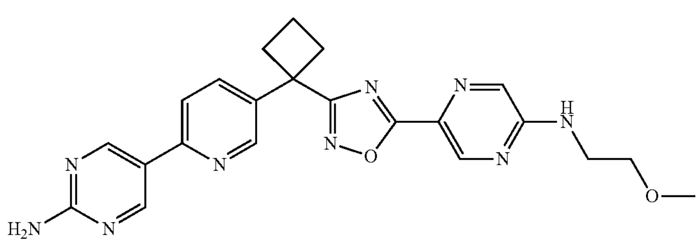 [SMILES: COCCNc1cnc(-c2nc(C3(c4ccc(-c5cnc(N)nc5)nc4)CCC3)no2)cn1] | 27 | 3.41 | 445 | G |

TABLE 1-continued

Final compounds.

| Example | Structure | Method | Retention time | m/z | LCMS method |
|---|---|---|---|---|---|
| 57 | 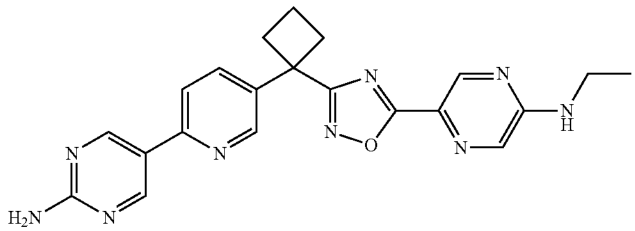 [SMILES: CCNc1cnc(-c2nc(C3(c4ccc(-c5cnc(N)nc5)nc4)CCC3)no2)cn1] | 1 | 3.51 | 415 | G |
| 58 | 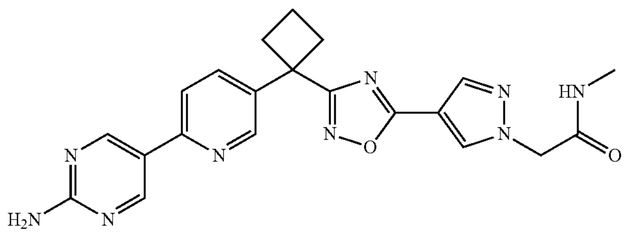 [SMILES: CNC(=O)Cn1cc(-c2nc(C3(c4ccc(-c5cnc(N)nc5)nc4)CCC3)no2)cn1] | 27 | 3.07 | 432.2 | G |
| 59 | 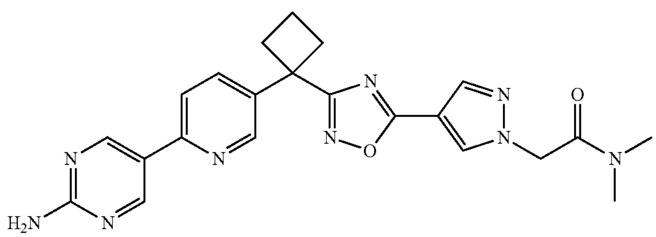 [SMILES: CN(C)C(=O)Cn1cc(-c2nc(C3(c4ccc(-c5cnc(N)nc5)nc4)CCC3)no2)cn1] | 27 | 3.15 | 446 | G |
| 60 | 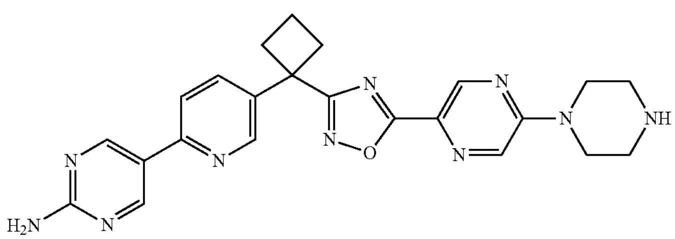 [SMILES: Nc1ncc(-c2ccc(C3(c4noc(-c5cnc(N6CCNCC6)cn5)n4)CCC3)cn2)cn1] | 20 | 0.60 | 457.3 | F |
| 61 | 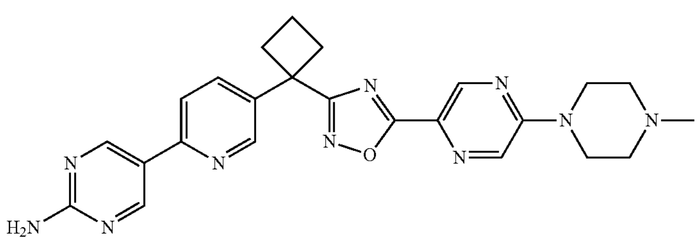 [SMILES: CN1CCN(c2cnc(-c3nc(C4(c5ccc(-c6cnc(N)nc6)nc5)CCC4)no3)cn2)CC1] | 8 | 2.75 | 470.2 | G |
| 62 | 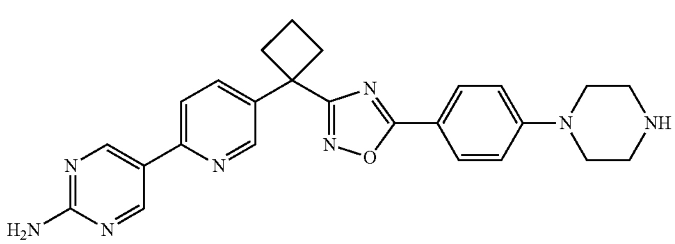 [SMILES: Nc1ncc(-c2ccc(C3(c4noc(-c5ccc(N6CCNCC6)cc5)n4)CCC3)cn2)cn1] | 19 | 1.75 | 455.4 | C |

TABLE 1-continued

Final compounds.

| Example | Structure | Method | Retention time | m/z | LCMS method |
|---|---|---|---|---|---|
| 63 | 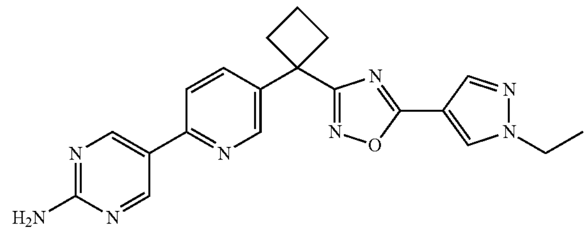 [SMILES: CCn1cc(-c2nc(C3(c4ccc(-c5cnc(N)nc5)nc4)CCC3)no2)cn1] | 11 | 1.37 | 389.4 | A |
| 64 | 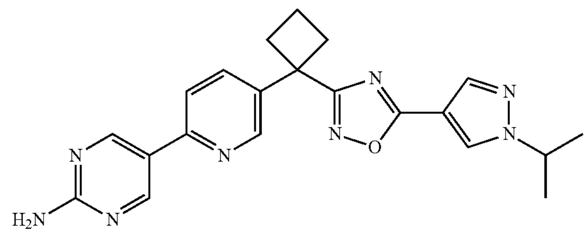 [SMILES: CC(C)n1cc(-c2nc(C3(c4ccc(-c5cnc(N)nc5)nc4)CCC3)no2)cn1] | 11 | 1.47 | 403.4 | A |
| 65 | 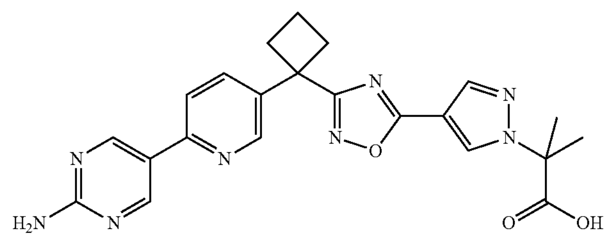 [SMILES: CC(C)(C(=O)O)n1cc(-c2nc(C3(c4ccc(-c5cnc(N)nc5)nc4)CCC3)no2)cn1] | 16 | 1.31 | 447.4 | A |
| 66 | 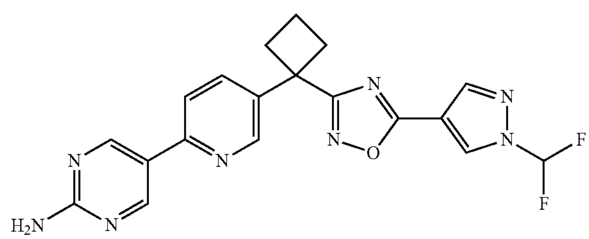 [SMILES: Nc1ncc(-c2ccc(C3(c4noc(-c5cnn(C(F)F)c5)n4)CCC3)cn2)cn1] | 15 | 1.43 | 411.4 | A |
| 67 | 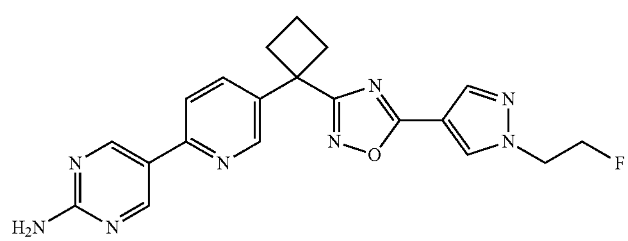 [SMILES: Nc1ncc(-c2ccc(C3(c4noc(-c5cnn(CCF)c5)n4)CCC3)cn2)cn1] | 11 | 1.33 | 407.4 | A |
| 68 | 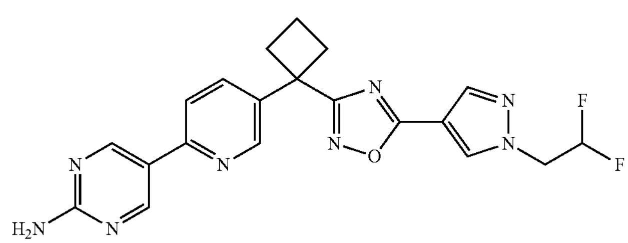 [SMILES: Nc1ncc(-c2ccc(C3(c4noc(-c5cnn(CC(F)F)c5)n4)CCC3)cn2)cn1] | 11 | 1.38 | 425.5 | A |

TABLE 1-continued

Final compounds.

| Example | Structure | Method | Retention time | m/z | LCMS method |
|---|---|---|---|---|---|
| 69 | 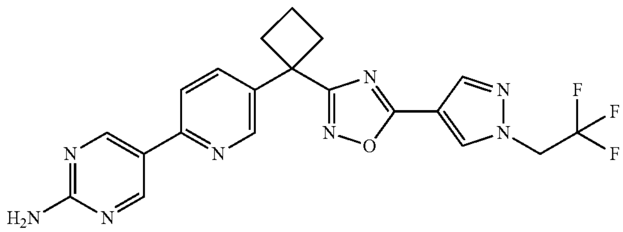 [SMILES: Nc1ncc(-c2ccc(C3(c4noc(-c5cnn(CC(F)(F)F)c5)n4)CCC3)cn2)cn1] | 11 | 1.48 | 443.4 | A |
| 70 | 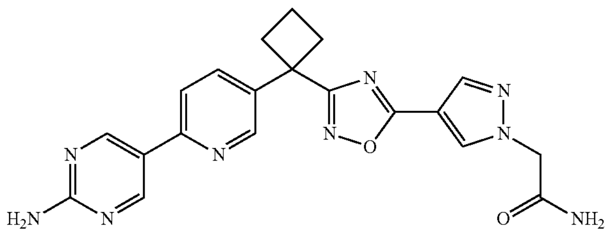 [SMILES: NC(=O)Cn1cc(-c2nc(C3(c4ccc(-c5cnc(N)nc5)nc4)CCC3)no2)cn1] | 11 | 3.97 | 418.3 | E |
| 71 | 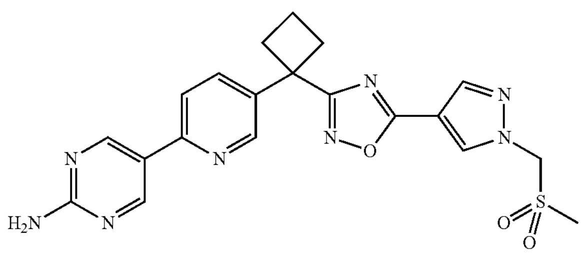 [SMILES: CS(=O)(=O)Cn1cc(-c2nc(C3(c4ccc(-c5cnc(N)nc5)nc4)CCC3)no2)cn1] | 14 | 1.72 | 453.4 | C |
| 72 | 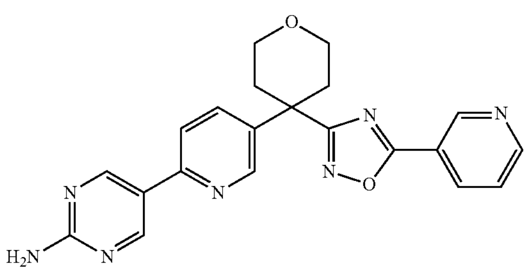 [SMILES: Nc1ncc(-c2ccc(C3(c4noc(-c5cccnc5)n4)CCOCC3)cn2)cn1] | 27 | 3.10 | 402 | G |
| 73 | 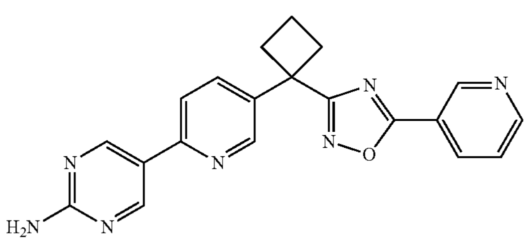 [SMILES: Nc1ncc(-c2ccc(C3(c4noc(-c5cccnc5)n4)CCC3)cn2)cn1] | 28 | 1.69 | 372 | H |
| 74 | 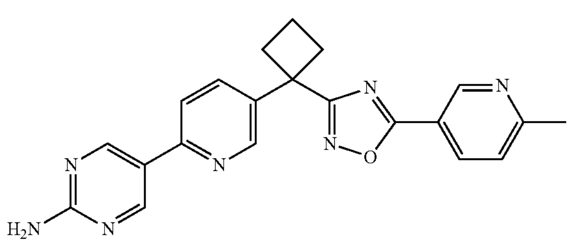 [SMILES: Cc1ccc(-c2nc(C3(c4ccc(-c5cnc(N)nc5)nc4)CCC3)no2)cn1] | 10 | 6.45 | 386.5 | B |

TABLE 1-continued

Final compounds.

| Example | Structure | Method | Retention time | m/z | LCMS method |
|---|---|---|---|---|---|
| 75 | 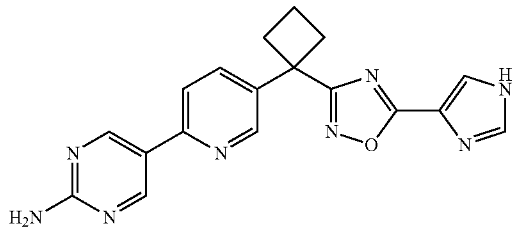 [SMILES: Nc1ncc(-c2ccc(C3(c4noc(-c5c[nH]cn5)n4)CCC3)cn2)cn1] | 10 | 2.94 | 361 | G |
| 76 | 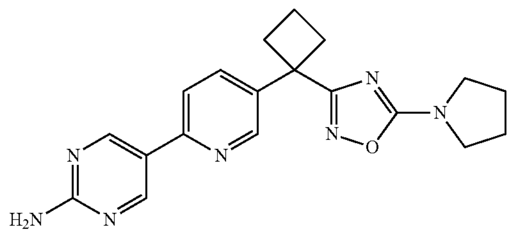 [SMILES: Nc1ncc(-c2ccc(C3(c4noc(N5CCCC5)n4)CCC3)cn2)cn1] | 25 | 3.53 | 364 | G |
| 77 | 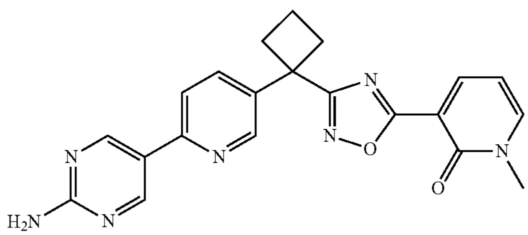 [SMILES: Cn1cccc(-c2nc(C3(c4ccc(-c5cnc(N)nc5)nc4)CCC3)no2)c1=O] | 10 | 2.96 | 402 | G |
| 78 | 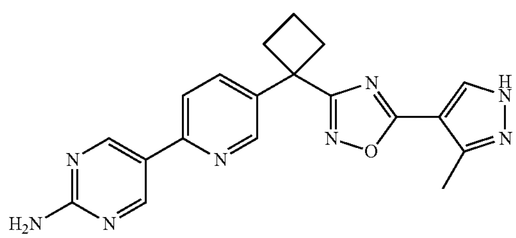 [SMILES: Cc1n[nH]cc1-c1nc(C2(c3ccc(-c4cnc(N)nc4)nc3)CCC2)no1] | 10 | 3.26 | 375 | G |
| 79 | 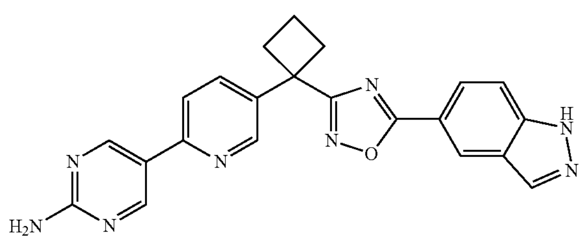 [SMILES: Nc1ncc(-c2ccc(C3(c4noc(-c5ccc6[nH]ncc6c5)n4)CCC3)cn2)cn1] | 10 | 3.59 | 410 | G |
| 80 | 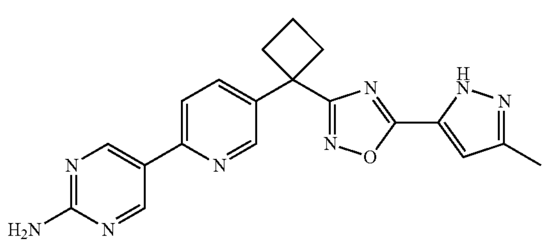 | 10 | 3.34 | 375 | G |

TABLE 1-continued

Final compounds.

| Example | Structure | Method | Retention time | m/z | LCMS method |
|---|---|---|---|---|---|
| 81 | 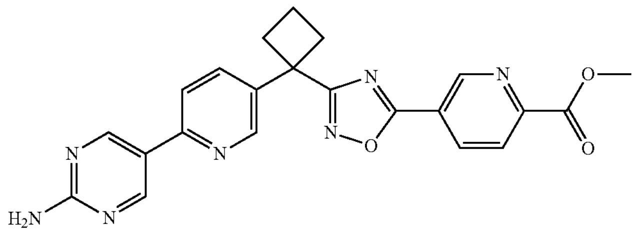 [SMILES: COC(=O)c1ccc(-c2nc(C3(c4ccc(-c5cnc(N)nc5)nc4)CCC3)no2)cn1] | 1 | 1.25 | 430.2 | F |
| 82 | 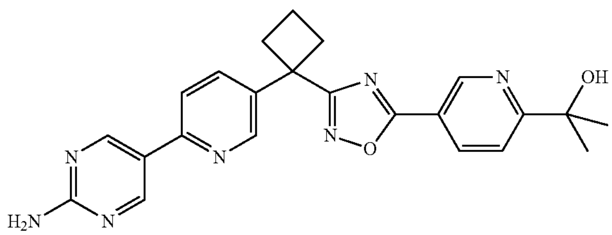 [SMILES: CC(C)(O)c1ccc(-c2nc(C3(c4ccc(-c5cnc(N)nc5)nc4)CCC3)no2)cn1] | 17 | 1.33 | 430.2 | F |
| 83 | 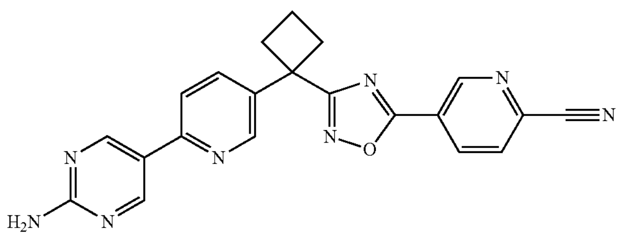 [SMILES: N#Cc1ccc(-c2nc(C3(c4ccc(-c5cnc(N)nc5)nc4)CCC3)no2)cn1] | 1 | 1.58 | 397.6 | F |
| 84 | 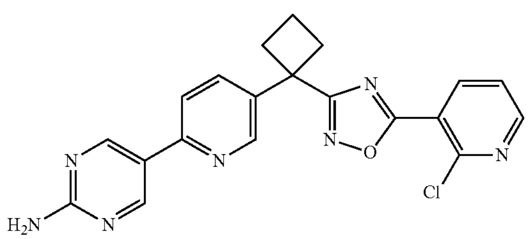 [SMILES: Nc1ncc(-c2ccc(C3(c4noc(-c5cccnc5Cl)n4)CCC3)cn2)cn1] | 21 | 5.57 | 406.4 | D |
| 85 | 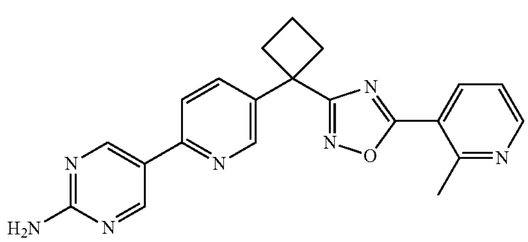 [SMILES: Cc1ncccc1-c1nc(C2(c3ccc(-c4cnc(N)nc4)nc3)CCC2)no1] | 21 | 2.34 | 386.2 | F |
| 86 | 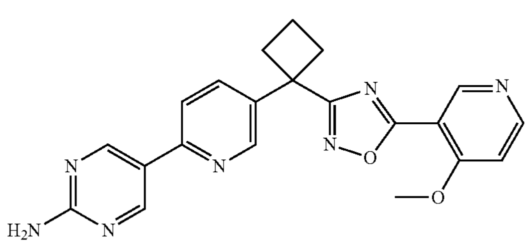 | 10 | 2.02 | 402.2 | C |

TABLE 1-continued

Final compounds.

| Example | Structure | Method | Retention time | m/z | LCMS method |
|---|---|---|---|---|---|
| 87 | 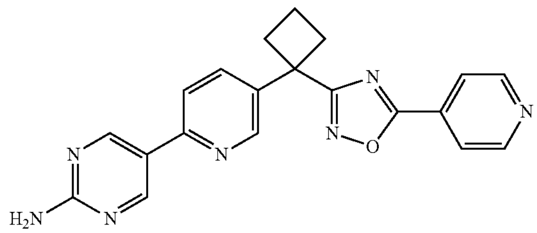 | 21 | 5.14 | 372.4 | D |
| 88 | 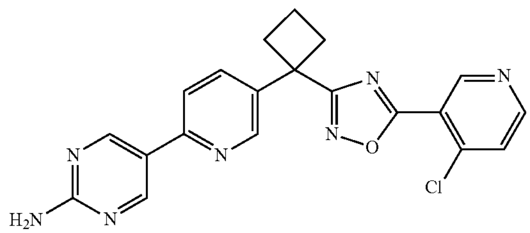 [SMILES: Nc1ncc(-c2ccc(C3(c4noc(-c5cnccc5Cl)n4)CCC3)cn2)cn1] | 1 | 6.66 | 406.5 | B |
| 89 | 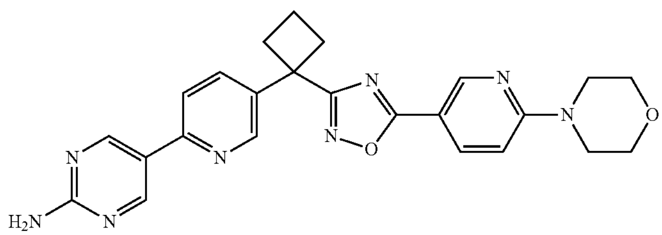 [SMILES: Nc1ncc(-c2ccc(C3(c4noc(-c5ccc(N6CCOCC6)nc5)n4)CCC3)cn2)cn1] | 10 | 1.23 | 457.2 | F |
| 90 | 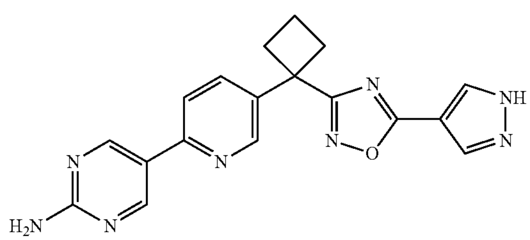 [SMILES: Nc1ncc(-c2ccc(C3(c4noc(-c5cn[nH]c5)n4)CCC3)cn2)cn1] | 10 | 4.84 | 361.6 | D |
| 91 | 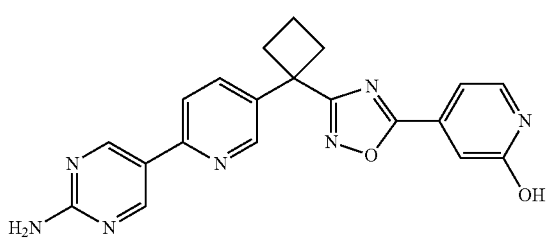 [SMILES: Nc1ncc(-c2ccc(C3(c4noc(-c5ccnc(O)c5)n4)CCC3)cn2)cn1] | 10 | 1.74 | 388.2 | E |
| 92 | 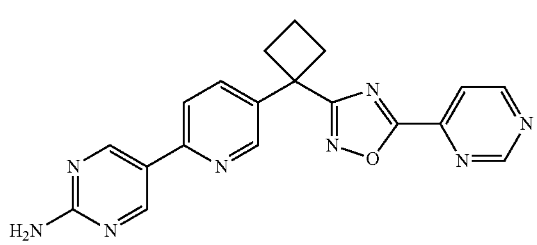 [SMILES: Nc1ncc(-c2ccc(C3(c4noc(-c5ccncn5)n4)CCC3)cn2)cn1] | 10 | 1.86 | 373.2 | C |

TABLE 1-continued

Final compounds.

| Example | Structure | Method | Retention time | m/z | LCMS method |
|---|---|---|---|---|---|
| 93 | 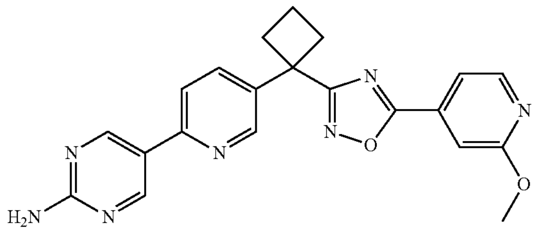 [SMILES: COc1cc(-c2nc(C3(c4ccc(-c5cnc(N)nc5)nc4)CCC3)no2)ccn1] | 10 | 2.53 | 402.2 | C |
| 94 | 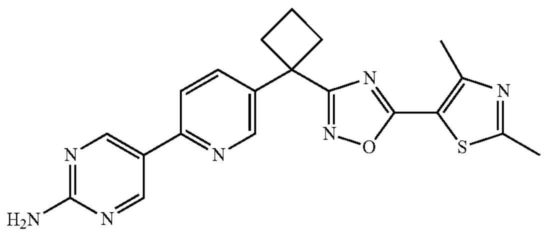 [SMILES: Cc1nc(C)c(-c2nc(C3(c4ccc(-c5cnc(N)nc5)nc4)CCC3)no2)s1] | 1 | 6.78 | 406.5 | B |
| 95 | 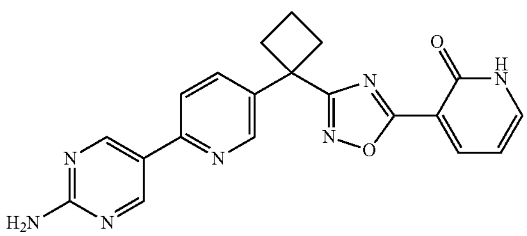 [SMILES: Nc1ncc(-c2ccc(C3(c4noc(-c5ccc[nH]c5=O)n4)CCC3)cn2)cn1] | 24 | 5.57 | 388.5 | B |
| 96 | 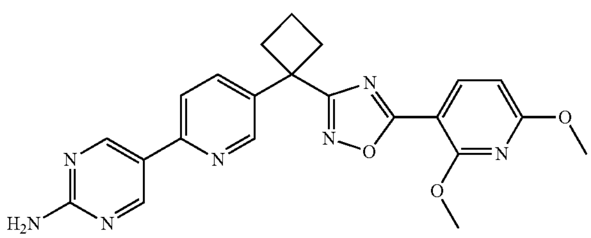 | 10 | 2.72 | 432.2 | C |
| 97 | 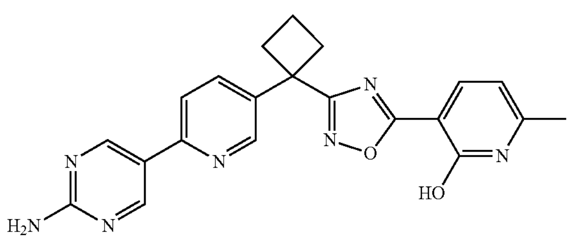 [SMILES: Cc1ccc(-c2nc(C3(c4ccc(-c5cnc(N)nc5)nc4)CCC3)no2)c(O)n1] | 10 | 1.75 | 402.2 | C |
| 98 | 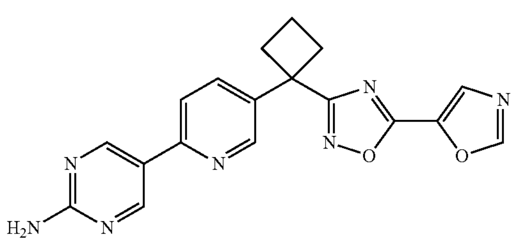 [SMILES: Nc1ncc(-c2ccc(C3(c4noc(-c5cnco5)n4)CCC3)cn2)cn1] | 10 | 1.92 | 362.2 | C |

TABLE 1-continued

Final compounds.

| Example | Structure | Method | Retention time | m/z | LCMS method |
|---|---|---|---|---|---|
| 99 | 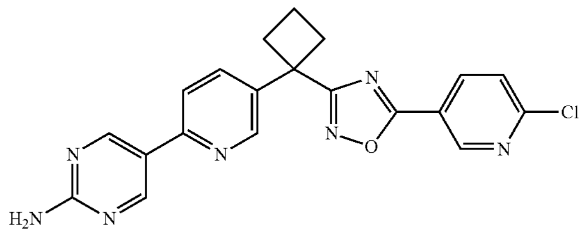 [SMILES: Nc1ncc(-c2ccc(C3(c4noc(-c5ccc(Cl)nc5)n4)CCC3)cn2)cn1] | 1 | 1.58 | 406.2 | A |
| 100 | 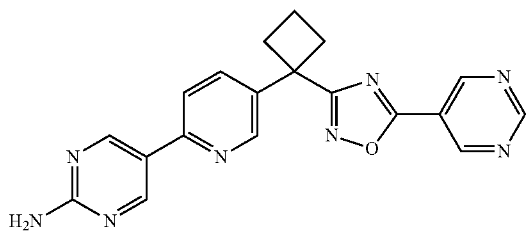 | 10 | 4.88 | 373.5 | D |
| 101 | 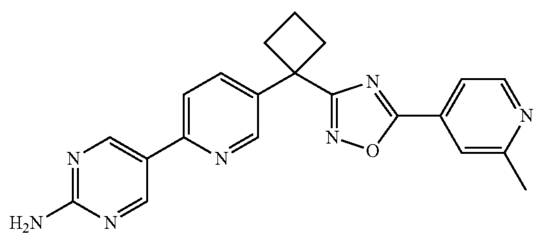 [SMILES: Cc1cc(-c2nc(C3(c4ccc(-c5cnc(N)nc5)nc4)CCC3)no2)ccn1] | 10 | 2.13 | 386.2 | C |
| 102 | 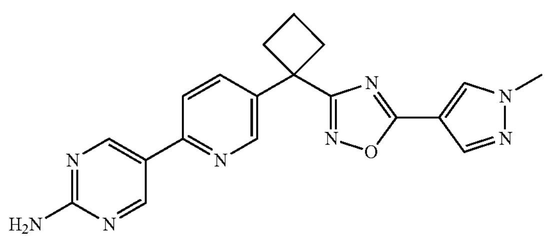 [SMILES: Cn1cc(-c2nc(C3(c4ccc(-c5cnc(N)nc5)nc4)CCC3)no2)cn1] | 10 | 1.92 | 375.2 | C |
| 103 | 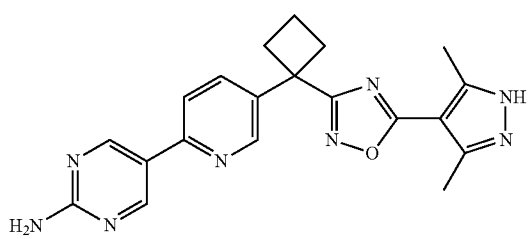 [SMILES: Cc1n[nH]c(C)c1-c1nc(C2(c3ccc(-c4cnc(N)nc4)nc3)CCC2)no1] | 10 | 2.08 | 389.2 | F |
| 104 | 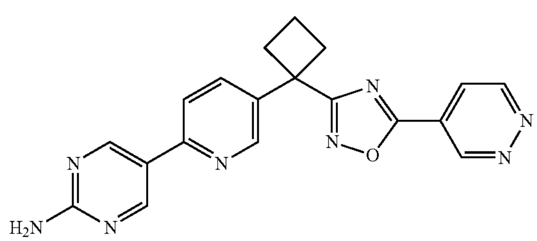 | 10 | 1.80 | 373.2 | C |

TABLE 1-continued
Final compounds.
| Example | Structure | Method | Retention time | m/z | LCMS method |
|---|---|---|---|---|---|
| 105 | 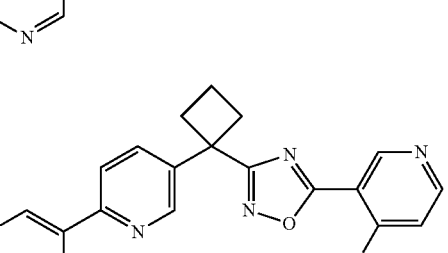 | 22 | 5.97 | 387.6 | B |
| 106 | 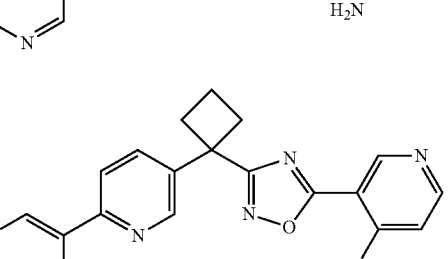 | 22 | 4.43 | 387.6 | D |
| 107 | 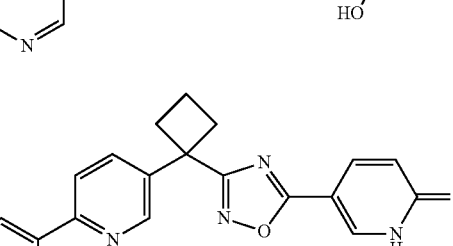 | 24 | 4.34 | 388.6 | D |
| 108 | 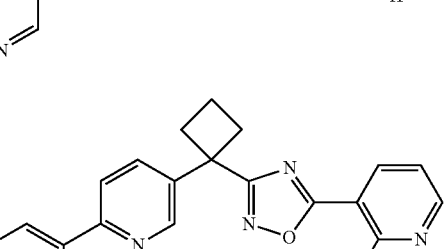 | 24 | 5.75 | 388.5 | B |
| 109 | 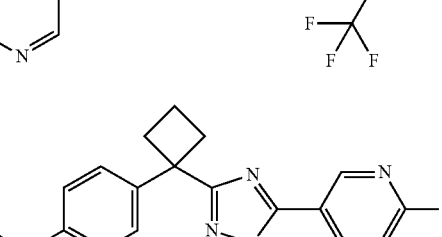 | 10 | 5.75 | 440.5 | D |
| 110 | 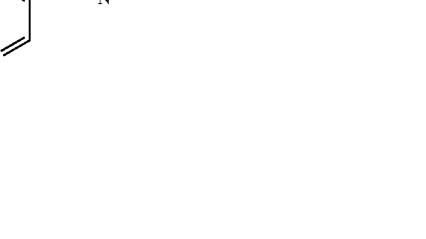 | 2 | 5.50 | 415.7 | D |

TABLE 1-continued

Final compounds.

| Example | Structure | Method | Retention time | m/z | LCMS method |
|---|---|---|---|---|---|
| 111 | 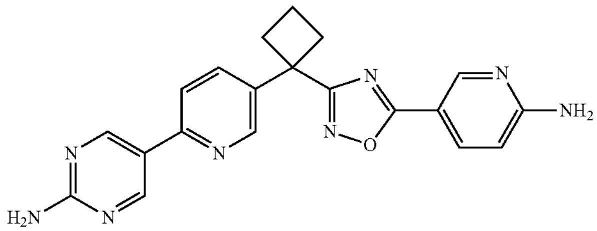 [SMILES: Nc1ccc(-c2nc(C3(c4ccc(-c5cnc(N)nc5)nc4)CCC3)no2)cn1] | 2 | 5.59 | 387.5 | B |
| 112 | 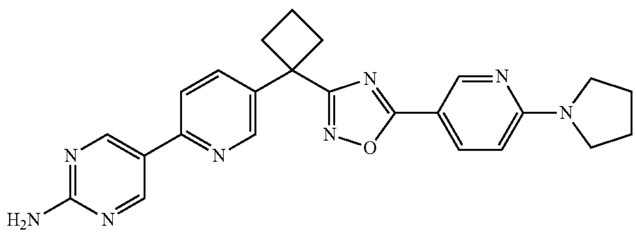 [SMILES: Nc1ncc(-c2ccc(C3(c4noc(-c5ccc(N6CCCC6)nc5)n4)CCC3)cn2)cn1] | 2 | 6.35 | 441.6 | B |
| 113 | 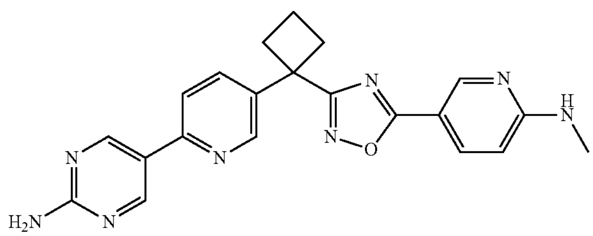 [SMILES: CNc1ccc(-c2nc(C3(c4ccc(-c5cnc(N)nc5)nc4)CCC3)no2)cn1] | 2 | 4.55 | 401.6 | D |
| 114 | 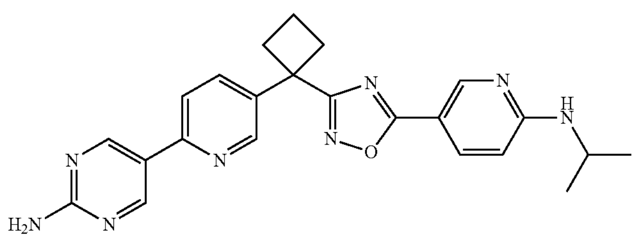 [SMILES: CC(C)Nc1ccc(-c2nc(C3(c4ccc(-c5cnc(N)nc5)nc4)CCC3)no2)cn1] | 2 | 6.36 | 429.6 | B |
| 115 | 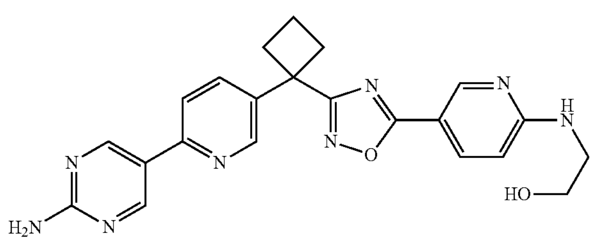 [SMILES: Nc1ncc(-c2ccc(C3(c4noc(-c5ccc(NCCO)nc5)n4)CCC3)cn2)cn1] | 2 | 4.47 | 431.7 | D |
| 116 | 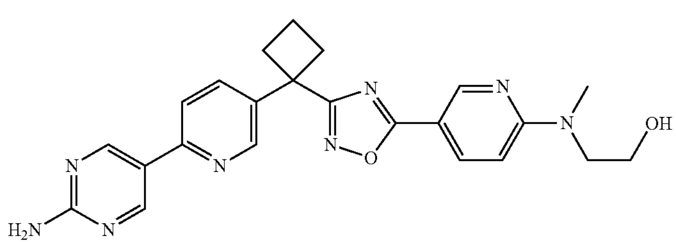 [SMILES: CN(CCO)c1ccc(-c2nc(C3(c4ccc(-c5cnc(N)nc5)nc4)CCC3)no2)cn1] | 2 | 2.04 | 445.2 | C |

TABLE 1-continued

Final compounds.

| Example | Structure | Method | Retention time | m/z | LCMS method |
|---|---|---|---|---|---|
| 117 | 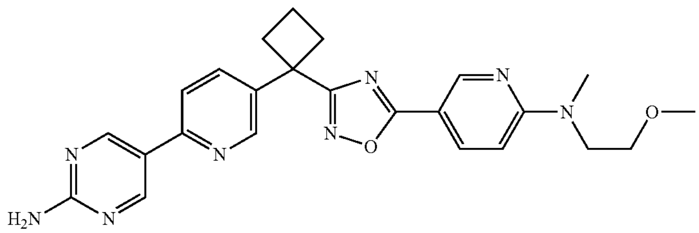 [SMILES: COCCN(C)c1ccc(-c2nc(C3(c4ccc(-c5cnc(N)nc5)nc4)CCC3)no2)cn1] | 2 | 2.51 | 459.2 | C |
| 118 | 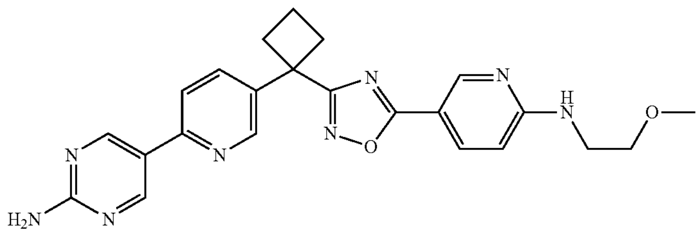 [SMILES: COCCNc1ccc(-c2nc(C3(c4ccc(-c5cnc(N)nc5)nc4)CCC3)no2)cn1] | 2 | 2.14 | 445.2 | C |
| 119 | 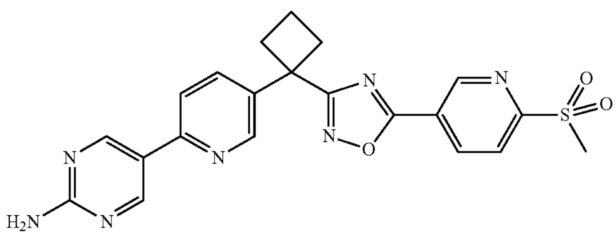 [SMILES: CS(=O)(=O)c1ccc(-c2nc(C3(c4ccc(-c5cnc(N)nc5)nc4)CCC3)no2)cn1] | 9 | 2.04 | 450.2 | C |
| 120 | 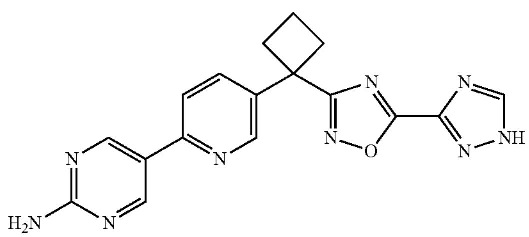 [SMILES: Nc1ncc(-c2ccc(C3(c4noc(-c5nc[nH]n5)n4)CCC3)cn2)cn1] | 1 | 3.99 | 362.6 | E |
| 121 | 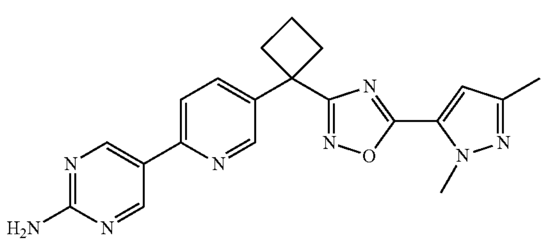 [SMILES: Cc1cc(-c2nc(C3(c4ccc(-c5cnc(N)nc5)nc4)CCC3)no2)n(C)n1] | 21 | 6.78 | 389.5 | E |
| 122 | 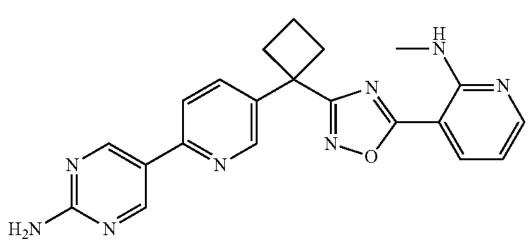 [SMILES: CNc1ncccc1-c1nc(C2(c3ccc(-c4cnc(N)nc4)nc3)CCC2)no1] | 23 | 5.32 | 401.7 | D |

TABLE 1-continued

Final compounds.

| Example | Structure | Method | Retention time | m/z | LCMS method |
|---|---|---|---|---|---|
| 123 | 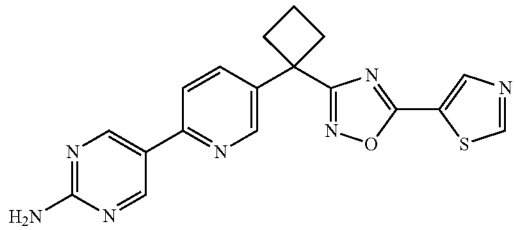 [SMILES: Nc1ncc(-c2ccc(C3(c4noc(-c5cncs5)n4)CCC3)cn2)cn1] | 10 | 4.86 | 378.5 | E |
| 124 | 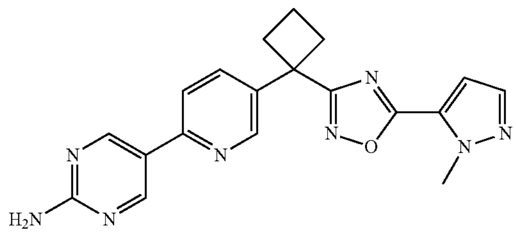 [SMILES: Cn1nccc1-c1nc(C2(c3ccc(-c4cnc(N)nc4)nc3)CCC2)no1] | 10 | 4.53 | 375.6 | E |
| 125 | 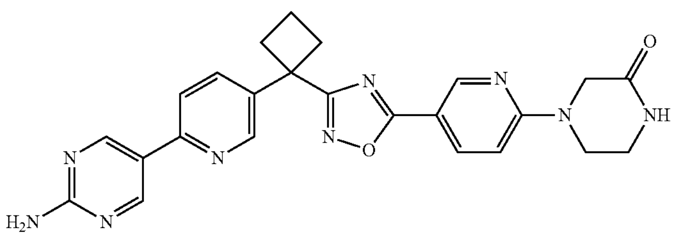 [SMILES: Nc1ncc(-c2ccc(C3(c4noc(-c5ccc(N6CCNC(=O)C6)nc5)n4)CCC3)cn2)cn1] | 2 | 4.78 | 470.7 | D |
| 126 | 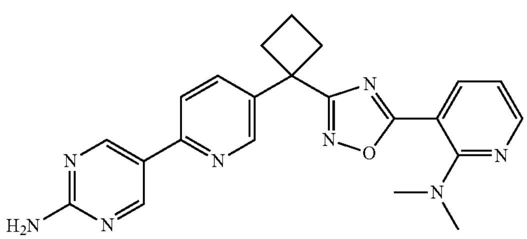 [SMILES: CN(C)c1ncccc1-c1nc(C2(c3ccc(-c4cnc(N)nc4)nc3)CCC2)no1] | 23 | 6.60 | 415.6 | B |
| 127 | 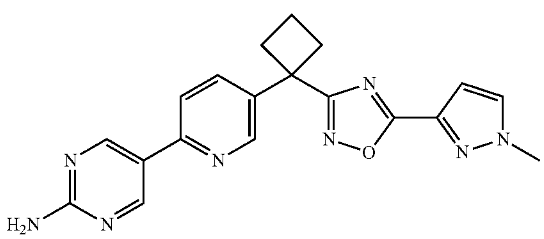 [SMILES: Cn1ccc(-c2nc(C3(c4ccc(-c5cnc(N)nc5)nc4)CCC3)no2)n1] | 10 | 4.64 | 375.6 | E |
| 128 | 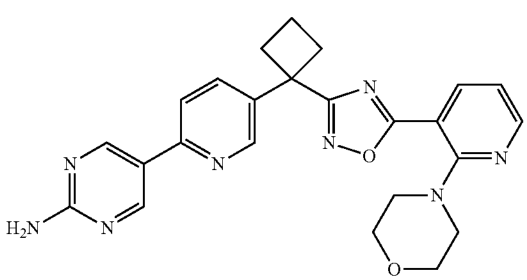 [SMILES: Nc1ncc(-c2ccc(C3(c4noc(-c5cccnc5N5CCOCC5)n4)CCC3)cn2)cn1] | 23 | 5.14 | 457.7 | E |

TABLE 1-continued

Final compounds.

| Example | Structure | Method | Retention time | m/z | LCMS method |
|---|---|---|---|---|---|
| 129 | 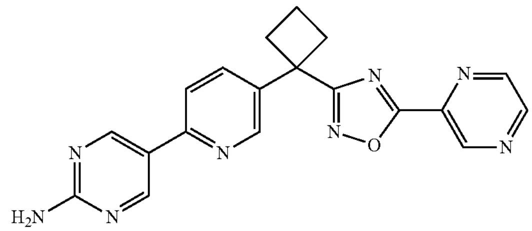 [SMILES: Nc1ncc(-c2ccc(C3(c4noc(-c5cnccn5)n4)CCC3)cn2)cn1] | 10 | 3.40 | 373 | G |
| 130 | 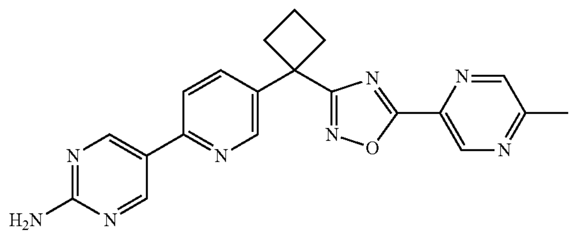 [SMILES: Cc1cnc(-c2nc(C3(c4ccc(-c5cnc(N)nc5)nc4)CCC3)no2)cn1] | 10 | 3.47 | 387 | G |
| 131 | 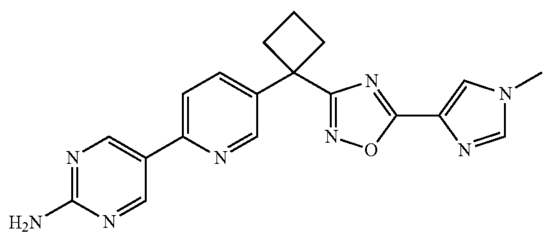 [SMILES: Cn1cnc(-c2nc(C3(c4ccc(-c5cnc(N)nc5)nc4)CCC3)no2)c1] | 10 | 3.10 | 375 | G |
| 132 | 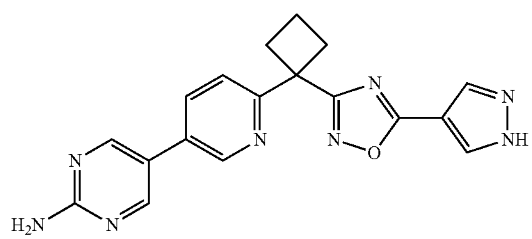 [SMILES: Nc1ncc(-c2ccc(C3(c4noc(-c5cn[nH]c5)n4)CCC3)nc2)cn1] | 1 | 1.56 | 361.2 | I |
| 133 | 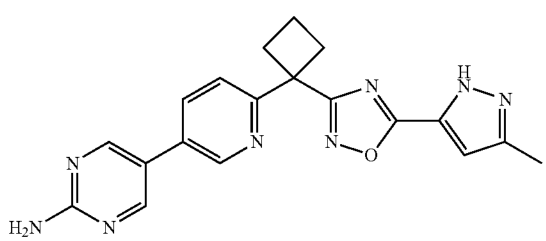 [SMILES: Cc1cc(-c2nc(C3(c4ccc(-c5cnc(N)nc5)cn4)CCC3)no2)[nH]n1] | 10 | 1.77 | 375.2 | I |
| 134 | 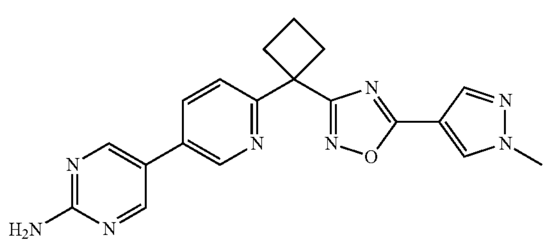 [SMILES: Cn1cc(-c2nc(C3(c4ccc(-c5cnc(N)nc5)cn4)CCC3)no2)cn1] | 10 | 1.71 | 375.2 | I |

TABLE 1-continued

Final compounds.

| Example | Structure | Method | Retention time | m/z | LCMS method |
|---|---|---|---|---|---|
| 135 | 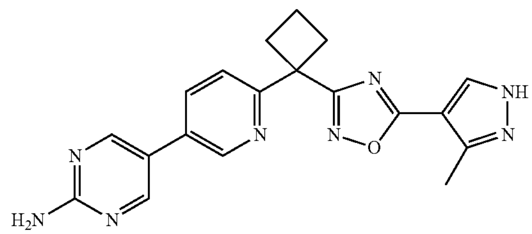 [SMILES: Cc1n[nH]cc1-c1nc(C2(c3ccc(-c4cnc(N)nc4)cn3)CCC2)no1] | 10 | 1.68 | 375.2 | I |
| 136 | 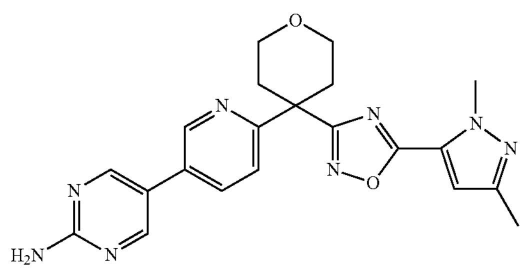 | 28 | 3.47 | 419.2 | G |
| 137 | 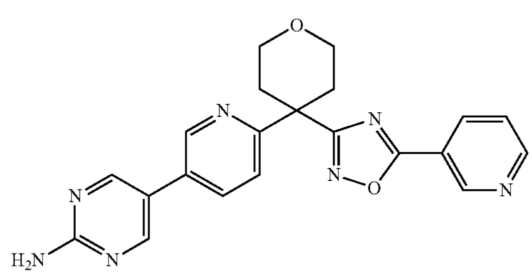 [SMILES: Nc1ncc(-c2ccc(C3(c4noc(-c5cccnc5)n4)CCOCC3)nc2)cn1] | 28 | 3.12 | 402.2 | G |
| 138 | 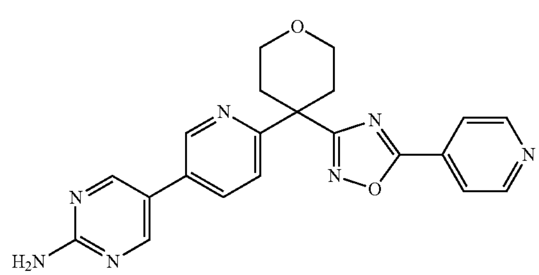 [SMILES: Nc1ncc(-c2ccc(C3(c4noc(-c5ccncc5)n4)CCOCC3)nc2)cn1] | 28 | 3.11 | 402.1 | G |
| 139 | 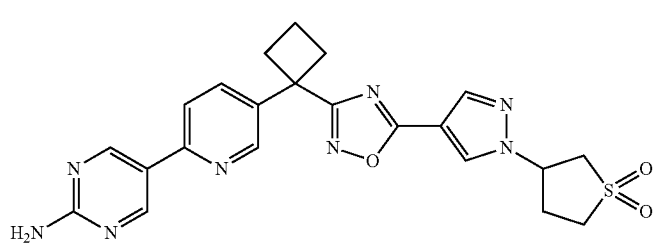 [SMILES: Nc1ncc(-c2ccc(C3(c4noc(-c5cnn(C6CCS(=O)(=O)C6)c5)n4)CCC3)cn2)cn1] | 29 | 1.06 | 479.2 | F |

TABLE 1-continued

Final compounds.

| Example | Structure | Method | Retention time | m/z | LCMS method |
|---|---|---|---|---|---|
| 140 | 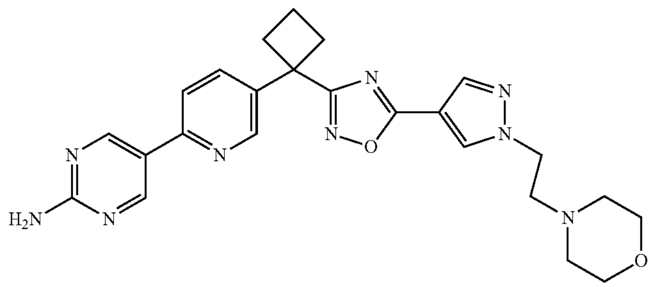 [SMILES: Nc1ncc(-c2ccc(C3(c4noc(-c5cnn(CCN6CCOCC6)c5)n4)CCC3)cn2)cn1] | 29 | 0.94 | 474.4 | F |
| 141 | 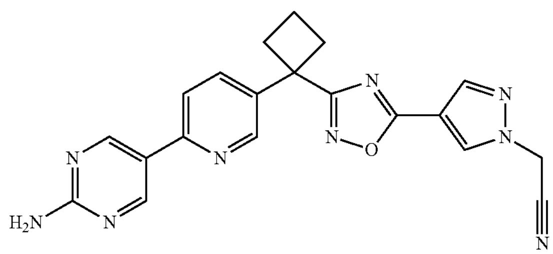 [SMILES: N#CCn1cc(-c2nc(C3(c4ccc(-c5cnc(N)nc5)nc4)CCC3)no2)cn1] | 29 | 1.08 | 400.4 | F |
| 142 | 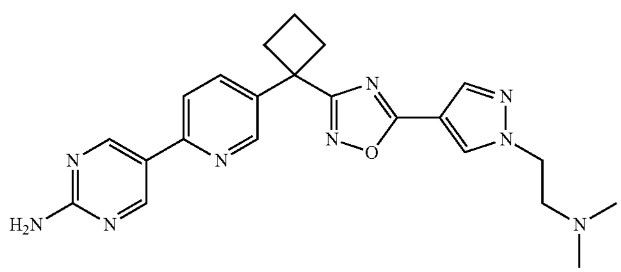 [SMILES: CN(C)CCn1cc(-c2nc(C3(c4ccc(-c5cnc(N)nc5)nc4)CCC3)no2)cn1] | 29 | 0.88 | 432.4 | F |
| 143 | 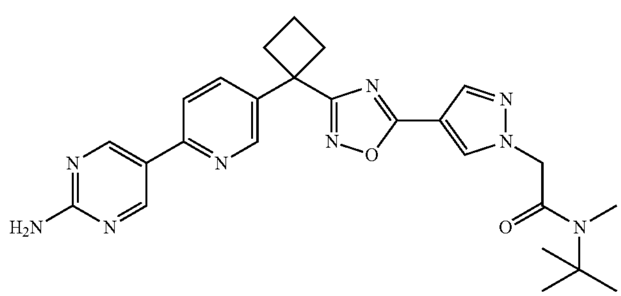 [SMILES: CN(C(=O)Cn1cc(-c2nc(C3(c4ccc(-c5cnc(N)nc5)nc4)CCC3)no2)cn1)C(C)(C)C] | 30 | 0.91 | 474.3 | J |
| 144 | 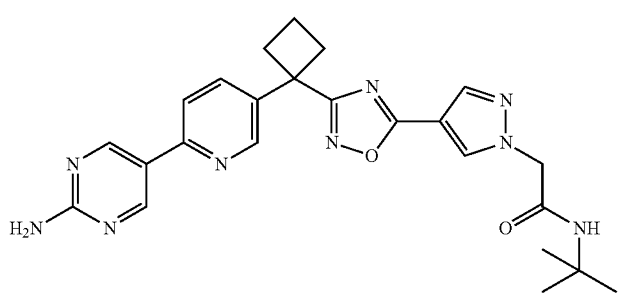 [SMILES: CC(C)(C)NC(=O)Cn1cc(-c2nc(C3(c4ccc(-c5cnc(N)nc5)nc4)CCC3)no2)cn1] | 30 | 0.95 | 488.4 | J |

TABLE 1-continued

Final compounds.

| Example | Structure | Method | Retention time | m/z | LCMS method |
|---|---|---|---|---|---|
| 145 | 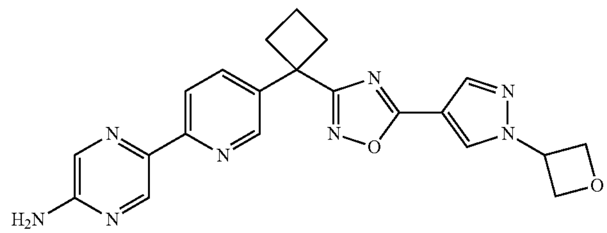 [SMILES: Nc1cnc(-c2ccc(C3(c4noc(-c5cnn(C6COC6)c5)n4)CCC3)cn2)cn1] | 31 | 0.65 | 417.3 | J |
| 146 | 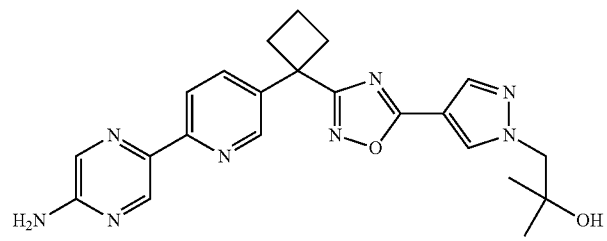 [SMILES: CC(C)(O)Cn1cc(-c2nc(C3(c4ccc(-c5cnc(N)cn5)nc4)CCC3)no2)cn1] | 31 | 1.05 | 433.4 | F |
| 147 | 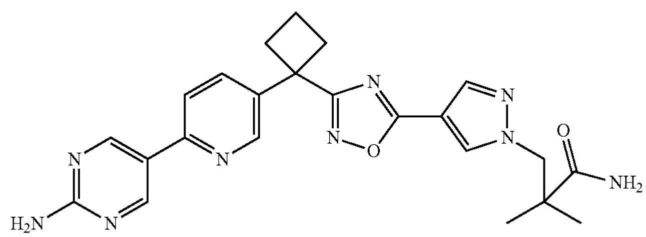 [SMILES: CC(C)(Cn1cc(-c2nc(C3(c4ccc(-c5cnc(N)nc5)nc4)CCC3)no2)cn1)C(N)=O] | 33 | 1.08 | 460.4 | F |
| 148 | 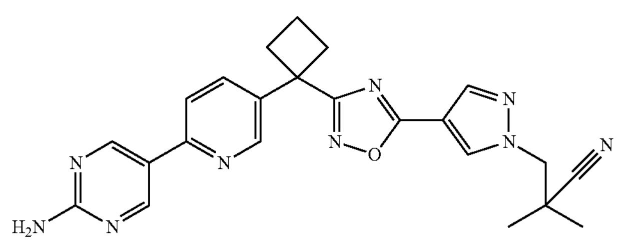 [SMILES: CC(C)(C#N)Cn1cc(-c2nc(C3(c4ccc(-c5cnc(N)nc5)nc4)CCC3)no2)cn1] | 34 | 1.2 | 442.4 | F |
| 149 | 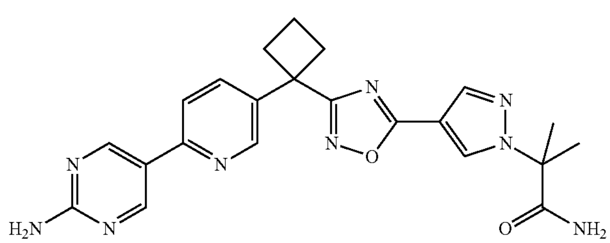 [SMILES: CC(C)(C(N)=O)n1cc(-c2nc(C3(c4ccc(-c5cnc(N)nc5)nc4)CCC3)no2)cn1] | 33 | 1.06 | 446.4 | F |
| 150 | 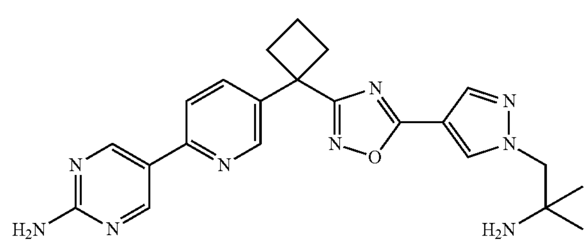 [SMILES: CC(C)(N)Cn1cc(-c2nc(C3(c4ccc(-c5cnc(N)nc5)nc4)CCC3)no2)cn1] | 35 | 0.95 | 432.4 | F |

TABLE 1-continued

Final compounds.

| Example | Structure | Method | Retention time | m/z | LCMS method |
|---|---|---|---|---|---|
| 151 | 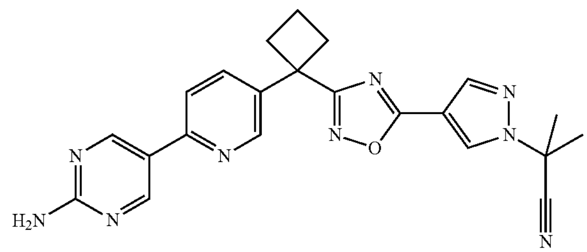 [SMILES: CC(C)(C#N)n1cc(-c2nc(C3(c4ccc(-c5cnc(N)nc5)nc4)CCC3)no2)cn1] | 34 | 0.76 | 428.3 | J |
| 152 | 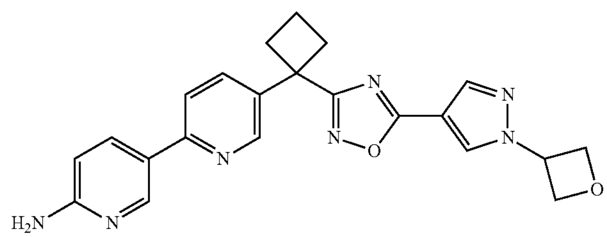 | 27 | 0.58 | 416.3 | J |
| 153 | 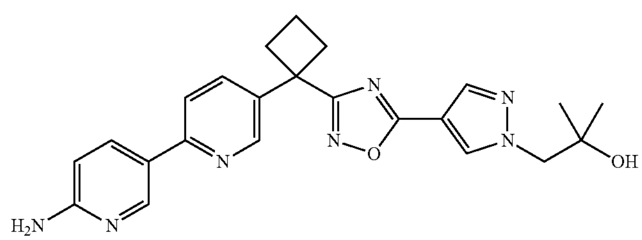 | 27 | 0.59 | 432.3 | J |
| 154 | 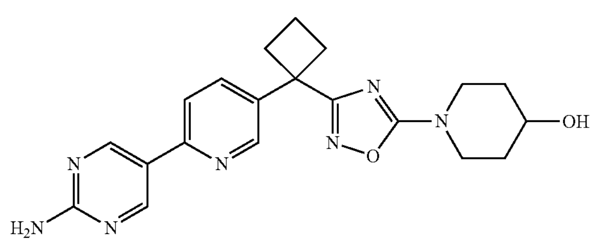 [SMILES: Nc1ncc(-c2ccc(C3(c4noc(N5CCC(O)CC5)n4)CCC3)cn2)cn1] | 32 | 0.59 | 394.2 | J |
| 155 | 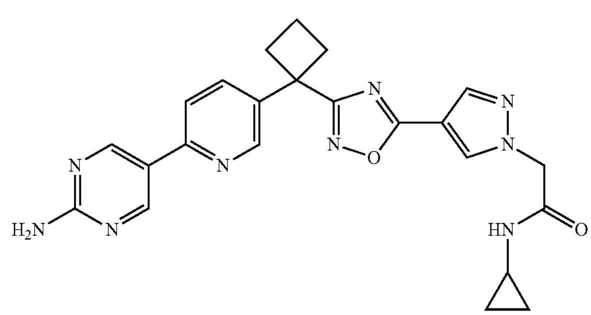 [SMILES: Nc1ncc(-c2ccc(C3(c4noc(-c5cnn(CC(=O)NC6CC6)c5)n4)CCC3)cn2)cn1] | 30 | 0.73 | 458.3 | J |

TABLE 1-continued

Final compounds.

| Example | Structure | Method | Retention time | m/z | LCMS method |
|---|---|---|---|---|---|
| 156 | 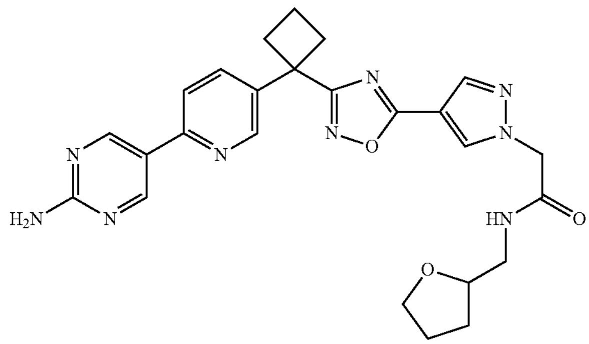 [SMILES: Nc1ncc(-c2ccc(C3(c4noc(-c5cnn(CC(=O)NCC6CCCO6)c5)n4)CCC3)cn2)cn1] | 30 | 0.75 | 502.3 | J |
| 157 | 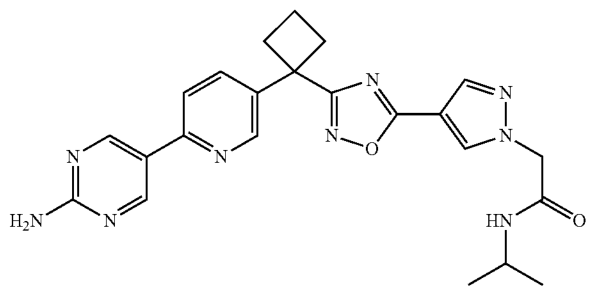 [SMILES: CC(C)NC(=O)Cn1cc(-c2nc(C3(c4ccc(-c5cnc(N)nc5)nc4)CCC3)no2)cn1] | 30 | 0.78 | 460.3 | J |
| 158 | 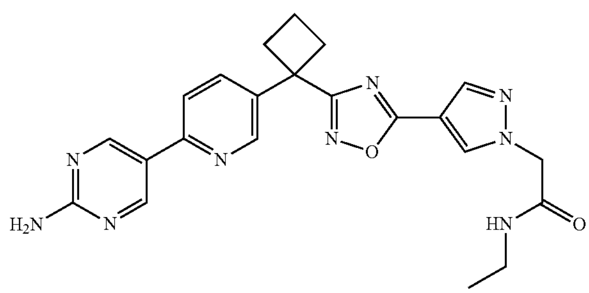 [SMILES: CCNC(=O)Cn1cc(-c2nc(C3(c4ccc(-c5cnc(N)nc5)nc4)CCC3)no2)cn1] | 30 | 0.73 | 466.3 | J |
| 159 | 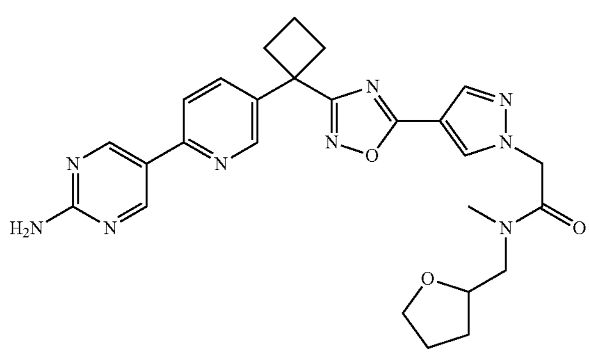 [SMILES: CN(CC1CCCO1)C(=O)Cn1cc(-c2nc(C3(c4ccc(-c5cnc(N)nc5)nc4)CCC3)no2)cn1] | 30 | 0.79 | 516.4 | J |

TABLE 1-continued

Final compounds.

| Example | Structure | Method | Retention time | m/z | LCMS method |
|---|---|---|---|---|---|
| 160 | 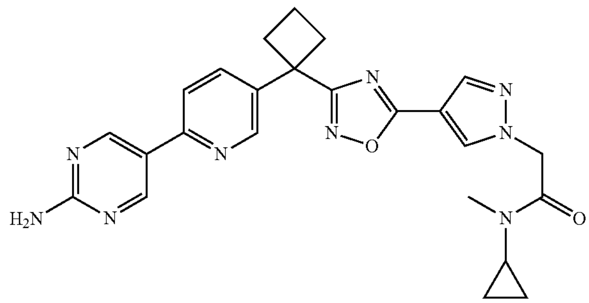 [SMILES: CN(C(=O)Cn1cc(-c2nc(C3(c4ccc(-c5cnc(N)nc5)nc4)CCC3)no2)cn1)C1CC1] | 30 | 0.8 | 472.3 | J |
| 161 | 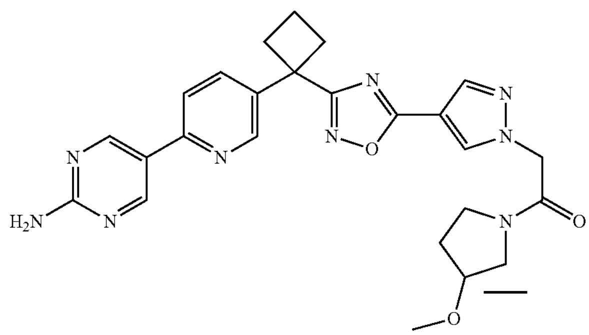 | 30 | 0.75 | 502.3 | J |
| 162 | 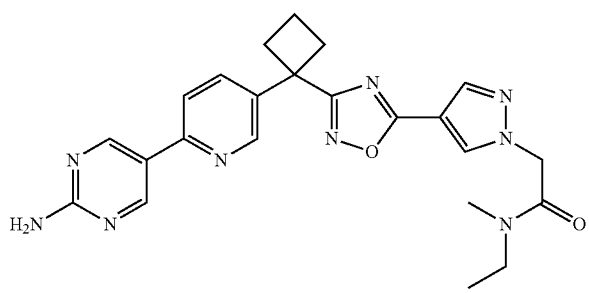 [SMILES: CCN(C)C(=O)Cn1cc(-c2nc(C3(c4ccc(-c5cnc(N)nc5)nc4)CCC3)no2)cn1] | 30 | 0.77 | 460.3 | J |
| 163 | 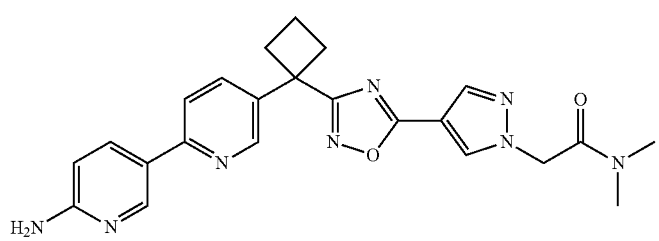 [SMILES: CN(C)C(=O)Cn1cc(-c2nc(C3(c4ccc(-c5ccc(N)nc5)nc4)CCC3)no2)cn1] | 27 | 0.52 | 445.2 | J |
| 164 | 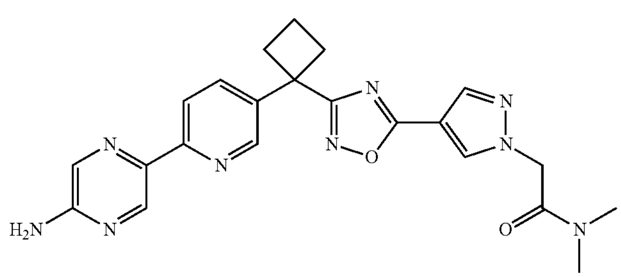 [SMILES: CN(C)C(=O)Cn1cc(-c2nc(C3(c4ccc(-c5cnc(N)cn5)nc4)CCC3)no2)cn1] | 31 | 0.56 | 446.3 | J |

TABLE 1-continued

Final compounds.

| Example | Structure | Method | Retention time | m/z | LCMS method |
|---|---|---|---|---|---|
| 165 | 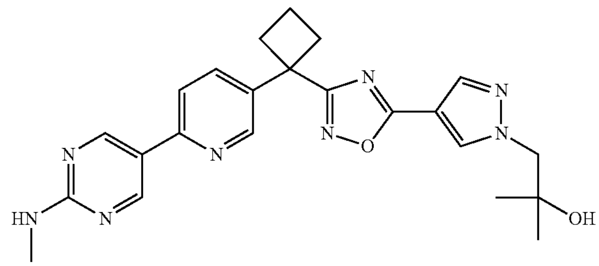 [SMILES: CNc1ncc(-c2ccc(C3(c4noc(-c5cnn(CC(C)(C)O)c5)n4)CCC3)cn2)cn1] | 11 | 0.93 | 447.3 | J |
| 166 | 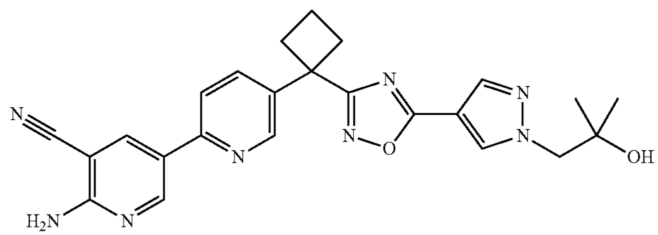 [SMILES: CC(C)(O)Cn1cc(-c2nc(C3(c4ccc(-c5cnc(N)c(C#N)c5)nc4)CCC3)no2)cn1] | 27 | 1.58 | 457.2 | I |
| 167 | 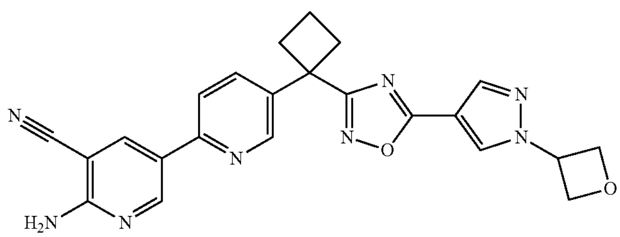 [SMILES: N#Cc1cc(-c2ccc(C3(c4noc(-c5cnn(C6COC6)c5)n4)CCC3)cn2)cnc1N] | 27 | 1.53 | 441.2 | I |
| 168 | 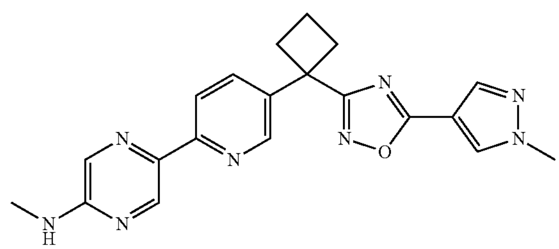 | 10 | 0.66 | 389.3 | J |
| 169 | 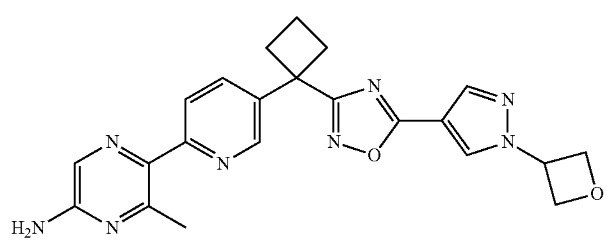 [SMILES: Cc1nc(N)cnc1-c1ccc(C2(c3noc(-c4cnn(C5COC5)c4)n3)CCC2)cn1] | 10 | 0.61 | 431 | J |
| 170 | 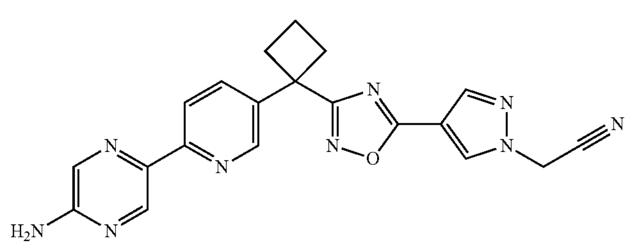 [SMILES: N#CCn1cc(-c2nc(C3(c4ccc(-c5cnc(N)cn5)nc4)CCC3)no2)cn1] | 11 | 0.64 | 401.3 | J |

TABLE 1-continued

Final compounds.

| Example | Structure | Method | Retention time | m/z | LCMS method |
|---|---|---|---|---|---|
| 171 | 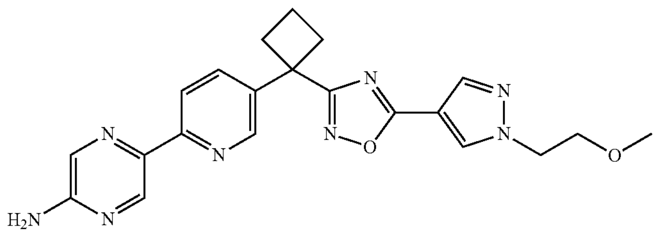 [SMILES: COCCn1cc(-c2nc(C3(c4ccc(-c5cnc(N)cn5)nc4)CCC3)no2)cn1] | 11 | 0.67 | 419.3 | J |
| 172 | 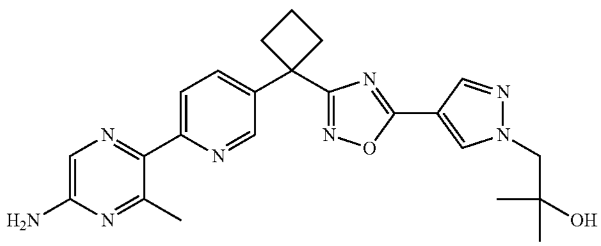 [SMILES: Cc1nc(N)cnc1-c1ccc(C2(c3noc(-c4cnn(CC(C)(C)O)c4)n3)CCC2)cn1] | 11 | 0.62 | 447.4 | J |
| 173 | 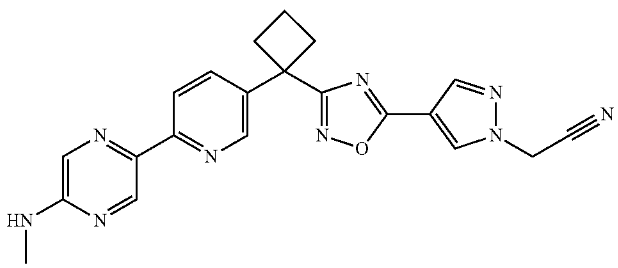 [SMILES: CNc1cnc(-c2ccc(C3(c4noc(-c5cnn(CC#N)c5)n4)CCC3)cn2)cn1] | 11 | 0.66 | 415.5 | J |
| 174 | 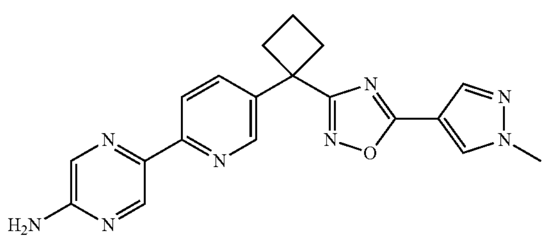 [SMILES: Cn1cc(-c2nc(C3(c4ccc(-c5cnc(N)cn5)nc4)CCC3)no2)cn1] | 10 | 0.9 | 375.2 | J |
| 175 | 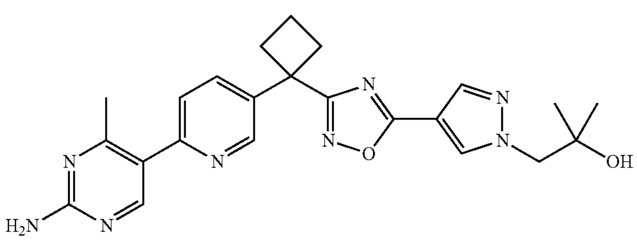 [SMILES: Cc1nc(N)ncc1-c1ccc(C2(c3noc(-c4cnn(CC(C)(C)O)c4)n3)CCC2)cn1] | 27 | 0.61 | 447.4 | J |
| 176 | 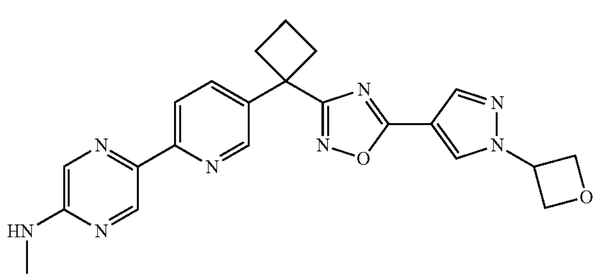 [SMILES: CNc1cnc(-c2ccc(C3(c4noc(-c5cnn(C6COC6)c5)n4)CCC3)cn2)cn1] | 12 | 0.65 | 431.3 | J |

TABLE 1-continued

Final compounds.

| Example | Structure | Method | Retention time | m/z | LCMS method |
|---|---|---|---|---|---|
| 177 | 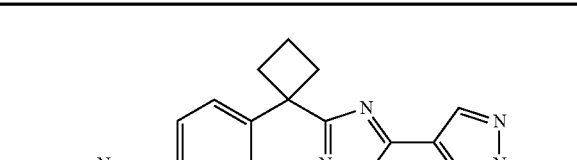 | 11 | 0.66 | 447.2 | J |

Analytical Methods

LC-MS Method A

| Column | Agilent Zorbax C18 SB |
| --- | --- |
| | 3.5 μm, 4.6 × 30 mm |
| | Ambient temperature |
| Mobile phase | A = Formic acid (aq) 0.1% |
| | B = Formic acid (acetonitrile) 0.1% |
| Flow rate | 2.5 ml/min |
| Injection volume | 7 μl |
| Detector | 200-600 nm (nominal) |

| Gradient | Time (mins) | % B |
| --- | --- | --- |
| | 0 | 5 |
| | 1.7 | 95 |
| | 2 | 95 |
| | 2.1 | 5 |
| | 2.3 | 5 |

LC-MS Method B

| Column | Agilent Zorbax Eclipse XDB-C8 |
| --- | --- |
| | 5 μm, 4.6 × 150 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 7 μl |
| Detector | 200-600 nm (nominal) |

| Gradient | Time (mins) | % B |
| --- | --- | --- |
| | 0 | 1 |
| | 2 | 20 |
| | 7 | 95 |
| | 9 | 95 |
| | 9.3 | 1 |
| | 10 | 1 |

LC-MS Method C

| Column | Agilent SB-C18 |
| --- | --- |
| | 1.8 μm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μl |
| Detector | 220 and 254 nm (nominal) |

| Gradient | Time (mins) | % B |
| --- | --- | --- |
| | 0 | 5 |
| | 3.8 | 90 |
| | 4.5 | 100 |

LC-MS Method D

| Column | Agilent Zorbax Eclipse XDB-C8 |
| --- | --- |
| | 5 μm, 4.6 × 150 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 7 μl |
| Detector | 200-600 nm (nominal) |

| Gradient | Time (mins) | % B |
| --- | --- | --- |
| | 0 | 1 |
| | 2 | 1 |
| | 7 | 5 |
| | 9 | 95 |
| | 9.3 | 95 |
| | 10 | 5 |

LC-MS Method E

| Column | Agilent Zorbax Eclipse XDB-C8 |
| --- | --- |
| | 5 μm, 4.6 × 150 mm |
| | Ambient temperature |
| Mobile phase | A = Formic acid (aq) 0.1% |
| | B = Formic acid (acetonitrile) 0.1% |

-continued

| | | |
|---|---|---|
| Flow rate | 1.5 ml/min | |
| Injection volume | 7 μl | |
| Detector | 200-600 nm (nominal) | |
| | Time (mins) | % B |
| Gradient | 0 | 5 |
| | 7 | 95 |
| | 9 | 95 |
| | 9.3 | 5 |
| | 10 | 5 |

LC-MS Method F

| | | |
|---|---|---|
| Column | Agilent SB-C18 | |
| | 1.8 μm, 3 × 50 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 3 μl | |
| Detector | 220 and 254 nm (nominal) | |
| | Time (mins) | % B |
| Gradient | 0 | 12 |
| | 0.25 | 30 |
| | 0.3 | 40 |
| | 1.19 | 95 |
| | 1.75 | 100 |

LC-MS Method G

| | | |
|---|---|---|
| Column | Waters Atlantis dC18 | |
| | 100 × 2.1 mm, 3 μm column | |
| | 40° C. | |
| Mobile phase | A - 0.1% Formic acid (water) | |
| | B - 0.1% Formic acid (acetonitrile) | |
| Flow rate | 0.6 ml/min | |
| Injection volume | 3 μl | |
| Detector | 215 nm (nominal) | |
| | Time (mins) | % B |
| Gradient | 0 | 5 |
| | 5 | 100 |
| | 5.4 | 100 |
| | 5.42 | 5 |

LC-MS Method H

| | | |
|---|---|---|
| Column | Atlantis dC18 | |
| | 2.1 × 50 mm, 3 m | |
| Mobile phase | A = Formic acid (aq) 0.1% | |
| | B = Formic acid (acetonitrile) 0.1% | |
| Flow rate | 1 ml/min | |
| Injection volume | 3 μl | |
| Detector | 215 nm (nominal) | |
| | Time (mins) | % B |
| Gradient | 0 | 5 |
| | 2.5 | 100 |
| | 2.7 | 100 |
| | 2.71 | 5 |
| | 3 | 5 |

LC-MS Method I

| | | |
|---|---|---|
| Column | Waters BEH C18 | |
| | 1.7 μm, 2.1 × 50 mm | |
| | Ambient temperature | |
| Mobile phase | A = Formic acid (aq) 0.1% | |
| | B = Formic acid (acetonitrile) 0.1% | |
| Flow rate | 0.8 ml/min | |
| Injection volume | 3 μl | |
| Detector | 254 nm (nominal) | |
| | Time (mins) | % B |
| Gradient | 0 | 10 |
| | 4.5 | 95 |
| | 4.58 | 95 |

LC-MS Method J

| | | |
|---|---|---|
| Column | Waters BEH C18 | |
| | 1.7 μm, 2.1 × 50 mm | |
| | Ambient temperature | |
| Mobile phase | A = Formic acid (aq) 0.1% | |
| | B = Formic acid (acetonitrile) 0.1% | |
| Flow rate | 0.8 ml/min | |
| Injection volume | 3 μl | |
| Detector | 254 nm (nominal) | |
| | Time (mins) | % B |
| Gradient | 0 | 10 |
| | 1.19 | 95 |
| | 1.7 | 95 |

Assessment of Biological Properties

1. Binding Assay:

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 μl, 5 μg) is mixed with WGA SPA beads (Amersham) and stirred for 1 h. To an assay plate (Perkin Elmer FlexiPlate) is added 25 μl of test compound prepared in Binding buffer [100 mM Tris (pH 7.5), 140 mM NaCl, 5% glycerol, 2 mM EDTA, 0.5 mM TCEP, 0.05% Tween 20], 25 μl of [$^{125}$I]L-691,831 (an iodinated analog of MK-591, Charleson et al. Mol. Pharmacol., 41, 873-879, 1992) and finally 50 μl of the bead/protein mixture. (final concentrations: beads, 200 μg/well; protein, 5 μg/well; [$^{125}$I] probe, 0 08 nM/well (17 nCi/well). The plates are shaken for 2 h before reading on a Microbeta plate reader. Non-specific binding is determined by the addition of 10 μM cold L-691,831 compound.

In general, the preferred potency range (IC$_{50}$) of compounds in the above assay is between 0.1 nM to 10 μM, the more preferred potency range is 0.1 nM to 1 μM, and the most preferred potency range is 0.1 nM to 100 nM.

2. Whole Blood Assay:

Compounds are additionally tested in a human whole blood assay to determine their ability to inhibit the synthesis of LTB$_4$ in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB$_4$ concentrations are then measured using an antibody-based homogenous time-resolved fluorescence method (CisBio, Bedford, Mass.).

In general, the preferred potency range (IC$_{50}$) of compounds in the above assay is between 10 nM to 10 µM, the more preferred potency range is 10 nM to 1 µM, and the most preferred potency range is 10 nM to 100 nM.

Method of Use

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease, multiple sclerosis, inflammatory pain, systemic lupus erythematosus, transplant rejection, inflammatory and allergic ocular diseases;

Cancer including solid tumors, leukemias and lymphomas; and

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: *The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula I:

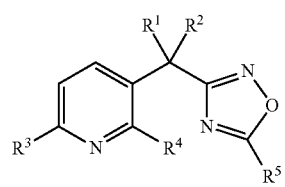

wherein:

$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;

$R^3$ is 5-11 membered heteroaryl ring containing one to three heteroatoms selected from nitrogen, oxygen and sulfur, wherein each $R^3$ is optionally independently substituted with one to three groups selected from $C_{1-5}$ alkyl, $C_{1-5}$ alkoxy, $C_{1-3}$ alkylhydroxy, —CN, amino, $C_{1-3}$ alkylamino and $C_{1-3}$ dialkylamino;

$R^4$ is hydrogen, halogen, $C_{1-3}$ alkyl or nitrile;

$R^5$ is $C_{1-6}$ alkyl, $C_{3-10}$ carbocycle, 5-11 membered heterocycle, aryl, 5-11 membered heteroaryl, —C(O)—$R^6$ or —NR$^7$R$^8$, wherein each $R^5$ is optionally independently substituted with one to three groups selected from $R^9$, $R^{10}$ and $R^{11}$;

$R^6$ is $C_{3-8}$ heterocycle, amino, $C_{1-3}$ alkylamino, $C_{1-3}$ dialkylamino or —NH-5-6 membered heterocycle, each optionally independently substituted with one to three groups selected from $R^9$, $R^{10}$ and $R^{11}$;

$R^7$ and $R^8$ are each independently hydrogen, —S(O)$_n$C$_{1-6}$ alkyl or $C_{1-6}$ alkyl;

$R^9$, $R^{10}$ and $R^{11}$ are independently selected from
(a) —H,
(b) —OH,
(c) halogen,
(d) —CN,
(e) —CF$_3$,
(f) $C_{1-6}$alkyl optionally substituted with one to three —OH, —N(R$^{12}$)(R$^{13}$), aryl, —O—C$_{1-2}$ alkyl-aryl, 3-6 membered heterocycle, —C(O)-3-6 membered heterocycle, $C_{1-6}$alkoxy, —S(O)$_n$C$_{1-6}$alkyl, —CO$_2$R$^{12}$, halogen, —CN or —C(O)N(R$^{12}$)(R$^{13}$),
(g) $C_{1-6}$alkoxy,
(h) —N(R$^{12}$)(R$^{13}$),
(i) —S(O)$_n$C$_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) a 3-10 membered heterocyclic group optionally substituted with one to three groups selected from —OH, $C_{1-6}$ alkyl, $C_{1-6}$alkylhydroxy, $C_{1-6}$ alkyl-CO$_2$R$^{12}$, —S(O)$_n$C$_{1-6}$alkyl, oxo, —C(O)N(R$^{12}$)(R$^{13}$), and —CO$_2$R$^{12}$,
(n') oxo,
(o) —C(O)—C$_{1-3}$ alkyl,
(p) —C(O)-3-6 membered heterocycle optionally substituted with one to three groups selected from halogen hydroxy and $C_{1-6}$alkoxy,
(q) —OR$^{12}$,
(r) 5-11 membered heteroaryl;

$R^{12}$ and $R^{13}$ are each independently selected from —H, —C$_{1-6}$alkyl, —C(O)—C$_{1-6}$ alkyl, $C_{3-10}$ carbocycle and a 3-6 membered heterocyclic group, each of which is optionally independently substituted with one to three —OH, $C_{1-6}$ alkyl, $C_{1-6}$alkoxy, —C(O)N(R$^{14}$)(R$^{15}$), —S(O)$_n$C$_{1-6}$alkyl, CN, $C_{3-10}$ carbocycle, —CO$_2$R$^{14}$, CF$_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkoxy or oxo;

$R^{14}$ and $R^{15}$ are each independently selected from —H and —C$_{1-6}$alkyl;

n is 0, 1 or 2;

or a pharmaceutically acceptable salt thereof.

2. A compound according to claim 1, wherein:

$R^1$ and $R^2$ together with the carbon atom to which they are attached is cyclopropyl, cyclobutyl, cyclopentyl, cyclohexyl, cycloheptyl, cyclooctyl, 2.2.1 bicycloheptyl, oxetanyl, tetrahydrofuranyl, tetrahydropyranyl, pyrrolidinyl, piperidinyl, tetrahydrothienyl, wherein each carbocycle or heterocycle is optionally independently substituted with one to two groups selected from $C_{1-6}$ alkyl and halogen;

$R^3$ is pyridinyl, pyrimidinyl, pyrazinyl, pyridazinyl, pyrrolyl, imidazolyl, thienyl, furanyl or thiazolyl, wherein each $R^3$ is optionally independently substituted with one to three groups selected from $C_{1-3}$ alkyl, $C_{1-3}$ alkoxy, $C_{1-3}$ alkylhydroxy, —CN, amino, $C_{1-3}$ alkylamino and $C_{1-3}$ dialkylamino;

$R^4$ is hydrogen, halogen or methyl;

$R^5$ is methyl, ethyl, propyl, isopropyl, butyl, isobutyl, tert, butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, dihydropyridinyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—R$^6$, hydroxy or —NR$^7$R$^8$, wherein each $R^5$ is optionally independently substituted with one to three groups selected from $R^9$, $R^{10}$ and $R^{11}$;

$R^6$ is azetidinyl, pyrrolidinyl, piperidinyl, piperazinyl, tetrahydropyranyl, morpholinyl, thiomorpholinyl, amino, $C_{1-3}$ alkylamino, $C_{1-3}$ dialkylamino or —NH-5-6 membered heterocycle, each optionally independently substituted with one to three groups selected from $R^9$, $R^{10}$ and $R^{11}$;

$R^7$ and $R^8$ are each independently hydrogen, $C_{1-5}$ alkyl or —S(O)$_n$C$_{1-6}$alkyl;

$R^9$, $R^{10}$ and $R^{11}$ are independently selected from
(a) —H,
(b) —OH,
(c) halogen,
(d) —CN,
(e) —CF$_3$,
(f) $C_{1-6}$alkyl optionally substituted with one to three —OH, —N(R$^{12}$)(R$^{13}$), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_n$C$_{1-6}$alkyl, —CO$_2$R$^{12}$, halogen, —CN or —C(O)N(R$^{12}$)(R$^{13}$),
(g) $C_{1-6}$alkoxy,
(h) —N(R$^{12}$)(R$^{13}$),
(i) —S(O)$_n$C$_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) oxetanyl, tetrahydrofuranyl, tetrahydropyranyl, azetidinyl, pyrrolidinyl, tetrahydrothienyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$ alkylhydroxy, $C_{1-6}$ alkyl-CO$_2$R$^{12}$, —S(O)$_n$C$_{1-6}$alkyl, oxo, —C(O)N(R$^{12}$)(R$^{13}$), and —CO$_2$R$^{12}$,
(n') oxo,
(o) —C(O)—C$_{1-3}$ alkyl,
(p) —C(O)-3-6 membered heterocycle optionally substituted with one to three groups selected from halogen hydroxy and $C_{1-6}$alkoxy,
(q) —OR$^{12}$,
(r) imidazolyl, pyrrolyl, pyrazolyl, thienyl or furanyl;

$R^{12}$ and $R^{13}$ are each independently selected from —H, —C$_{1-6}$alkyl, —C(O)—C$_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —S(O)$_n C_{1-6}$alkyl, CN, cyclopropyl, cyclobutyl, cyclopentyl, cyclohexyl, —CO$_2 R^{14}$, CF$_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkoxy or oxo;

$R^{14}$ and $R^{15}$ are each independently selected from —H and —$C_{1-6}$alkyl;

n is 0 or 2;

or a pharmaceutically acceptable salt thereof.

3. A compound according to claim 1, wherein:

$R^1$ and $R^2$ together with the carbon atom to which they are attached is cyclobutyl, cyclopentyl cyclohexyl, or tetrahydropyranyl wherein each carbocycle or heterocycle is optionally independently substituted with one to two groups selected from $C_{1-3}$ alkyl and halogen;

or a pharmaceutically acceptable salt thereof.

4. A compound according to claim 1, wherein:

$R^3$ is pyridinyl, pyrimidinyl, pyrazinyl or pyridazinyl, wherein each $R^3$ is optionally independently substituted with one to three groups selected from $C_{1-3}$ alkyl, $C_{1-3}$ alkoxy, $C_{1-3}$ alkylhydroxy, —CN, amino, $C_{1-3}$ alkylamino and $C_{1-3}$ dialkylamino;

or a pharmaceutically acceptable salt thereof.

5. A compound according to claim 1, wherein:

$R^5$ is methyl, ethyl, propyl, isopropyl, butyl, isobutyl, tert, butyl, pentyl, hexyl, phenyl, piperidinyl, piperazinyl, morpholinyl, thiomorpholinyl, pyrrolidinyl, furanyl, thiazolyl, oxazolyl, isoxazolyl, pyrazolyl, imidazolyl, triazolyl, dihydropyridinyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—$R^6$, hydroxy or —N$R^7 R^8$, wherein each $R^5$ is optionally independently substituted with one to three groups selected from $R^9$, $R^{10}$ and $R^{11}$;

$R^6$ is azetidinyl, pyrrolidinyl, piperidinyl, piperazinyl, morpholinyl, amino, $C_{1-3}$ alkylamino or $C_{1-3}$ dialkylamino;

$R^7$ and $R^8$ are each independently hydrogen, $C_{1-5}$ alkyl or —S(O)$_2 C_{1-6}$alkyl;

$R^9$, $R^{10}$ and $R^{11}$ are independently selected from
(a) —H,
(b) —OH,
(c) halogen,
(d) —CN,
(e) —CF$_3$,
(f) $C_{1-6}$alkyl optionally substituted with one to three —OH, —N($R^{12}$)($R^{13}$), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_n C_{1-6}$alkyl, —CO$_2 R^{12}$, halogen, —CN or —C(O)N($R^{12}$)($R^{13}$),
(g) $C_{1-6}$alkoxy,
(h) —N($R^{12}$)($R^{13}$),
(i) —S(O)$_2 C_{1-6}$alkyl,
(j) —CO$_2 R^{12}$,
(k) —C(O)N($R^{12}$)($R^{13}$),
(l) —S(O)$_2$N($R^{12}$)($R^{13}$),
(m) oxetanyl, tetrahydrofuranyl, tetrahydropyranyl, tetrahydrothienyl, azetidinyl, pyrrolidinyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$alkylhydroxy, $C_{1-6}$alkyl-CO$_2 R^{12}$, —S(O)$_n C_{1-6}$alkyl, oxo, —C(O)N($R^{12}$)($R^{13}$), and —CO$_2 R^{12}$,
(n') oxo,
(o) —C(O)—$C_{1-3}$ alkyl,
(p) —C(O)-3-6 membered heterocycle optionally substituted with one to three groups selected from halogen hydroxy and $C_{1-6}$alkoxy,
(q) —O$R^{12}$,
(r) imidazolyl, pyrrolyl, pyrazolyl, thienyl or furanyl;

$R^{12}$ and $R^{13}$ are each independently selected from —H, —$C_{1-6}$alkyl, —C(O)—$C_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —S(O)$_n C_{1-6}$alkyl, CN, cyclopropyl, cyclobutyl, cyclopentyl, cyclohexyl, —CO$_2 R^{14}$, CF$_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkoxy or oxo;

$R^{14}$ and $R^{15}$ are each independently selected from —H and —$C_{1-6}$alkyl;

n=2;

or a pharmaceutically accepted salt thereof.

6. A compound according to claim 1, wherein:

$R^1$ and $R^2$ together with the carbon atom to which they are attached is cyclobutyl or tetrahydropyranyl each optionally independently substituted with one to two groups selected from methyl and fluoro;

$R^3$ is pyridinyl, pyrimidinyl, pyrazinyl or pyridazinyl, wherein each $R^3$ is optionally independently substituted with one to three groups selected from methyl, —CN, —NH—CH$_3$ and an amino group;

$R^4$ is hydrogen;

$R^5$ is phenyl, piperidinyl, piperazinyl, pyrrolidinyl, thiazolyl, oxazolyl, isoxazolyl, pyrazolyl, imidazolyl, triazolyl, dihydropyridinyl, pyridinyl, pyrimidinyl, pyrazinyl, pyridazinyl, pyrazolopyrimidinyl, imidazopyridinyl, indazolyl, or —N$R^7 R^8$, wherein each $R^5$ is optionally independently substituted with one to three groups selected from $R^9$, $R^{10}$ and $R^{11}$;

$R^7$ and $R^8$ are each independently hydrogen or $C_{1-3}$ alkyl;

$R^9$, $R^{10}$ and $R^{11}$ are independently selected from
(a) —H,
(b) —OH,
(c) halogen,
(d) —CN,
(e) —CF$_3$,
(f) $C_{1-6}$alkyl optionally substituted with one to three —OH, —N($R^{12}$)($R^{13}$), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_2 C_{1-6}$alkyl, —CO$_2 R^{12}$, halogen, —CN or —C(O)N($R^{12}$)($R^{13}$),
(g) $C_{1-6}$alkoxy,
(h) —N($R^{12}$)($R^{13}$),
(i) —S(O)$_2 C_{1-6}$ alkyl,
(j) —CO$_2 R^{12}$,
(k) —C(O)N($R^{12}$)($R^{13}$),
(l) —S(O)$_2$N($R^{12}$)($R^{13}$),
(m) oxetanyl, tetrahydrothienyl, pyrrolidinyl, piperidinyl, piperazinyl, morpholinyl, thiomorpholinyl or thiomorpholinyldioxide, optionally substituted with one to three groups selected from —OH, $C_{1-6}$ alkyl, $C_{1-6}$ alkylhydroxy, $C_{1-6}$ alkyl-CO$_2 R^{12}$, —S(O)$_2 C_{1-6}$ alkyl, oxo, —C(O)N($R^{12}$)($R^{13}$), and —CO$_2 R^{12}$,
(n') oxo,
(o) —C(O)—$C_{1-3}$ alkyl, (p) —C(O)-piperidinyl or —C(O)-pyrrolidinyl each optionally substituted with one to three groups selected from halogen hydroxy and $C_{1-6}$alkoxy, (q) —$OR^{12}$, (r) imidazolyl, pyrrolyl or pyrazolyl;

$R^{12}$ and $R^{13}$ are each independently selected from —H, —$C_{1-6}$alkyl, —C(O)—$C_{1-6}$ alkyl, cyclopropyl, cyclobutyl, cyclopentyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —$S(O)_2C_{1-6}$alkyl, CN, cyclopropyl, cyclobutyl, cyclopentyl, cyclohexyl, —$CO_2R^{14}$, $CF_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkoxy or oxo;

$R^{14}$ and $R^{15}$ are each independently selected from —H and —$C_{1-6}$alkyl;

or a pharmaceutically accepted salt thereof.

7. A compound according to claim 6, wherein:

$R^1$ and $R^2$ together with the carbon atom to which they are attached is cyclobutyl;

or a pharmaceutically acceptable salt thereof.

8. A compound according to claim 6, wherein:

$R^1$ and $R^2$ together with the carbon atom to which they are attached is tetrahydropyranyl;

or a pharmaceutically acceptable salt thereof.

9. A compound according to claim 6, wherein:

$R^3$ is selected from

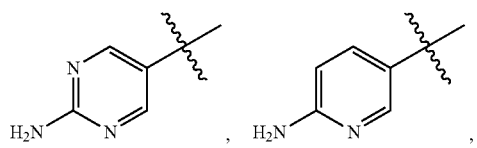

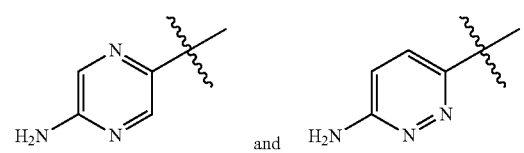

or a pharmaceutically acceptable salt thereof.

10. A compound according to claim 6, wherein:

$R^5$ is selected from imidazolyl, pyrazolyl, triazolyl, thiazolyl, oxazolyl, pyrazolopyrimidinyl, imidazopyridinyl, indazolyl, dihydropyridinyl, pyridinyl, pyrimidinyl, pyrazinyl, pyridazinyl, pyrrolidinyl, and phenyl, wherein each $R^5$ is optionally independently substituted with one to three groups selected from $R^9$, $R^{10}$ and $R^{11}$;

or a pharmaceutically acceptable salt thereof.

11. A compound according to claim 6, wherein:

$R^5$ is —$NR^7R^8$, optionally substituted with one to three groups selected from $R^9$, $R^{10}$ and $R^{11}$;

or a pharmaceutically acceptable salt thereof.

12. A compound according to claim 6, wherein:

$R^1$ and $R^2$ together with the carbon atom to which they are attached is cyclobutyl or tetrahydropyranyl;

$R^3$ is selected from

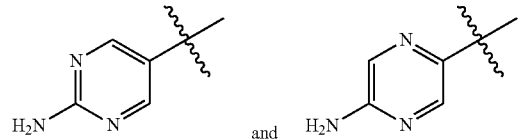 [SMILES: *c1cnc(N)nc1 ; *c1cnc(N)cn1 ; "and"]

$R^4$ is hydrogen;

$R^5$ is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, and phenyl, wherein each $R^5$ is optionally independently substituted with one to three groups selected from $R^9$, $R^{10}$ and $R^{11}$;

or a pharmaceutically acceptable salt thereof.

13. A compound according to claim 6, wherein:

$R^1$ and $R^2$ together with the carbon atom to which they are attached is cyclobutyl or tetrahydropyranyl;

$R^3$ is selected from

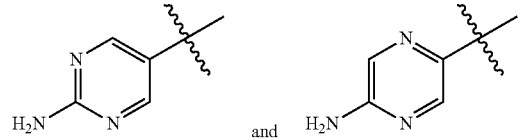 [SMILES: *c1cnc(N)nc1 ; *c1cnc(N)cn1 ; "and"]

$R^4$ is hydrogen;

$R^5$ is —$NR^7R^8$ optionally substituted with one to three groups selected from $R^9$, $R^{10}$ and $R^{11}$;

or a pharmaceutically acceptable salt thereof.

14. A compound of formula IA:

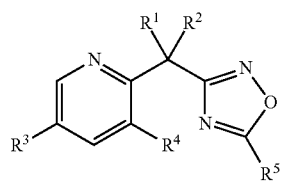

IA wherein:

$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;

$R^3$ is 5-11 membered heteroaryl ring containing one to three heteroatoms selected from nitrogen, oxygen and sulfur, wherein each $R^3$ is optionally independently substituted with one to three amino groups;

$R^4$ is hydrogen, $C_{1-3}$ alkyl or halogen;

$R^5$ is 5-11 membered heteroaryl optionally independently substituted with one to three $C_{1-6}$ alkyl groups;

or a pharmaceutically acceptable salt thereof.

15. A compound of formula (IA) according to claim 14, wherein:
- $R^1$ and $R^2$ together with the carbon atom to which they are attached is cyclopropyl, cyclobutyl, cyclopentyl, tetrahydrofuranyl, tetrahydropyranyl, wherein each carbocycle or heterocycle is optionally independently substituted with one to two groups selected from $C_{1-6}$ alkyl and halogen;
- $R^3$ is pyridinyl, pyrimidinyl, pyrazinyl, pyridazinyl, wherein each $R^3$ is optionally independently substituted with one to three amino groups;
- $R^4$ is hydrogen;
- $R^5$ is pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, wherein each $R^5$ is optionally substituted with one to three $C_{1-6}$ alkyl groups;

or a pharmaceutically acceptable salt thereof.

16. A compound of formula (IA) according to claim 14, wherein:
- $R^1$ and $R^2$ together with the carbon atom to which they are attached is cyclobutyl or tetrahydropyranyl;

or a pharmaceutically acceptable salt thereof.

17. A compound of formula (IA) according to claim 14, wherein:
- $R^3$ is pyrimidinyl substituted with an amino group;

or a pharmaceutically acceptable salt thereof.

18. A compound of formula (IA) according to claim 14, wherein:
- $R^5$ is pyrazolyl or, pyridinyl, each optionally substituted with one to three $C_{1-3}$ alkyl groups;

or a pharmaceutically acceptable salt thereof.

19. A compound of formula (IA) according to claim 14, wherein:
- $R^1$ and $R^2$ together with the carbon atom to which they are attached is cyclobutyl or tetrahydropyranyl;
- $R^3$ is pyrimidinyl substituted with an amino group;
- $R^4$ is H
- $R^5$ is pyrazolyl or, pyridinyl, each optionally substituted with one to three methyl groups;

or a pharmaceutically acceptable salt thereof.

20. A compound selected from the group consisting of:

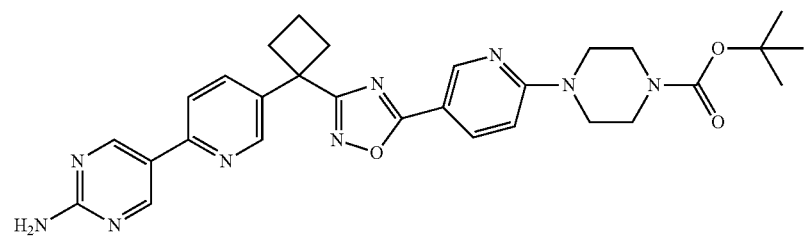

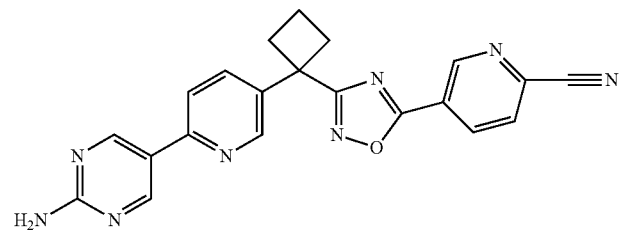

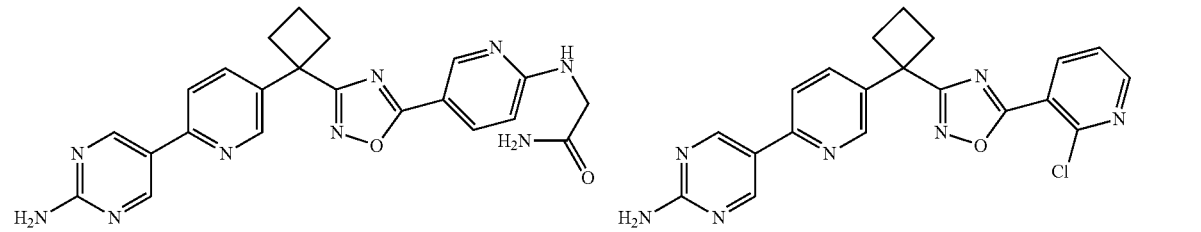

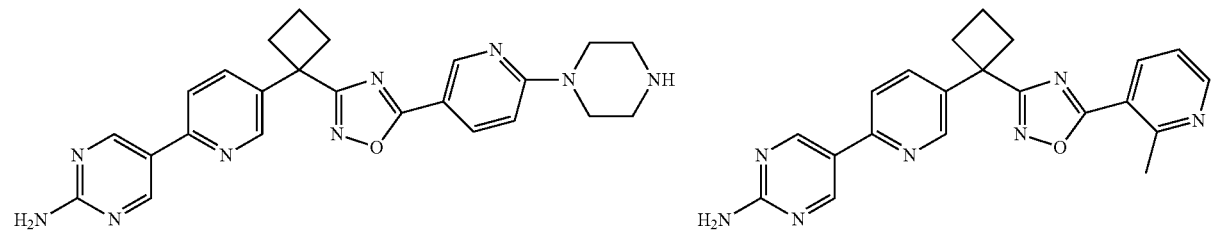

213 214
-continued
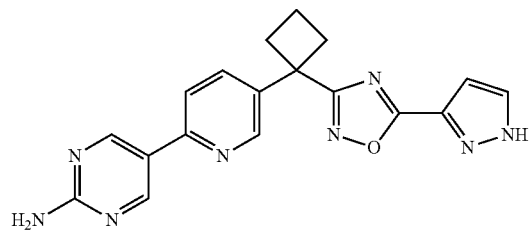 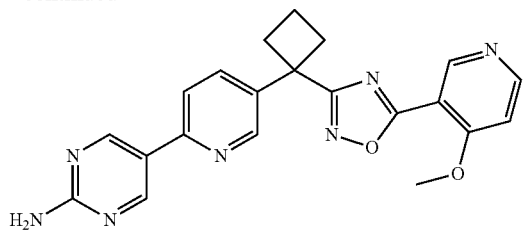
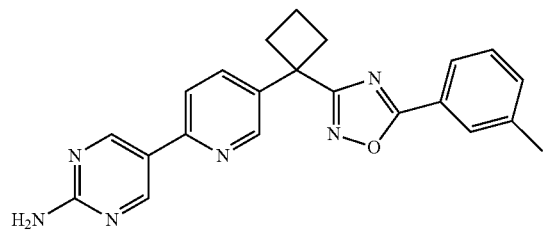 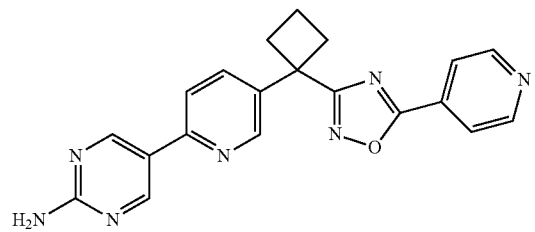
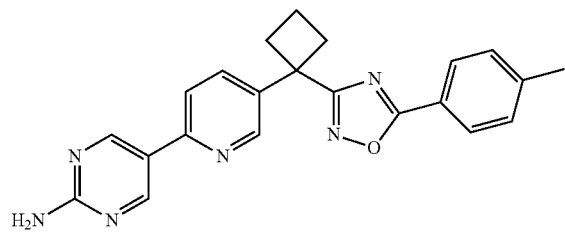 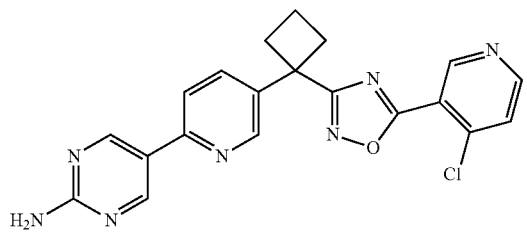
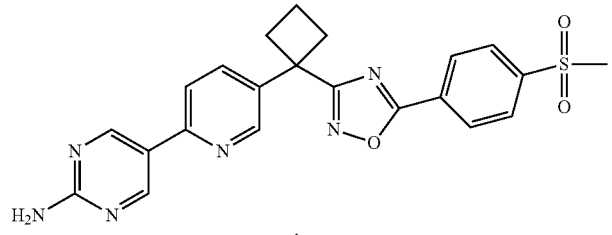
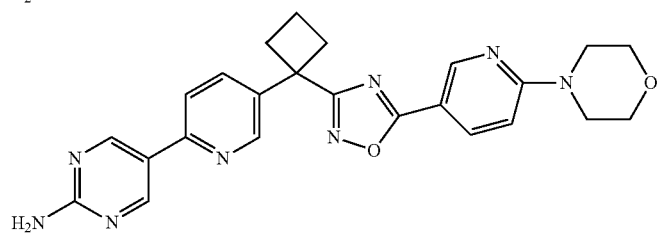
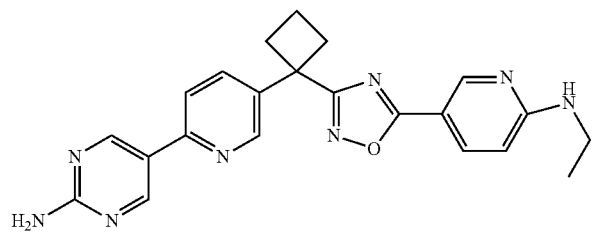 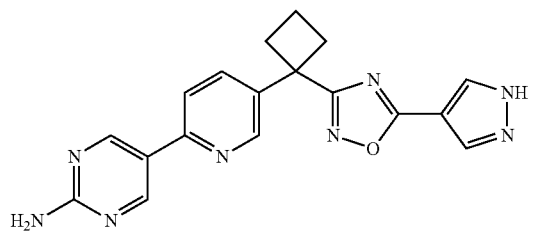
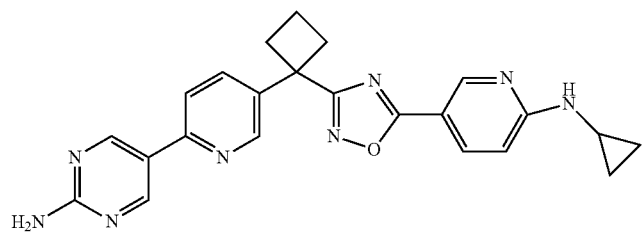

215 216
-continued
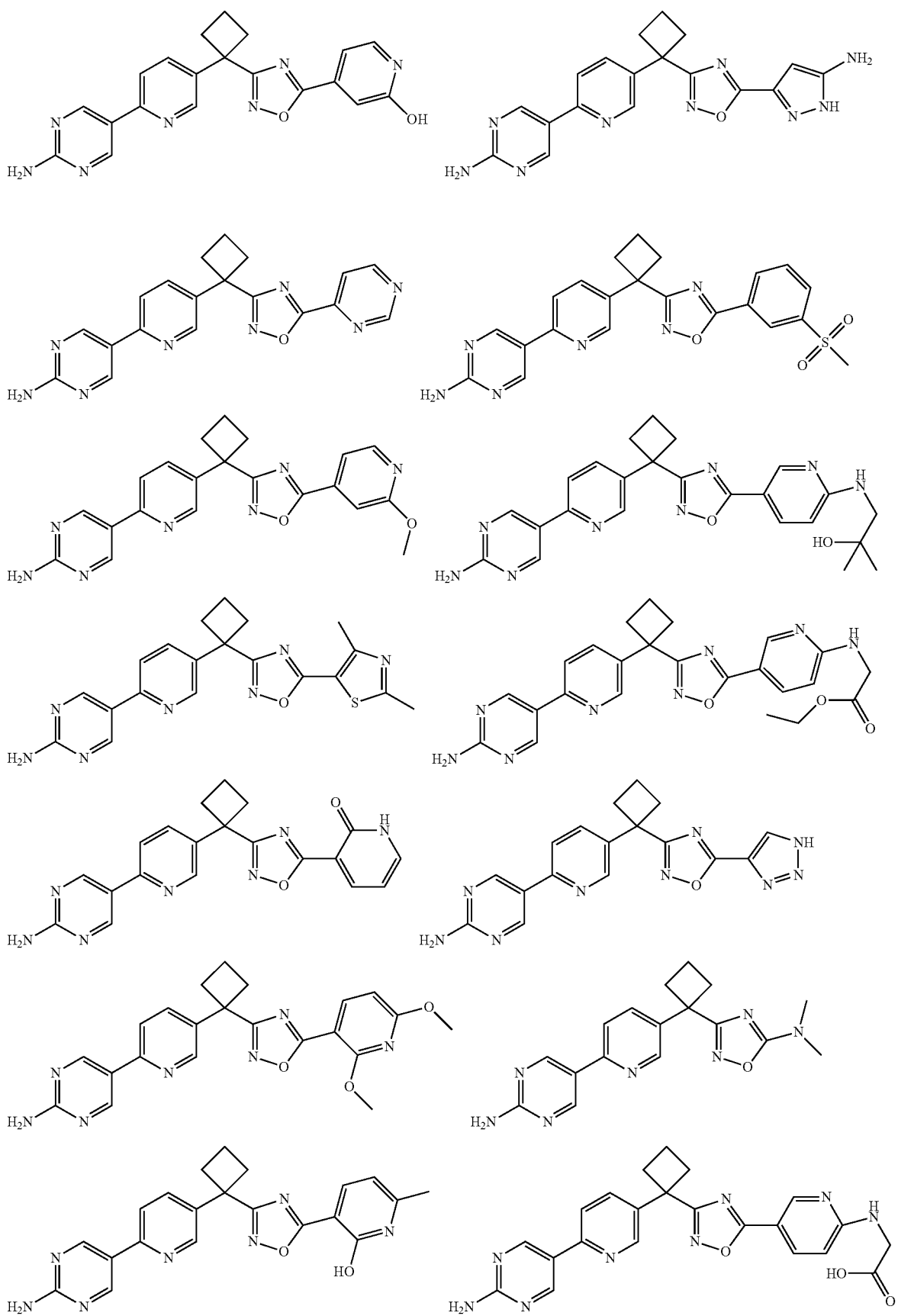

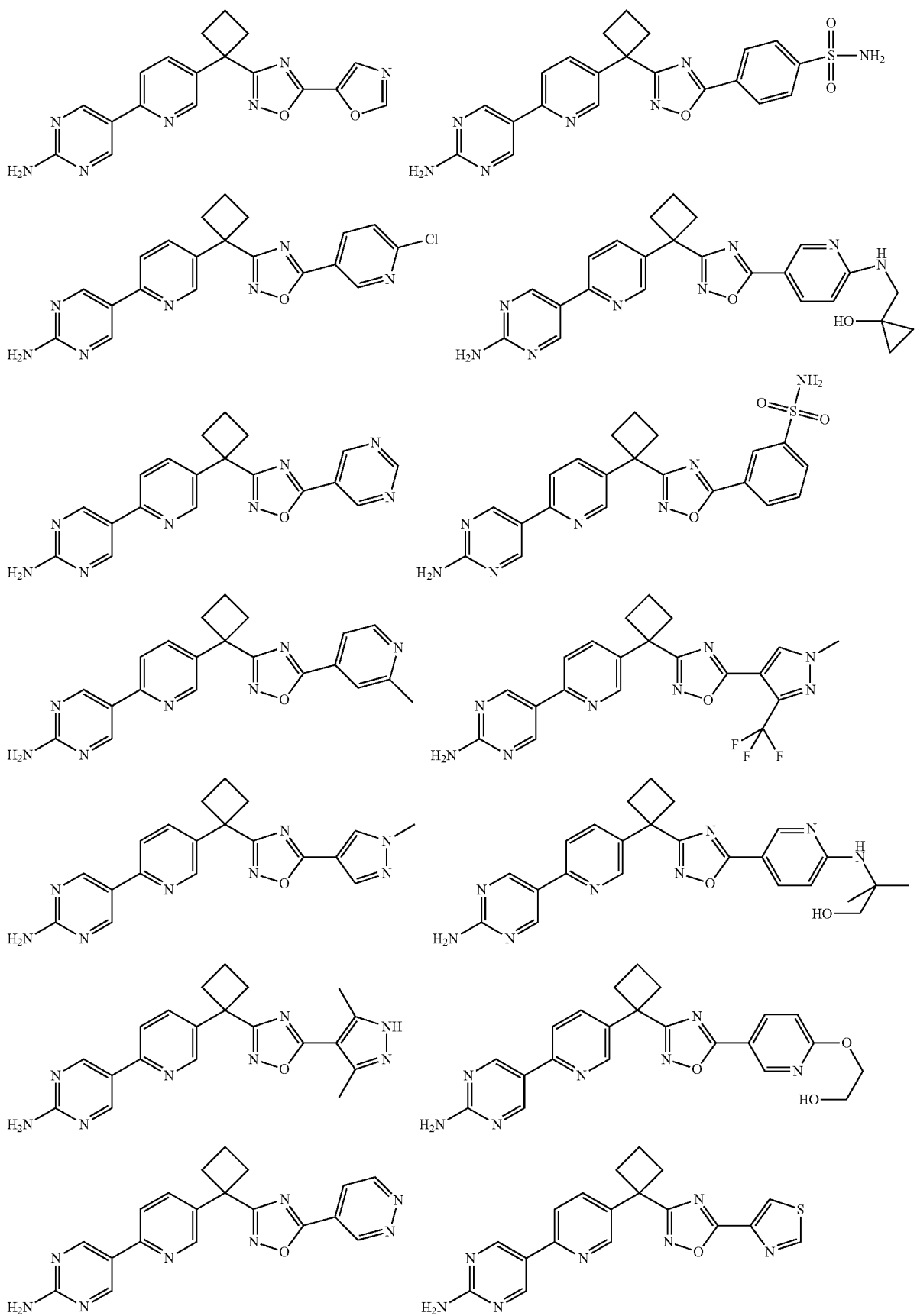

219 220
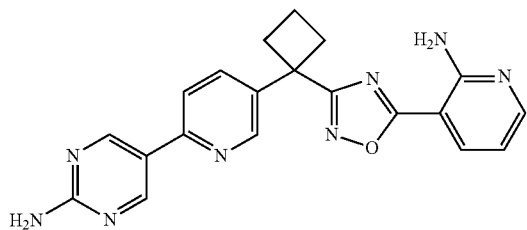 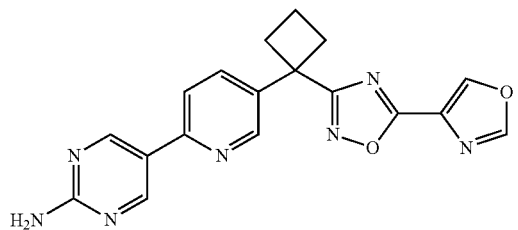
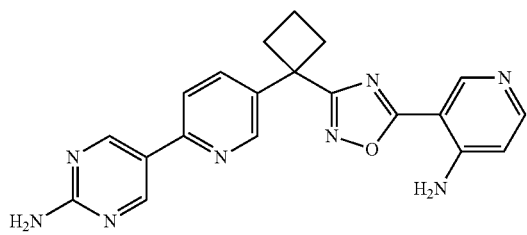 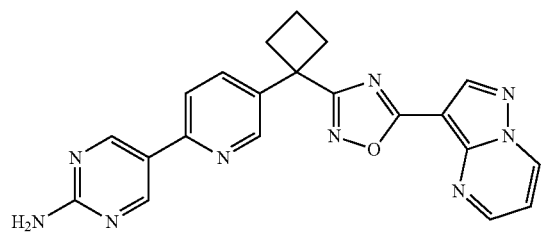
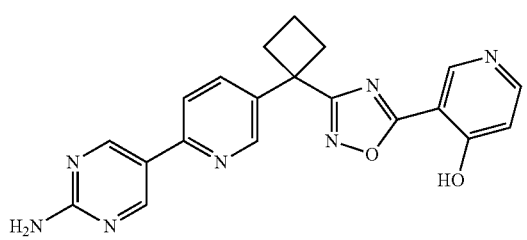 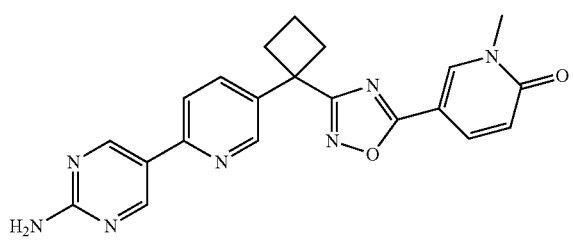
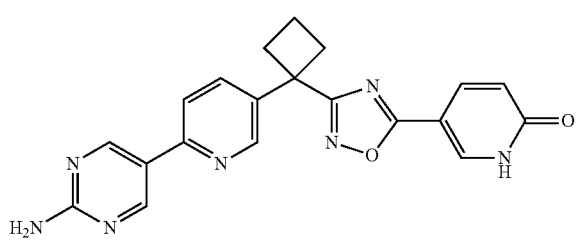 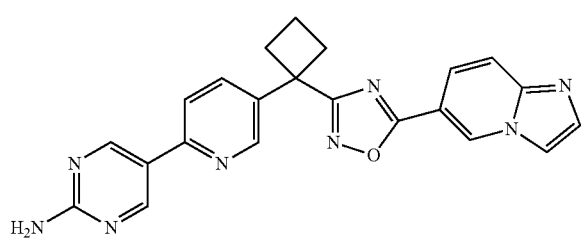
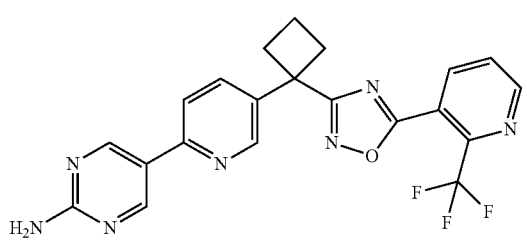 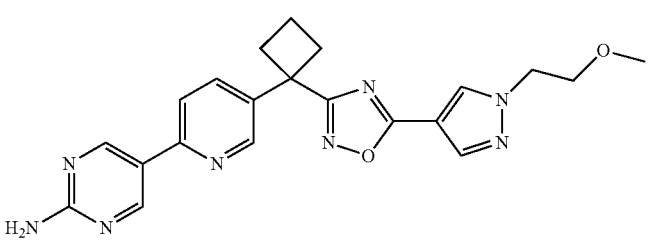
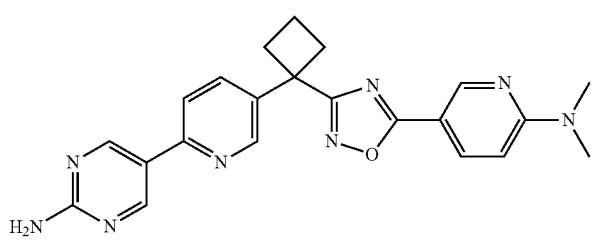
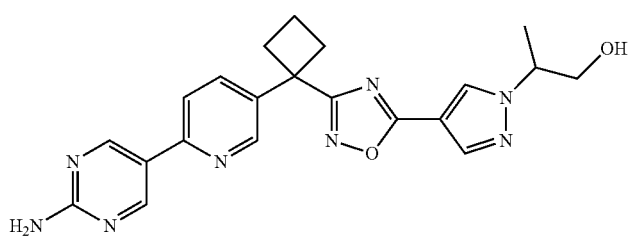

221
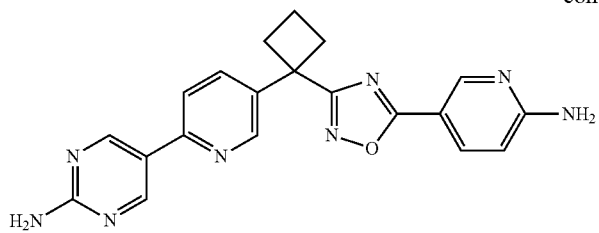
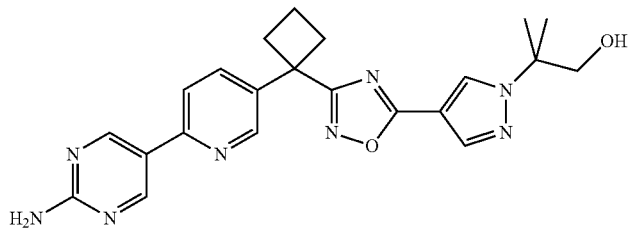
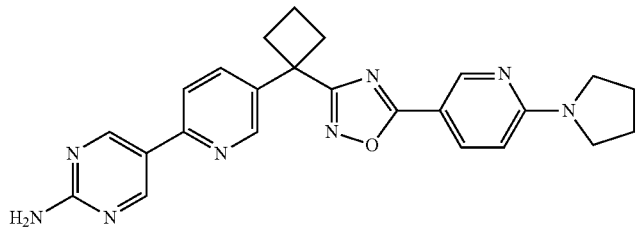
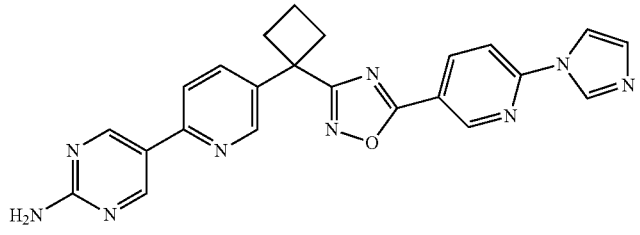
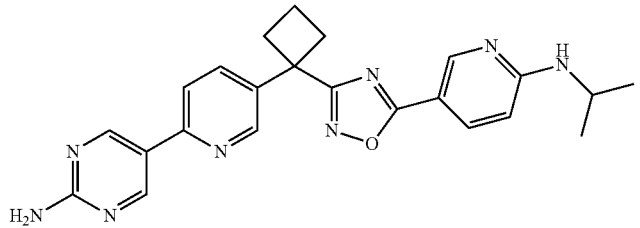
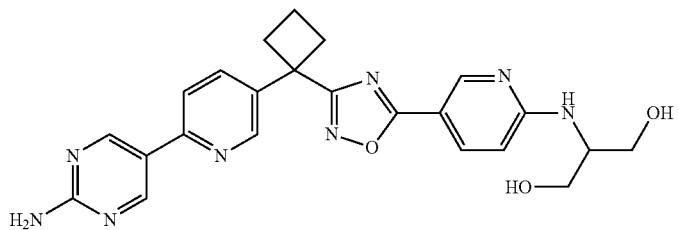
222
-continued
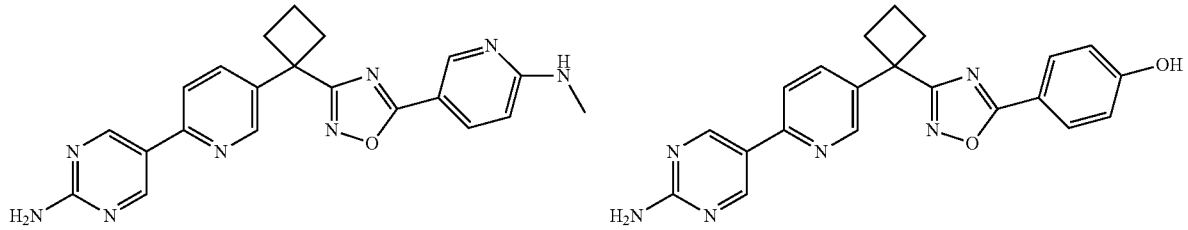

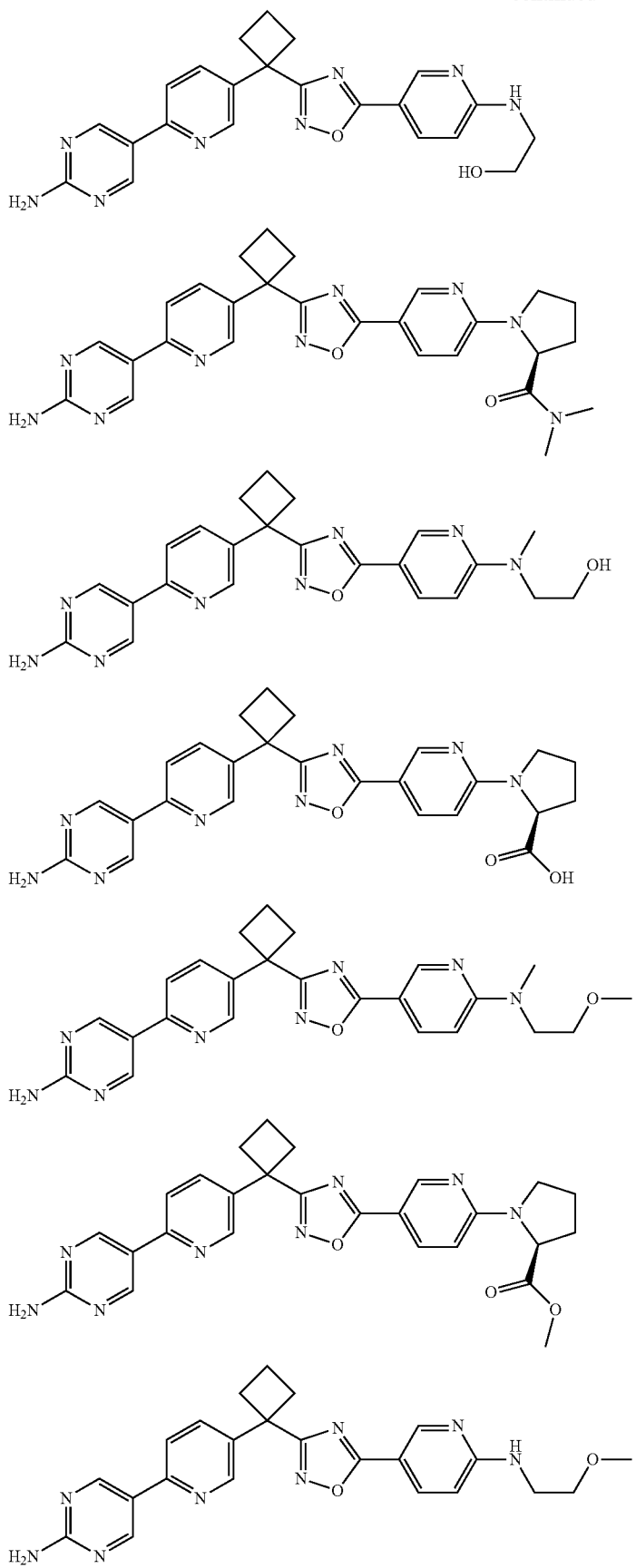

-continued
| 225 | 226 |
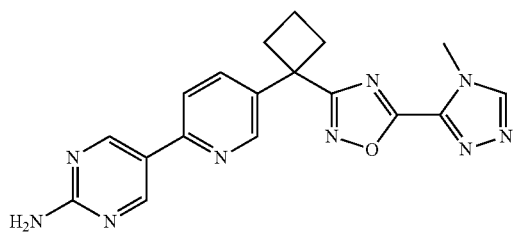 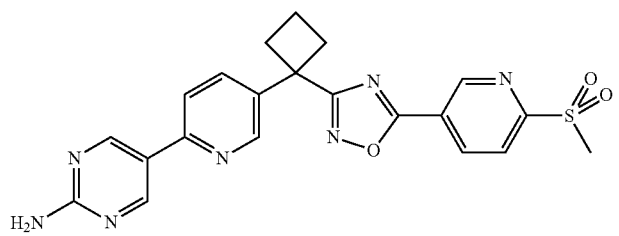
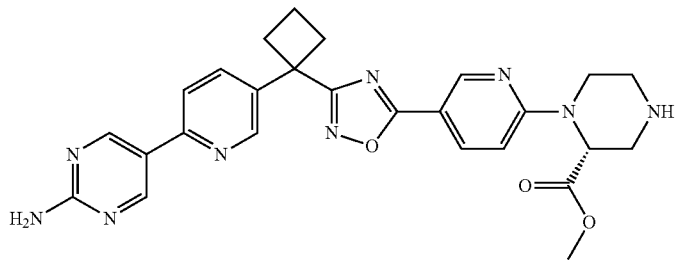
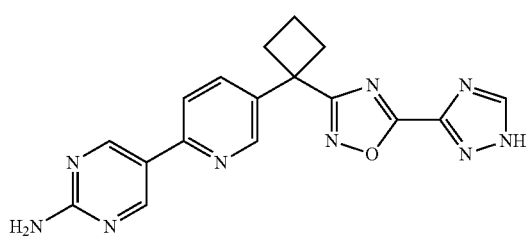
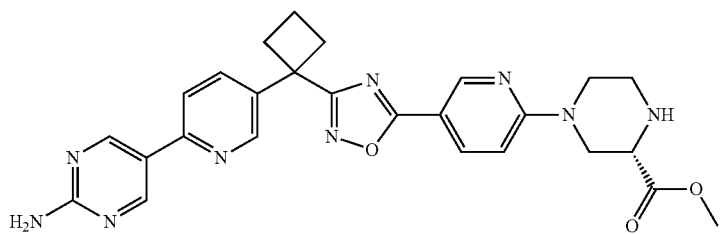
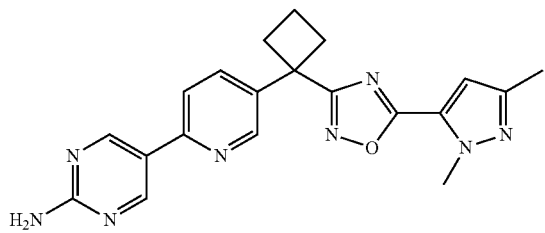
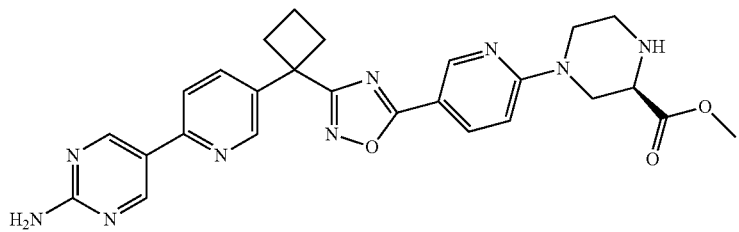
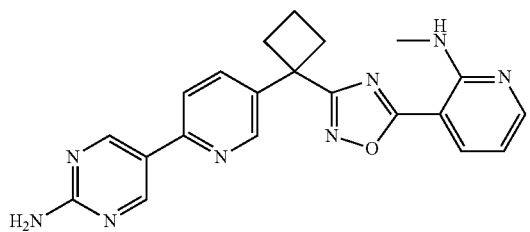

-continued
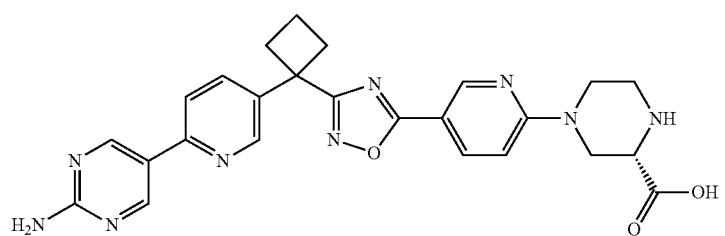
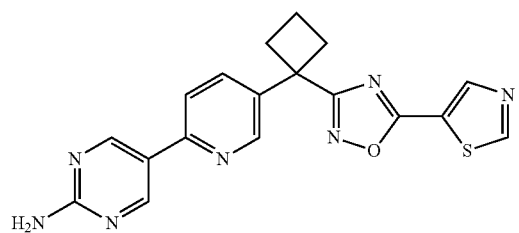
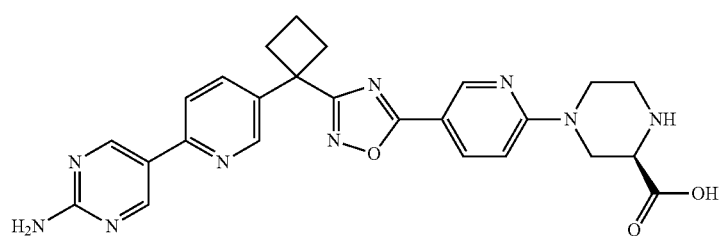
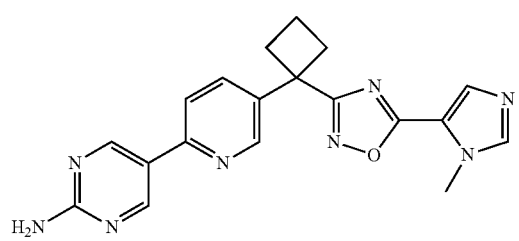
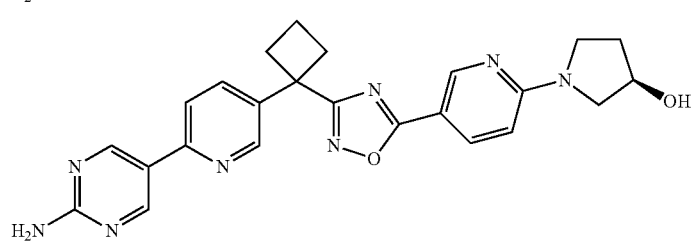
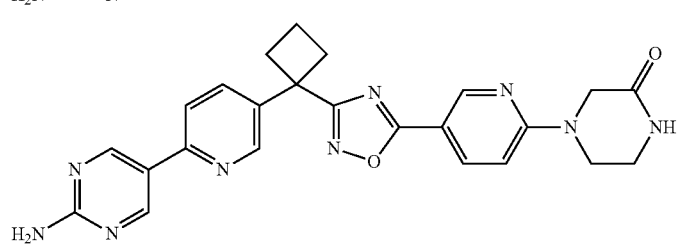
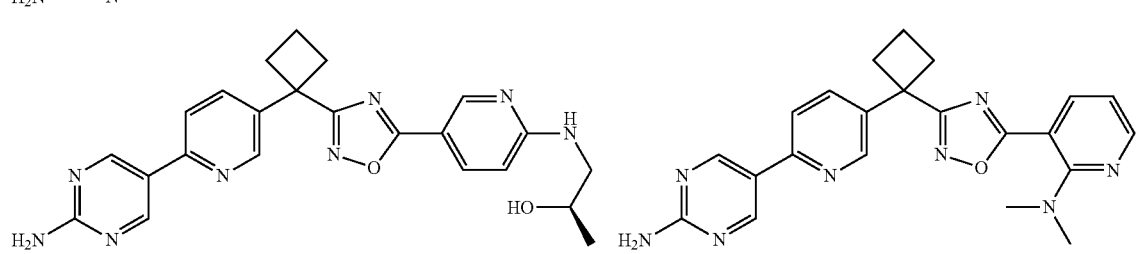

229 230
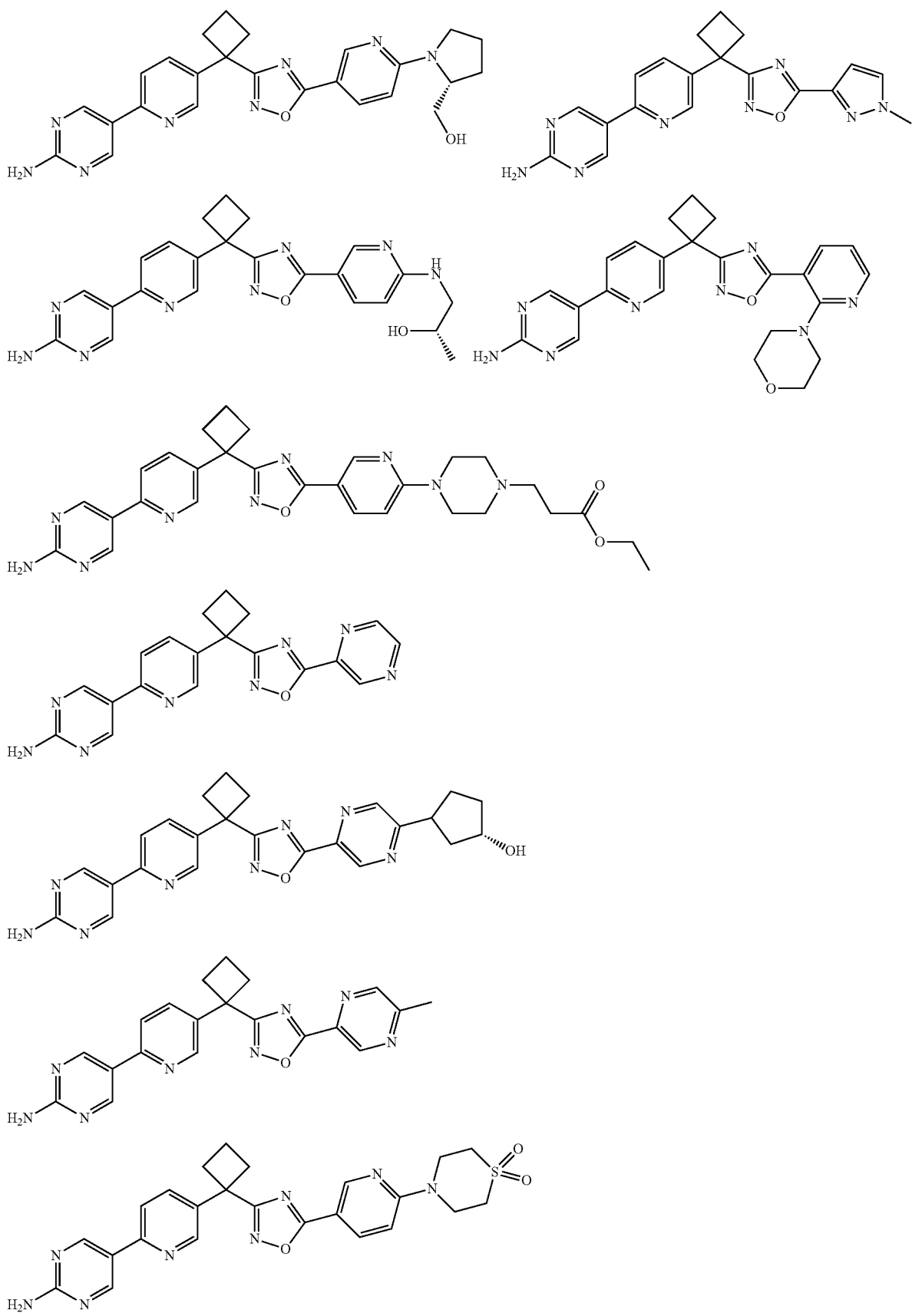

-continued
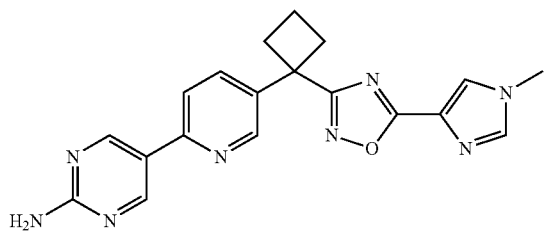
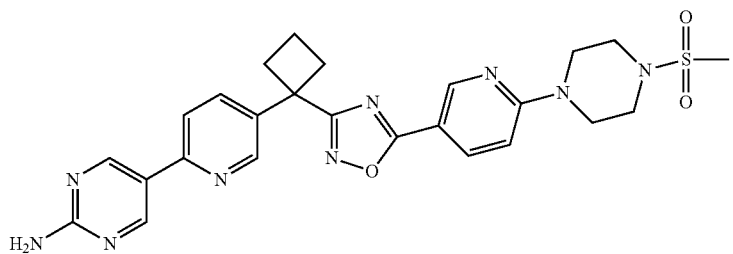
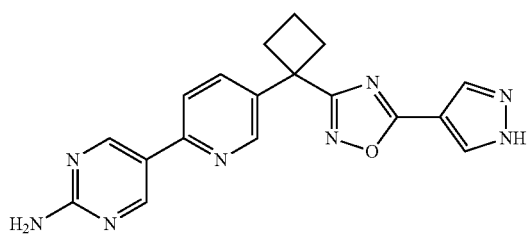
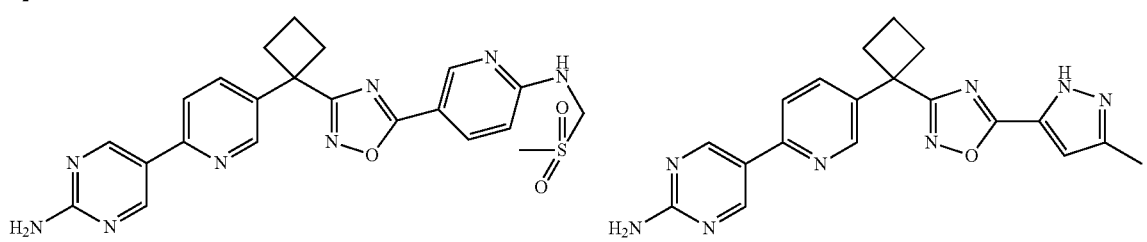
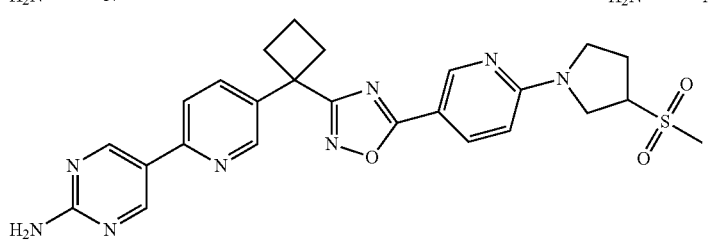
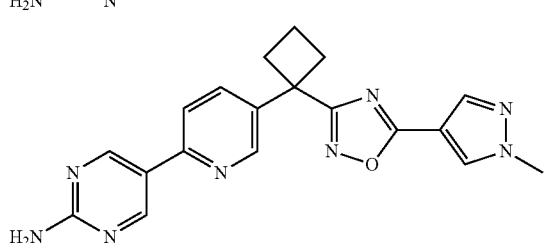
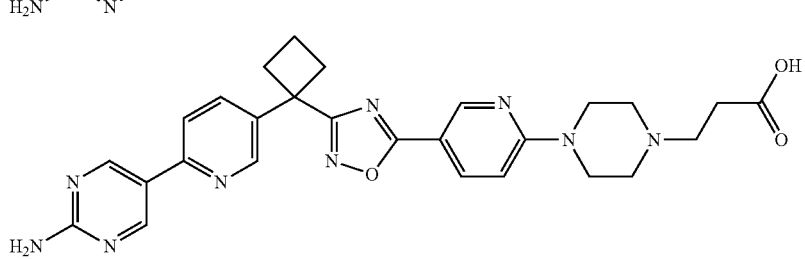

-continued
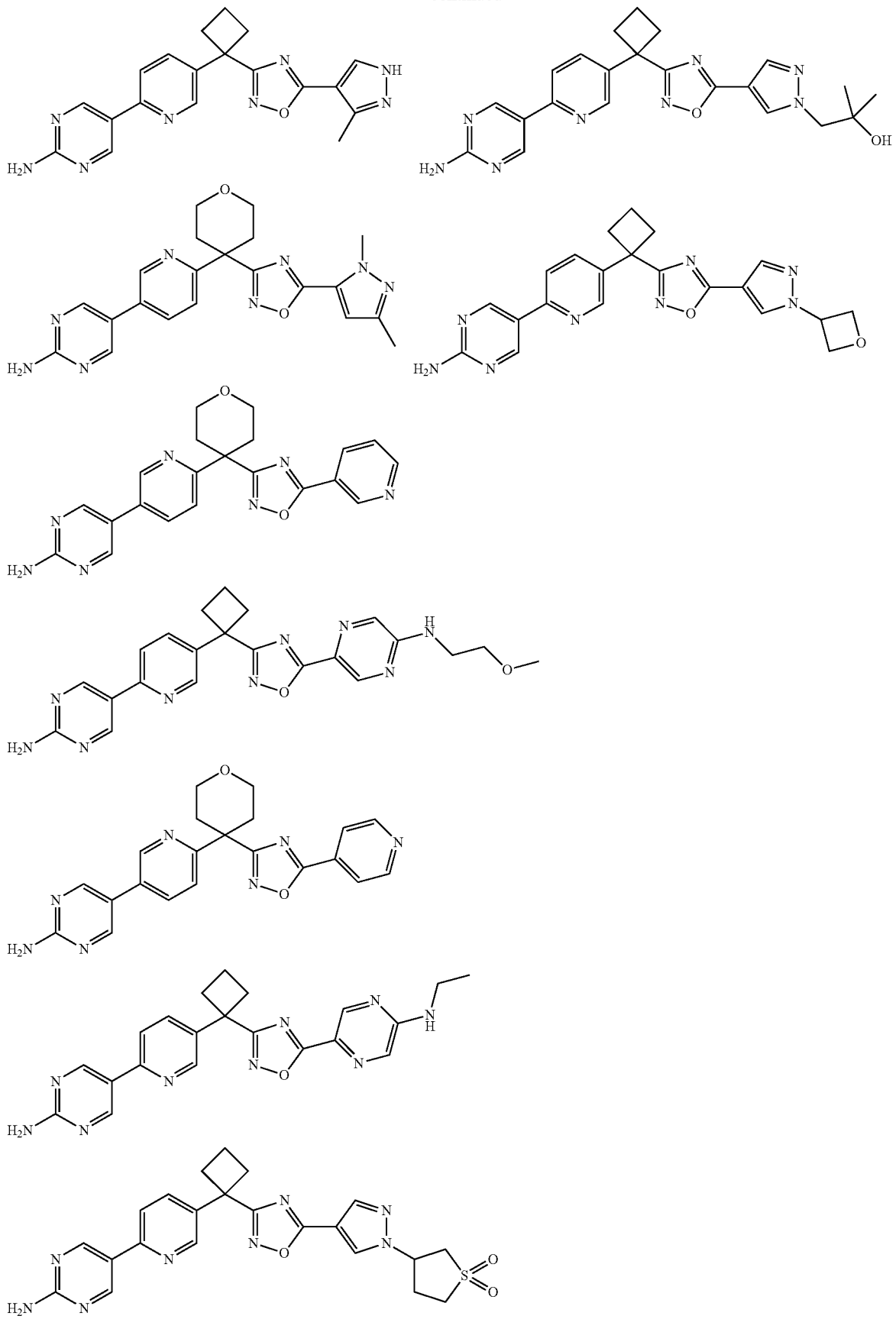

-continued
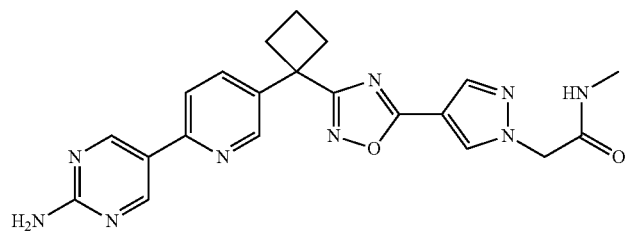
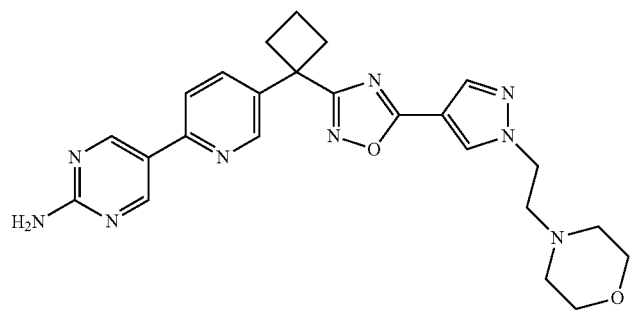
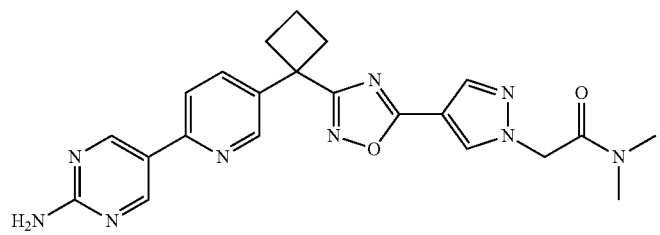
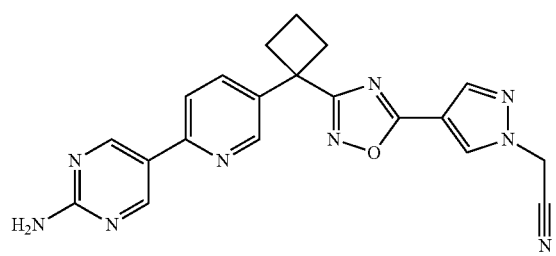
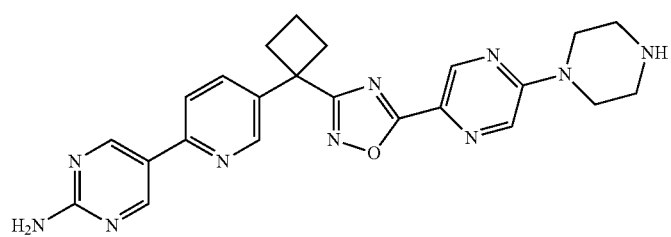
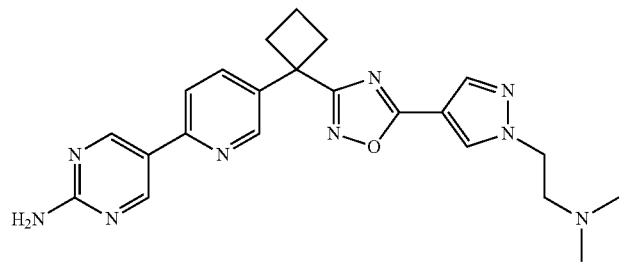

237                                                                 238
-continued
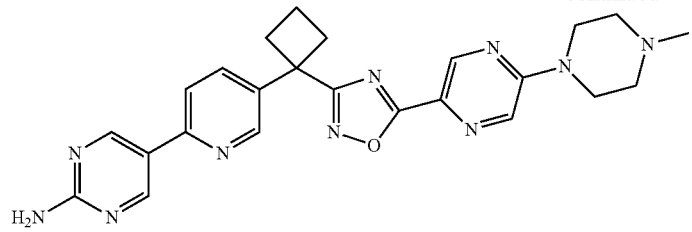
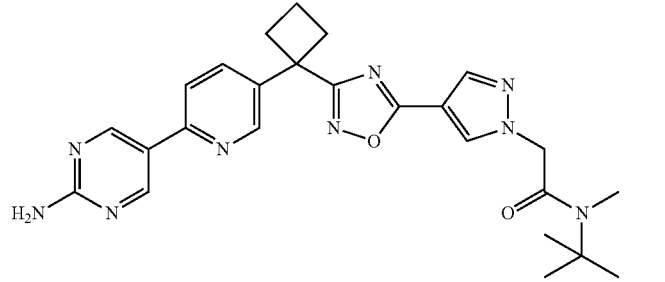
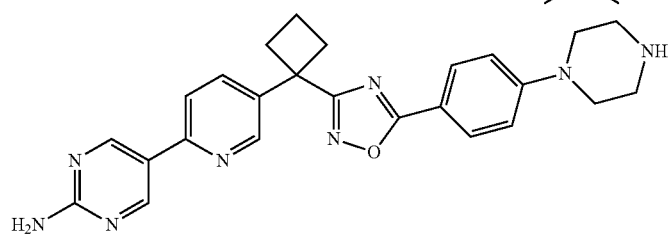
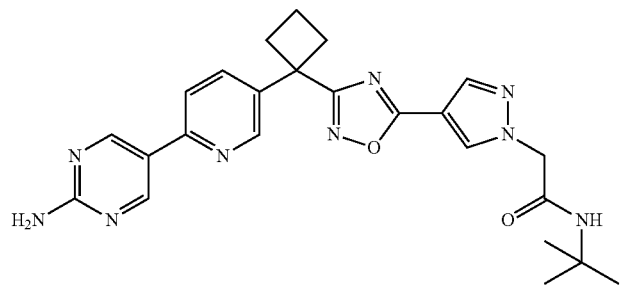
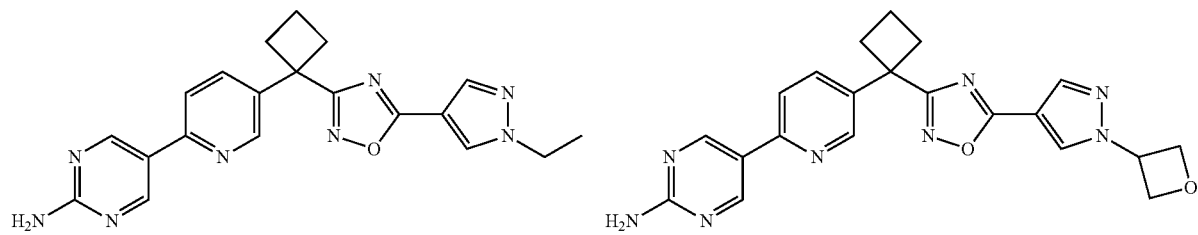
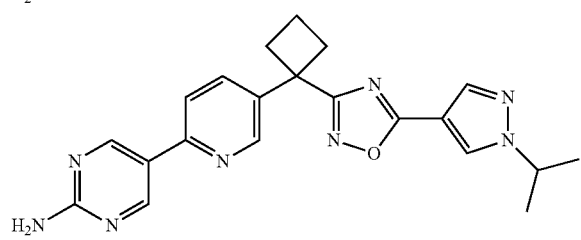      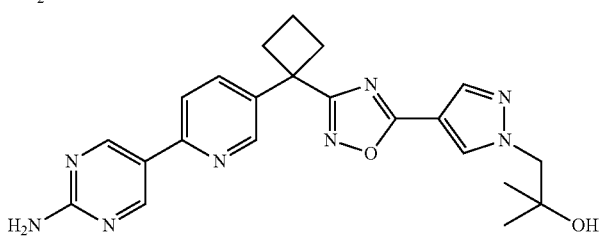
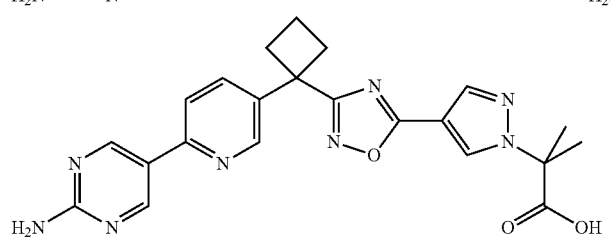

-continued
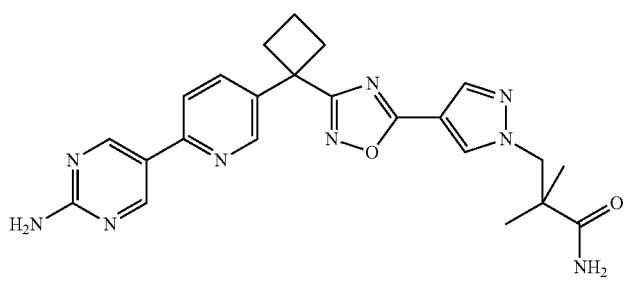
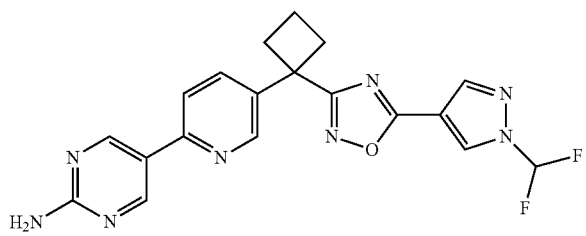
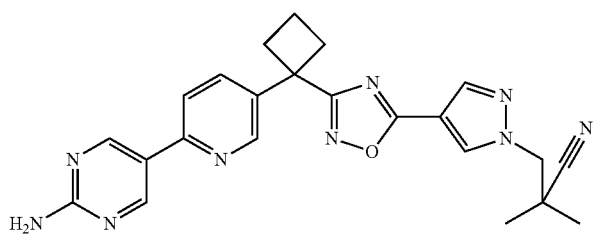
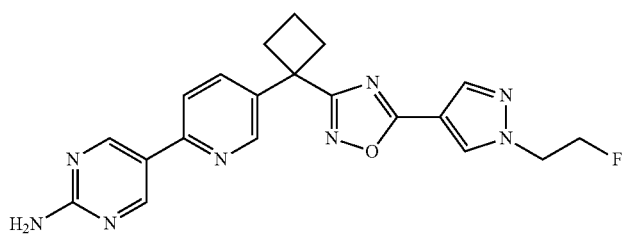
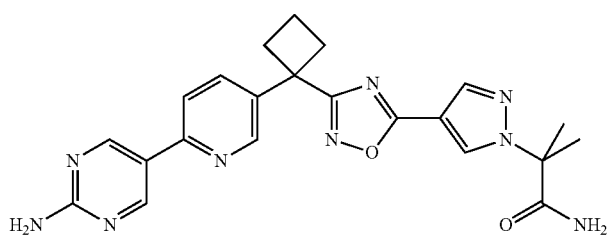
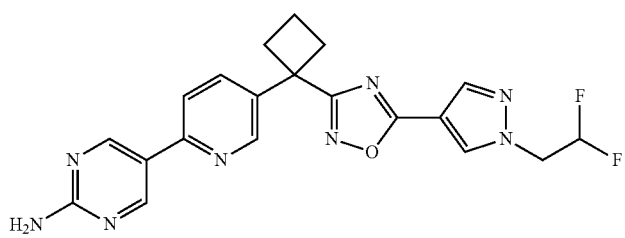
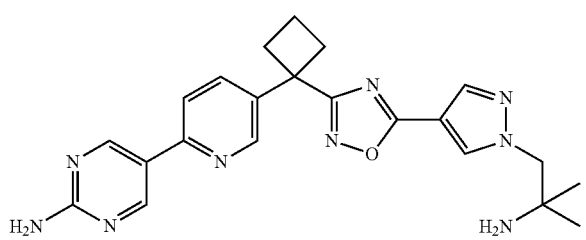

241
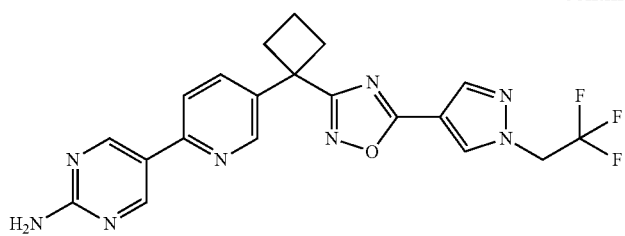
242
-continued
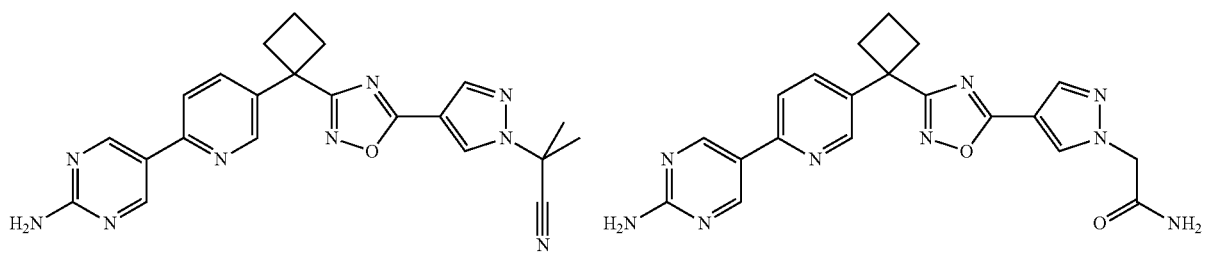
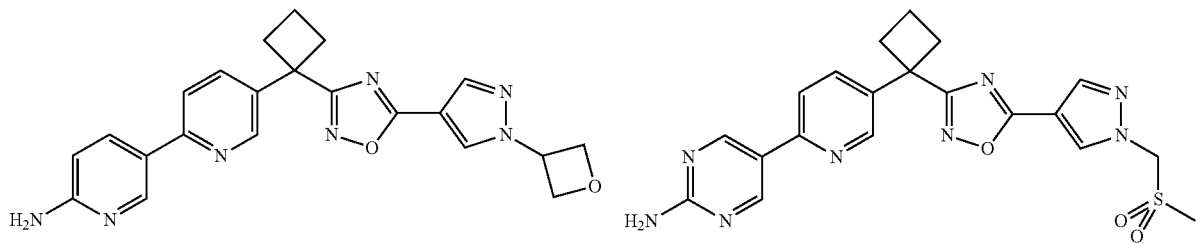
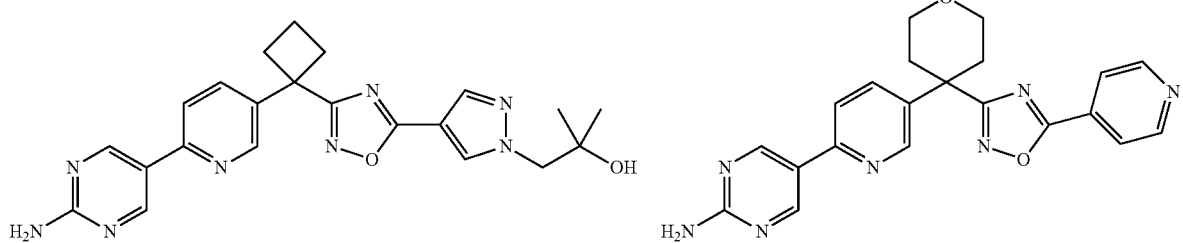
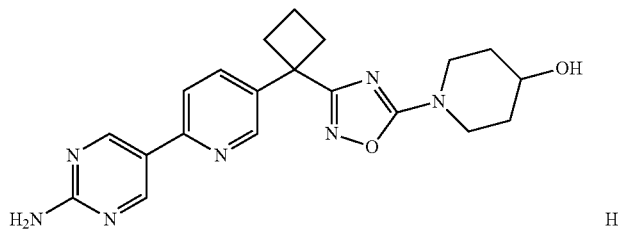
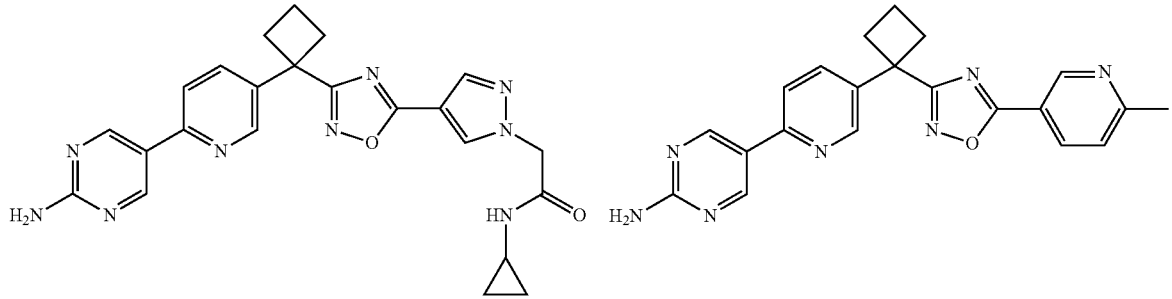

243 244
-continued
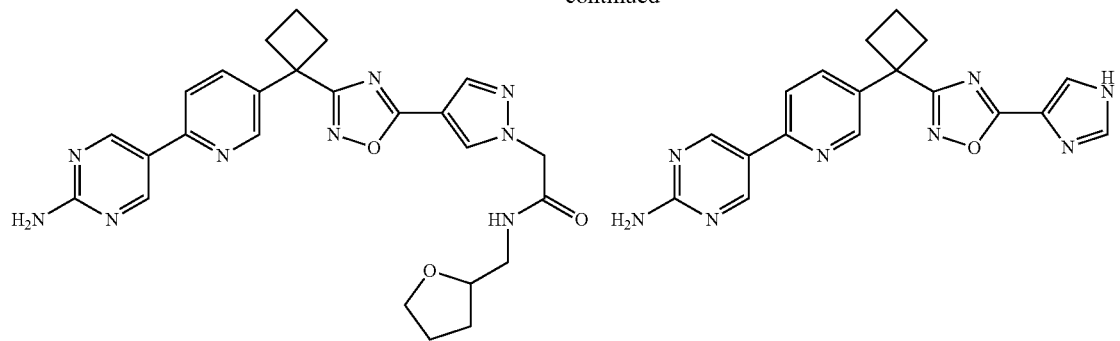
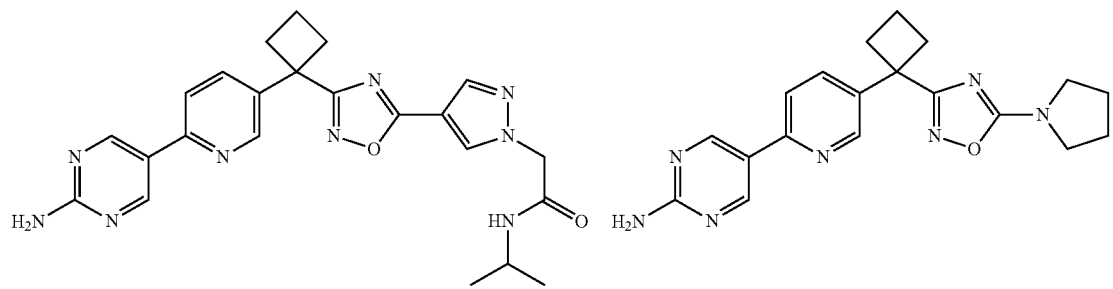
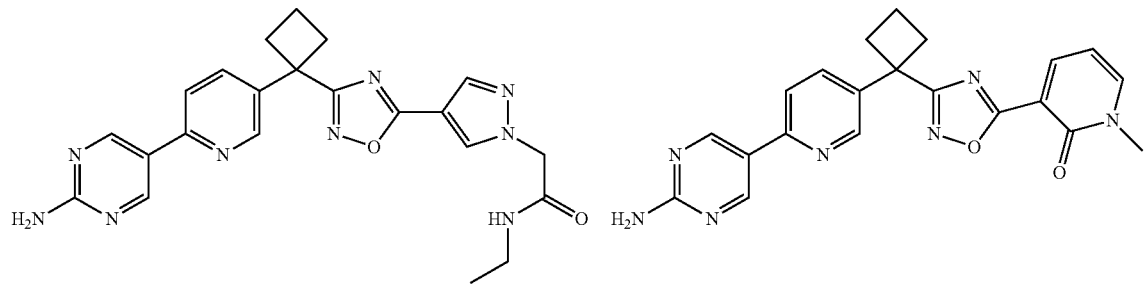
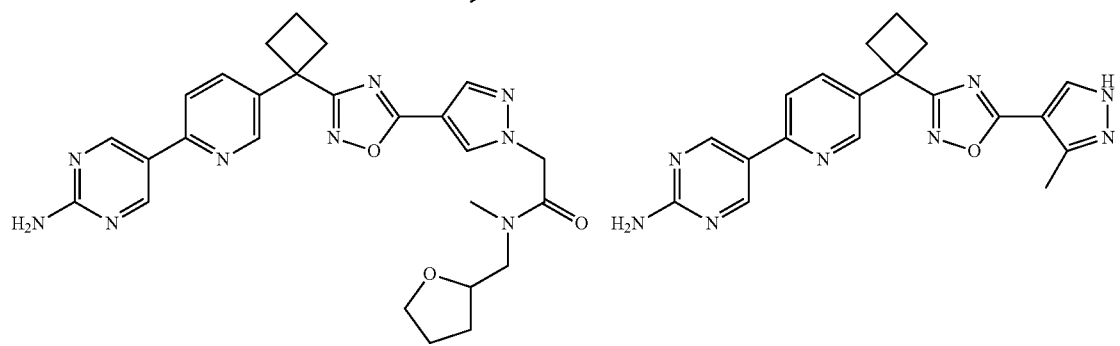
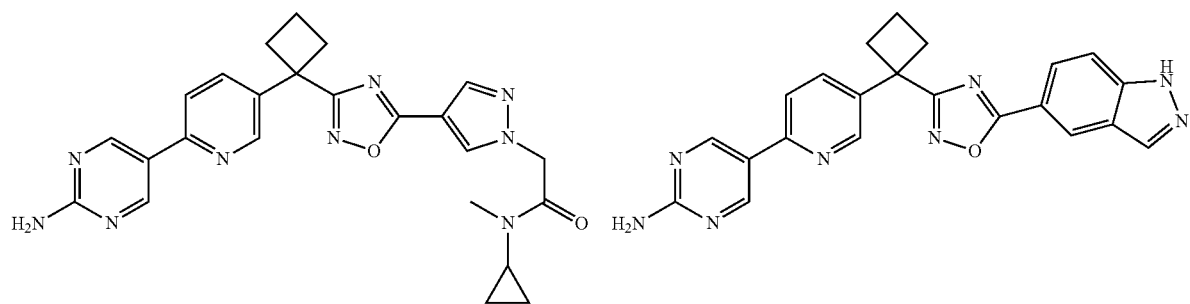

-continued
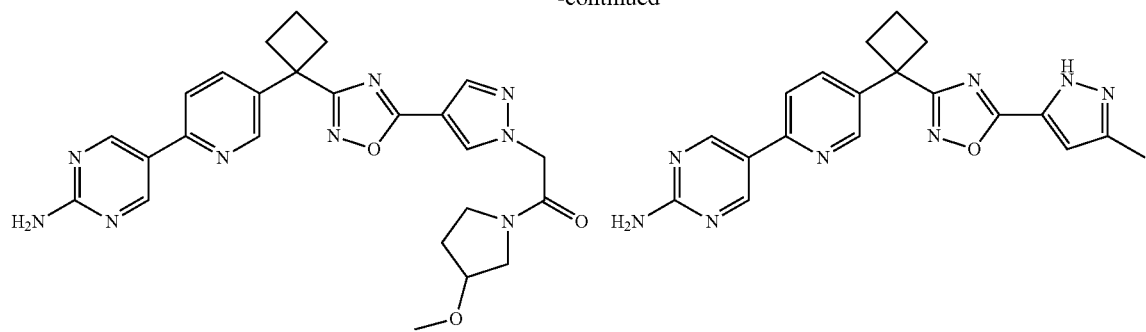
245
246
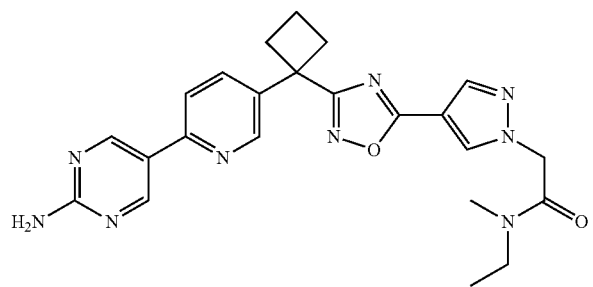
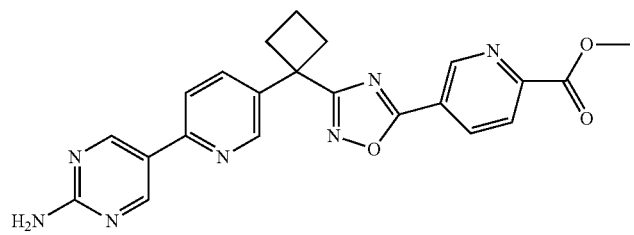
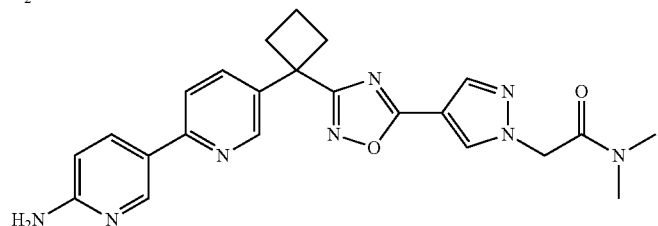
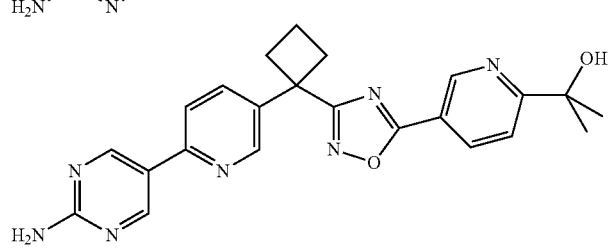
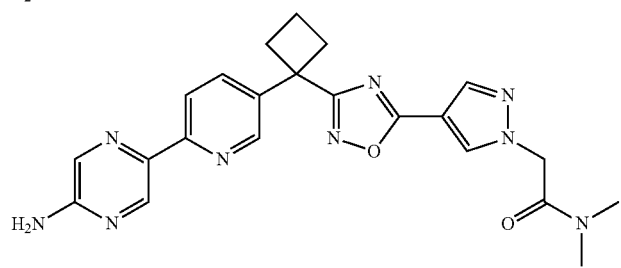

-continued
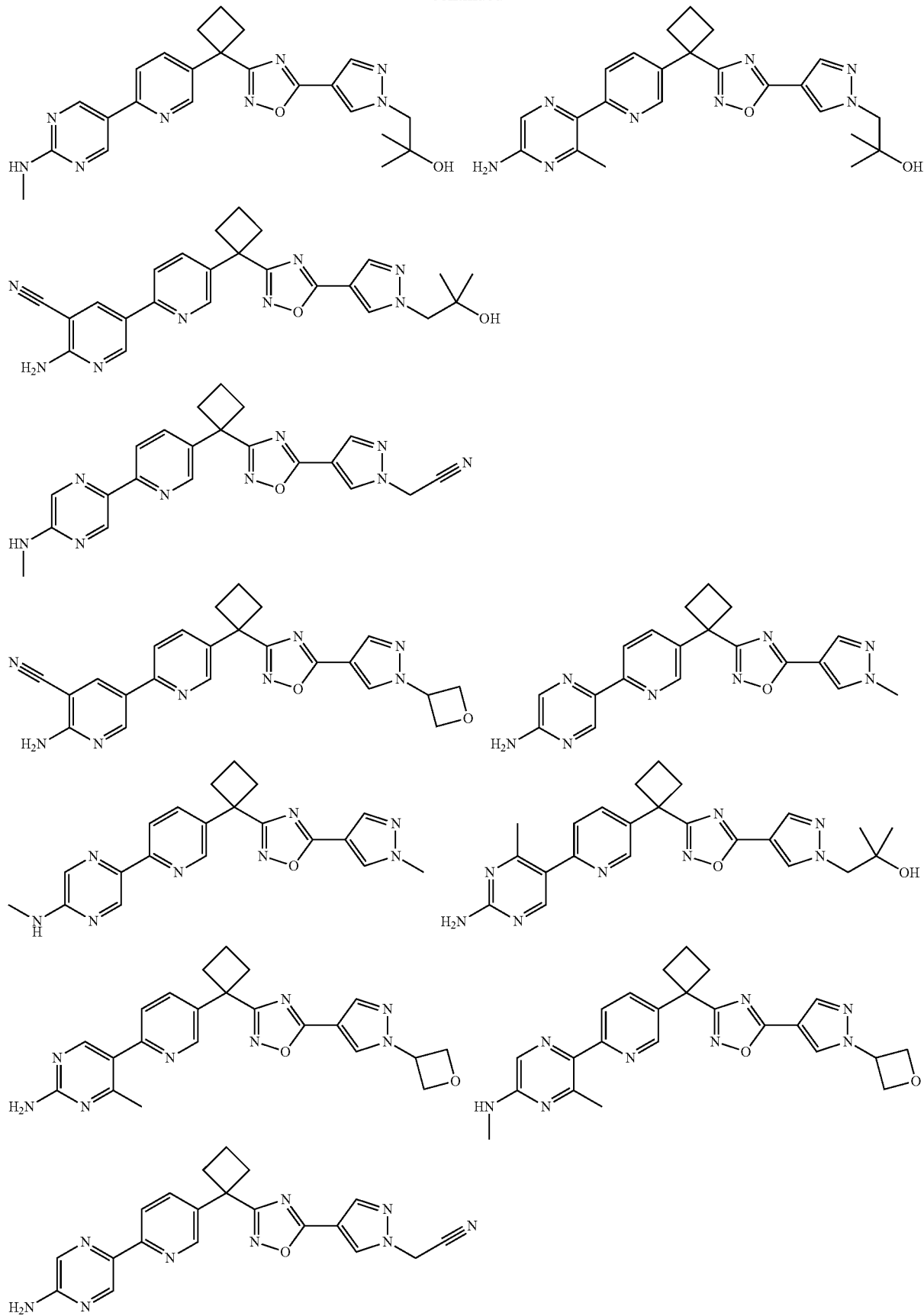

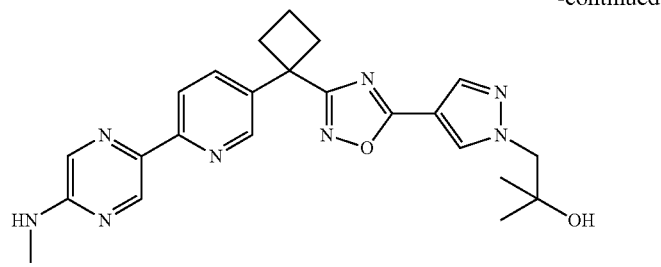
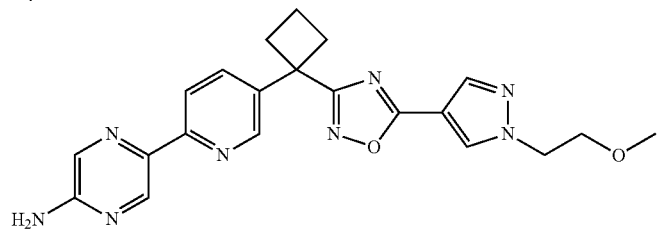
or pharmaceutically acceptable salts thereof.
21. A compound according to claim 20 selected from a group consisting of:
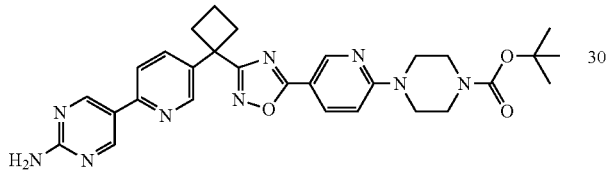
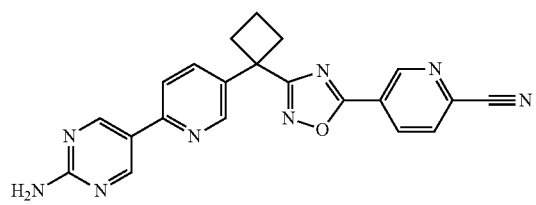
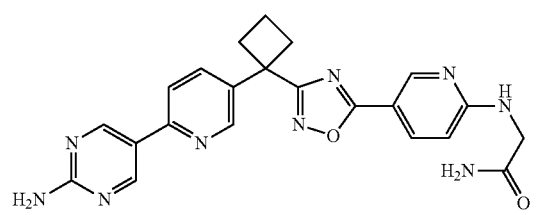
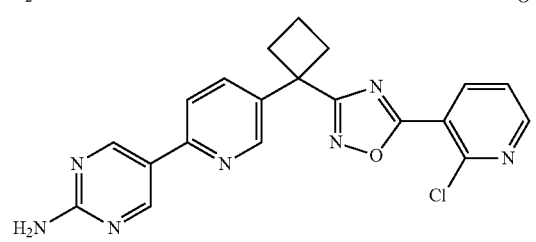
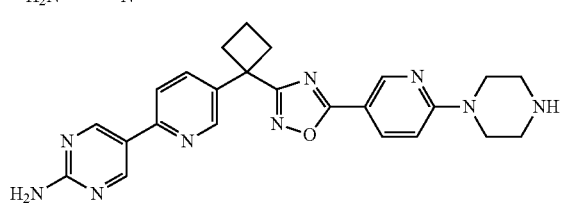
-continued
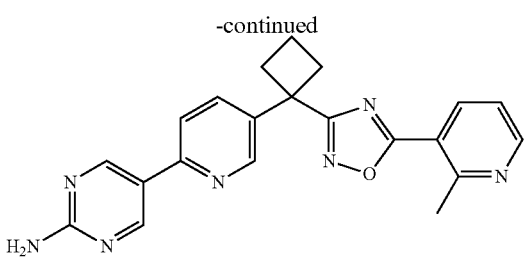
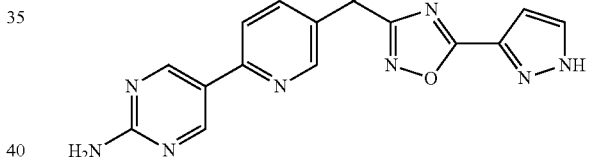
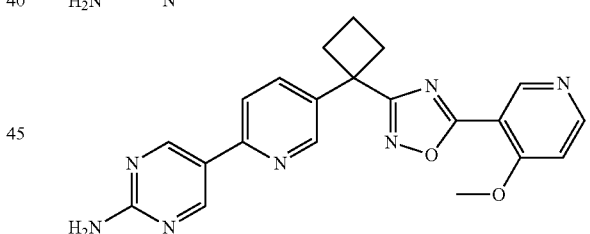
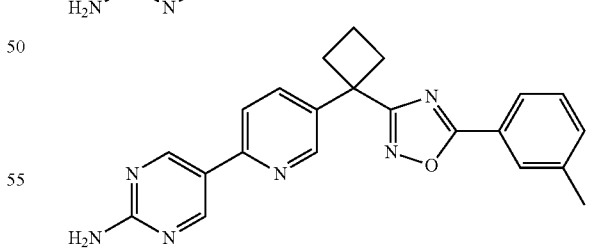
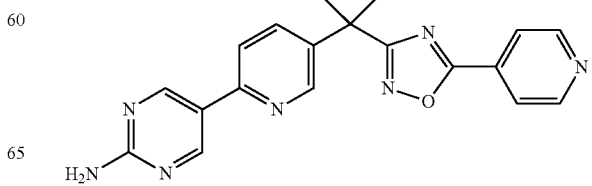

251
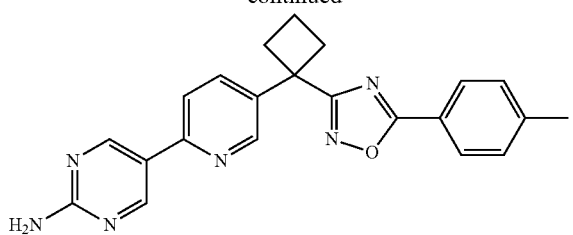
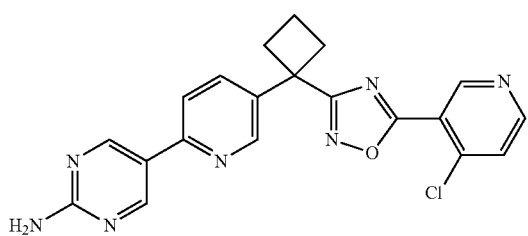
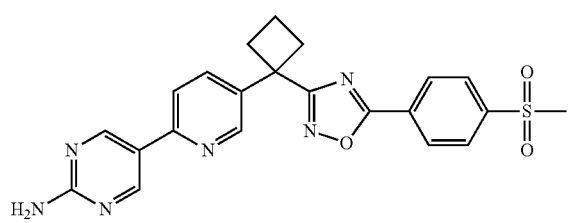
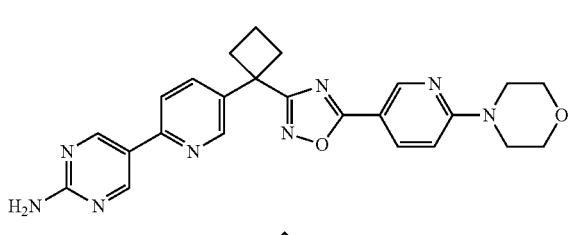
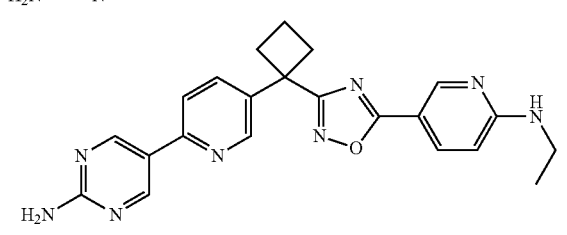
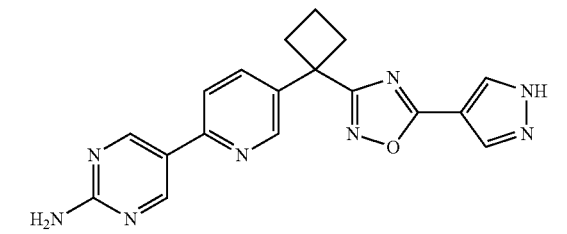
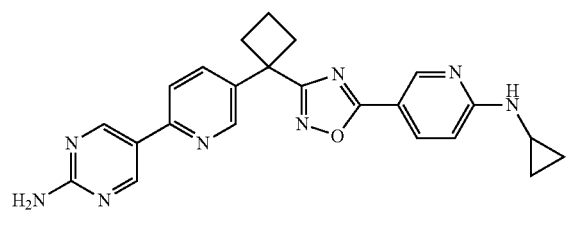
252
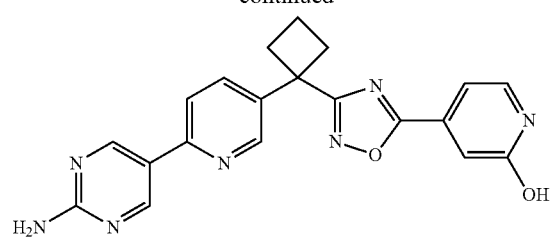
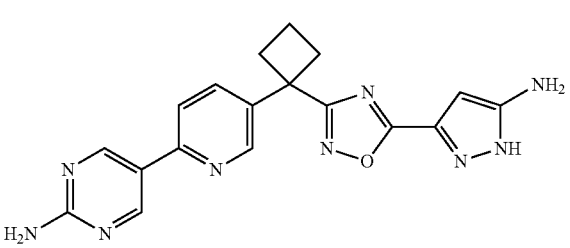
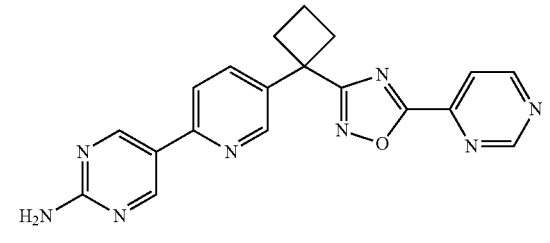
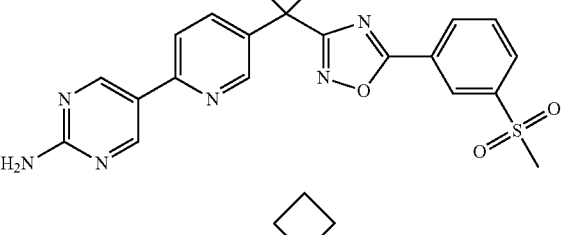
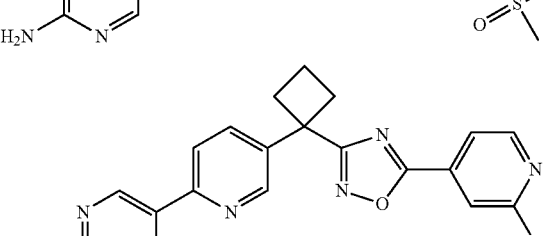
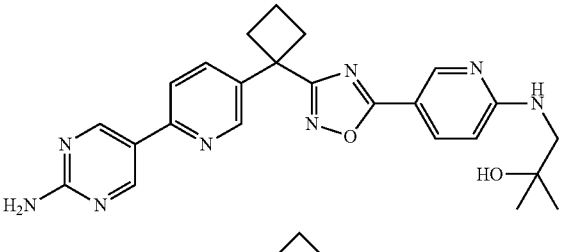
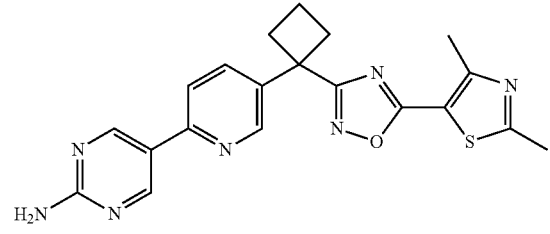

253
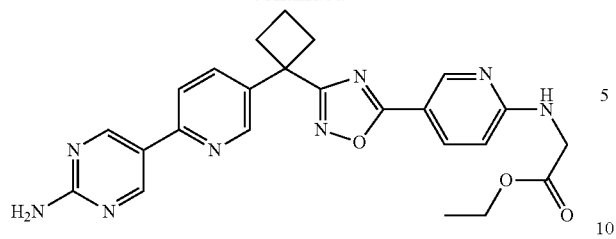
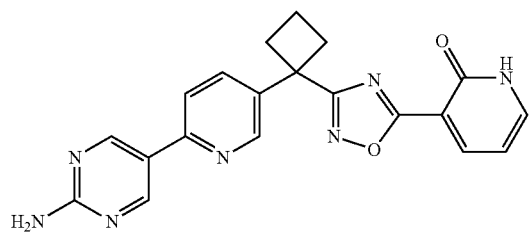
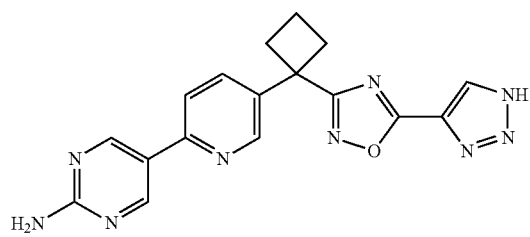
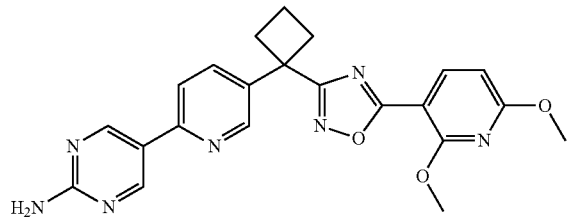
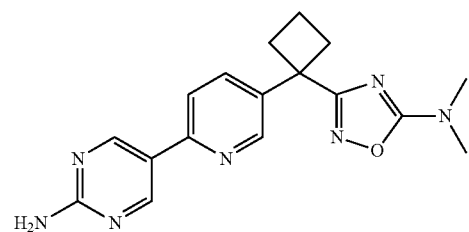
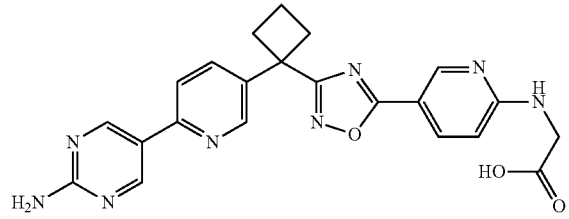
254
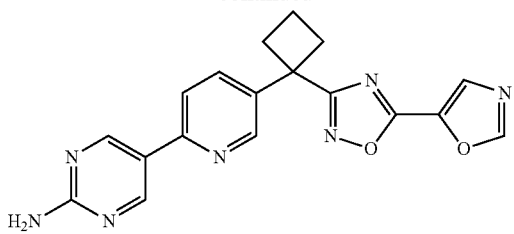
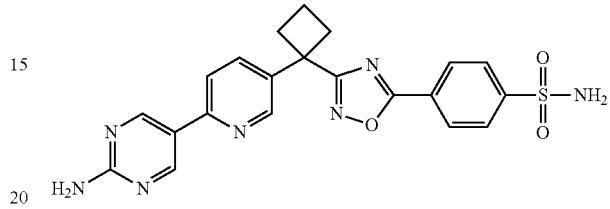
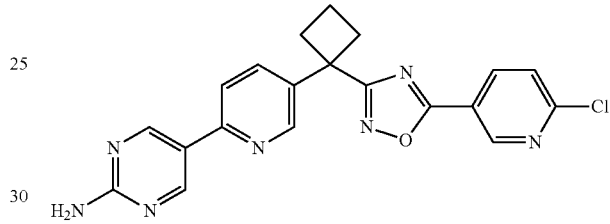
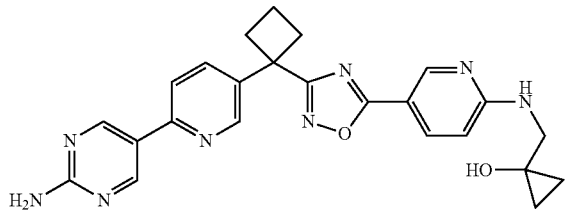
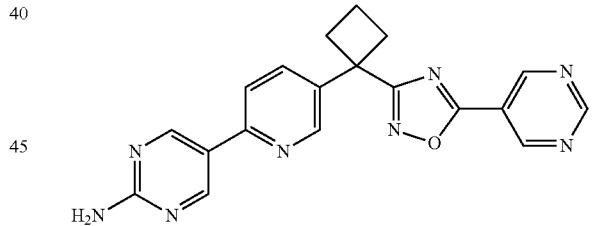
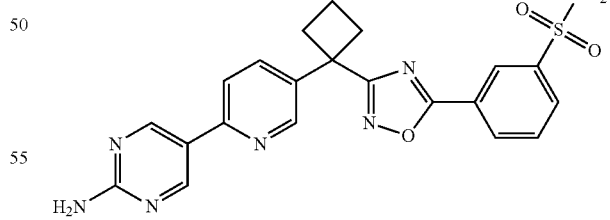
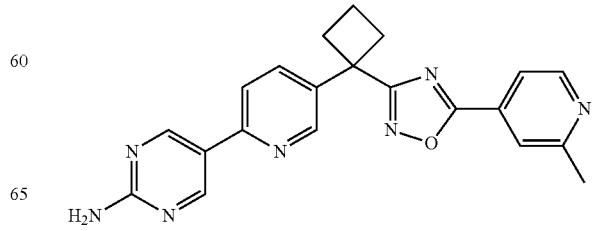

255
-continued
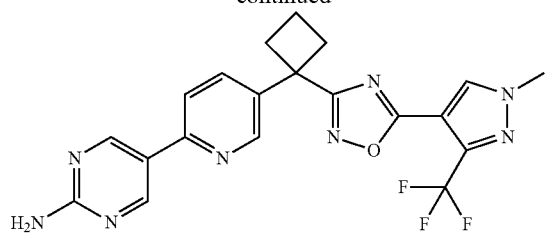
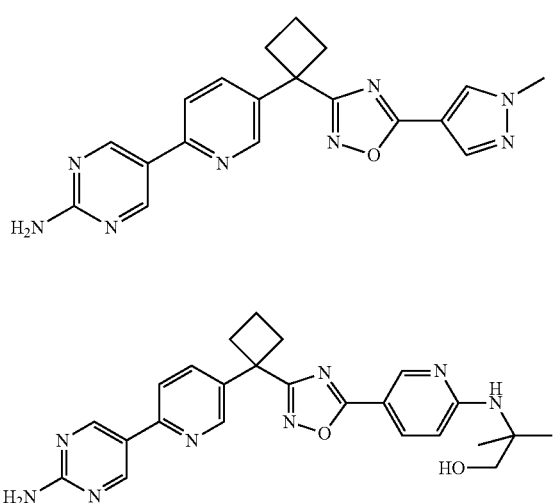
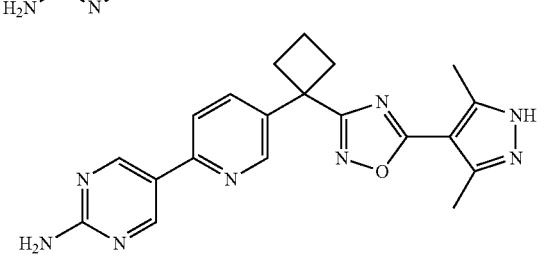
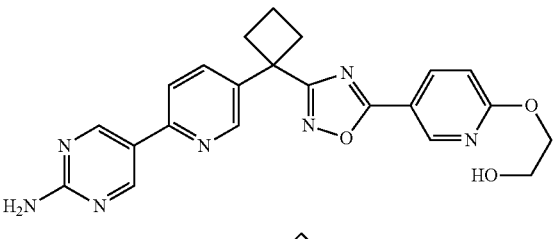
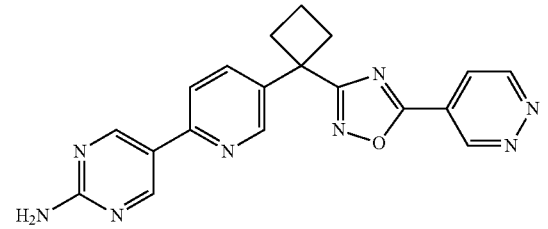
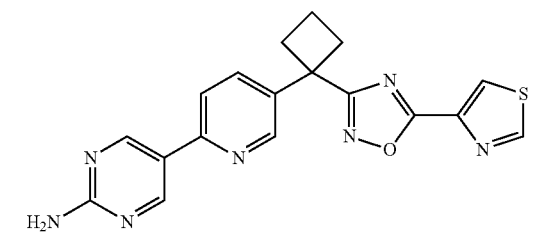
256
-continued
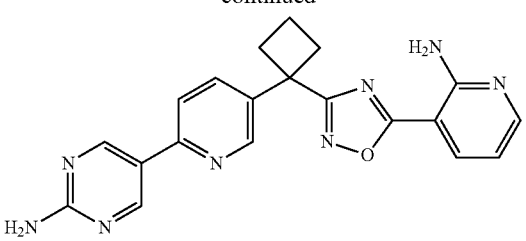
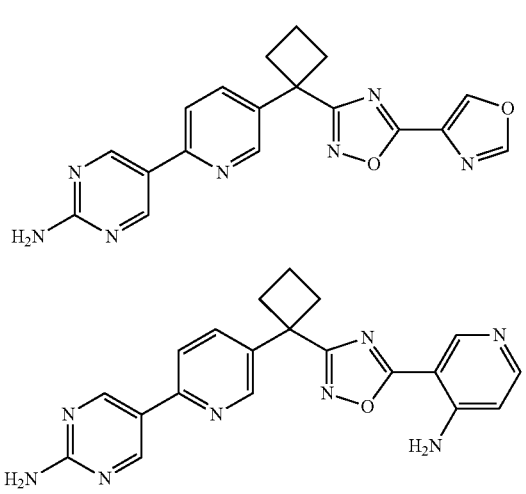
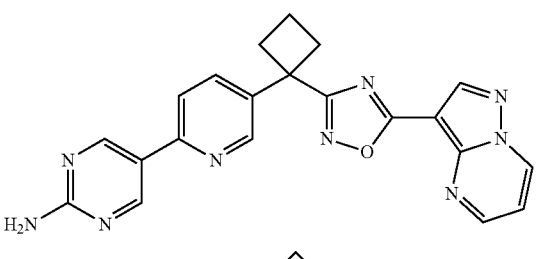
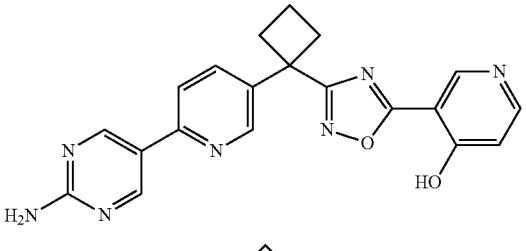
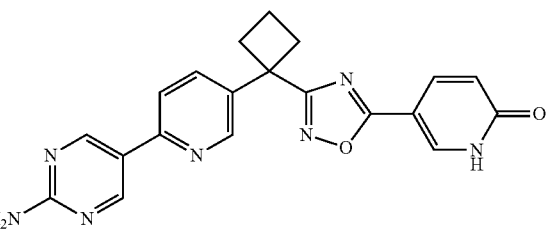

257 -continued

258 -continued

-continued
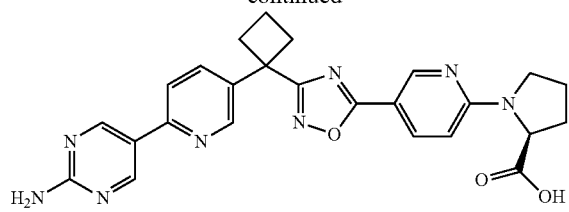
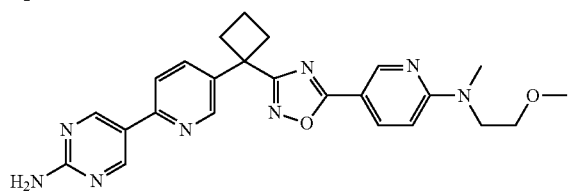
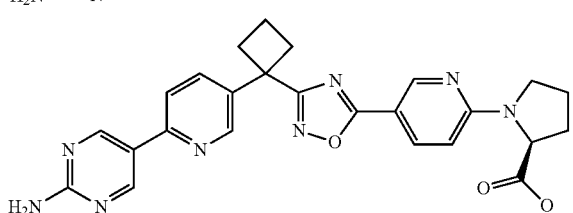
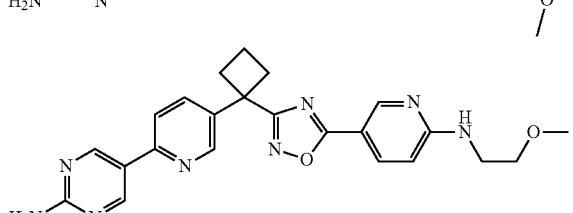
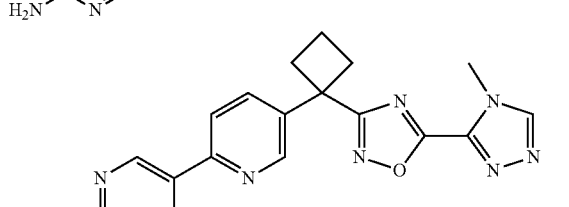
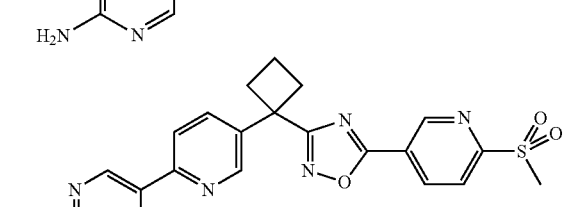
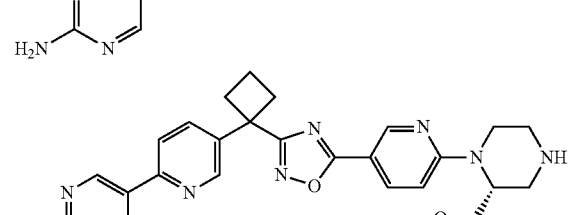
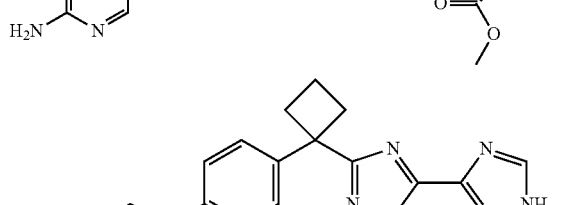
-continued
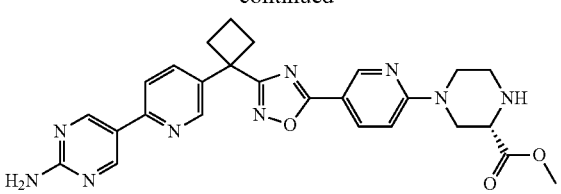
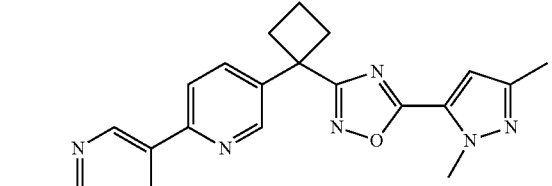
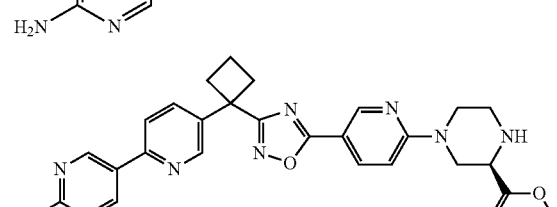
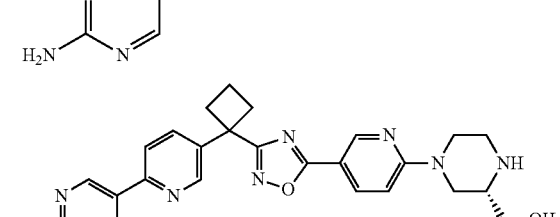
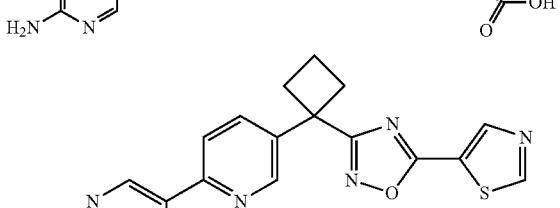
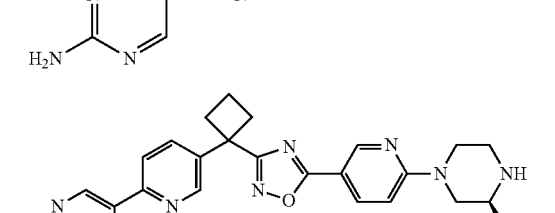
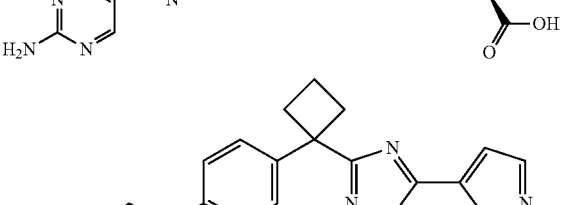

261
-continued
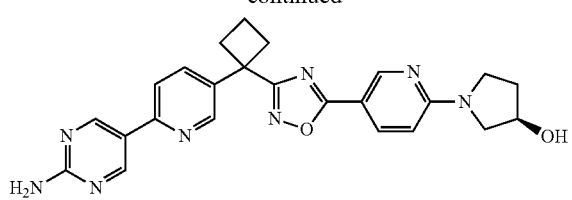
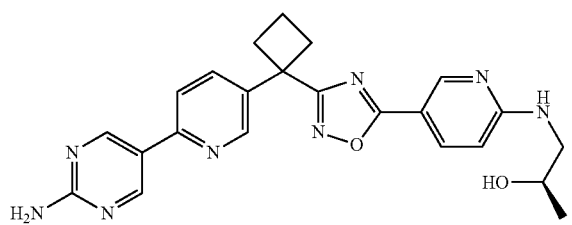
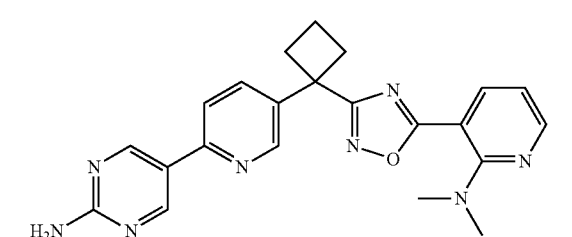
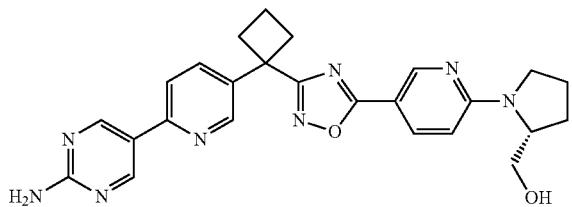
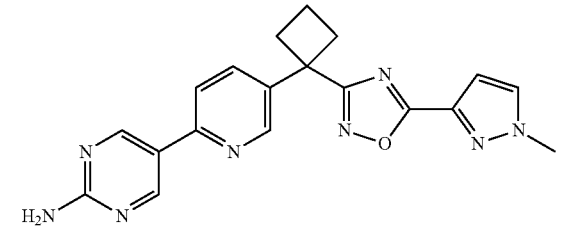
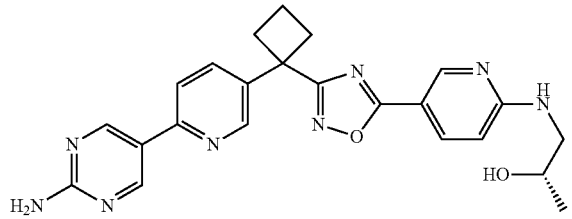
262
-continued
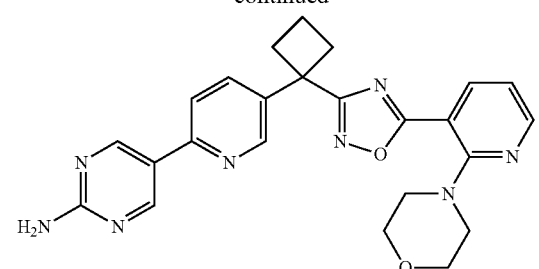
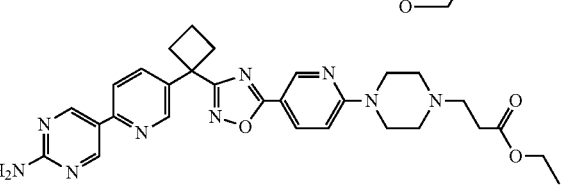
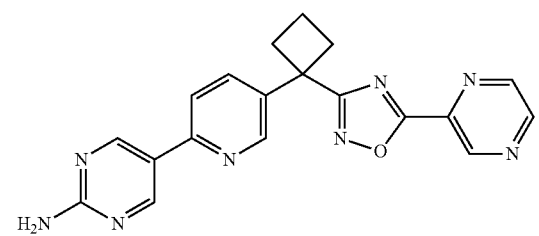
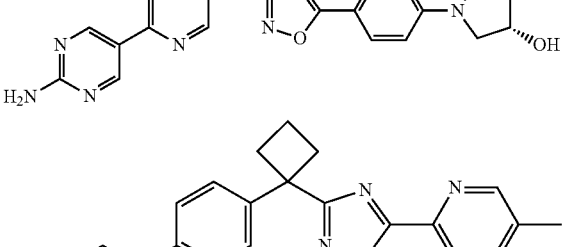
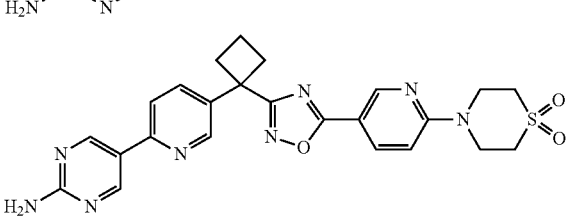
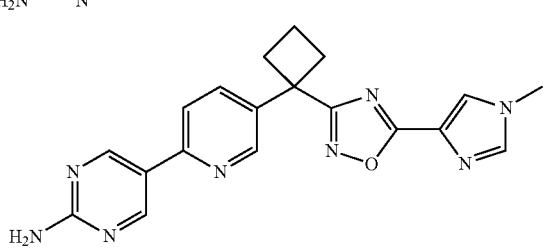
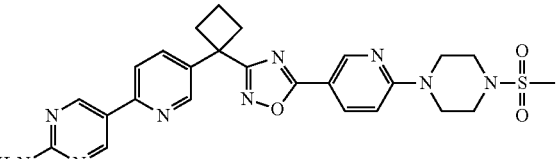

263
-continued
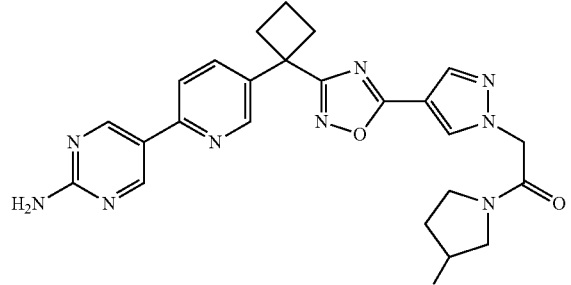
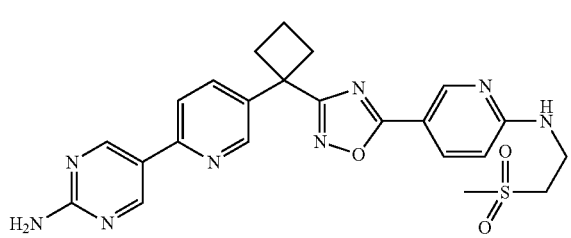
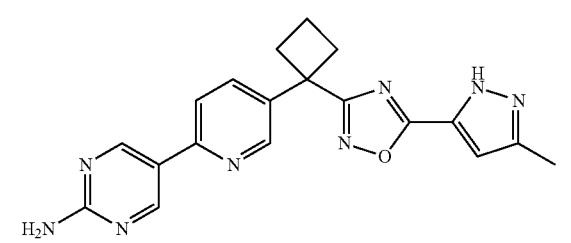
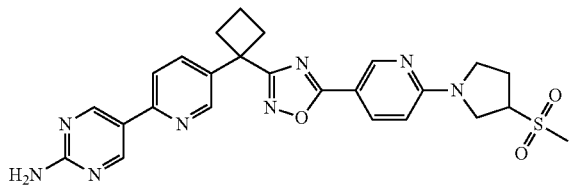
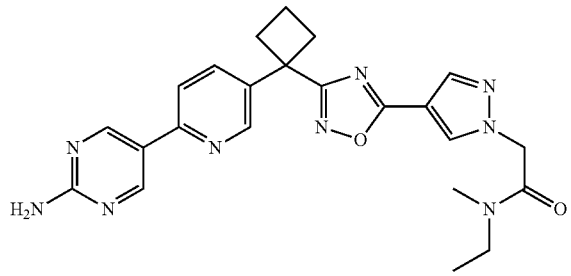
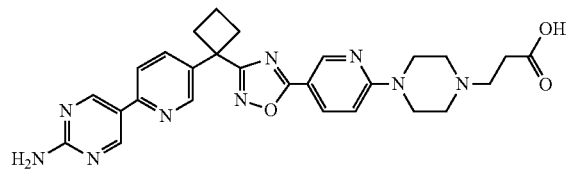
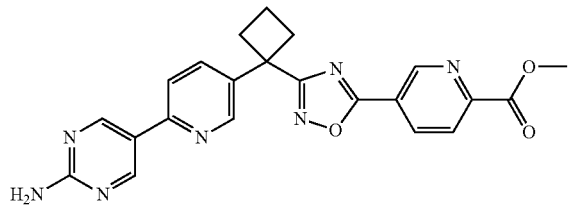
264
-continued
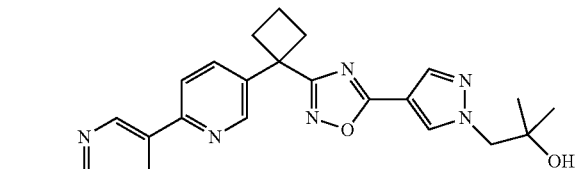
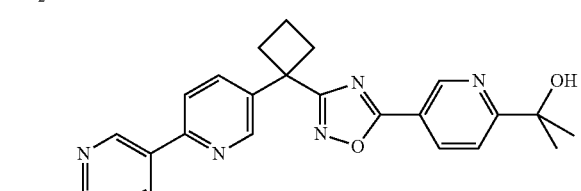
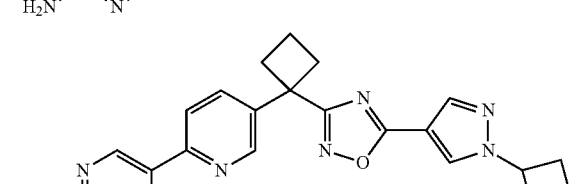
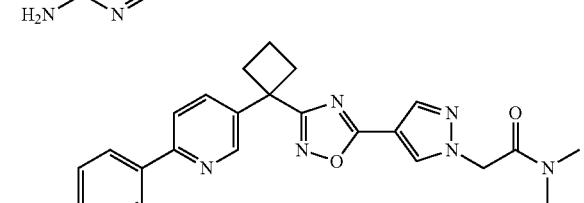
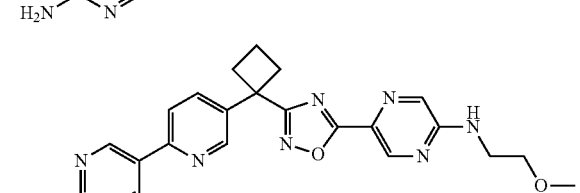
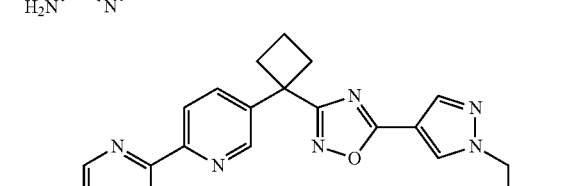
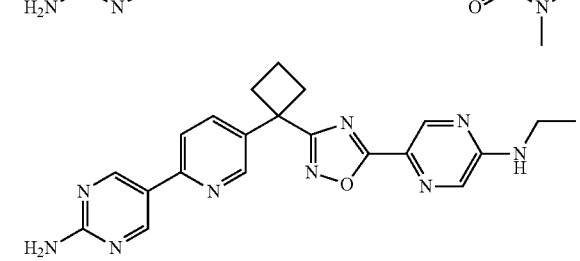
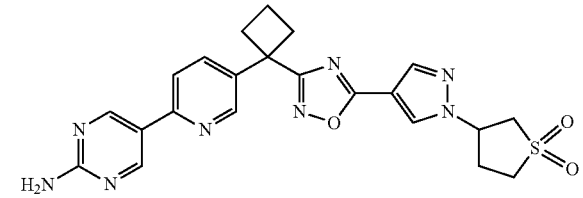

265
-continued
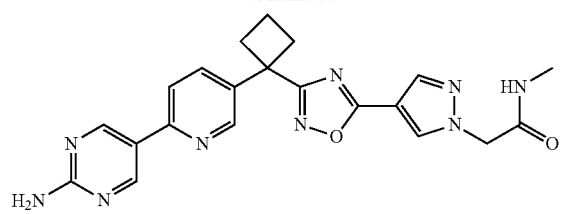
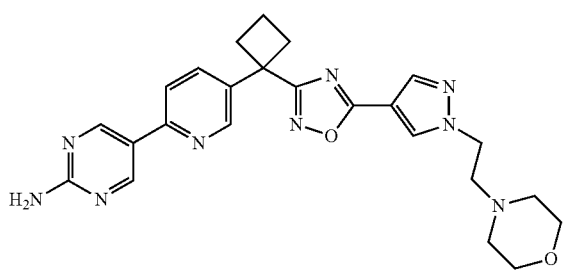
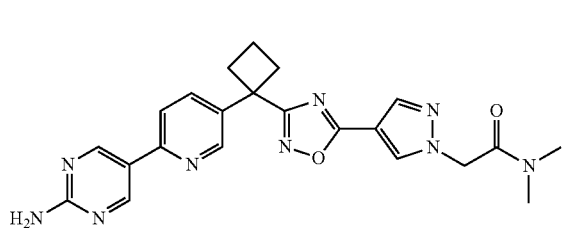
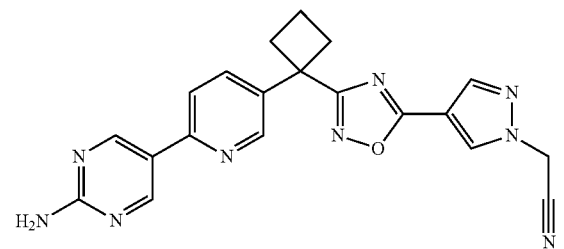
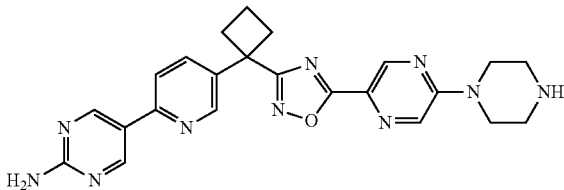
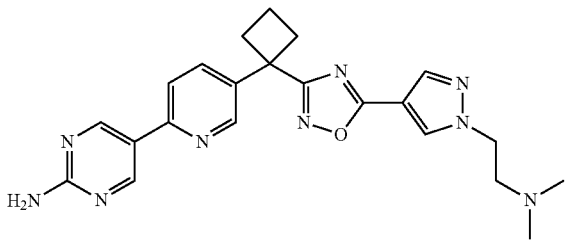
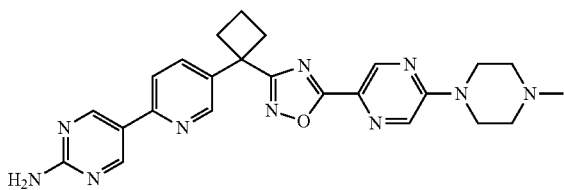
266
-continued
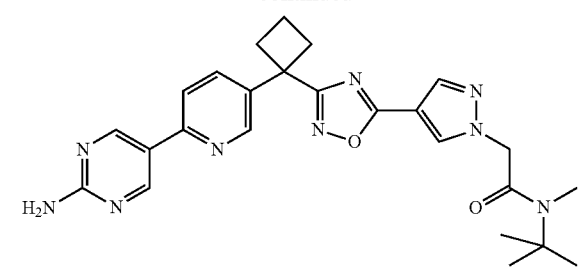
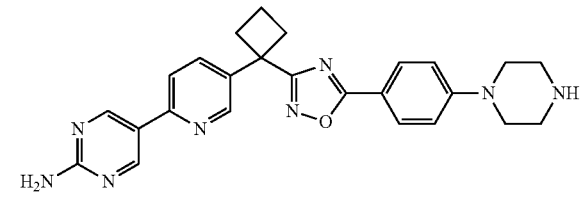
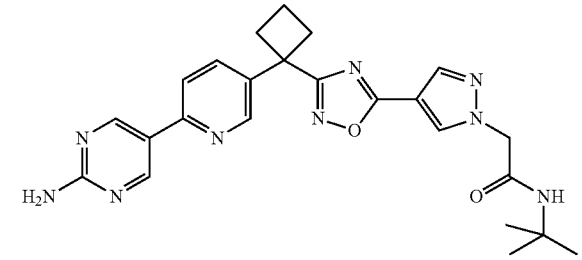
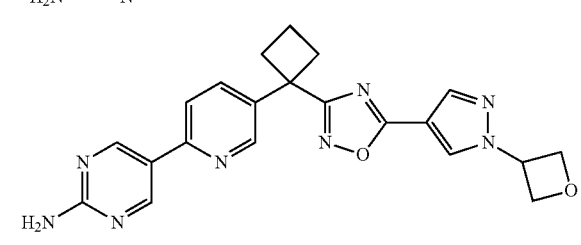
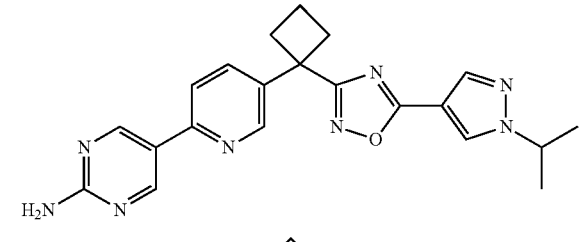
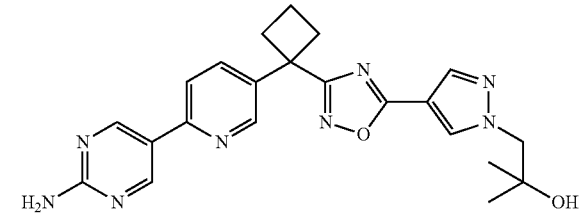

267
-continued
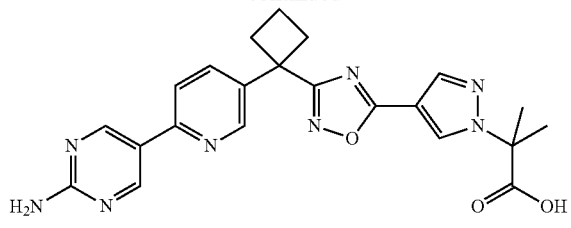
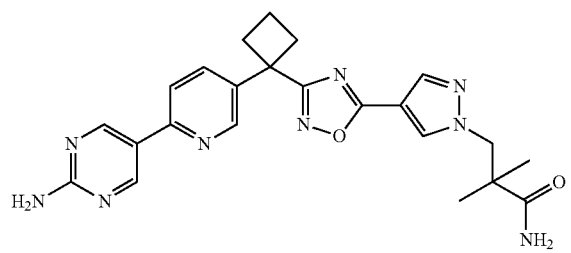
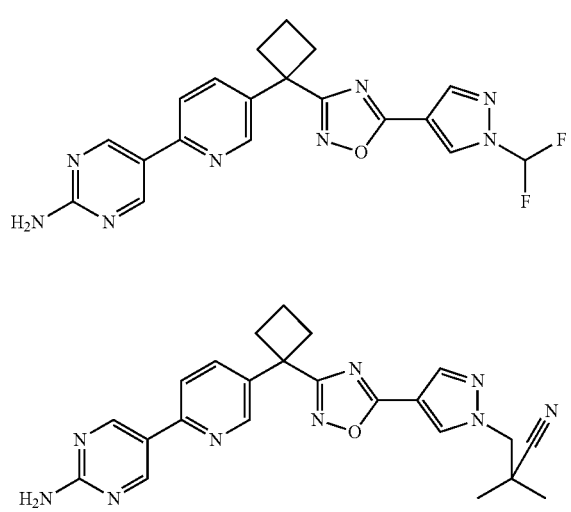
268
-continued
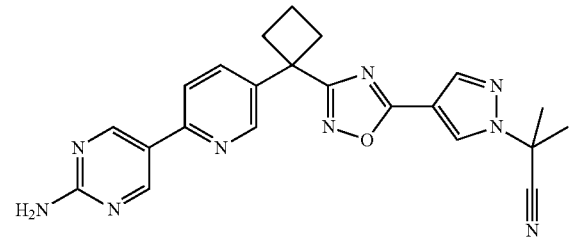
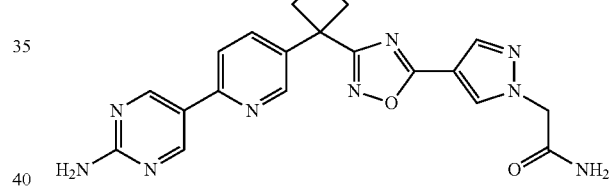
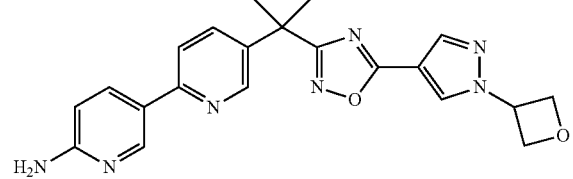
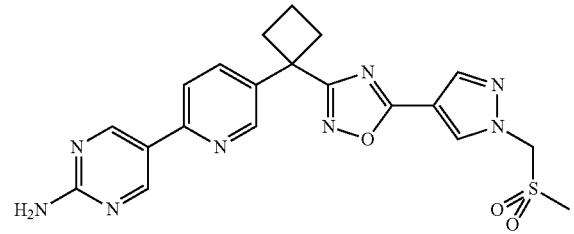
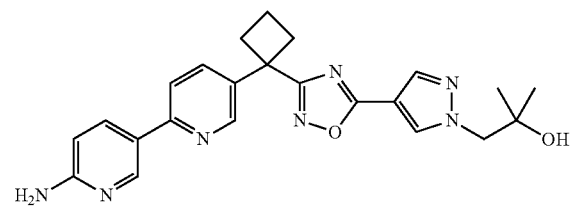

269
-continued
270
-continued
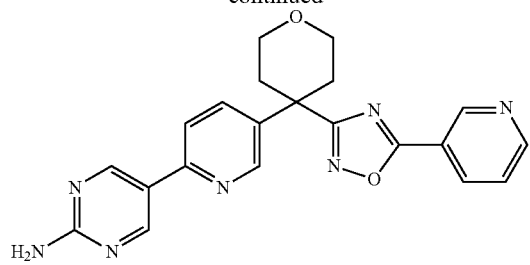
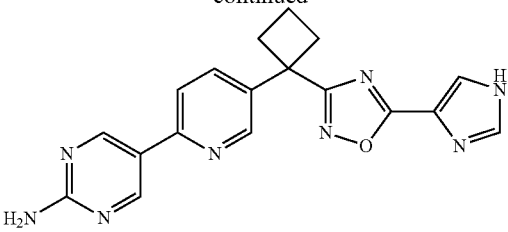

-continued
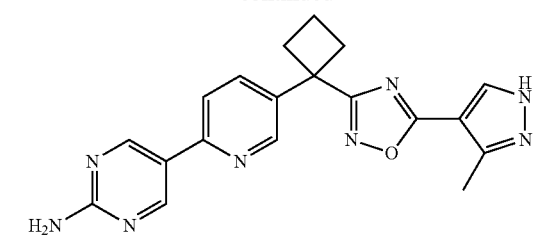
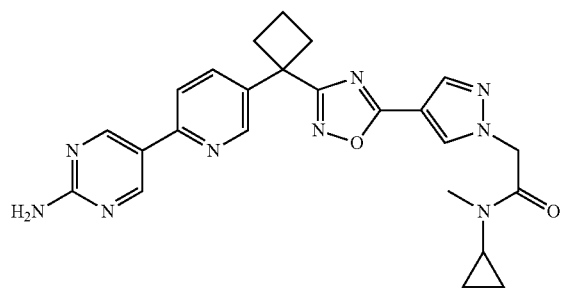
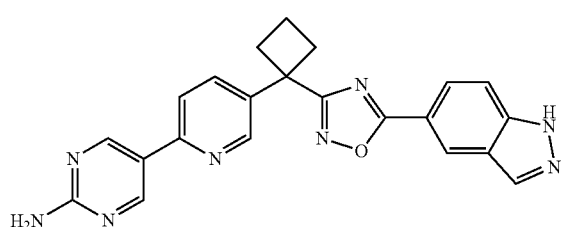
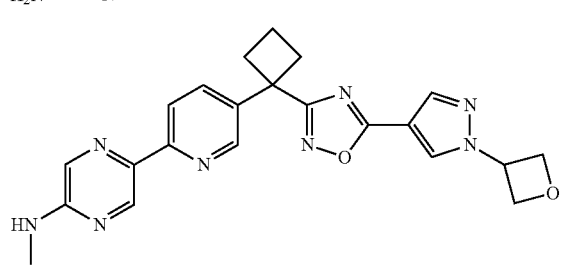
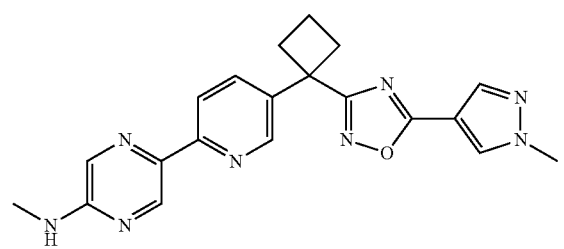
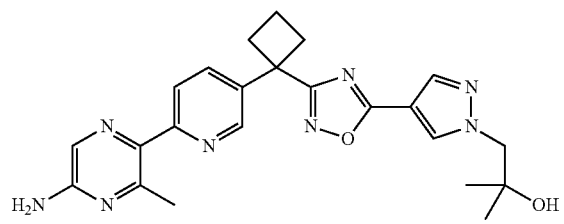
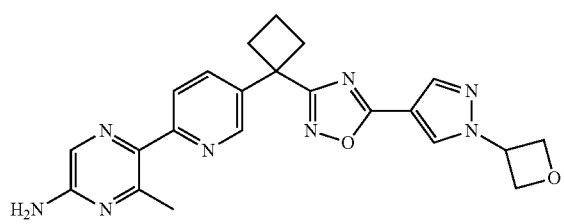
-continued
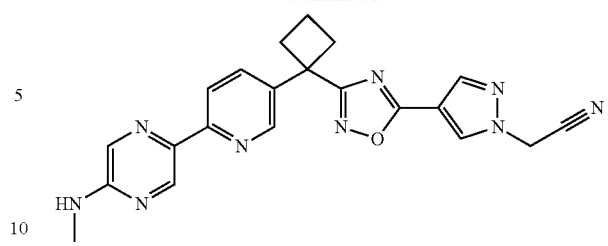
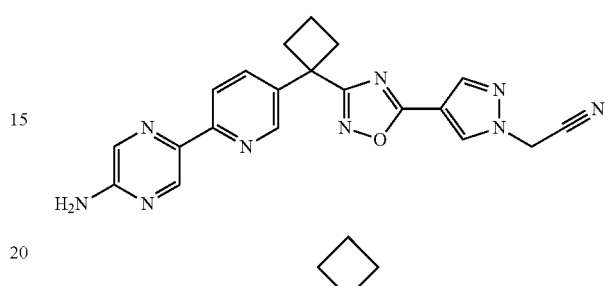
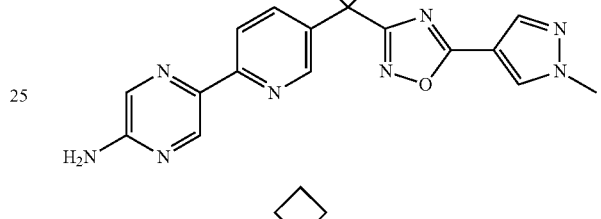
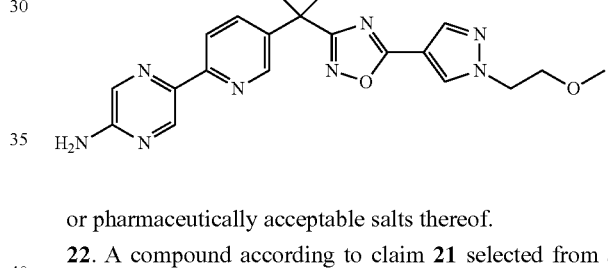
or pharmaceutically acceptable salts thereof.
22. A compound according to claim 21 selected from a group consisting of:
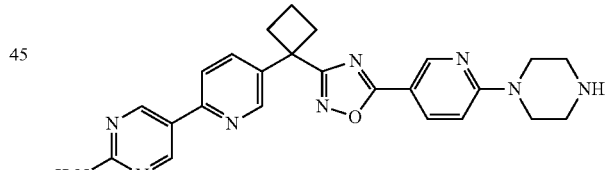
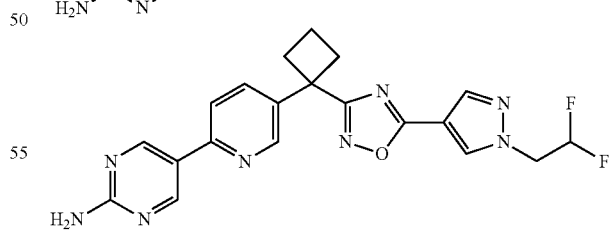
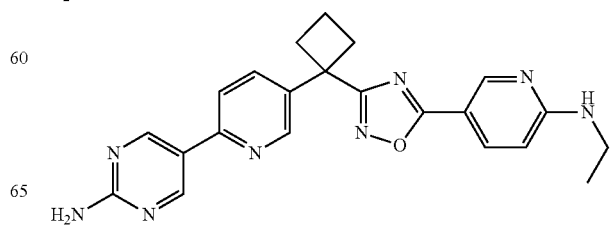

273
-continued
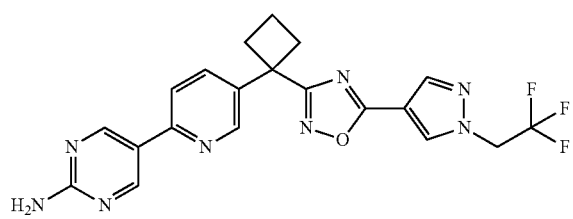
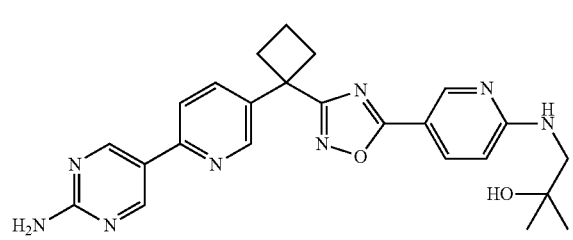
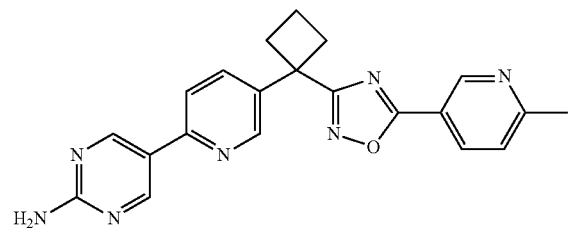
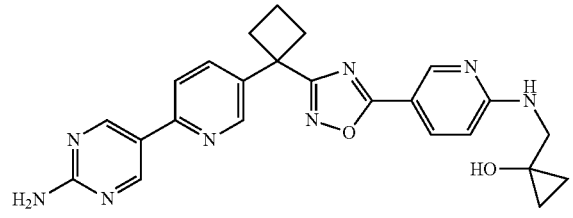
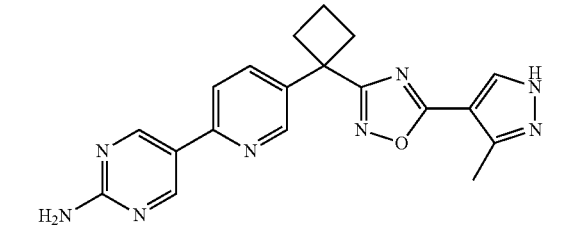
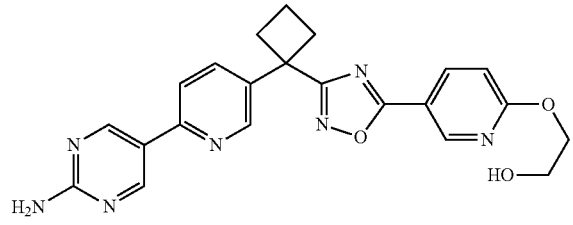
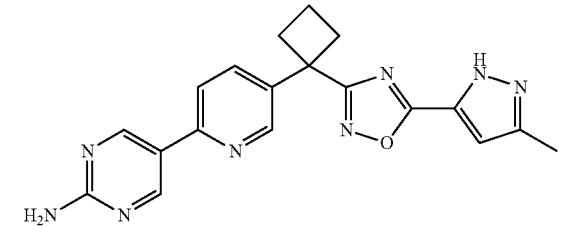
274
-continued
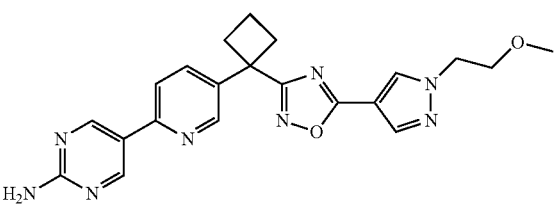
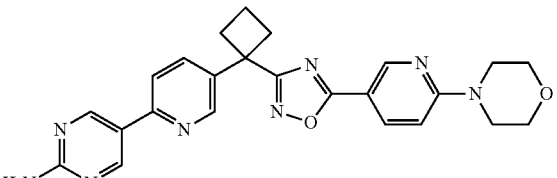
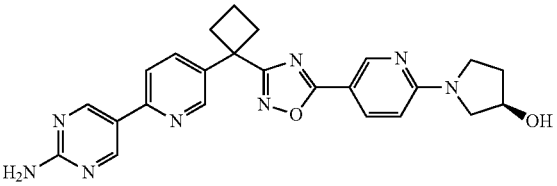
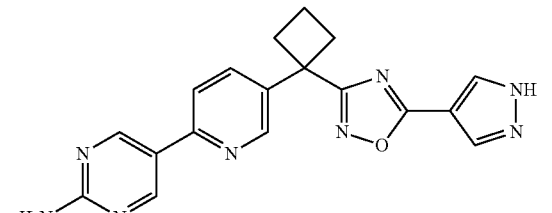
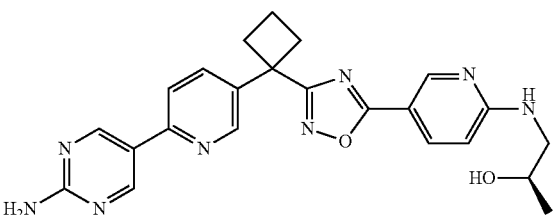
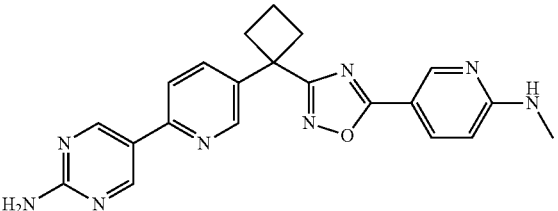
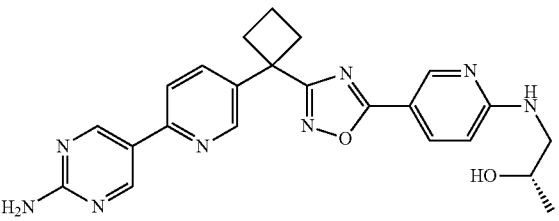
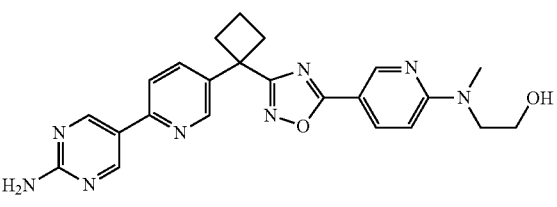

275
-continued
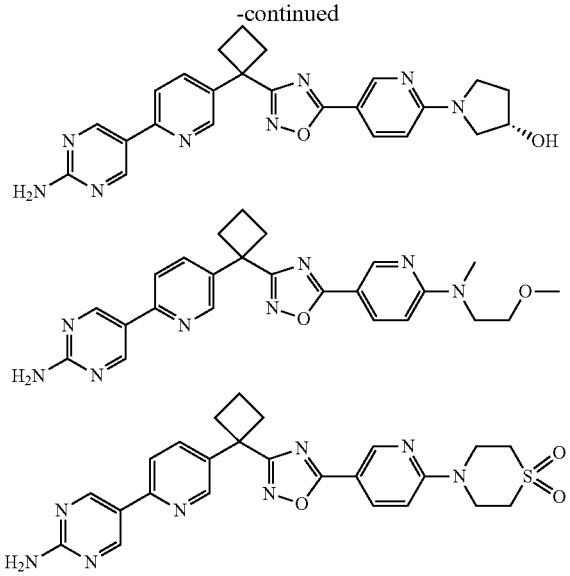
276
-continued
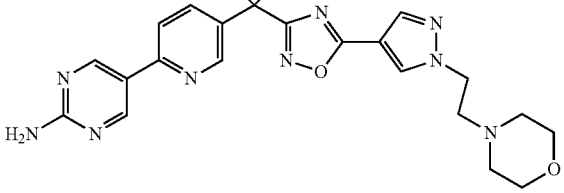
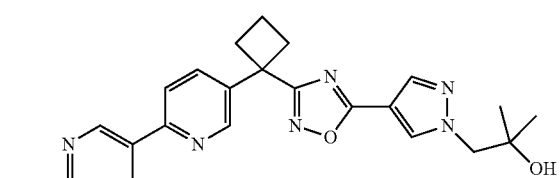
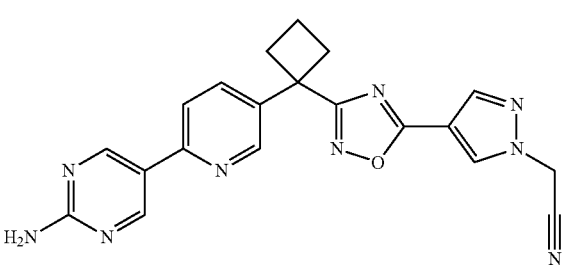
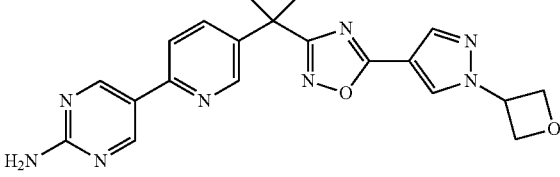
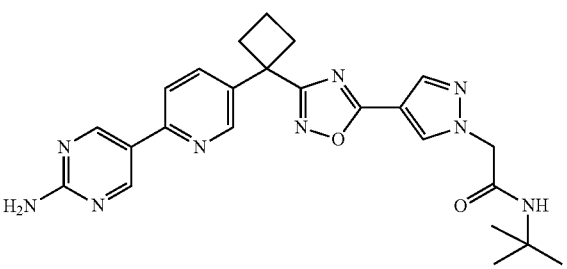
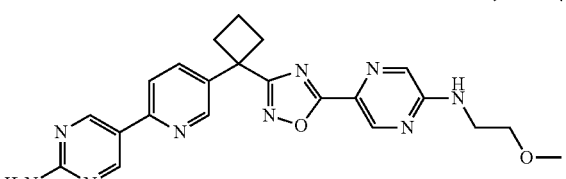
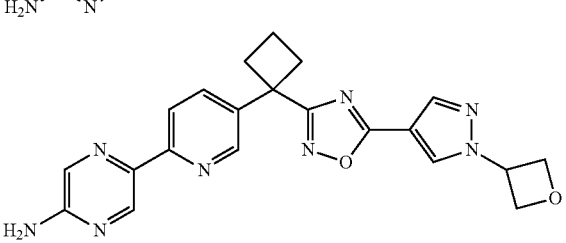

277
-continued
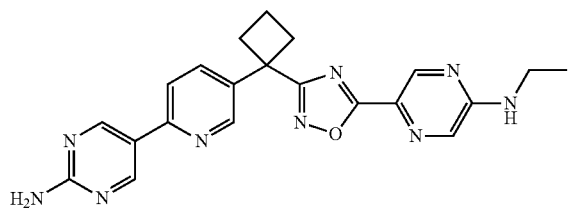
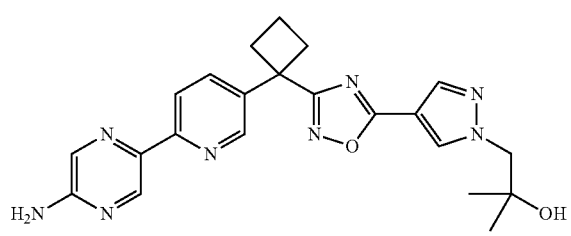
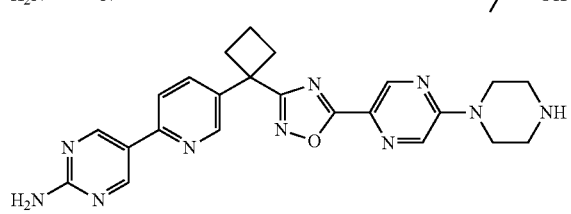
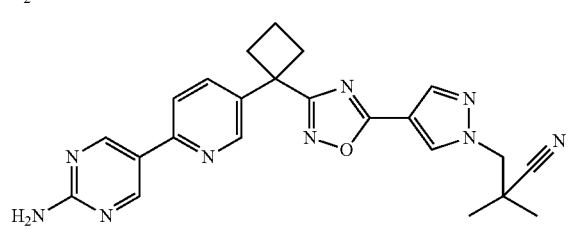
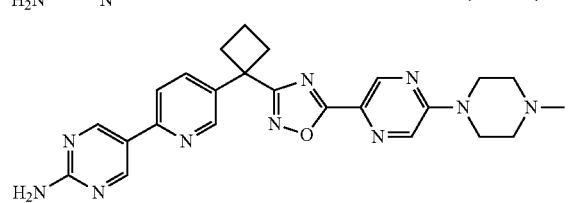
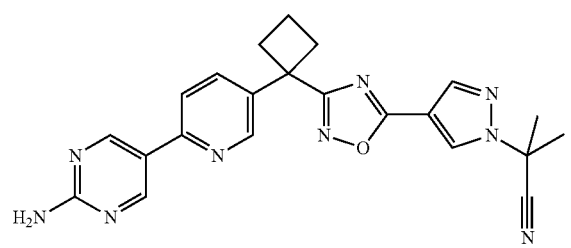
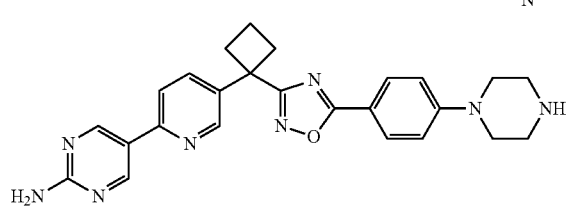
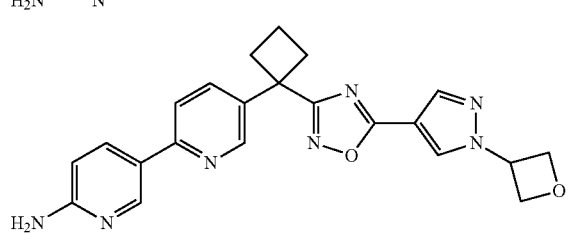
278
-continued
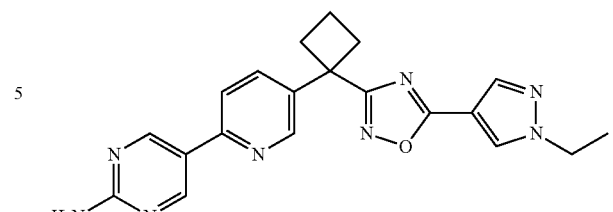
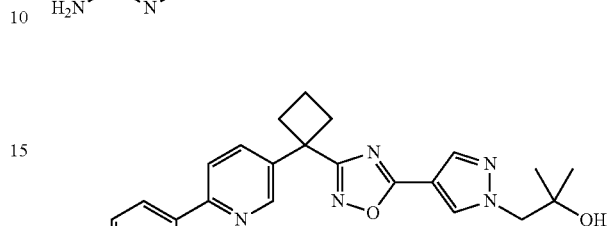
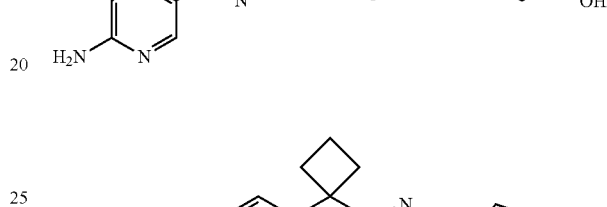
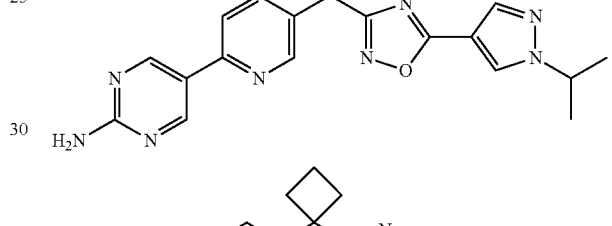
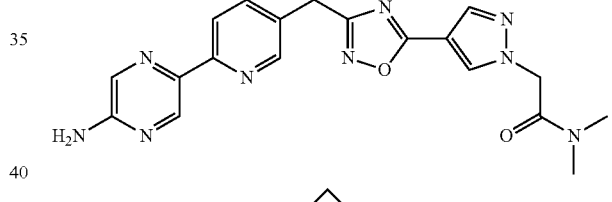
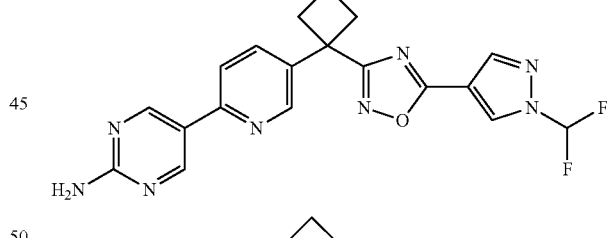
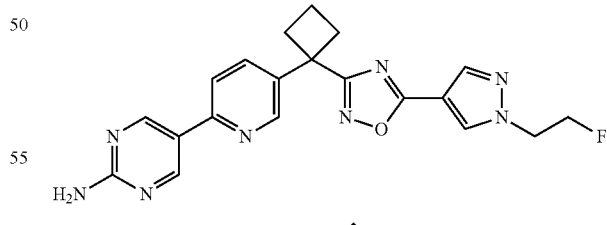
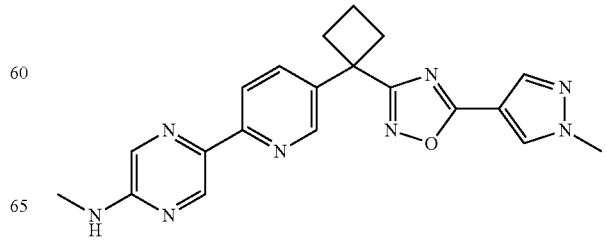

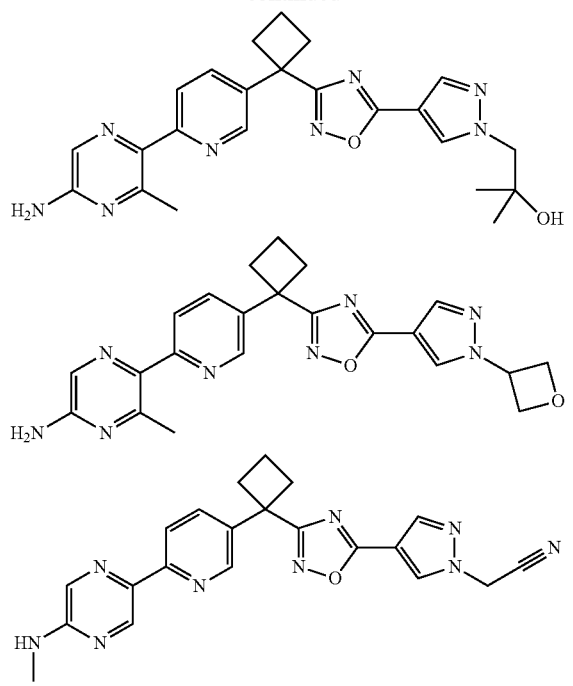

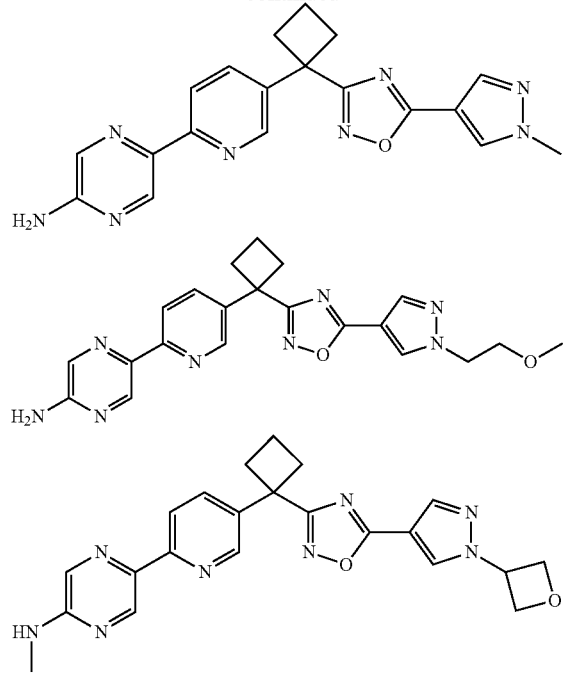

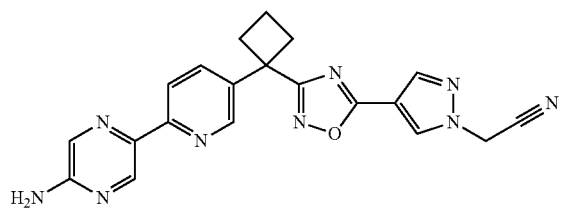

or pharmaceutically acceptable salts thereof.

23. A pharmaceutical composition comprising a compound according to claim 1, or a pharmaceutically acceptable salt thereof, and a pharmaceutically acceptable excipient and/or carrier.

24. A method of treating atherosclerosis comprising administering an effective amount of a compound according to claim 1 or a pharmaceutically acceptable salt thereof, to a patient in need thereof.

* * * * *